US011851460B2

United States Patent
Finlay

(10) Patent No.: US 11,851,460 B2
(45) Date of Patent: Dec. 26, 2023

(54) PD1 BINDING AGENTS

(71) Applicant: ULTRAHUMAN EIGHT LIMITED, Sandwich (GB)

(72) Inventor: William James Jonathan Finlay, Sandwich (GB)

(73) Assignee: ULTRAHUMAN EIGHT LIMITED, Sandwich (GB)

( * ) Notice: Subject to any disclaimer, the term of this patent is extended or adjusted under 35 U.S.C. 154(b) by 323 days.

(21) Appl. No.: 17/086,762

(22) Filed: Nov. 2, 2020

(65) Prior Publication Data

US 2021/0047415 A1    Feb. 18, 2021

Related U.S. Application Data

(60) Division of application No. 16/911,826, filed on Jun. 25, 2020, now Pat. No. 10,858,434, which is a continuation of application No. PCT/EP2019/055901, filed on Mar. 8, 2019.

(30) Foreign Application Priority Data

| Mar. 8, 2018 | (GB) | ...................................... | 1803745 |
| May 1, 2018 | (GB) | ...................................... | 1807176 |
| Jul. 10, 2018 | (GB) | ...................................... | 1811302 |
| Oct. 8, 2018 | (GB) | ...................................... | 1816372 |
| Oct. 29, 2018 | (GB) | ...................................... | 1817652 |

(51) Int. Cl.
C07K 16/28    (2006.01)

(52) U.S. Cl.
CPC ...... C07K 16/2818 (2013.01); *C07K 2317/24* (2013.01); *C07K 2317/33* (2013.01); *C07K 2317/52* (2013.01); *C07K 2317/55* (2013.01); *C07K 2317/565* (2013.01); *C07K 2317/76* (2013.01)

(58) Field of Classification Search
CPC ............ C07K 16/2818; C07K 2317/24; C07K 2317/33; C07K 2317/52; C07K 2317/55; C07K 2317/565; C07K 2317/76
See application file for complete search history.

(56) References Cited

U.S. PATENT DOCUMENTS

| 8,735,553 | B1 | 5/2014 | Li et al. |
| 10,858,434 | B2 | 12/2020 | Finlay et al. |
| 10,858,435 | B2 | 12/2020 | Finlay et al. |
| 2021/0101981 | A1 | 4/2021 | Finlay |

FOREIGN PATENT DOCUMENTS

| EP | 3 081 576 A1 | 10/2016 |
| WO | WO 2006/121168 A1 | 11/2006 |
| WO | WO-2013181452 A1 | 12/2013 |
| WO | WO 2017/055404 A1 | 4/2017 |
| WO | WO 2019/170885 A1 | 9/2019 |
| WO | WO 2019/170898 A1 | 9/2019 |

OTHER PUBLICATIONS

Lu, D. et al., "Abstract 572: A novel anti-PDL1 x anti-VEGFR2 bispecific antibody for enhanced antitumor immunity," Cancer Res (2016) 76 (14_Supplement): 572; https://doi.org/10.1158/1538-7445. AM2016-572, 1 page.
Tiller, T., et al., "A fully synthetic human Fab antibody library based on fixed VH/VL framework pairings with favorable biophysical properties", mAbs, 2013, vol. 5, No. 3, p. 445-470.
Zhou, F. et al., "A general user interface for prediction servers of proteins' post-translational modification sites," Nature Protocols, 1(3):1318-1321 (2006).
International Search Report and Written Opinion dated Jun. 7, 2019 for International Application No. PCT/EP2019/055901, 14 pages.
International Search Report and Written Opinion dated Jun. 11, 2019 for International Application No. PCT/EP2019/055927, 14 pages.
Finlay, W. J. J. et al., "Anti-PD1 'SHR-1210' aberrantly targets proangiogenic receptors and this polyspecificity can be ablated by paratope refinement," mAbs, 11(1):26-44 (2019).
Townsend, S. et al., "Augmented Binary Substitution: Single-pass CDR germlining and stabilization of therapeutic antibodies," PNAS, 112(50):15354-15359 (2015).

*Primary Examiner* — Amy E Juedes
*Assistant Examiner* — Brian Hartnett
(74) *Attorney, Agent, or Firm* — COOLEY LLP; Ivor Elrifi

(57) ABSTRACT

Provided herein are antibody molecules that bind specifically to Programmed cell death 1 (PD1) and related nucleic acid molecules, vectors and host cells. Also provided herein are medical uses of such antibody molecules.

17 Claims, 37 Drawing Sheets

Specification includes a Sequence Listing.

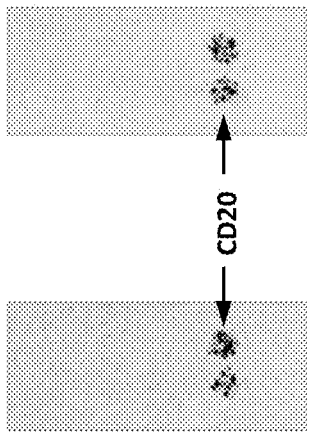
FIG. 11C
Rituximab IgG1 (1µg/ml)
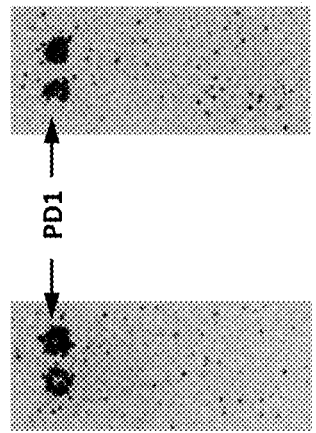
FIG. 11B
Pembrolizumab IgG1null (5µg/ml)
FIG. 11A
Key to spotting pattern /ZsGreen
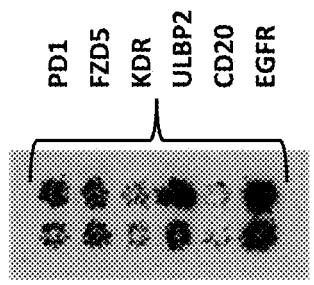
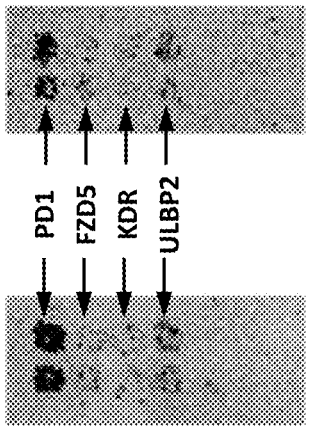
FIG. 11F
Mab005 IgG1null (5µg/ml)
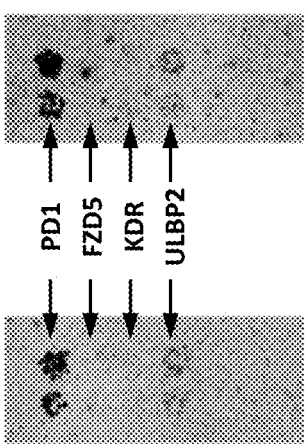
FIG. 11E
mVH/mVL Mab005 IgG1null (5µg/ml)
FIG. 11D
Isotype IgG1 (5µg/ml)
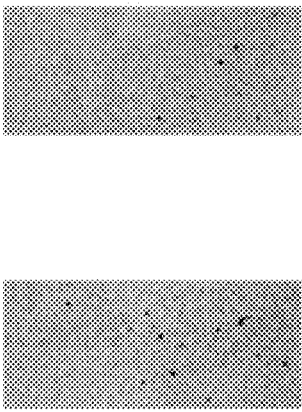

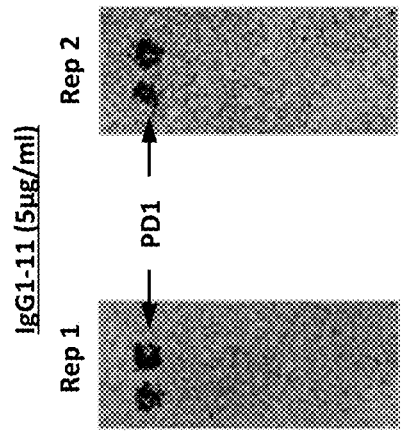
FIG. 11O
IgG1-11 (5μg/ml)
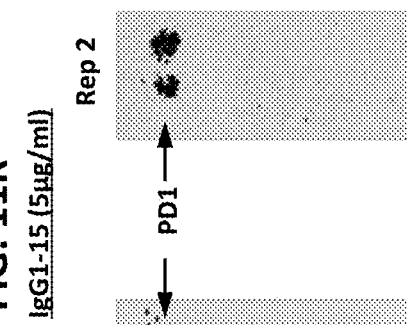
FIG. 11R
IgG1-15 (5μg/ml)
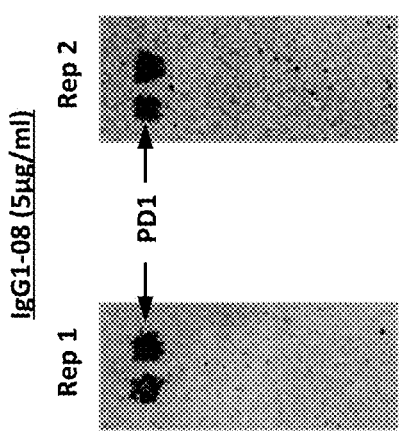
FIG. 11N
IgG1-08 (5μg/ml)
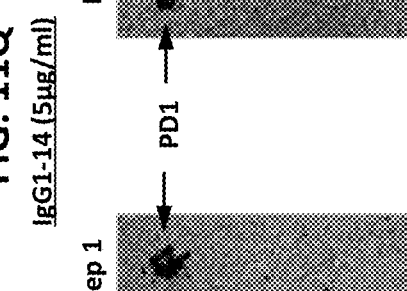
FIG. 11Q
IgG1-14 (5μg/ml)
FIG. 11M
IgG1-06 (5μg/ml)
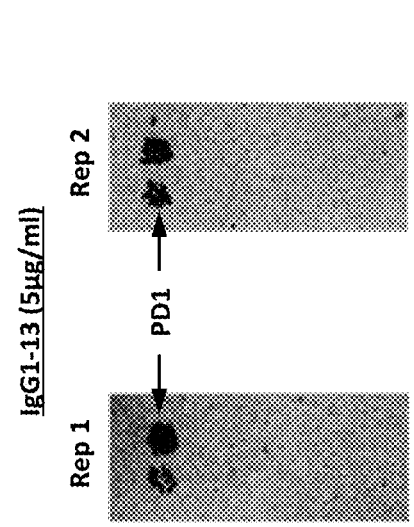
FIG. 11P
IgG1-13 (5μg/ml)

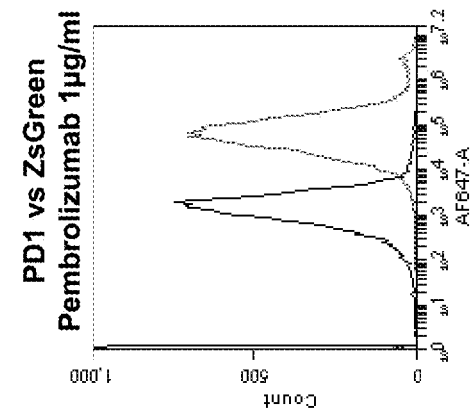
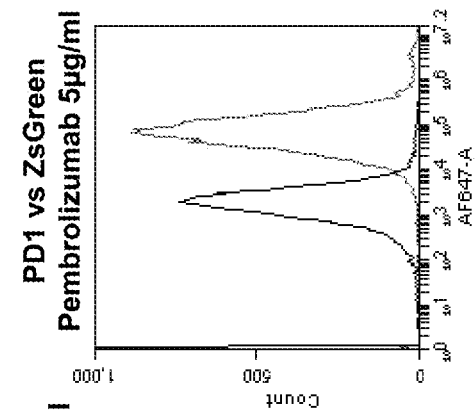
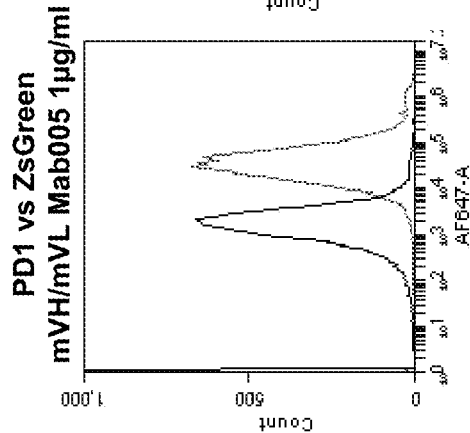
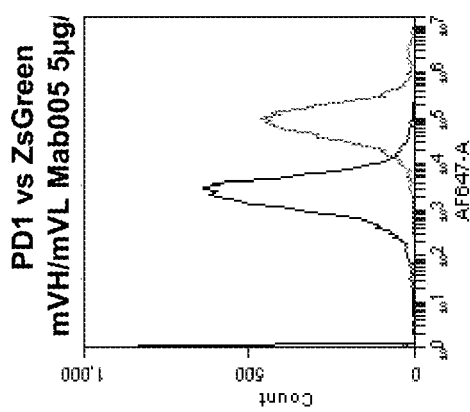
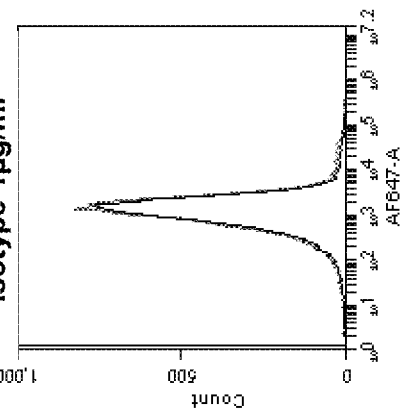
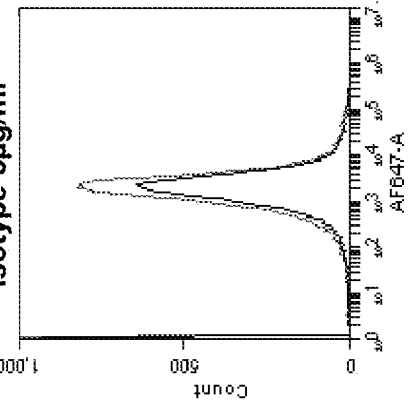
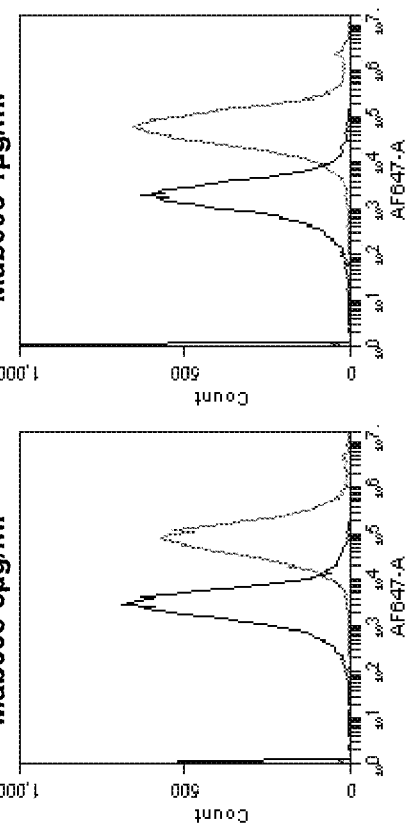

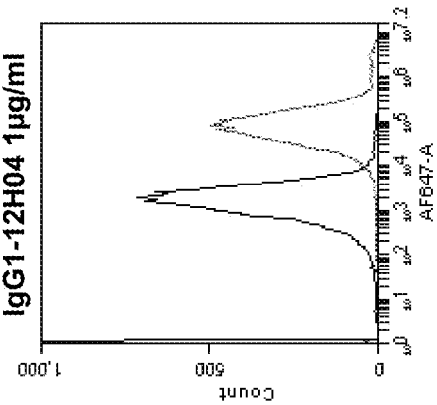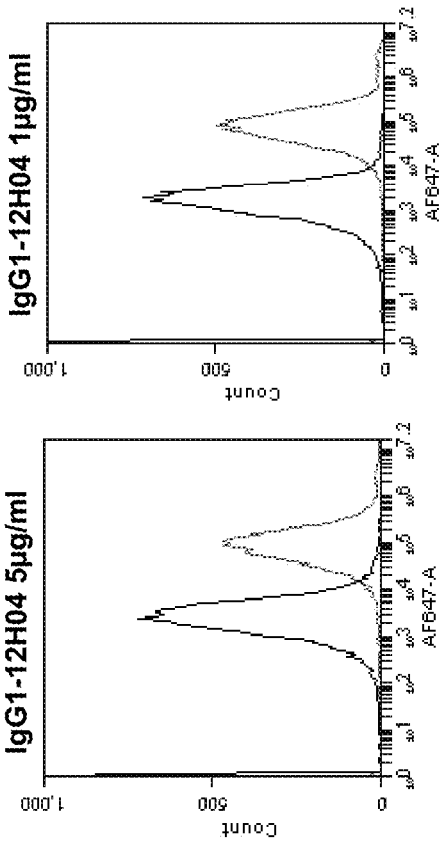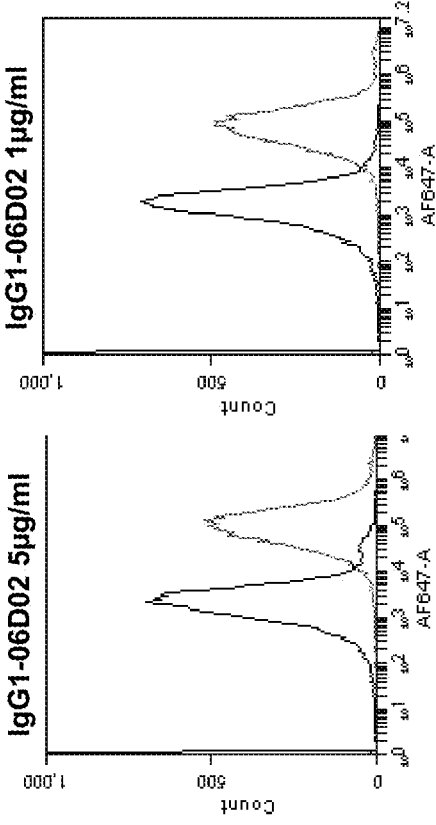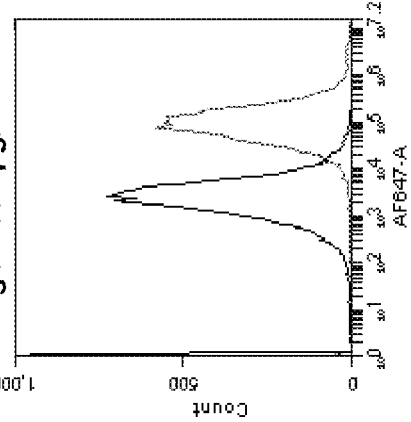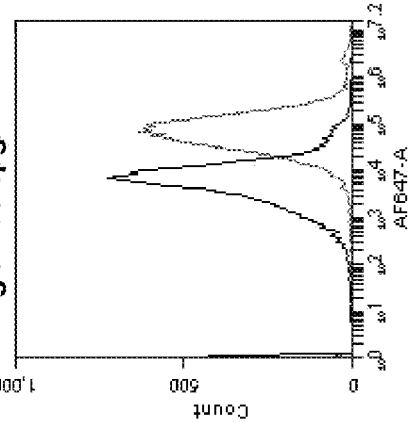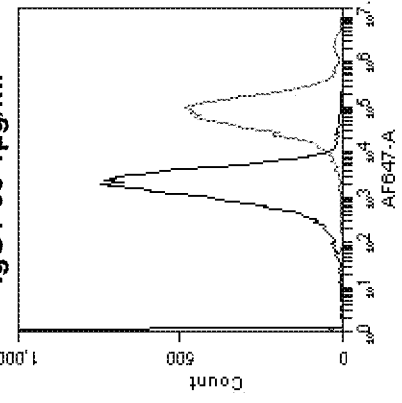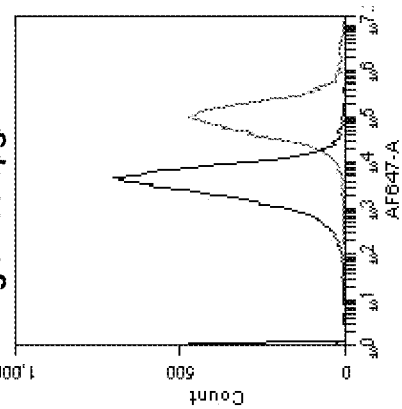
FIG. 12I, FIG. 12J, FIG. 12K, FIG. 12L, FIG. 12M, FIG. 12N, FIG. 12O, FIG. 12P

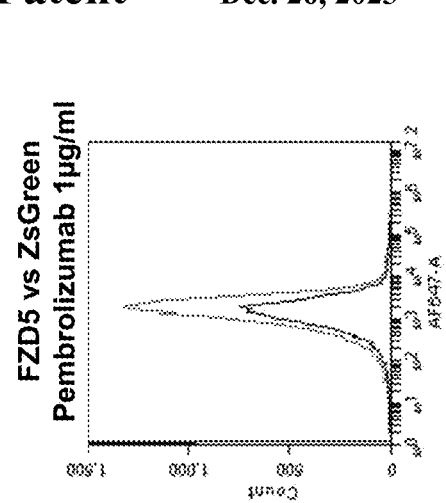
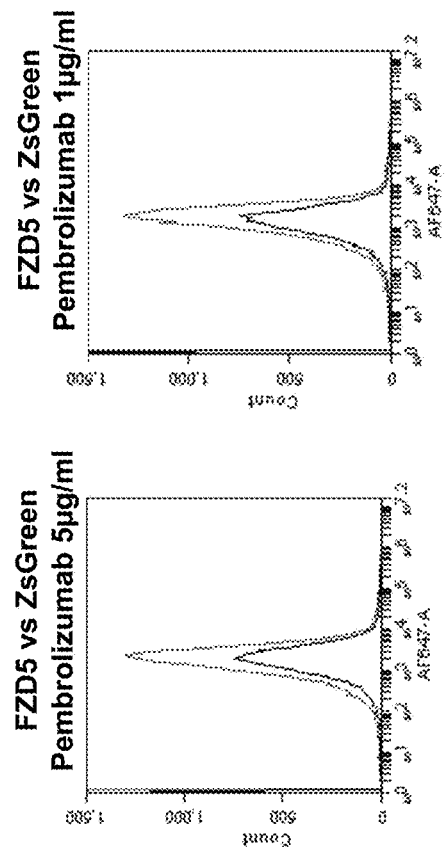
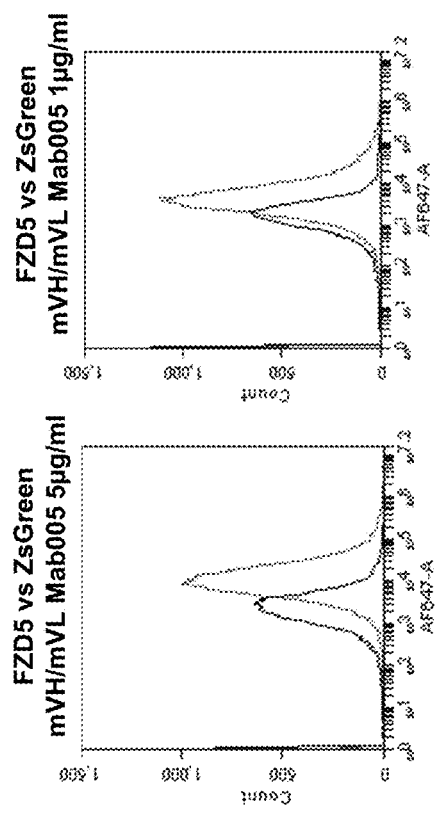
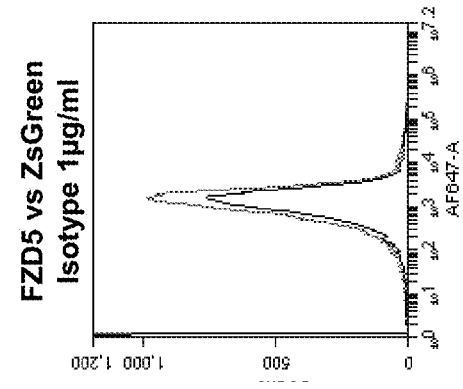
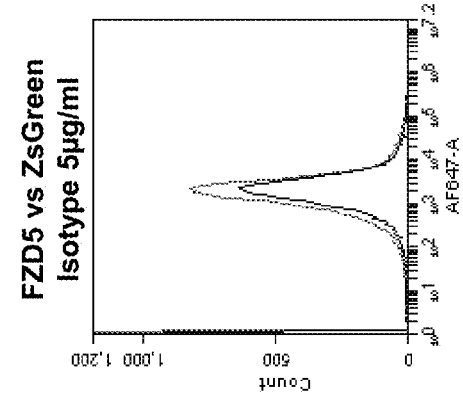
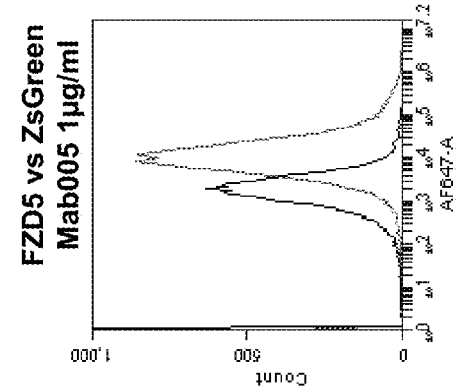
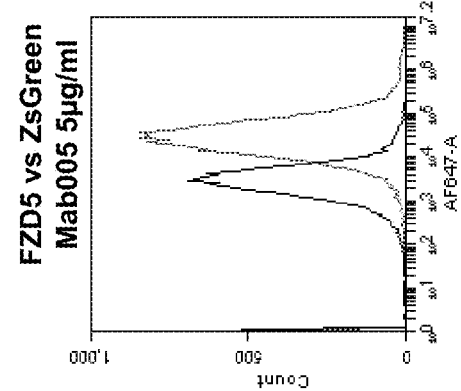

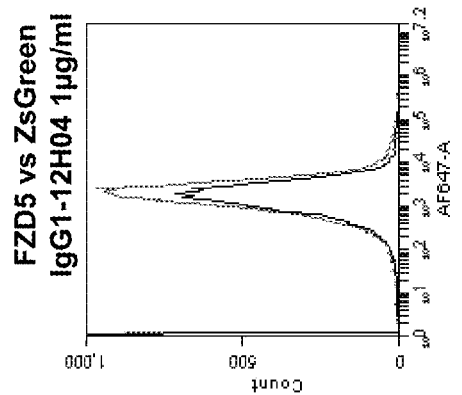
FIG. 13L
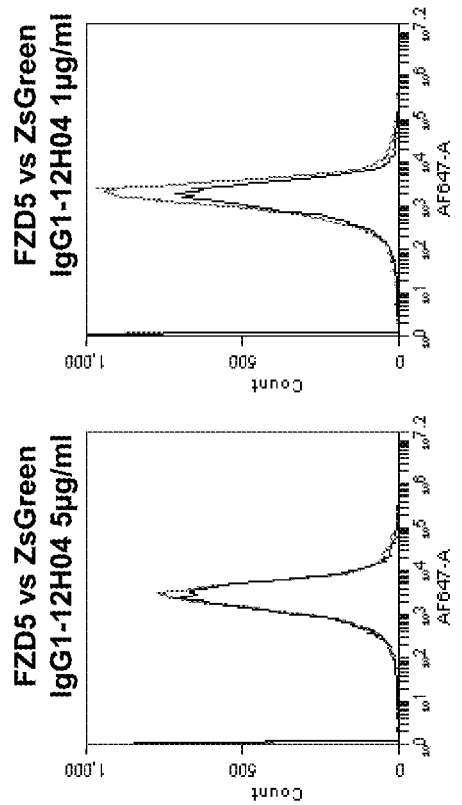
FIG. 13K
FIG. 13J
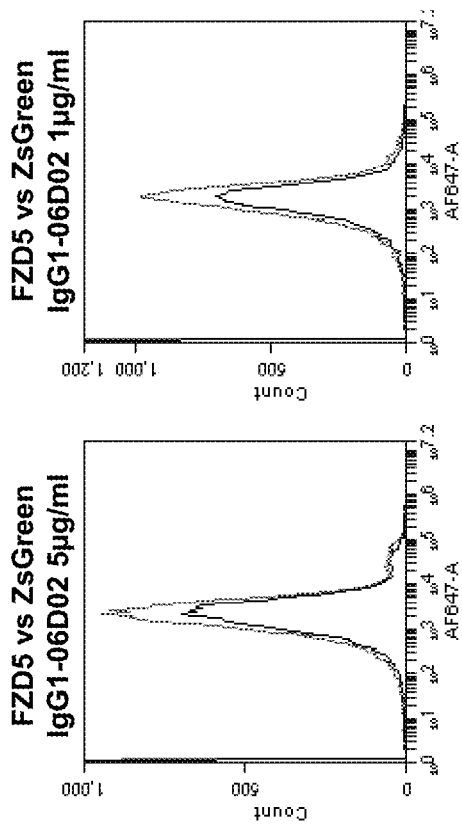
FIG. 13I
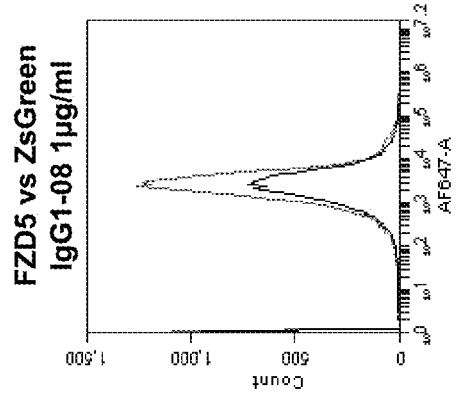
FIG. 13P
FIG. 13O
FIG. 13N
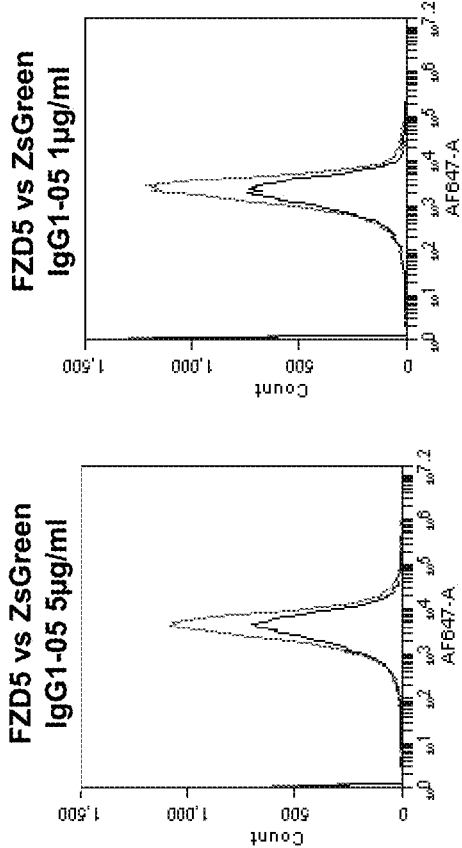
FIG. 13M

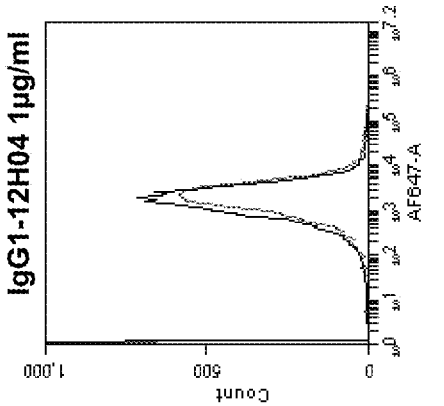
FIG. 14I KDR vs ZsGreen IgG1-06D02 5μg/ml
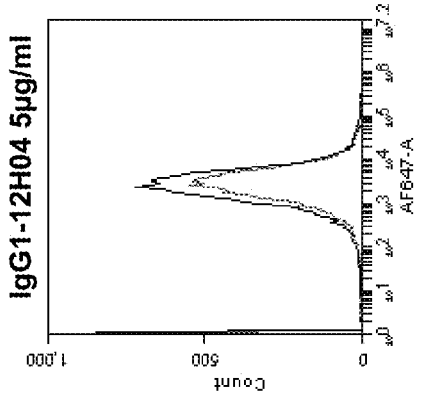
FIG. 14J KDR vs ZsGreen IgG1-06D02 1μg/ml
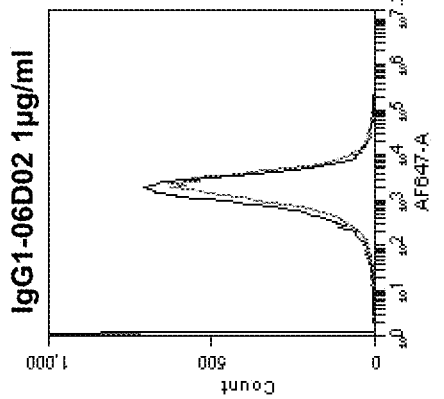
FIG. 14K KDR vs ZsGreen IgG1-12H04 5μg/ml
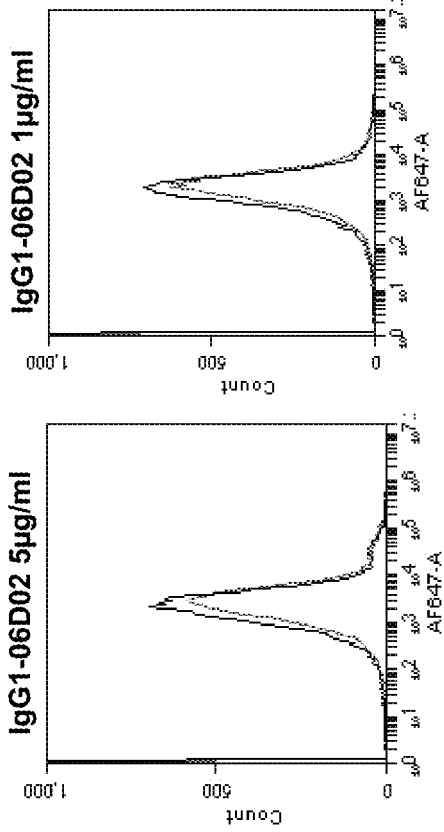
FIG. 14L KDR vs ZsGreen IgG1-12H04 1μg/ml
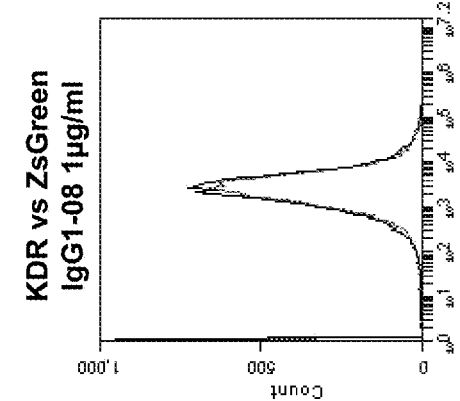
FIG. 14M KDR vs ZsGreen IgG1-05 5μg/ml
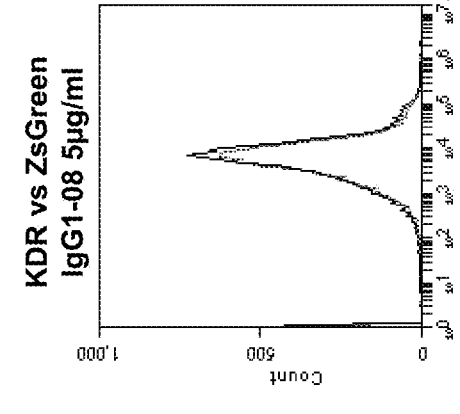
FIG. 14N KDR vs ZsGreen IgG1-05 1μg/ml
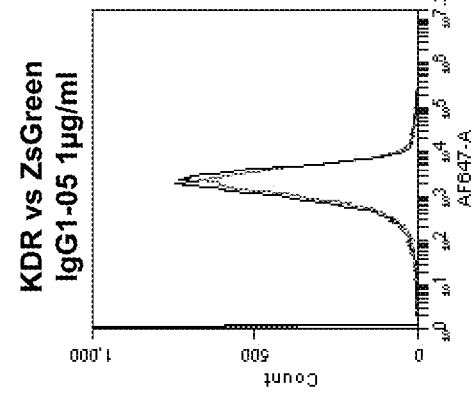
FIG. 14O KDR vs ZsGreen IgG1-08 5μg/ml
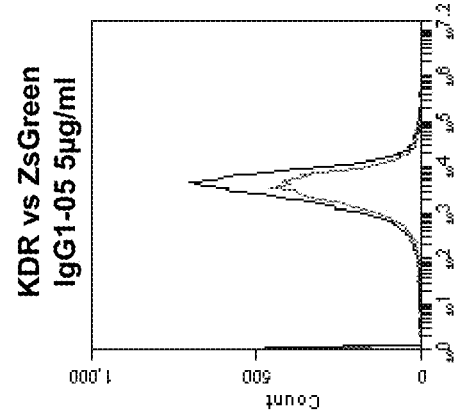
FIG. 14P KDR vs ZsGreen IgG1-08 1μg/ml

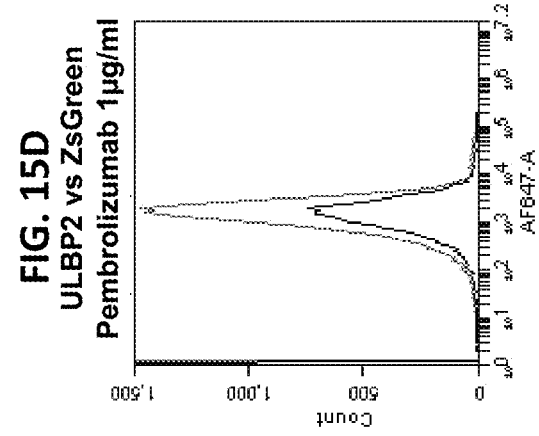
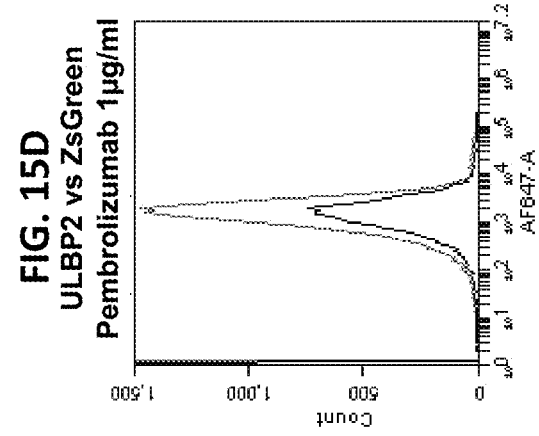
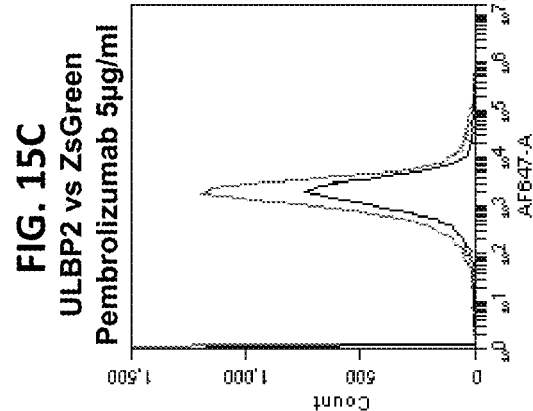
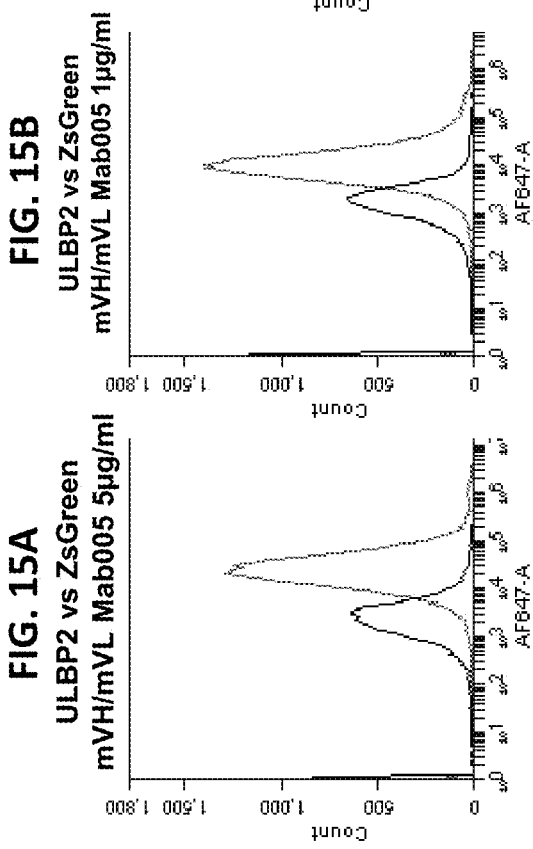
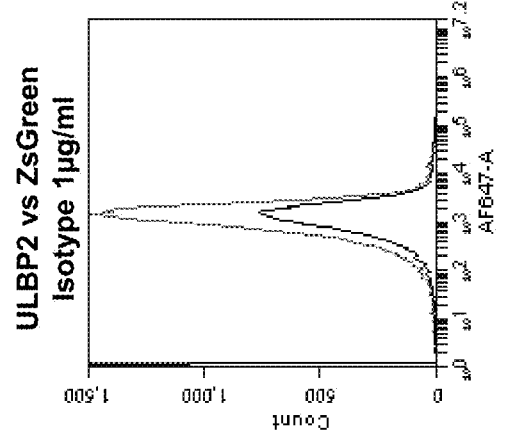
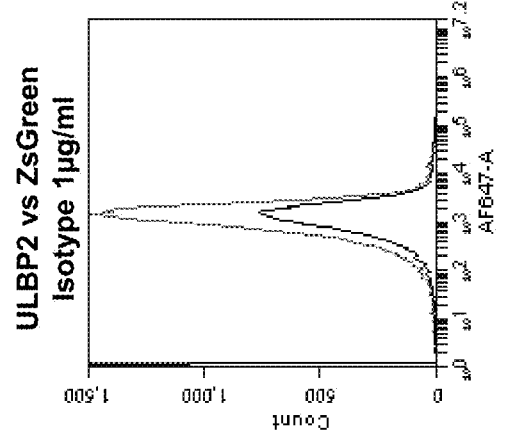
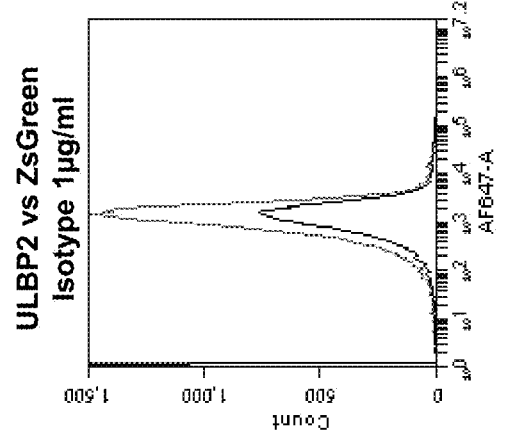
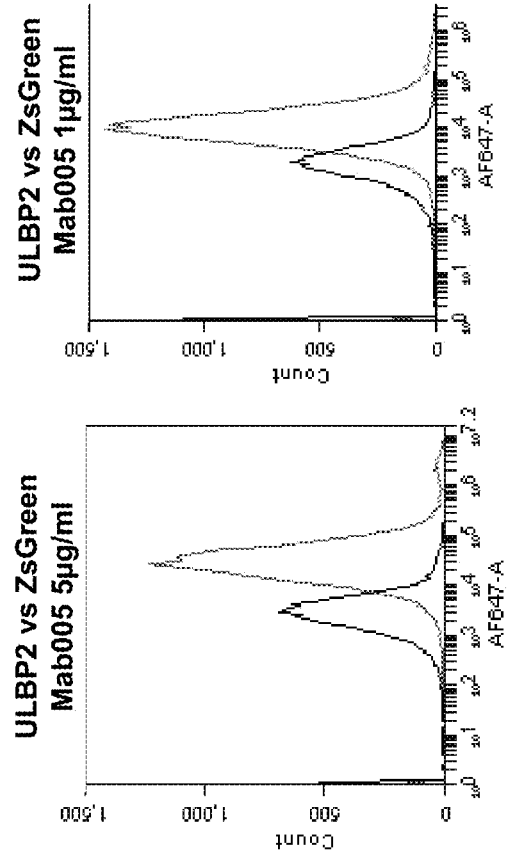

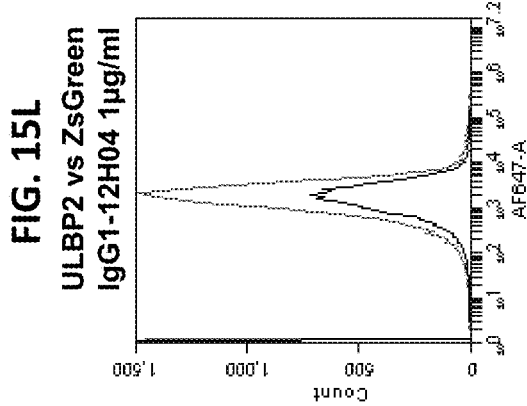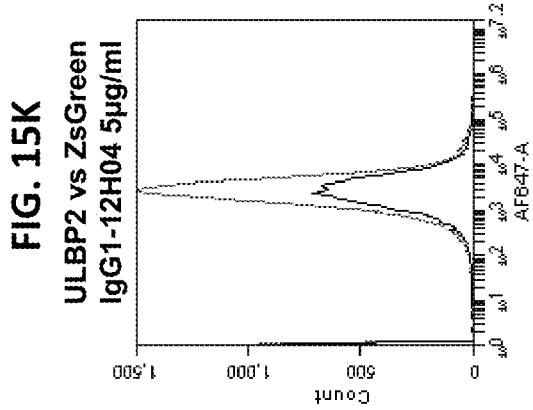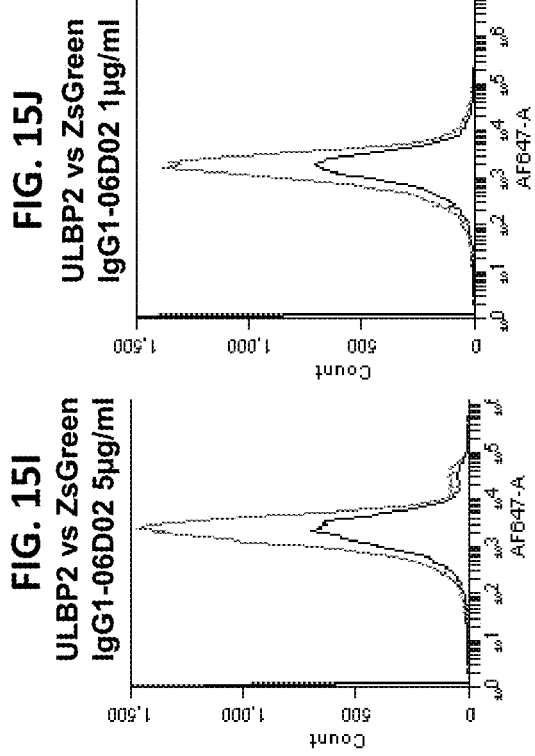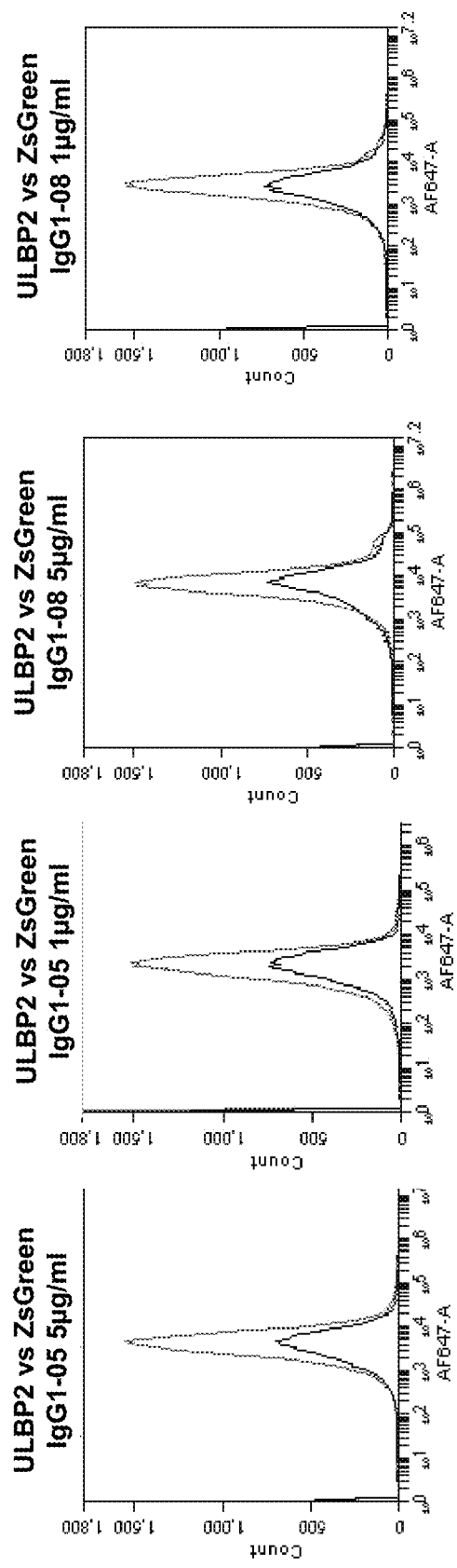

PD1 BINDING AGENTS

CROSS-REFERENCE TO RELATED APPLICATIONS

This application is a division of U.S. patent application Ser. No. 16/911,826, filed on Jun. 25, 2020 and issued as U.S. Pat. No. 10,858,434, which is a continuation of International Patent Application No. PCT/EP2019/055901, filed on Mar. 8, 2019, which claims the benefit of GB Patent Application No. 1817652.9, filed on Oct. 29, 2018, GB Patent Application No. 1816372.5, filed on Oct. 8, 2018, GB Patent Application No. 1811302.7, filed on Jul. 10, 2018, GB Patent Application No. 1807176.1, filed on May 1, 2018, and GB Patent Application No. 1803745.7, filed on Mar. 8, 2018, the disclosure of each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: UHEL_001_06US_SeqList_ST25.txt, date recorded: Nov. 2, 2020, file size ~113,226 bytes).

FIELD OF THE INVENTION

The invention relates to antibody molecules binding specifically to PD1 (also known as Programmed cell death 1, PDCD1, CD279, PD-1, SLEB2, PD-I, SLE1) and medical uses thereof.

BACKGROUND OF THE INVENTION

PD1 is a cell surface receptor that is a member of the immunoglobulin superfamily and is principally expressed on T cells, but has also been observed on pro-B cells. PD1 binds two known ligands, PD-L1 and PD-L2. The interaction of these ligands with PD1 on T cells down-regulates T cell inflammatory activity, which promotes immune self-tolerance. PD1 is, therefore, described as being an immune "checkpoint". This checkpoint activity has been demonstrated to minimise autoimmunity risk by promoting apoptosis (programmed cell death) in lymph node-resident T cells that are reactive to self-antigens. Importantly, PD1 ligation also promotes the survival of regulatory (anti-inflammatory) T cells.

While the role of PD1/PD-L1(2) binding in non-disease states is important for self-tolerance, it is also a key mechanism by which tumour cells escape identification as "foreign" during immune surveillance. Indeed, PD-L1 has been shown to be highly expressed in several cancers. Monoclonal antibodies that target PD1 and antagonise its function can therefore be of significant potential value in treating cancer, by boosting the immune response against malignant cells with high PD-L1 expression and/or which exhibit high levels of mutation. A significant body of preclinical and more recently, clinical, evidence suggests that blocking PD1/PD-L1(2) binding can enhance the anti-tumour activity of T cells and inhibit the growth of both haematological and solid malignancies. As PD1/PD-L1 activity can also be induced in chronic diseases such as HIV, anti-PD1 antagonistic antibodies may also have therapeutic value in infectious disease settings. Hence, antagonistic anti-PD1 mAbs have the potential to act as immunotherapeutic agents in cancer, immune and infectious disease settings, and to amplify the effectiveness of currently established therapies.

The majority of currently approved antibody therapeutics are derived from immunized rodents. Many of those antibodies have undergone a process known as "humanization", via the "grafting" of murine CDRs into human v-gene framework sequences (see Nelson et al., 2010, Nat Rev Drug Discov 9: 767-774). This process is often inaccurate and leads to a reduction in target binding affinity of the resulting antibody. To return the binding affinity of the original antibody, murine residues are usually introduced at key positions in the variable domain frameworks of the grafted v-domains (also known as "back-mutations").

While antibodies humanized via CDR grafting and back mutations have been shown to induce lower immune response rates in the clinic in comparison to those with fully murine v-domains, antibodies humanized using this basic grafting method still carry significant clinical development risks due to the potential physical instability and immunogenicity motifs still housed in the grafted CDR loops. As animal testing of protein immunogenicity is often non-predictive of immune responses in man, antibody engineering for therapeutic use focuses on minimizing predicted human T-cell epitope content, non-human germline amino acid content and aggregation potential in the purified protein.

The ideal humanized agonistic anti-PD1 antibody would therefore have as many identical residues as possible in the v-domains to those found in both the frameworks and CDRs of well-characterized human germline sequences. Townsend et al. (2015; PNAS 112: 15354-15359) describe a method for generating antibodies in which CDRs derived from rat, rabbit and mouse antibodies were grafted into preferred human frameworks and then subject to a human germ-lining approach termed "Augmented Binary Substitution". Although the approach demonstrated a fundamental plasticity in the original antibody paratopes, even when an investigator is in possession of highly accurate antibody-antigen co-crystal structural data, it is still not possible to reliably predict which individual residues in the CDR loops of any given antibody can be converted to human germline, and in what combination. Additionally, the Townsend et al. study did not address the addition of mutagenesis beyond the residues found in the human germline at positions where the removal of development risk motifs might be beneficial. This is a technological limitation which renders the process inherently inefficient, requiring an extra stage of modification of the starting antibody sequence. In addition, it cannot currently be accurately predicted what modifications in distal positions of the protein sequence of an individual v-domain, or even on the partner v-domain, might facilitate the removal of risk motifs while maintaining antigen binding affinity and specificity.

CDR germ-lining and development quality optimisation is thus a complex, multifactorial problem, as multiple functional properties of the molecule should preferably be maintained or improved, including in this instance: target binding specificity, PD1/PD-L1 signalling antagonism, affinity to PD1 from both human and animal test species (e.g. cynomolgus monkey, also known as the crab-eating macaque, i.e. *Macaca fascicularis*) should be as similar as possible to facilitate highly accurate preclinical safety testing, v-domain biophysical stability and/or IgG expression yield should be optimal for manufacturing purposes. Antibody engineering studies have shown that mutation of even single residue positions in key CDRs can have dramatic negative effects on all of these desired molecular properties.

WO2015/085847A1 describes an antagonistic murine anti-PD1 IgG molecule termed "MAb005", and also the preparation of humanized forms of MAb005. Those humanized forms of MAb005 were produced using classical humanization techniques, i.e. by grafting of Kabat-defined murine CDRs into human heavy and light chain framework sequences, with some of the human framework residues being potentially back-mutated to the correspondingly positioned MAb005 murine residues. For reasons noted above, such humanized forms of MAb005 described in WO2015/085847A1 are not ideal.

SUMMARY OF THE INVENTION

The present invention provides a number of anti-PD1 antibodies and medical uses thereof.

According to one aspect of the invention, there is provided an antibody molecule which specifically binds to human PD1, and optionally also to cynomolgus monkey PD1, or an antigen-binding portion thereof, wherein the antibody molecule or antigen-binding portion comprises a heavy chain variable region with:
- an HCDR1 having amino acids in sequence in the following order: G-F-T-F-S-S-Y-L or any amino acid (for example A/D/E/F/G/H/I/N/P/Q/S/T/V/W/Y)-M-S (SEQ ID NO: 26);
- an HCDR2 having amino acids in sequence in the following order: V or a conservative substitution of V-A-T/N-I-S-G-G-G-A/S-E/N-T/K-Y-Y-P/V-D-S-V-K-G (SEQ ID NO: 27); and an HCDR3 having amino acids in sequence in the following order: Q or any amino acid (for example T/L/M/N)-L or any amino acid (for example G/K/M/Q/S/V)-Y or a conservative substitution of Y (for example H)-Y or any amino acid (for example A/D/F/G/M-A/D/E/F/I/K/M/S/W)-F or any amino acid (for example A/D/E/K/M/S/W)-D-Y (SEQ ID NO: 28).

In aspects of the invention, the HCDR1 of the antibody molecule or antigen-binding portion may exclude the sequences GFTFSSYMMS (SEQ ID NO: 29; MAb005 murine/humanized antibody HCDR1 disclosed in WO2015/085847A1; US2016/376367A1), TISGGGAN-TYYPDSVKG (SEQ ID NO: 30; MAb005 murine/humanized antibody HCDR2 disclosed in WO2015/085847A1; US2016/376367A1), and/or the HCDR3 of the antibody molecule or antigen-binding portion may exclude the sequence QLYYFDY (SEQ ID NO: 31; MAb005 murine/humanized antibody HCDR3 disclosed in WO2015/085847A1; US2016/376367A1).

The antibody molecule or antigen-binding portion may further comprise a light chain variable region with:
- an LCDR1 having amino acids in sequence in the following order: R-A-S-Q-S-I-S or a conservative substitution of S-S or a conservative substitution of S-Y or a conservative substitution of Y-L or a conservative substitution of L-N/T or a conservative substitution of N or T (SEQ ID NO: 32);
- an LCDR2 having amino acids in sequence in the following order: A/T or a conservative substitution of A or T-A-S or a conservative substitution of S-S-L-Q or any amino acid (for example, A/H)-S or any amino acid (for example, D, Y) (SEQ ID NO: 33); and
- an LCDR3 having amino acids in sequence in the following order: Q-Q-S or any amino acid (for example, V)-Y-S-T or any amino acid (for example, I)-P-W or any amino acid (for example, L)-T (SEQ ID NO: 34).

In aspects of the invention, the LCDR1 of the antibody molecule or antigen-binding portion may exclude the sequence LASQTIGTWLT (SEQ ID NO: 35; MAb005 murine/humanized antibody LCDR1 disclosed in WO2015/085847A1; US2016/376367A1), and/or the LCDR2 of the antibody molecule or antigen-binding portion may exclude the sequence TATSLAD (SEQ ID NO: 36; MAb005 murine/humanized antibody LCDR2 disclosed in WO2015/085847A1; US2016/376367A1) and/or the LCDR3 of the antibody molecule or antigen-binding portion may exclude the sequence QQVYSIPWT (SEQ ID NO: 37; MAb005 murine/humanized antibody LCDR3 disclosed in WO2015/085847A1; US2016/376367A1).

In some aspects, disclosed herein is an anti-PD1 antibody or an antigen-binding portion thereof, wherein the antibody comprises a heavy chain variable (VH) region comprising HCDR1, HCDR2, and HCDR3 and a light chain variable (VL) region comprising LCDR1, LCDR2, and LCDR3, wherein
(a) the HCDR1 comprises the amino acid sequence G-F-T-F-S-S-Y-$X_1$-M-S, wherein $X_1$ is L or any other amino acid (SEQ ID NO: 26);
(b) the HCDR2 comprises the amino acid sequence $X_1$-A-$X_2$-I-S-G-G-G-$X_3$-$X_4$-$X_5$-Y-Y-$X_6$-D-S-V-K-G, wherein $X_1$ is V or a conservative substitution of V, $X_2$ is T or N, $X_3$ is A or S, $X_4$ is E or N, $X_5$ is T or K, and $X_6$ is P or V (SEQ ID NO: 27);
(c) the HCDR3 comprises the amino acid sequence $X_1$-$X_2$-$X_3$-$X_4$-$X_5$-D-Y, wherein $X_1$ is Q or any other amino acid (for example, T, L, M, or N), $X_2$ is L or any other amino acid (for example, G, K, M, Q, S, or V), $X_3$ is Y or a conservative substitution of Y (for example, H), $X_4$ is Y or any other amino acid (for example, A, D, F, G, M, E, I, K, S, or W) and $X_5$ is F or any other amino acid (for example A, D, E, I, K, M, S, or W) (SEQ ID NO: 28);
(d) the LCDR1 comprises the amino acid sequence R-A-S-Q-S-I-$X_1$-$X_2$-$X_3$-$X_4$-$X_5$, wherein $X_1$ is S or a conservative substitution of S, $X_2$ is S or a conservative substitution of S, $X_3$ is Y or a conservative substitution of Y, $X_4$ is L or a conservative substitution of L, and $X_5$ is N or T or a conservative substitution of N or T (SEQ ID NO: 32);
(e) the LCDR2 comprises the amino acid sequence $X_1$-A-$X_2$-S-L-$X_3$-$X_4$, wherein $X_1$ is A or T or a conservative substitution of A or T, $X_2$ is S or a conservative substitution of S, $X_3$ is Q or any other amino acid, and $X_4$ is S or any other amino acid (SEQ ID NO: 33); and
(f) the LCDR3 comprises the amino acid sequence Q-Q-$X_1$-Y-S-$X_2$-P-$X_3$-T, wherein $X_1$ is S or any other amino acid, $X_2$ is T or any other amino acid, and $X_3$ is W or any other amino acid (SEQ ID NO: 34).

In some aspects, the invention provides an anti-PD1 antibody or an antigen-binding portion thereof, wherein the antibody comprises a heavy chain variable (VH) region and a light chain variable (VL) region, wherein
(a) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QLYGFDY (SEQ ID NO: 40); and the VL region amino acid sequence comprises LCDR1 of RASQSISSWLN (SEQ ID NO: 41), LCDR2 of AASSLQS (SEQ ID NO: 42) and LCDR3 of QQSYS-TPWT (SEQ ID NO: 43);
(b) the VH region amino acid sequence comprises HCDR1 of GFTFSSYLMS (SEQ ID NO: 38), HCDR2 of VATISGGGSEKYYVDSVKG (SEQ ID NO: 39)

and HCDR3 of QVYYFDY (SEQ ID NO: 44); and the VL region amino acid sequence comprises LCDR1 of RASQSISSWLN (SEQ ID NO: 41), LCDR2 of AASSLQS (SEQ ID NO: 42) and LCDR3 of QQSYS-TPWT (SEQ ID NO: 43);

(c) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QLYFFDY (SEQ ID NO: 45); and the VL region amino acid sequence comprises LCDR1 of RASQSISSWLN (SEQ ID NO: 41), LCDR2 of AASSLQS (SEQ ID NO: 42) and LCDR3 of QQSYS-TPWT (SEQ ID NO: 43);

(d) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QLYAFDY (SEQ ID NO: 46); and the VL region amino acid sequence comprises LCDR1 of RASQSISSWLN (SEQ ID NO: 41), LCDR2 of AASSLQS (SEQ ID NO: 42) and LCDR3 of QQSYS-TPWT (SEQ ID NO: 43);

(e) the VH region amino acid sequence comprises HCDR1 of GFTFSSYLMS (SEQ ID NO: 38), HCDR2 of VATISGGGSETYYVDSVKG (SEQ ID NO: 48) and HCDR3 of QLYGFDY (SEQ ID NO: 40); and the VL region amino acid sequence comprises LCDR1 of RASQSISSWLN (SEQ ID NO: 41), LCDR2 of AASSLQS (SEQ ID NO: 42) and LCDR3 of QQSY-SIPWT (SEQ ID NO: 47);

(f) the VH region amino acid sequence comprises HCDR1 of GFTFSSYLMS (SEQ ID NO: 38), HCDR2 of VATISGGGAEKYYVDSVKG (SEQ ID NO: 49) and HCDR3 of QLYGFDY (SEQ ID NO: 40); and the VL region amino acid sequence comprises LCDR1 of RASQSISSWLN (SEQ ID NO: 41), LCDR2 of AASSLQD (SEQ ID NO: 50) and LCDR3 of QQSYS-TPWT (SEQ ID NO: 43);

(g) the VH region amino acid sequence comprises HCDR1 of GFTFSSYLMS (SEQ ID NO: 38), HCDR2 of VATISGGGSETYYVDSVKG (SEQ ID NO: 48), and HCDR3 of QLYGFDY (SEQ ID NO: 40); and the VL region amino acid sequence comprises LCDR1 of RASQSISSWLN (SEQ ID NO: 41), LCDR2 of AASSLQS (SEQ ID NO: 42), and LCDR3 of QQSY-SIPWT (SEQ ID NO: 47);

(h) the VH region amino acid sequence comprises HCDR1 of GFTFSSYLMS (SEQ ID NO: 38), HCDR2 of VATISGGGAEKYYVDSVKG (SEQ ID NO: 49), and HCDR3 of QLYGFDY (SEQ ID NO: 40); and the VL region amino acid sequence comprises LCDR1 of RASQSISSWLN (SEQ ID NO: 41), LCDR2 of AASSLQD (SEQ ID NO: 50), and LCDR3 of QQSYS-TPWT (SEQ ID NO: 43);

(i) the VH region amino acid sequence comprises HCDR1 of GFTFSSYLMS (SEQ ID NO: 38), HCDR2 of VATISGGGSNTYYVDSVKG (SEQ ID NO: 51), and HCDR3 of QLYGFDY (SEQ ID NO: 40); and the VL region amino acid sequence comprises LCDR1 of RASQSISTWLN (SEQ ID NO: 52), LCDR2 of AASSLAS (SEQ ID NO: 53), and LCDR3 of QQSYS-TPWT (SEQ ID NO: 43);

(j) the VH region amino acid sequence comprises HCDR1 of GFTFSSYLMS (SEQ ID NO: 38), HCDR2 of VATISGGGSEKYYVDSVKG (SEQ ID NO: 39), and HCDR3 of QVYYFDY (SEQ ID NO: 44); and the VL region amino acid sequence comprises LCDR1 of RASQSISSWLN (SEQ ID NO: 41), LCDR2 of AASSLHS (SEQ ID NO: 54), and LCDR3 of QQSYS-TPWT (SEQ ID NO: 43); or (k) the VH region amino acid sequence comprises HCDR1 of GFTFSSYLMS (SEQ ID NO: 38), HCDR2 of VATISGGGSEKYYVDSVKG (SEQ ID NO: 39), and HCDR3 of QVYYFDY (SEQ ID NO: 44); and the VL region amino acid sequence comprises LCDR1 of RASQSISSWLN (SEQ ID NO: 41), LCDR2 of AASSLQS (SEQ ID NO: 42), and LCDR3 of QQSYS-TPWT (SEQ ID NO: 43).

In some aspects, disclosed herein is an anti-PD1 antibody or an antigen-binding portion thereof, wherein the antibody comprises a heavy chain variable (VH) region and a light chain variable (VL) region, wherein the VH region amino acid sequence comprises:
(a) HCDR1 of SEQ ID NO: 38;
(b) HCDR2 of SEQ ID NO: 39, SEQ ID NO: 48, SEQ ID NO: 49 or SEQ ID NO: 51; and
(c) HCDR3 of SEQ ID NO: 40, SEQ ID NO: 44, SEQ ID NO: 45 or SEQ ID NO: 46; and the VL region amino acid sequence comprises:
(a') LCDR1 of SEQ ID NO: 41 or SEQ ID NO: 52;
(b') LCDR2 of SEQ ID NO: 42, SEQ ID NO: 50, SEQ ID NO: 53 or SEQ ID NO: 54; and
(c') LCDR3 of SEQ ID NO: 43 or SEQ ID NO: 47.

In some aspects, disclosed herein is an anti-PD1 antibody or an antigen-binding portion thereof, wherein the antibody comprises a heavy chain variable (VH) region and a light chain variable (VL) region, wherein (a) the VH region amino acid sequence comprises SEQ ID NO:1 and the VL region amino acid sequence comprises SEQ ID NO:2;
(b) the VH region amino acid sequence comprises SEQ ID NO:3 and the VL region amino acid sequence comprises SEQ ID NO:4;
(c) the VH region amino acid sequence comprises SEQ ID NO:5 and the VL region amino acid sequence comprises SEQ ID NO:6;
(d) the VH region amino acid sequence comprises SEQ ID NO:7 and the VL region amino acid sequence comprises SEQ ID NO:8;
(e) the VH region amino acid sequence comprises SEQ ID NO:9 and the VL region amino acid sequence comprises SEQ ID NO:10; or
(f) the VH region amino acid sequence comprises SEQ ID NO:11 and the VL region amino acid sequence comprises SEQ ID NO:12.

Also provided according to the invention is an immunoconjugate comprising the antibody molecule or antigen-binding portion thereof as defined herein linked, fused or conjugated to a therapeutic agent.

In another aspect the invention provides a nucleic acid molecule encoding the antibody molecule or antigen-binding portion thereof as defined herein.

Further provided is a vector comprising the nucleic acid molecule of the invention.

Also provided is a host cell comprising the nucleic acid molecule or the vector of the invention as defined herein.

In a further aspect there is provided a method of producing an anti-PD1 antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

Further provided herein is an antibody molecule or antigen-binding portion thereof as defined herein, or the immunoconjugate as defined herein, or the nucleic acid molecule as defined herein, or the vector as defined herein, or the pharmaceutical composition as defined herein, for use as a medicament. The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an infectious disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

The infectious disease may be selected in all aspects from the group consisting of: viral, bacterial, fungal or parasitic. In one embodiment, the infectious disease is human immunodeficiency virus (HIV) infection.

Also provided is an antibody molecule or antigen-binding portion thereof as defined herein, or the immunoconjugate as defined herein, or the nucleic acid molecule as defined herein, or the vector as defined herein, or the pharmaceutical composition as defined herein, for use in the treatment of an infectious disease.

Further provided is the use of an antibody molecule or antigen-binding portion thereof as defined herein, or an immunoconjugate as defined herein, or a nucleic acid molecule as defined herein, or a vector as defined herein, or a pharmaceutical composition as defined herein, in the manufacture of a medicament for the treatment of an infectious disease.

The invention also provides a method for treating or preventing an infectious disease in a subject, comprising administering an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

The invention also provides a method of producing an antibody molecule which specifically binds to human PD1 and optionally also to cynomolgus monkey PD1, or an antigen-binding portion thereof, comprising the steps of:
(1) grafting anti-PD1 CDRs from a non-human source into a human v-domain framework to produce a humanized anti-PD1 antibody molecule or antigen-binding portion thereof;
(2) generating a library of clones of the humanized anti-PD1 antibody molecule or antigen-binding portion thereof comprising one or more mutations in the CDRs;
(3) screening the library for binding to human PD1 and optionally also to cynomolgus monkey PD1;
(4) selecting clones from the screening step (3) having binding specificity to human PD1 and optionally also to cynomolgus monkey PD1; and
(5) producing an antibody molecule which specifically binds to human PD1 and optionally also to cynomolgus monkey PD1, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

BRIEF DESCRIPTION OF THE FIGURES

FIG. 12A-FIG. 12P. PD1 binding analysis by flow cytometry using transiently-transfected HEK293 cells. Analyses of binding specificity were performed on HEK293 cells transiently transfected with plasmids encoding either human PD1 (grey line) or ZS green marker (black line). Transfected cells were then stained using mVH/mVL Mab005-IgG1, IgG1-Mab005 (humanized), Pembrolizumab analog, isotype IgG1 and a subset of lead antibodies (IgG1-06D02, IgG1-12HO4, IgG1-05, IgG1-08). Each antibody was used in repeat staining at high (5 µg/ml) and moderate (1 µg/ml) concentration. These analyses confirmed that all antibodies (other than the isotype control IgG1) exhibited binding to PD1, but no antibody exhibited measurable signal on ZS-green transfected cells.

FIG. 13A-FIG. 13P. FZD5 binding analysis by flow cytometry using transiently-transfected HEK293 cells. Analyses of binding specificity were performed on HEK293 cells transiently transfected with plasmids encoding either human FZD5 (grey line) or ZS green marker (black line). Transfected cells were then stained using mVH/mVL Mab005-IgG1, IgG1-Mab005 (humanized), Pembrolizumab analog, isotype IgG1 and a subset of lead antibodies (IgG1-06D02, IgG1-12HO4, IgG1-05, IgG1-08). Each antibody was used in repeat staining at high (5 µg/ml) and moderate (1 µg/ml) concentration. These analyses confirmed that the only antibodies which exhibited binding to FZD5-expressing cells were mVH/mVL Mab005-IgG1 and IgG1-Mab005 (humanized).

FIG. 15A-FIG. 15P. ULBP2 binding analysis by flow cytometry using transiently-transfected HEK293 cells. Analyses of binding specificity were performed on HEK293 cells transiently transfected with plasmids encoding either human ULBP2 (grey line) or ZS green marker (black line).

Transfected cells were then stained using mVH/mVL Mab005-IgG1, IgG1-Mab005 (humanized), Pembrolizumab analog, isotype IgG1 and a subset of lead antibodies (IgG1-06D02, IgG1-12HO4, IgG1-05, IgG1-08). Each antibody was used in repeat staining at high (5 µg/ml) and moderate (1 µg/ml) concentration. These analyses confirmed that the only antibodies which exhibited binding to ULBP2-expressing cells were mVH/mVL Mab005-IgG1 and IgG1-Mab005 (humanized).

FIG. 16A-FIG. 16F. Off-target binding analysis ELISA assay. IgG1-Mab005 (humanized), mVH/mVL Mab005-IgG1, library-derived clones and designer clones in human IgG1null format were titrated (in µg/ml) in a direct binding ELISA against human PD1 (FIG. 16A) and cyno PD1 (FIG. 16B), human VEGFR2 (FIG. 16C) and rhesus VEGFR2 (FIG. 16D), human FZD5 (FIG. 16E) and BSA (FIG. 16F) proteins. These analyses confirmed that all anti-PD1 antibodies exhibited binding to PD1, but only IgG1-Mab005 (humanized) and mVH/mVL Mab005-IgG1 exhibited measurable off-target binding to VEGFR2 and FZD5 proteins.

Figure 17:
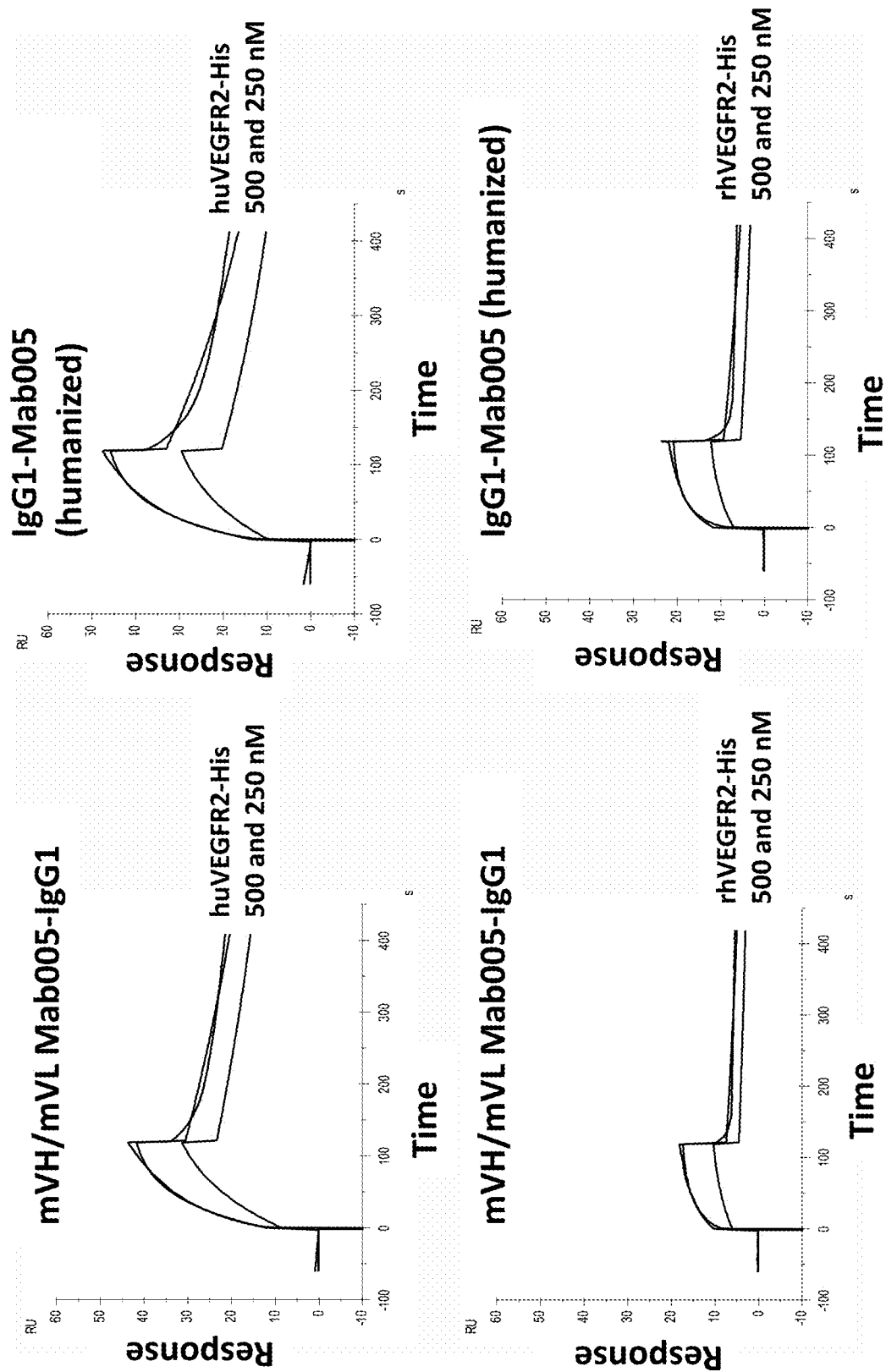

FIG. 17. VEGFR2 binding for mVH/mVL Mab005-IgG1 and IgG1-Mab005 (humanized) by Biacore. Human and rhesus monomeric VEGFR2-his proteins were titrated (in nM) in a direct binding ELISA against mVH/mVL Mab005-IgG1 and IgG1-Mab005 (humanized), captured by anti-human IgG1-Fc antibody. These analyses confirmed that both anti-PD1 antibodies exhibited binding to VEGFR2 recombinant protein, but binding was only observed at high concentrations of soluble analyte. As a result, reliable KD values could not be generated.

Figure 18:
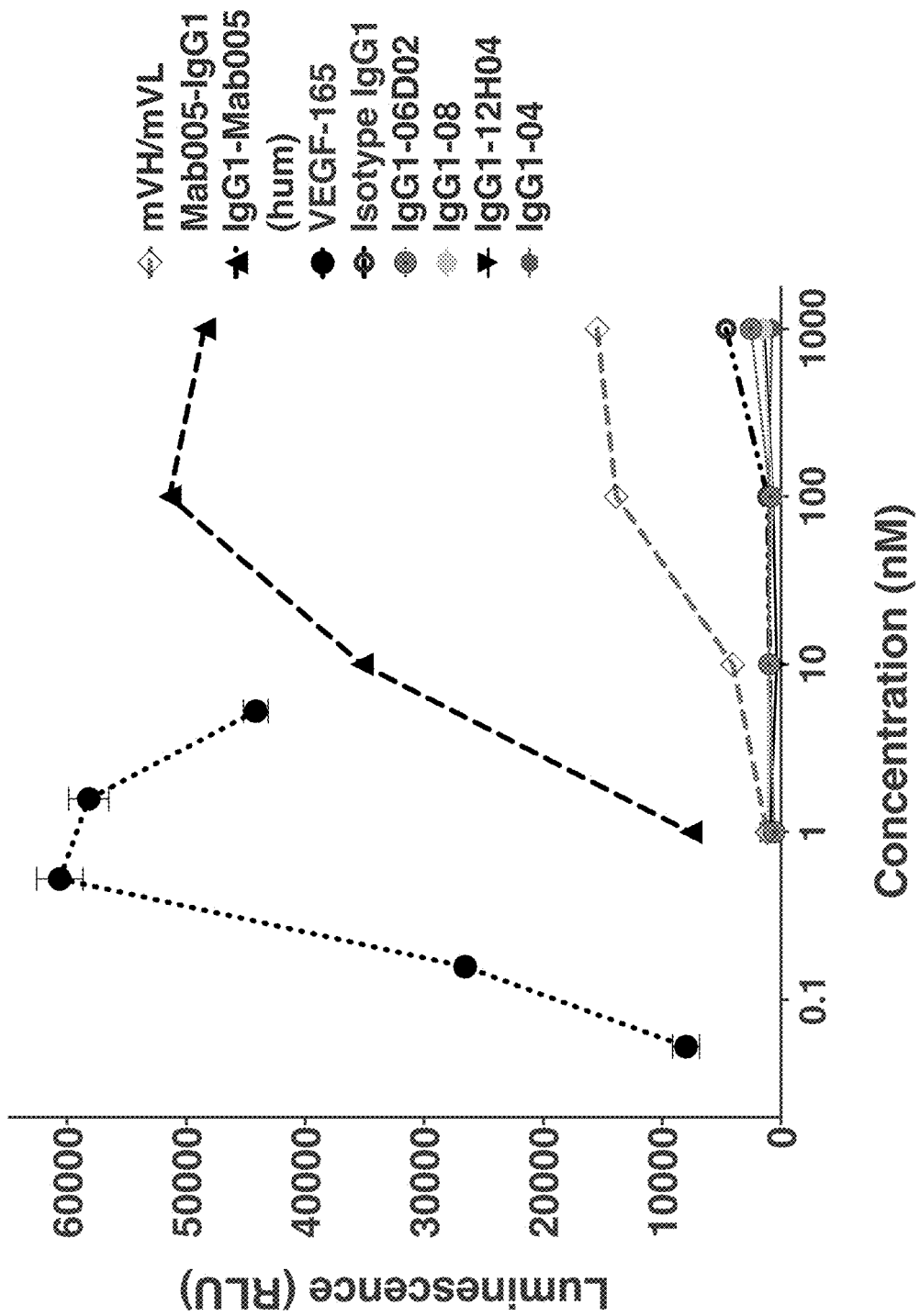

FIG. 18. Cell-based VEGFR2 agonism assay. mVH/mVL Mab005-IgG1, IgG1-Mab005 (humanized), library-derived clones and designer clones in human IgG1null format were titrated (in nM) in a human VEGFR2 signalling assay. mVH/mVL Mab005-IgG1, IgG1-Mab005 (humanized) and the positive control protein (human VEGF-165) all induced strong, concentration-dependent VEGFR2 agonism. Lead clones IgG1-04, IgG1-08, IgG1-06D02, and IgG1-12H04 showed no measurable agonism, even at concentrations as high as 1 µM.

Figure 19:
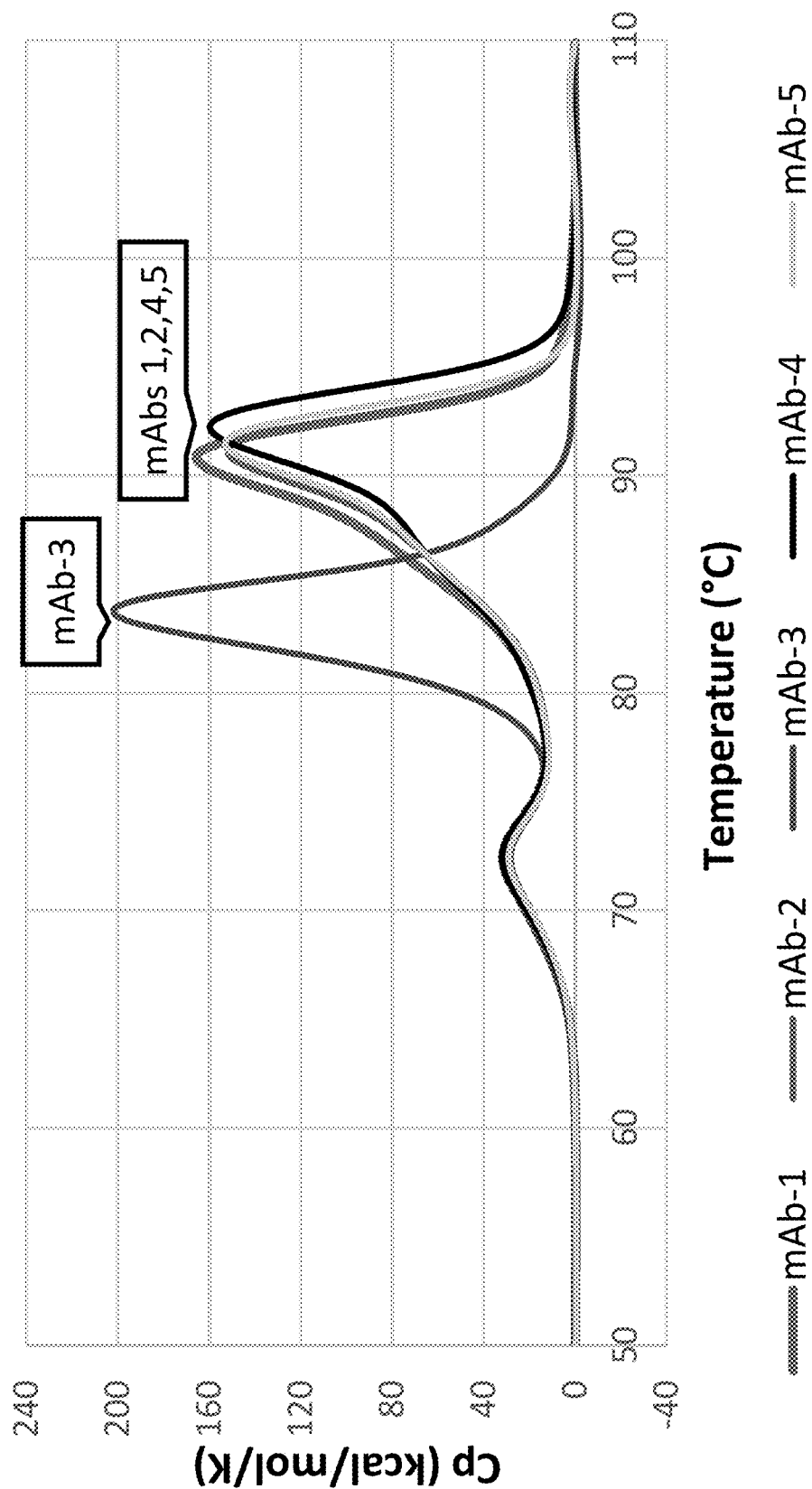

FIG. 19. Differential Scanning Calorimetry (DSC) of IgGs. DSC assay data for the following antibodies in IgG1null form: (mAb-1) IgG1-05, (mAb-2) IgG1-08, (mAb-3) IgG1-Mab005 (humanized), (mAb-4) IgG1-06D02, and (mAb-5) IgG1-12H04.

Figure 20A:
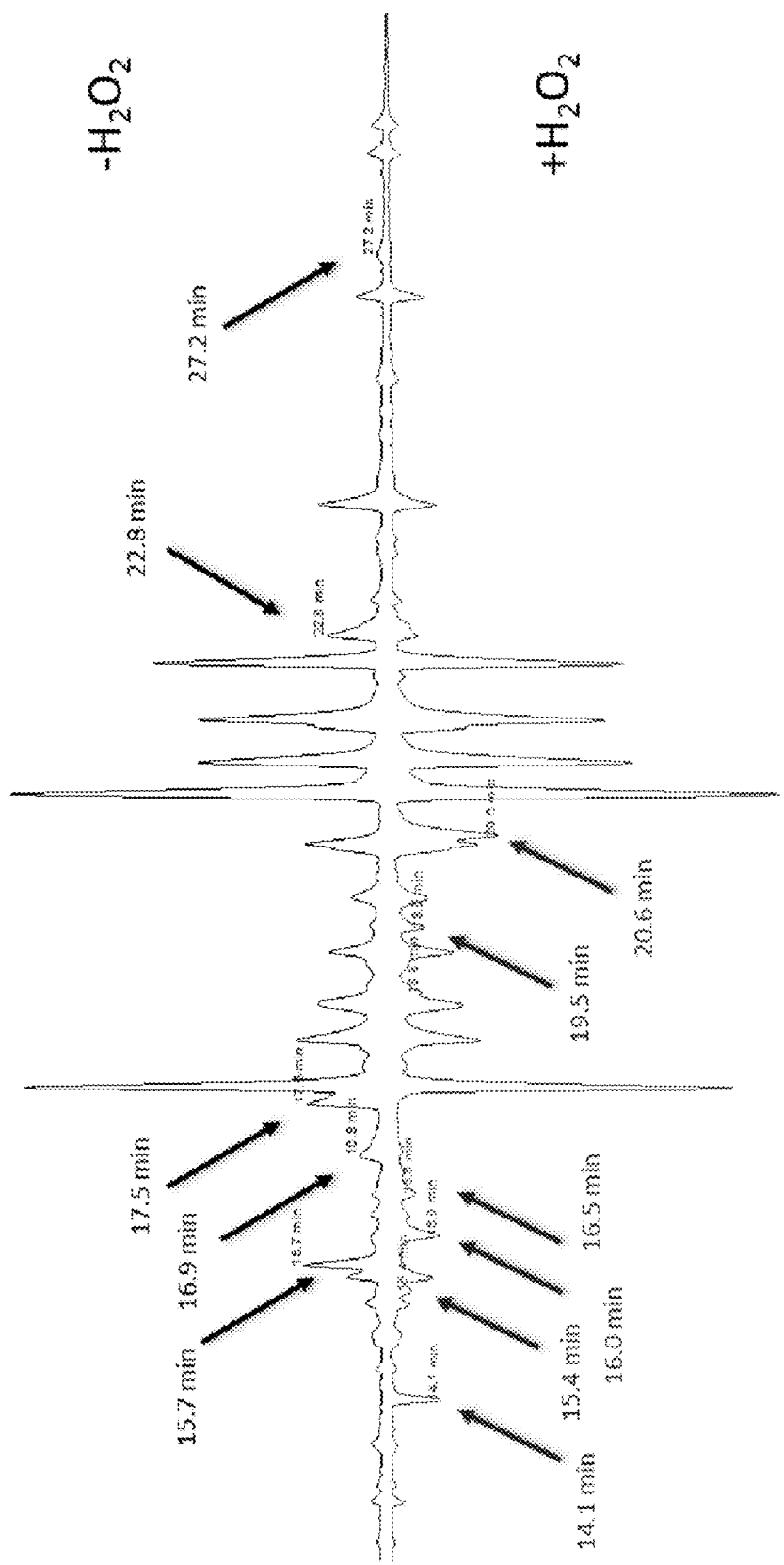
Figure 20B:
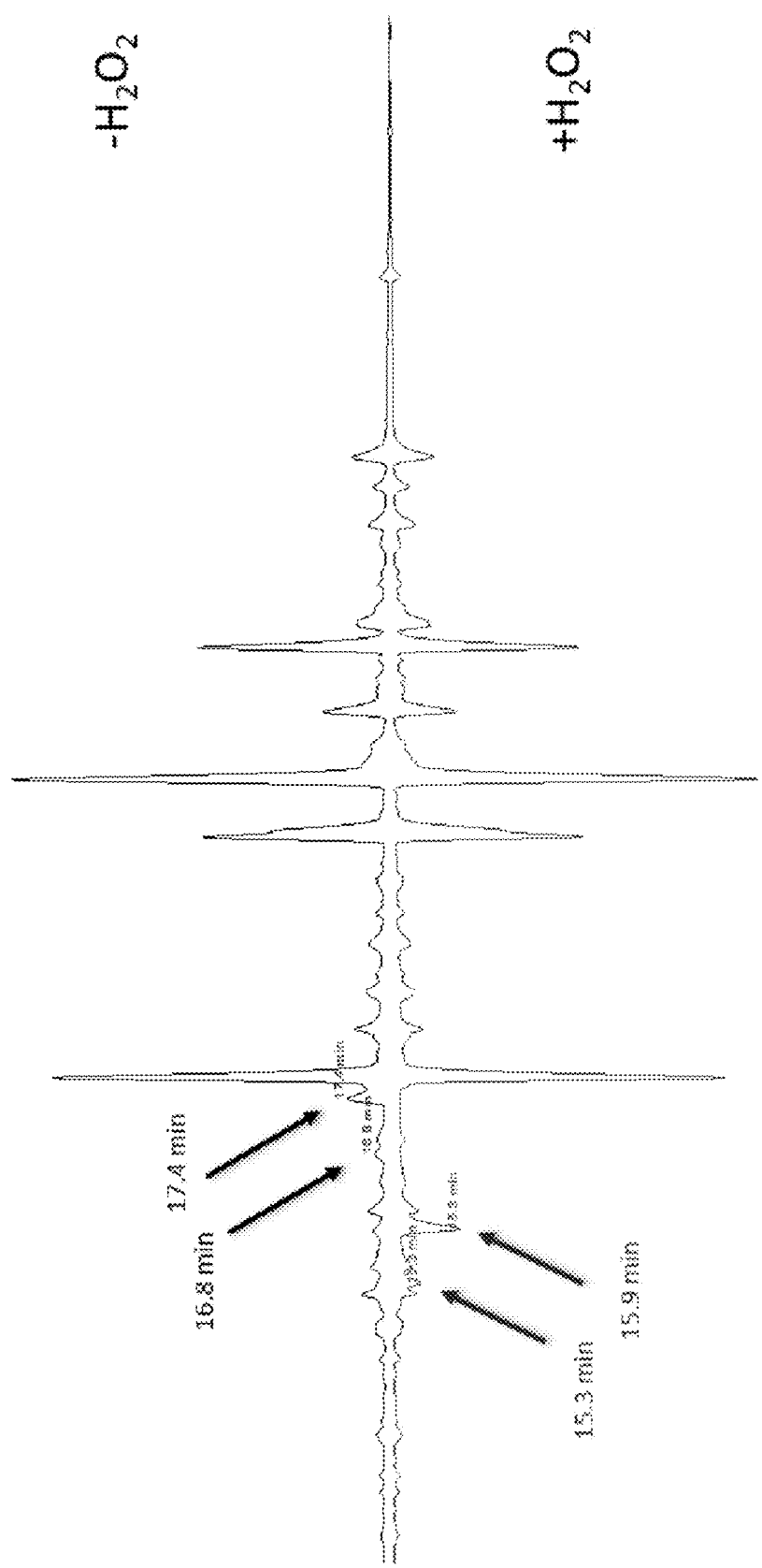

FIG. 20A-FIG. 20B. Reverse Phase Chromatography analyses of tryptic peptides from IgGs before and after forced oxidation. Reverse phase chromatograms showed that for antibodies in IgG1null form: IgG1-Mab005 (humanized) (FIG. 20A) demonstrated up to 6 peptide changes post-oxidation, whereas lead clones such as IgG1-06D02 (FIG. 20B) showed greater resistance to oxidation with only 2 modifications.

DETAILED DESCRIPTION OF THE INVENTION

According to a first aspect of the invention, there is provided an antibody molecule which specifically binds to human PD1 and also to cynomolgus monkey PD1, or an antigen-binding portion thereof, wherein the antibody molecule or antigen-binding portion comprises a heavy chain variable region with:
    an HCDR1 having amino acids in sequence in the following order: G-F-T-F-S-S-Y-L or any amino acid (for example A/D/E/F/G/H/I/N/P/Q/S/T/V/W/Y)-M-S (SEQ ID NO: 26);
    an HCDR2 having amino acids in sequence in the following order: V or a conservative substitution of V-A-T/N-I-S-G-G-G-A/S-E/N-T/K-Y-Y-P/V-D-S-V-K-G (SEQ ID NO: 27); and
    an HCDR3 having amino acids in sequence in the following order: Q or any amino acid (for example T/L/M/N)-L or any amino acid (for example G/K/M/Q/S/V)-Y or a conservative substitution of Y (for example H)-Y or any amino acid (for example A/D/F/G/M-A/D/E/F/I/K/M/S/W)-F or any amino acid (for example A/D/E/K/M/S/W)-D-Y (SEQ ID NO: 28).

In some aspects an anti-PD1 antibody or antigen-binding portion provided herein specifically binds to a PD1 protein comprising or consisting of SEQ ID NO:20 or SEQ ID NO:21. In some aspects an anti-PD1 antibody or antigen-binding portion provided herein specifically binds to a PD1 protein having an amino acid sequence that is at least about 90%, at least about 91%, at least about 92%, at least about 93%, at least about 94%, at least about 95%, at least about 96%, at least about 97%, at least about 98% or at least about 99% identical to SEQ ID NO:20 or SEQ ID NO:21.

In aspects of the invention, the HCDR1 of the antibody molecule or antigen-binding portion may exclude the sequence GFTFSSYMMS (SEQ ID NO: 29; MAb005 murine/humanized antibody HCDR1 disclosed in WO2015/085847A1; US2016/376367A1), and/or the HCDR2 of the antibody molecule or antigen-binding portion may exclude the sequence TISGGGANTYYPDSVKG (SEQ ID NO: 30; MAb005 murine/humanized antibody HCDR2 disclosed in WO2015/085847A1; US2016/376367A1), and/or the HCDR3 of the antibody molecule or antigen-binding portion may exclude the sequence QLYYFDY (SEQ ID NO: 31; MAb005 murine/humanized antibody HCDR3 disclosed in WO2015/085847A1; US2016/376367A1).

The antibody molecule or antigen-binding portion thereof according to the invention may further comprise a light chain variable region with:
    an LCDR1 having amino acids in sequence in the following order: R-A-S-Q-S-I-S or a conservative substitution of S-S or a conservative substitution of S-Y or a conservative substitution of Y-L or a conservative substitution of L-N/T or a conservative substitution of N or T (SEQ ID NO: 32);
    an LCDR2 having amino acids in sequence in the following order: A/T or a conservative substitution of A or T-A-S or a conservative substitution of S-S-L-Q or any amino acid (for example, A/H)-S or any amino acid (for example, D, Y) (SEQ ID NO: 33); and
    an LCDR3 having amino acids in sequence in the following order: Q-Q-S or any amino acid (for example, V)-Y-S-T or any amino acid (for example, I)-P-W or any amino acid (for example, L)-T (SEQ ID NO: 34).

In aspects of the invention, the LCDR1 of the antibody molecule or antigen-binding portion may exclude the sequence LASQTIGTWLT (SEQ ID NO: 35; MAb005 murine/humanized antibody LCDR1 disclosed in WO2015/085847A1; US2016/376367A1), and/or the LCDR2 of the antibody molecule or antigen-binding portion may exclude the sequence TATSLAD (SEQ ID NO: 36; MAb005 murine/humanized antibody LCDR2 disclosed in WO2015/085847A1; US2016/376367A1) and/or the LCDR3 of the antibody molecule or antigen-binding portion may exclude the sequence QQVYSIPWT (SEQ ID NO: 37; MAb005 murine/humanized antibody LCDR3 disclosed in WO2015/085847A1; US2016/376367A1).

In some aspects, disclosed herein is an anti-PD1 antibody or an antigen-binding portion thereof, wherein the antibody comprises a heavy chain variable (VH) region comprising HCDR1, HCDR2, and HCDR3 and a light chain variable (VL) region comprising LCDR1, LCDR2, and LCDR3, wherein
  (a) the HCDR1 comprises the amino acid sequence G-F-T-F-S-S-Y-$X_1$-M-S, wherein $X_1$ is L or any other amino acid (for example, A, D, E, F, G, H, I, N, P, Q, S, T, V, W, or Y) (SEQ ID NO: 26);
  (b) the HCDR2 comprises the amino acid sequence $X_1$-A-$X_2$-I-S-G-G-G-$X_3$-$X_4$-$X_5$-Y-Y-$X_6$-D-S-V-K-G, wherein $X_1$ is V or a conservative substitution of V, $X_2$ is T or N, $X_3$ is A or S, $X_4$ is E or N, $X_5$ is T or K, and $X_6$ is P or V (SEQ ID NO: 27);
  (c) the HCDR3 comprises the amino acid sequence $X_1$-$X_2$-$X_3$-$X_4$-$X_5$-D-Y, wherein $X_1$ is Q or any other amino acid (for example, T, L, M, or N), $X_2$ is L or any other amino acid (for example, G, K, M, Q, S, or V), $X_3$ is Y or a conservative substitution of Y (for example, H), $X_4$ is Y or any other amino acid (for example, A, D, F, G, M, E, I, K, S, or W) and $X_5$ is F or any other amino acid (for example A, D, E, I, K, M, S, or W) (SEQ ID NO: 28);
  (d) the LCDR1 comprises the amino acid sequence R-A-S-Q-S-I-$X_1$-$X_2$-$X_3$-$X_4$-$X_5$, wherein $X_1$ is S or a conservative substitution of S, $X_2$ is S or a conservative substitution of S, $X_3$ is Y or a conservative substitution of Y, $X_4$ is L or a conservative substitution of L, and $X_5$ is N or T or a conservative substitution of N or T (SEQ ID NO: 32);
  (e) the LCDR2 comprises the amino acid sequence $X_1$-A-$X_2$-S-L-$X_3$-$X_4$, wherein $X_1$ is A or T or a conservative substitution of A or T, $X_2$ is S or a conservative substitution of S, $X_3$ is Q or any other amino acid (for example, A or H), and $X_4$ is S or any other amino acid (for example, D or Y) (SEQ ID NO: 33); and
  (f) the LCDR3 comprises the amino acid sequence Q-Q-$X_1$-Y-S-$X_2$-P-$X_3$-T, wherein $X_1$ is S or any other amino acid (for example, V), $X_2$ is T or any other amino acid (for example, I), and $X_3$ is W or any other amino acid (for example, L) (SEQ ID NO: 34).

In some aspects, disclosed herein is an anti-PD1 antibody or an antigen-binding portion thereof, wherein the antibody comprises a heavy chain variable (VH) region comprising, in amino-terminal to carboxyl-terminal order, FR1-HCDR1-FR2-HCDR2-FR3-HCDR3-FR4 and a light chain variable (VL) region comprising, in amino-terminal to carboxyl-terminal order, FR1-LCDR1-FR2-LCDR2-FR3-LCDR3-FR4, wherein the HCDR1 is SEQ ID NO:26, the HCDR2 is SEQ ID NO:27, the HCDR3 is SEQ ID NO:28, the LCDR1 is SEQ ID NO:32, the LCDR2 is SEQ ID NO:33 and the LCDR3 is SEQ ID NO:34, wherein the heavy chain FR1, FR2, FR3 and FR4 amino acid sequences are the heavy chain FR1, FR2, FR3 and FR4 amino acid sequences in SEQ ID NO: 120 (see Table 2) and wherein the light chain FR1, FR2, FR3 and FR4 amino acid sequences are the light chain FR1, FR2, FR3 and FR4 amino acid sequences in SEQ ID NO: 122 (see Table 2).

As elaborated herein, the present inventors have succeeded for the first time in generating a number of optimized anti-PD1 antibody molecules using CDR sequences derived from the murine anti-PD1 antibody MAb005 disclosed in WO2015/085847A1; US2016/376367A1. In embodiments of the present invention, these antibody molecules have been selected to have equivalency in binding specificity and affinity to both human PD1 as well as cynomolgus monkey PD1 (to facilitate maximally accurate primate toxicology and pk studies). Further refining of the optimized antibody molecules as described herein has provided improved binding to the cynomolgus monkey orthologues of PD1, improved potency in neutralisation of PD1/PD-L1 signalling, improved variable domain stability, high expression yields, and/or reduced immunogenicity potential. Critically, these antibodies also dramatically improved the specificity of PD1 binding in comparison to MAb005, by ablating off-target binding to the human receptors KDR (also known as VEGFR2), FZD5 and ULBP2.

In some aspects, optimized anti-PD1 antibody molecules of the present invention do not necessarily have the maximum number of human germline substitutions at corresponding murine CDR or other (such as framework) amino acid positions. As elaborated in the experimental section below, we have found that "maximally humanized" antibody molecules are not necessary "maximally optimized" in terms of anti-PD1 binding characteristics and/or other desirable features.

In some embodiments, optimized anti-PD1 antibody molecules of the present invention are improved over the Mab005 antibody (WO2015/085847A1; US2016/376367A1) in their binding of a functionally identical epitope on cyno PD1. As elaborated in the experimental section below, we have found that some optimized clones exhibit Biacore KD values lower than 32 nM for binding to monomeric cyno PD1 protein (e.g. between 2.7 and 15 nM) and EC50 values lower than 6.5 nM (e.g. 0.86-2.17 nM) in flow cytometric staining of cyno PD1-expressing CHO cells.

The present invention encompasses modifications to the amino acid sequence of the antibody molecule or antigen-binding portion thereof as defined herein. For example, the invention includes antibody molecules and corresponding antigen-binding portions thereof comprising functionally equivalent variable regions and CDRs which do not significantly affect their properties as well as variants which have enhanced or decreased activity and/or affinity. For example, the amino acid sequence may be mutated to obtain an antibody with the desired binding affinity to PD1. Insertions which include amino- and/or carboxyl-terminal fusions ranging in length from one residue to polypeptides containing a hundred or more residues, as well as intrasequence insertions of single or multiple amino acid residues, are envisaged. Examples of terminal insertions include an antibody molecule with an N-terminal methionyl residue or the antibody molecule fused to an epitope tag. Other insertional variants of the antibody molecule include the fusion to the N- or C-terminus of the antibody of an enzyme or a polypeptide which increases the half-life of the antibody in the blood circulation.

The antibody molecule or antigen-binding portion of the invention may include glycosylated and nonglycosylated polypeptides, as well as polypeptides with other post-translational modifications, such as, for example, glycosylation with different sugars, acetylation, and phosphorylation. The antibody molecule or antigen-binding portion of the invention may be mutated to alter such post-translational modifications, for example by adding, removing or replacing one or more amino acid residues to form or remove a glycosylation site.

The antibody molecule or antigen-binding portion of the invention may be modified for example by amino acid substitution to remove potential proteolytic sites in the antibody.

In the antibody molecule or antigen-binding portion thereof, the HCDR1 may have the amino acid sequence: G-F-T-F-S-S-Y-A/D/E/F/H/I/L/N/P/Q/S/T/V/W/Y-M-S (SEQ ID NO: 55); the HCDR2 may have the amino acid sequence: V-A-T/N-I-S-G-G-G-S/A-E/N-T/K-Y-Y-V/P-D-S-V-K-G (SEQ ID NO: 56); and the HCDR3 may have the amino acid sequence: Q/L/M/N/T-L/G/K/Q/M/S/V-Y/H-Y/A/D/G/F/M-F/A/D/E/I/K/M/S/W/Y-D-Y (SEQ ID NO: 57).

For example, the HCDR1 may have the amino acid sequence: G-F-T-F-S-S-Y-L/A/S-M-S (SEQ ID NO: 58); the HCDR2 may have the amino acid sequence: V-A-T-I-S-G-G-G-S/A-E/N-T/K-Y-Y-V-D-S-V-K-G (SEQ ID NO: 59); and the HCDR3 may have the amino acid sequence: Q-L/V-Y-Y/G/F/A-F/Y/A-D-Y (SEQ ID NO: 60).

In the antibody molecule or antigen-binding portion thereof, the LCDR1 may have the amino acid sequence: R-A-S-Q-T/S-I-G/S-T/S-W/Y-L-T/N (SEQ ID NO: 61); the LCDR2 may have the amino acid sequence T/A-A-T/S-S-L-A/Q/H-D/S (SEQ ID NO: 62); and the LCDR3 may have the amino acid sequence: Q-Q-V/S-Y-S-I/T-P-W/L-T (SEQ ID NO: 63).

For example, the LCDR1 may have the amino acid sequence: R-A-S-Q-S-I-G/S-T/S-W/Y-L-N (SEQ ID NO: 64); the LCDR2 may have the amino acid sequence A-A-S-S-L-Q/H-S(SEQ ID NO: 65); and the LCDR3 may have the amino acid sequence: Q-Q-S-Y-S-I/T-P-W-T (SEQ ID NO: 66).

In specific embodiments of the invention, the antibody molecule or antigen-binding portion may comprise:

(a) the amino acid sequences

GFTFSSYLMS, (SEQ ID NO: 38; HCDR1)

VATISGGGSETYYVDSVKG, (SEQ ID NO: 48; HCDR2)

QLYGFDY, (SEQ ID NO: 40; HCDR3)

RASQSISSWLN, (SEQ ID NO: 41; LCDR1)

AASSLQS
and (SEQ ID NO: 42; LCDR2)

QQSYSIPWT [Clone 06D02]; (SEQ ID NO: 47; LCDR3)
or (b) the amino acid sequences

GFTFSSYAMS, (SEQ ID NO: 67; HCDR1)

VATISGGGSNKYYVDSVKG, (SEQ ID NO: 68; HCDR2)

QLYGFDY, (SEQ ID NO: 40; HCDR3)

RASQSISTWLN, (SEQ ID NO: 52; LCDR1)

AATSLAS
and (SEQ ID NO: 69; LCDR2)

QQSYSIPWT [Clone 08F04]; (SEQ ID NO: 47; LCDR3)

(c) the amino acid sequences

GFTFSSYLMS, (SEQ ID NO: 38; HCDR1)

VATISGGGAETYYVDSVKG, (SEQ ID NO: 70; HCDR2)

QLYFFDY, (SEQ ID NO: 45; HCDR3)

RASQSISSWLN, (SEQ ID NO: 41; LCDR1)

TASSLQD
and (SEQ ID NO: 71; LCDR2)

QQSYSTPWT [Clone 11G05]; (SEQ ID NO: 43; LCDR3)

(d) the amino acid sequences

GFTFSSYAMS, (SEQ ID NO: 67; HCDR1)

VATISGGGSEKYYVDSVKG, (SEQ ID NO: 39; HCDR2)

QLYYADY, (SEQ ID NO: 72; HCDR3)

RASQSISSWLN, (SEQ ID NO: 41; LCDR1)

TASSLAD
and (SEQ ID NO: 73; LCDR2)

QQSYSIPWT [Clone 12E02]; (SEQ ID NO: 47; LCDR3)

(e) the amino acid sequences

GFTFSSYLMS, (SEQ ID NO: 38; HCDR1)

VATISGGGAEKYYVDSVKG, (SEQ ID NO: 49; HCDR2)

QLYGFDY, (SEQ ID NO: 40; HCDR3)

RASQSISSWLN, (SEQ ID NO: 41; LCDR1)

AASSLQD
and (SEQ ID NO: 50; LCDR2)

QQSYSTPWT [Clone 12H04]; (SEQ ID NO: 43; LCDR3)

(f) the amino acid sequences

GFTFSSYLMS, (SEQ ID NO: 38; HCDR1)

VATISGGGSNTYYVDSVKG, (SEQ ID NO: 51; HCDR2)

QLYGFDY, (SEQ ID NO: 40; HCDR3)

RASQSISTWLN, (SEQ ID NO: 52; LCDR1)

AASSLAS
and (SEQ ID NO: 53; LCDR2)

QQSYSTPWT [Clone 12B07]; (SEQ ID NO: 43; LCDR3)

(g) the amino acid sequences

GFTFSSYLMS, (SEQ ID NO: 38; HCDR1)

VATISGGGAEKYYVDSVKG, (SEQ ID NO: 49; HCDR2)

-continued

QLYGFDY, (SEQ ID NO: 40; HCDR3)

RASQSISSYLN, (SEQ ID NO: 74; LCDR1)

AASSLQS (SEQ ID NO: 42; LCDR2)
and

QQSYSTPWT [Clone 13G02]; (SEQ ID NO: 43; LCDR3)

(h) the amino acid sequences

GFTFSSYSMS, (SEQ ID NO: 75; HCDR1)

VATISGGGAETYYVDSVKG, (SEQ ID NO: 70; HCDR2)

QLYGFDY, (SEQ ID NO: 40; HCDR3)

RASQSISSWLN, (SEQ ID NO: 41; LCDR1)

AASSLQS (SEQ ID NO: 42; LCDR2)
and

QQSYSIPWT [Clone 14C07]; (SEQ ID NO: 47; LCDR3)

(i) the amino acid sequences

GFTFSSYLMS, (SEQ ID NO: 38; HCDR1)

VATISGGGSNKYYVDSVKG, (SEQ ID NO: 68; HCDR2)

QLYGFDY, (SEQ ID NO: 40; HCDR3)

RASQSIGTYLN, (SEQ ID NO: 76; LCDR1)

AATSLQS (SEQ ID NO: 77; LCDR2)
and

QQSYSIPWT [Clone 15C10]; (SEQ ID NO: 47; LCDR3)

(j) the amino acid sequences

GFTFSSYLMS, (SEQ ID NO: 38; HCDR1)

VATISGGGAEKYYVDSVKG, (SEQ ID NO: 49; HCDR2)

QLYAFDY, (SEQ ID NO: 46; HCDR3)

RASQSIGSYLN, (SEQ ID NO: 78; LCDR1)

TASSLQS (SEQ ID NO: 79; LCDR2)
and

QQSYSIPWT [Clone 16C07]; (SEQ ID NO: 47; LCDR3)

(k) the amino acid sequences

GFTFSSYLMS, (SEQ ID NO: 38; HCDR1)

VATISGGGSEKYYVDSVKG, (SEQ ID NO: 39; HCDR2)

QVYYFDY, (SEQ ID NO: 44; HCDR3)

RASQSISSWLN, (SEQ ID NO: 41; LCDR1)

AASSLHS (SEQ ID NO: 54; LCDR2)
and

QQSYSTPWT [Clone 16H10]; (SEQ ID NO: 43; LCDR3)

(l) the amino acid sequences

GFTFSSYPMS, (SEQ ID NO: 80; HCDR1)

VATISGGGSETYYVDSVKG, (SEQ ID NO: 48; HCDR2)

QLYYYDY, (SEQ ID NO: 81; HCDR3)

RASQSISTWLN, (SEQ ID NO: 52; LCDR1)

AASSLQY (SEQ ID NO: 82; LCDR2)
and

QQSYSTPWT [Clone 17B11]; (SEQ ID NO: 43; LCDR3)

(m) the amino acid sequences

GFTFSSYAMS, (SEQ ID NO: 67; HCDR1)

VATISGGGSEKYYVDSVKG, (SEQ ID NO: 39; HCDR2)

QLYYADY, (SEQ ID NO: 72; HCDR3)

RASQSISSWLN, (SEQ ID NO: 41; LCDR1)

AASSLQS (SEQ ID NO: 42; LCDR2)
and

QQSYSTPWT (SEQ ID NO: 43; LCDR3)

[Clone IgG1-01 (VL domain contains JK4 sequence)];

(n) the amino acid sequences

GFTFSSYAMS, (SEQ ID NO: 67; HCDR1)

VATISGGGSEKYYVDSVKG, (SEQ ID NO: 39; HCDR2)

QLYYADY, (SEQ ID NO: 72; HCDR3)

RASQSISSWLN, (SEQ ID NO: 41; LCDR1)

AASSLQS (SEQ ID NO: 42; LCDR2)
and

QQSYSTPWT (SEQ ID NO: 43; LCDR3)

-continued

[Clone IgG1-02 (VL domain contains JK1 sequence)];

(o) the amino acid sequences

GFTFSSYAMS, (SEQ ID NO: 67; HCDR1)

VATISGGGSEKYYVDSVKG, (SEQ ID NO: 39; HCDR2)

QLYYADY, (SEQ ID NO: 72; HCDR3)

RASQSISSYLN, (SEQ ID NO: 74; LCDR1)

AASSLQS (SEQ ID NO: 42; LCDR2)
and

QQSYSTPWT (SEQ ID NO: 43; LCDR3)

[Clone IgG1-03 (VL domain contains JK1 sequence)];

(p) the amino acid sequences

GFTFSSYLMS, (SEQ ID NO: 38; HCDR1)

VATISGGGSEKYYVDSVKG, (SEQ ID NO: 39; HCDR2)

QVYYFDY, (SEQ ID NO: 44; HCDR3)

RASQSISSWLN, (SEQ ID NO: 41; LCDR1)

AASSLQS (SEQ ID NO: 42; LCDR2)
and

QQSYSTPWT (SEQ ID NO: 43; LCDR3)

[Clone IgG1-04 (VL domain contains JK4 sequence)];

(q) the amino acid sequences

GFTFSSYLMS, (SEQ ID NO: 38; HCDR1)

VATISGGGSEKYYVDSVKG, (SEQ ID NO: 39; HCDR2)

QVYYFDY, (SEQ ID NO: 44; HCDR3)

RASQSISSWLN, (SEQ ID NO: 41; LCDR1)

AASSLQS (SEQ ID NO: 42; LCDR2)
and

QQSYSTPWT (SEQ ID NO: 43; LCDR3)

[Clone IgG1-05 (VL domain contains JK1 sequence)];

(r) the amino acid sequences

GFTFSSYLMS, (SEQ ID NO: 38; HCDR1)

VATISGGGSEKYYVDSVKG, (SEQ ID NO: 39; HCDR2)

QVYYFDY, (SEQ ID NO: 44; HCDR3)

RASQSISSYLN, (SEQ ID NO: 74; LCDR1)

AASSLQS (SEQ ID NO: 42; LCDR2)
and

QQSYSTPWT (SEQ ID NO: 43; LCDR3)

[Clone IgG1-06 (VL domain contains JK1 sequence)];

(s) the amino acid sequences

GFTFSSYLMS, (SEQ ID NO: 38; HCDR1)

VATISGGGSEKYYVDSVKG, (SEQ ID NO: 39; HCDR2)

QLYGFDY, (SEQ ID NO: 40; HCDR3)

RASQSISSWLN, (SEQ ID NO: 41; LCDR1)

AASSLQS (SEQ ID NO: 42; LCDR2)
and

QQSYSTPWT (SEQ ID NO: 43; LCDR3)

[Clone IgG1-07 (VL domain contains JK4 sequence)];

(t) the amino acid sequences

GFTFSSYLMS, (SEQ ID NO: 38; HCDR1)

VATISGGGSEKYYVDSVKG, (SEQ ID NO: 39; HCDR2)

QLYGFDY, (SEQ ID NO: 40; HCDR3)

RASQSISSWLN, (SEQ ID NO: 41; LCDR1)

AASSLQS (SEQ ID NO: 42; LCDR2)
and

QQSYSTPWT (SEQ ID NO: 43; LCDR3)

[Clone IgG1-08 (VL domain contains JK1 sequence)];

(u) the amino acid sequences

GFTFSSYLMS, (SEQ ID NO: 38; HCDR1)

VATISGGGSEKYYVDSVKG, (SEQ ID NO: 39; HCDR2)

QLYGFDY, (SEQ ID NO: 40; HCDR3)

RASQSISSYLN, (SEQ ID NO: 74; LCDR1)

AASSLQS (SEQ ID NO: 42; LCDR2)
and

QQSYSTPWT (SEQ ID NO: 43; LCDR3)

[Clone IgG1-09 (VL domain contains JK1 sequence)];

(v) the amino acid sequences

GFTFSSYLMS, (SEQ ID NO: 38; HCDR1)

VATISGGGSEKYYVDSVKG, (SEQ ID NO: 39; HCDR2)

QLYFFDY, (SEQ ID NO: 45; HCDR3)

RASQSISSWLN, (SEQ ID NO: 41; LCDR1)

AASSLQS (SEQ ID NO: 42; LCDR2)
and

QQSYSTPWT (SEQ ID NO: 43; LCDR3)

[Clone IgG1-10 (VL domain contains JK4 sequence)];

(w) the amino acid sequences

GFTFSSYLMS, (SEQ ID NO: 38; HCDR1)

VATISGGGSEKYYVDSVKG, (SEQ ID NO: 39; HCDR2)

QLYFFDY, (SEQ ID NO: 45; HCDR3)

RASQSISSWLN, (SEQ ID NO: 41; LCDR1)

AASSLQS (SEQ ID NO: 42; LCDR2)
and

QQSYSTPWT (SEQ ID NO: 43; LCDR3)

[Clone IgG1-11 (VL domain contains JK1 sequence)];

(x) the amino acid sequences

GFTFSSYLMS, (SEQ ID NO: 38; HCDR1)

VATISGGGSEKYYVDSVKG, (SEQ ID NO: 39; HCDR2)

QLYFFDY, (SEQ ID NO: 45; HCDR3)

RASQSISSYLN, (SEQ ID NO: 74; LCDR1)

AASSLQS (SEQ ID NO: 42; LCDR2)
and

QQSYSTPWT (SEQ ID NO: 43; LCDR3)

[Clone IgG1-12 (VL domain contains JK1 sequence)];

(y) the amino acid sequences

GFTFSSYLMS, (SEQ ID NO: 38; HCDR1)

VATISGGGSEKYYVDSVKG, (SEQ ID NO: 39; HCDR2)

QLYAFDY, (SEQ ID NO: 46; HCDR3)

RASQSISSWLN, (SEQ ID NO: 41; LCDR1)

AASSLQS (SEQ ID NO: 42; LCDR2)
and

QQSYSTPWT (SEQ ID NO: 43; LCDR3)

[Clone IgG1-13 (VL domain contains JK4 sequence)];

(z) the amino acid sequences

GFTFSSYLMS, (SEQ ID NO: 38; HCDR1)

VATISGGGSEKYYVDSVKG, (SEQ ID NO: 39; HCDR2)

QLYAFDY, (SEQ ID NO: 46; HCDR3)

RASQSISSWLN, (SEQ ID NO: 41; LCDR1)

AASSLQS (SEQ ID NO: 42; LCDR2)
and

QQSYSTPWT (SEQ ID NO: 43; LCDR3)

[Clone IgG1-14 (VL domain contains JK1 sequence)];

(z1) the amino acid sequences

GFTFSSYLMS, (SEQ ID NO: 38; HCDR1)

VATISGGGSEKYYVDSVKG, (SEQ ID NO: 39; HCDR2)

QLYAFDY, (SEQ ID NO: 46; HCDR3)

RASQSISSYLN, (SEQ ID NO: 74; LCDR1)

AASSLQS (SEQ ID NO: 42; LCDR2)
and

QQSYSTPWT (SEQ ID NO: 43; LCDR3)

[Clone IgG1-15 (VL domain contains JK1 sequence)].

In some aspects, the invention provides an anti-PD1 antibody or an antigen-binding portion thereof, wherein the antibody comprises a heavy chain variable (VH) region and a light chain variable (VL) region, wherein (a) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QLYGFDY (SEQ ID NO: 40); and the VL region amino acid sequence comprises LCDR1 of RASQSISSWLN (SEQ ID NO: 41), LCDR2 of AASSLQS (SEQ ID NO: 42) and LCDR3 of QQSYSTPWT (SEQ ID NO: 43);

(b) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QVYYFDY (SEQ ID NO: 44); and the VL region amino acid sequence comprises LCDR1 of RASQSISSWLN (SEQ ID NO: 41), LCDR2 of AASSLQS (SEQ ID NO: 42) and LCDR3 of QQSYSTPWT (SEQ ID NO: 43);

(c) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QLYFFDY (SEQ ID NO: 45); and the VL region amino acid sequence comprises LCDR1 of RASQSISSWLN (SEQ ID NO: 41), LCDR2 of AASSLQS (SEQ ID NO: 42) and LCDR3 of QQSYS-TPWT (SEQ ID NO: 43);

(d) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QLYAFDY (SEQ ID NO: 46); and the VL region amino acid sequence comprises LCDR1 of RASQSISSWLN (SEQ ID NO: 41), LCDR2 of AASSLQS (SEQ ID NO: 42) and LCDR3 of QQSYS-TPWT (SEQ ID NO: 43);

(e) the VH region amino acid sequence comprises HCDR1 of GFTFSSYLMS (SEQ ID NO: 38), HCDR2 of VATISGGGSETYYVDSVKG (SEQ ID NO: 48) and HCDR3 of QLYGFDY (SEQ ID NO: 40); and the VL region amino acid sequence comprises LCDR1 of RASQSISSWLN (SEQ ID NO: 41), LCDR2 of AASSLQS (SEQ ID NO: 42) and LCDR3 of QQSY-SIPWT (SEQ ID NO: 47);

(f) the VH region amino acid sequence comprises HCDR1 of GFTFSSYLMS (SEQ ID NO: 38), HCDR2 of VATISGGGAEKYYVDSVKG (SEQ ID NO: 49) and HCDR3 of QLYGFDY (SEQ ID NO: 40); and the VL region amino acid sequence comprises LCDR1 of RASQSISSWLN (SEQ ID NO: 41), LCDR2 of AASSLQD (SEQ ID NO: 50) and LCDR3 of QQSYS-TPWT (SEQ ID NO: 43);

(g) the VH region amino acid sequence comprises HCDR1 of GFTFSSYLMS (SEQ ID NO: 38), HCDR2 of VATISGGGSETYYVDSVKG (SEQ ID NO: 48), and HCDR3 of QLYGFDY (SEQ ID NO: 40); and the VL region amino acid sequence comprises LCDR1 of RASQSISSWLN (SEQ ID NO: 41), LCDR2 of AASSLQS (SEQ ID NO: 42), and LCDR3 of QQSY-SIPWT (SEQ ID NO: 47);

(h) the VH region amino acid sequence comprises HCDR1 of GFTFSSYLMS (SEQ ID NO: 38), HCDR2 of VATISGGGAEKYYVDSVKG (SEQ ID NO: 49), and HCDR3 of QLYGFDY (SEQ ID NO: 40); and the VL region amino acid sequence comprises LCDR1 of RASQSISSWLN (SEQ ID NO: 41), LCDR2 of AASSLQD (SEQ ID NO: 50), and LCDR3 of QQSYS-TPWT (SEQ ID NO: 43);

(i) the VH region amino acid sequence comprises HCDR1 of GFTFSSYLMS (SEQ ID NO: 38), HCDR2 of VATISGGGSNTYYVDSVKG (SEQ ID NO: 51), and HCDR3 of QLYGFDY (SEQ ID NO: 40); and the VL region amino acid sequence comprises LCDR1 of RASQSISTWLN (SEQ ID NO: 52), LCDR2 of AASSLAS (SEQ ID NO: 53), and LCDR3 of QQSYS-TPWT (SEQ ID NO: 43);

(j) the VH region amino acid sequence comprises HCDR1 of GFTFSSYLMS (SEQ ID NO: 38), HCDR2 of VATISGGGSEKYYVDSVKG (SEQ ID NO: 39), and HCDR3 of QVYYFDY (SEQ ID NO: 44); and the VL region amino acid sequence comprises LCDR1 of RASQSISSWLN (SEQ ID NO: 41), LCDR2 of AASSLHS (SEQ ID NO: 54), and LCDR3 of QQSYS-TPWT (SEQ ID NO: 43); or (k) the VH region amino acid sequence comprises HCDR1 of GFTFSSYLMS (SEQ ID NO: 38), HCDR2 of VATISGGGSEKYYVDSVKG (SEQ ID NO: 39), and HCDR3 of QVYYFDY (SEQ ID NO: 44); and the VL region amino acid sequence comprises LCDR1 of RASQSISSWLN (SEQ ID NO: 41), LCDR2 of AASSLQS (SEQ ID NO: 42), and LCDR3 of QQSYS-TPWT (SEQ ID NO: 43).

In some aspects, disclosed herein is anti-PD1 antibody or an antigen-binding portion thereof, wherein the antibody comprises a heavy chain variable (VH) region and a light chain variable (VL) region, wherein the VH region comprises any one of the VH region amino acid sequences in Table 17 and the VL region comprises any one of the VL region amino acid sequences in Table 17.

In some aspects, disclosed herein is an anti-PD1 antibody or an antigen-binding portion thereof, wherein the antibody comprises a heavy chain variable (VH) region and a light chain variable (VL) region, wherein (a) the VH region amino acid sequence comprises SEQ ID NO:1 and the VL region amino acid sequence comprises SEQ ID NO:2;

(b) the VH region amino acid sequence comprises SEQ ID NO:3 and the VL region amino acid sequence comprises SEQ ID NO:4;

(c) the VH region amino acid sequence comprises SEQ ID NO:5 and the VL region amino acid sequence comprises SEQ ID NO:6;

(d) the VH region amino acid sequence comprises SEQ ID NO:7 and the VL region amino acid sequence comprises SEQ ID NO:8;

(e) the VH region amino acid sequence comprises SEQ ID NO:9 and the VL region amino acid sequence comprises SEQ ID NO:10; or (f) the VH region amino acid sequence comprises SEQ ID NO:11 and the VL region amino acid sequence comprises SEQ ID NO:12.

In some aspects, disclosed herein is an anti-PD1 antibody or an antigen-binding portion thereof, wherein the antibody comprises a heavy chain variable (VH) region and a light chain variable (VL) region, wherein (a) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:1 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:2;

(b) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:3 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:4;

(c) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:5 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:6;

(d) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:7 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:8;

(e) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:9 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:10; or (f) the VH region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:11 and the VL region amino acid sequence is at least about 90%, at least about 91%, at least about 92%, at least about 93%, at least about 94%, at least about 95%, at least about 96%, at least about 97%, at least about 98% or at least about 99% identical to SEQ ID NO:12. In some aspects, the CDR amino acid sequences of an anti-PD1 antibody are 100% identical to the CDR amino acid sequences in the recited sequences while the FR amino acid sequences are less than 100% identical to the FR amino acid sequences in the recited sequences.

In some aspects, the antibody or antigen-binding portion as defined herein may be isolated.

The antibody molecule or antigen-binding portion as defined herein may cross-compete for binding to PD1 with an antibody or antigen-binding portion thereof comprising the sets of CDRs disclosed herein. In some embodiments, the invention provides an isolated anti-PD1 antibody or an antigen-binding portion thereof, wherein the antibody or antigen-binding portion cross-competes for binding to PD1 with the antibody or antigen-binding portion comprising the sets of CDRs disclosed herein; and (a) comprises fully germline human framework amino acid sequences; (b) binds specifically to human PD1 and cynomolgus PD1; (c) antagonizes binding of human PD1 to human PD-L1 with an EC50 lower than 260 ng/ml; (d) binds to monomeric cynomolgus PD1 with a KD lower than 32 nM; (e) binds to cyno PD1-expressing cells with an EC50 lower than 6.5 nM; (f) binds to a functionally identical epitope on cynomolgus PD1 and human PD1; (g) comprises a human germline peptide sequence with high MHC class I binding affinity in LCDR2; (h) comprises a reduced number of immunogenic peptides compared to an anti-PID1 antibody comprising the variable domain sequences of antibody Mab005; (i) exhibits reduced immunogenicity compared to an anti-PID1 antibody comprising the variable domain sequences of antibody Mab005; (j) comprises a deimmunized VL region (e.g., a fully deimmunized VL region); (k) exhibits no binding to one or more of KDR, FZD5, ULBP2 and EPHB6; and/or (1) does not agonise or minimally agonises one or more of KDR, FZD5, ULBP2 and EPHB6. In some embodiments, a KD value of an antibody or antigen-binding portion may be determined by Biacore analysis. In some embodiments, an EC50 value of an antibody or antigen-binding portion may be determined by flow cytometric staining of PD-1 expressing cells (e.g., CHO cells). In some embodiments, binding to KDR, FZD5, ULBP2 or EPHB6 may be determined by flow cytometry analysis.

In some embodiments, an anti-PID1 antibody or antigen-binding portion has low immunogenicity. In certain cases, an antibody or antigen-binding portion exhibits reduced immunogenicity compared to an anti-PID1 antibody comprising HCDR1 of GFTFSSYMMS (SEQ ID NO: 29), HCDR2 of TISGGGANTYYPDSVKG (SEQ ID NO: 30), HCDR3 of QLYYFDY (SEQ ID NO: 31), LCDR1 of LASQTIGTWLT (SEQ ID NO: 35), LCDR2 of TATSLAD (SEQ ID NO: 36), and LCDR3 of QQVYSIPWT (SEQ ID NO: 37). In some examples, immunogenicity risk of an antibody or antigen-binding portion may be determined in silico by identifying the location of T cell epitopes in the antibody or portion (e.g., in the variable regions of the antibody or portion).

For example, T cell epitopes in an antibody or antigen-binding portion may be identified by using iTope™. iTope™ can used to analyse VL and VH region sequences for peptides with promiscuous high affinity binding to human MHC class II. Promiscuous high affinity MHC class II binding peptides are thought to correlate with the presence of T cell epitopes that are high risk indicators for clinical immunogenicity of drug proteins. The iTope™ software predicts favourable interactions between amino acid side chains of a peptide and specific binding pockets (in particular pocket positions; p1, p4, p6, p7 and p9) within the open-ended binding grooves of 34 human MHC class II alleles. These alleles represent the most common HLA-DR alleles found world-wide with no weighting attributed to those found most prevalently in any particular ethnic population. Twenty of the alleles contain the 'open' p1 configuration and 14 contain the 'closed' configuration where glycine at position 83 is replaced by a valine. The location of key binding residues is achieved by the in silico generation of 9mer peptides that overlap by eight amino acids spanning the test protein sequence. This process successfully discriminates with high accuracy between peptides that either bind or do not bind MHC class molecules.

T cell epitopes in an antibody or antigen-binding portion may be identified by analysing VL and VH region sequences using TCED™ (T Cell Epitope Database™) to search for matches to T cell epitopes previously identified by in vitro human T cell epitope mapping analyses of other protein sequences. The TCED™ is used to search any test sequence against a large (>10,000 peptides) database of peptides derived from unrelated protein and antibody sequences.

In some embodiments, an anti-PID1 antibody or antigen-binding portion may exhibit a low immunogenicity because the antibody or portion has a low number of one or more of the following peptides in its sequences: High Affinity Foreign ('HAF'—high immunogenicity risk), Low Affinity Foreign ('LAF'—lower immunogenicity risk), and/or TCED+ (previously identified epitope in TCED™ database).

In some embodiments, an anti-PID1 antibody or antigen-binding portion may have high Germline Epitope (GE) content in its sequence. In some examples, an anti-PID1 antibody or antigen-binding portion has 3, 4, 5, 6, 7, 8, 9, 10, 11, 12, 13, 14, 15, 16, 17, 18, 19 or 20 (or greater than 20) germline epitopes in its sequence (e.g., in the VL and/or VH region sequence). Germline Epitope may be defined as a human germline peptide sequence with high MHC Class II binding affinity. Germline Epitope 9mer peptides are unlikely to have immunogenic potential due to T cell tolerance, as validated by previous studies with a wide range of germline peptides. Importantly, such germline v-domain epitopes (aided further by similar sequences in the human antibody constant regions) also compete for MHC Class II occupancy at the membrane of antigen presenting cells, reducing the risk of foreign peptide presentation being sufficient to achieve the 'activation threshold' required for T cell stimulation. High GE content is therefore a beneficial quality in clinical development of an antibody therapeutic and can provide low immunogenicity. In some examples, an anti-PID1 antibody or antigen-binding portion comprises a human germline peptide sequence with high MHC class II binding affinity (e.g., germline epitope) in the LCDR2.

In certain embodiments, an anti-PID1 antibody or antigen-binding portion may have a reduced number of HAF, LAF and/or TCED+ epitopes found in the frameworks of both the heavy and light chain variable regions compared to an anti-PID1 antibody comprising the variable domain sequences of antibody Mab005 (Table 2). In some embodiments, HAF, LAF and/or TCED+ epitopes are not present in the VL and/or VH region sequences of an anti-PD1 antibody or antigen-binding portion.

For example, a TCED+ and HAF peptide 'VTITCLASQ' (SEQ ID NO: 83) found in the LCDR-1 of Mab005 may be eliminated by the mutation L>R at position 6, converting this sequence to the light chain GE 'VTITCRASQ' (SEQ ID NO: 84) in an anti-PID1 antibody or antigen-binding portion.

In some embodiments, an LAF peptide 'IGTWLTWYQ' (SEQ ID NO: 85) found in the LCDR-1 of Mab005 may be eliminated by retaining only a single murine residue W at position 4, converting this sequence to 'ISSWLNWYQ' (SEQ ID NO: 86) in an anti-PD1 antibody or antigen-binding portion (Table 12).

In some embodiments, the Mab005 HAF peptides 'LLIYTATSL' (SEQ ID NO: 87) and 'LIYTATSLA' (SEQ ID NO: 88), and LAF peptide 'IYTATSLAD' (SEQ ID NO: 89) may be eliminated and converted to GE sequences by mutation of the LCDR2 from the murine sequence 'TATSLAD' (SEQ ID NO: 36) to the fully germline sequence 'AASSLQS' (SEQ ID NO: 42) in an anti-PID1 antibody or antigen-binding portion.

The Mab005 FW3/LCDR3 region also encodes a LAF peptide 'YYCQQVYSI' (SEQ ID NO: 90). In some embodiments, this epitope may be eliminated by the germlining mutation V>S at position 6 in an anti-PD1 antibody or antigen-binding portion.

In the VH region of Mab005, the peptide sequence 'LYYFDYWGQ' (SEQ ID NO:91) (spanning the HCDR3 and FW4) was found to be a LAF. In some embodiments, the mutation Y>A at position 3 in this peptide allows the elimination of this epitope in an anti-PD1 antibody or antigen-binding portion (Tables 4, 12).

The terms "cross-compete", "cross-competition", "cross-block", "cross-blocked" and "cross-blocking" are used interchangeably herein to mean the ability of an antibody or portion thereof to interfere with the binding directly or indirectly through allosteric modulation of the anti-PD1 antibodies of the invention to the target PD1 (e.g., human PD1). The extent to which an antibody or portion thereof is able to interfere with the binding of another to the target, and therefore whether it can be said to cross-block or cross-compete according to the invention, can be determined using competition binding assays. One example of a binding competition assay is Homogeneous Time Resolved Fluorescence (HTRF). One particularly suitable quantitative cross-competition assay uses a FACS- or an AlphaScreen-based approach to measure competition between the labelled (e.g. His tagged, biotinylated or radioactive labelled) antibody or portion thereof and the other antibody or portion thereof in terms of their binding to the target. In general, a cross-competing antibody or portion thereof is, for example, one which will bind to the target in the cross-competition assay such that, during the assay and in the presence of a second antibody or portion thereof, the recorded displacement of the immunoglobulin single variable domain or polypeptide according to the invention is up to 100% (e.g. in a FACS based competition assay) of the maximum theoretical displacement (e.g. displacement by cold (e.g. unlabeled) antibody or fragment thereof that needs to be cross-blocked) by the potentially cross-blocking antibody or fragment thereof that is present in a given amount. Preferably, cross-competing antibodies or portions thereof have a recorded displacement that is between 10% and 100%, or between 50% and 100%.

The anti-PD1 antibody molecule or antigen-binding portion as defined herein may be thermally stable. In some cases, an antibody molecule or antigen-binding portion may have substantially the same thermal stability as murine anti-PID1 antibody Mab005 or Mab005-IgG1 (humanized). In some cases, an antibody molecule or antigen-binding portion may be more thermally stable than murine anti-PID1 antibody Mab005 or Mab005-IgG1 (humanized). In some examples, an antibody molecule or antigen-binding portion may have a melting temperature (Tm) from about 90° C. to about 93° C. and may be in an IgG1 format. In some aspects, an antibody molecule or antigen-binding portion may have a Tm from about 90.8° C. to about 92.2° C. and may be in an IgG1 format. In some aspects, the antigen-binding portion may be in an Fab format. The melting temperature of an antibody molecule or antigen-binding portion thereof may be analysed by a differential scanning calorimetry (DSC) assay.

The anti-PID1 antibody molecule or antigen-binding portion as defined herein may be resistant to oxidation (e.g., resistant to oxidation of exposed amino acid residues). In some cases, an antibody molecule or antigen-binding portion may undergo reduced oxidation of exposed amino acid residues compared to murine anti-PID1 antibody Mab005 or Mab005-IgG1 (humanized), or an anti-PID1 antibody comprising the variable domain sequences of antibody Mab005-IgG1 (humanized). Oxidation resistance of an antibody molecule or antigen-binding portion thereof may be analysed by adding an oxidative reagent (e.g., $H_2O_2$) to the antibody molecule or antigen-binding portion and analysing changes induced by oxidation by Reverse Phase (RP) and Hydrophobic Interaction Chromatography (HIC) methods.

In certain embodiments, an antibody molecule or antigen-binding portion thereof binds specifically to PD1 and does not bind (or does not bind specifically) to one or more of the membrane receptors KDR (also known as VEGFR2), FZD5 (frizzled class receptor 5), ULBP2 (UL16 binding protein 2) and EPHB6. In some aspects, KDR, FZD5, ULBP2 and/or EPHB6 are human proteins. In some embodiments, KDR is a rhesus protein. In some embodiments, the human KDR protein comprises or consists of the amino acid sequence of SEQ ID NO:22 or an amino acid sequence that is at least about 90%, at least about 91%, at least about 92%, at least about 93%, at least about 94%, at least about 95%, at least about 96%, at least about 97%, at least about 98% or at least about 99% identical to SEQ ID NO:22. In some embodiments, the rhesus KDR protein comprises or consists of the amino acid sequence of SEQ ID NO:23 or an amino acid sequence that is at least about 90%, at least about 91%, at least about 92%, at least about 93%, at least about 94%, at least about 95%, at least about 96%, at least about 97%, at least about 98% or at least about 99% identical to SEQ ID NO:23. In some embodiments, the human FZD5 protein comprises or consists of the amino acid sequence of SEQ ID NO:24 or an amino acid sequence that is at least about 90%, at least about 91%, at least about 92%, at least about 93%, at least about 94%, at least about 95%, at least about 96%, at least about 97%, at least about 98% or at least about 99% identical to SEQ ID NO:24. In some embodiments, the human ULBP2 protein comprises or consists of the amino acid sequence of SEQ ID NO:25 or an amino acid sequence that is at least about 90%, at least about 91%, at least about 92%, at least about 93%, at least about 94%, at least about 95%, at least about 96%, at least about 97%, at least about 98% or at least about 99% identical to SEQ ID NO:25. In one embodiment, an antibody molecule or antigen-binding portion thereof does not bind to any of KDR, FZD5, ULBP2 and EPHB6. In some embodiments, an antibody molecule or antigen-binding portion thereof exhibits reduced binding to one or more of KDR, FZD5, ULBP2 and EPHB6 compared to the binding exhibited by antibody Mab005 or IgG1-Mab005 (humanized) to said membrane receptors. In some cases, binding of an antibody or antigen-binding portion thereof to PD1, KDR, FZD5, ULBP2 or EPHB6 may be determined by flow cytometry analysis.

In some embodiments, an antibody molecule or antigen-binding portion thereof disclosed herein binds specifically to PD1 and does not agonise or minimally agonises one or more of KDR, FZD5, ULBP2 and EPHB6 (e.g., human KDR, human FZD5, human ULBP2 or human EPHB6). In some embodiments, an antibody molecule or antigen-binding portion thereof disclosed herein binds specifically to PD1 and exhibits reduced agonism of one or more of KDR, FZD5, ULBP2 and EPHB6 (e.g., human KDR, human FZD5, human ULBP2 or human EPHB6) compared to the agonism of KDR, FZD5, ULBP2 or EPHB6 exhibited by antibody Mab005 or IgG1-Mab005 (humanized). In some cases, agonism of KDR, FZD5, ULBP2 or EPHB6 by an antibody molecule or antigen-binding portion thereof may be determined by a KDR (or VEGFR2), FZD5, ULBP2 or EPHB6 signaling reporter assay.

The antibody molecule or antigen-binding portion as defined herein may comprise one or more substitutions, deletions and/or insertions which remove a post-translational modification (PTM) site, for example a glycosylation site (N-linked or O-linked), a deamination site, a phosphorylation site or an isomerisation/fragmentation site.

More than 350 types of PTM are known. Key forms of PTM include phosphorylation, glycosylation (N- and O-linked), sumoylation, palmitoylation, acetylation, sulfation, myristoylation, prenylation and methylation (of K and R residues). Statistical methods to identify putative amino acid sites responsible for specific PTMs are well known in the art (see Zhou et al., 2016, Nature Protocols 1: 1318-1321). Removal of such a site for example by substitution, deletion and/or insertion and then optionally testing (experimentally and/or theoretically) for (a) binding activity and/or (b) loss of the PTM is contemplated.

For example, the MAb005 murine HCDR2 (as defined herein, i.e. the amino acid sequence VATISGGGAN-TYYPDSVKG (SEQ ID NO: 92)) has been identified to have a putative deamination site at residue 10 (N). Removal of this site at equivalent positions in an HCDR2 of the invention, for example by conservative or non-conservative substitution (such as to E, Q, S or D), is envisaged (as for example in clone 06D02 and other clones in Tables 3 and 4).

Similarly, the MAb005 murine HCDR1 (as defined herein, i.e. the amino acid sequence GFTFSSYMMS (SEQ ID NO: 29)) has been identified to have a putative oxidation site at residue 8 (M). Removal of this site at an equivalent position in an HCDR1 of the invention, for example by conservative or non-conservative substitution (such as to A/D/E/F/H/I/L/N/P/Q/S/T/V/W/Y), is envisaged (as exemplified in clone 06D02 and the further sequences found in Tables 3 and 4).

The antibody molecule or antigen-binding portion thereof may be human, humanized or chimeric.

The antibody molecule or antigen-binding portion thereof may comprise one or more human variable domain framework scaffolds into which the CDRs have been inserted. For example, the VH region, the VL region, or both the VH and the VL region may comprise one or more human framework region amino acid sequences.

The antibody molecule or antigen-binding portion thereof may comprise an IGHV3-7 human germline scaffold into which the corresponding HCDR sequences have been inserted. The antibody molecule or antigen-binding portion thereof may comprise a VH region that comprises an IGHV3-7 human germline scaffold amino acid sequence into which a set of corresponding HCDR1, HCDR2 and HCDR3 amino acid sequences have been inserted.

The antibody molecule or antigen-binding portion thereof may comprise an IGKV1-39 human germline scaffold into which the corresponding LCDR sequences have been inserted. The antibody molecule or antigen-binding portion thereof may comprise a VL region that comprises an IGKV1-39 human germline scaffold amino acid sequence into which a set of corresponding LCDR1, LCDR2 and LCDR3 amino acid sequences have been inserted.

The antibody molecule or antigen-binding portion thereof may comprise an IGHV3-7 human germline scaffold into which the corresponding HCDR sequences have been inserted and an IGKV1-39 human germline scaffold into which the corresponding LCDR sequences have been inserted. The antibody molecule or antigen-binding portion thereof may comprise a VH region that comprises an IGHV3-7 human germline scaffold amino acid sequence into which a set of corresponding HCDR1, HCDR2 and HCDR3 amino acid sequences have been inserted and a VL region that comprises an IGKV1-39 human germline scaffold amino acid sequence into which a set of corresponding LCDR1, LCDR2 and LCDR3 amino acid sequences have been inserted. The HCDR1, HCDR2, HCDR3, LCDR1, LCDR2 and LCDR3 amino acid sequences may be the HCDR1, HCDR2, HCDR3, LCDR1, LCDR2 and LCDR3 amino acid sequences of any one of the clones in Table 4 (with all six CDR sequences being from the same clone).

In some aspects, the antibody molecule or antigen-binding portion thereof may comprise an immunoglobulin constant region. In some embodiments, the immunoglobulin constant region is IgG1, IgG2, IgG3, IgG4, IgA1 or IgA2. In additional embodiments, the immunoglobulin constant region is IgG1, IgG2, IgG3, IgG4, IgA1 or IgA2. The antibody molecule or antigen-binding portion thereof may comprise an immunologically inert constant region. In some aspects, an anti-PD1 antibody or antigen-binding portion thereof may comprise an immunoglobulin constant region comprising a wild-type human IgG1 constant region, a human IgG1 constant region comprising the amino acid substitutions L234A, L235A and G237A or a human IgG1 constant region comprising the amino acid substitutions L234A, L235A, G237A and P331S. In some aspects, an anti-PD1 antibody or antigen-binding portion thereof may comprise an immunoglobulin constant region comprising a wild-type human IgG2 constant region or a wild-type human IgG4 constant region. In some aspects, an anti-PD1 antibody may comprise an immunoglobulin constant region comprising any one of the amino acid sequences in Table 18. The Fc region sequences in Table 18 begin at the CH1 domain. In some aspects, an anti-PD1 antibody may comprise an immunoglobulin constant region comprising an amino acid sequence of an Fc region of human IgG4, human IgG4 (S228P), human IgG2, human IgG1, human IgG1-3M or human IgG1-4M. For example, the human IgG4(S228P) Fc region comprises the following substitution compared to the wild-type human IgG4 Fc region: S228P. For example, the human IgG1-3M Fc region comprises the following substitutions compared to the wild-type human IgG1 Fc region: L234A, L235A and G237A, while the human IgG1-4M Fc region comprises the following substitutions compared to the wild-type human IgG1 Fc region: L234A, L235A, G237A and P331S. In some aspects, a position of an amino acid residue in a constant region of an immunoglobulin molecule is numbered according to EU nomenclature (Ward et al., 1995 *Therap. Immunol.* 2:77-94). In some aspects, an immunoglobulin constant region may comprise an RDELT (SEQ ID NO: 93) motif or an REEM (SEQ ID NO: 94) motif (underlined in Table 18). The REEM (SEQ ID NO: 94) allotype is found in a smaller human population than the RDELT (SEQ ID NO: 93) allotype. In some aspects, an anti-PD1 antibody may comprise an immunoglobulin constant region comprising any one of SEQ ID NOS:13-19. In some aspects, an anti-PD1 antibody may comprise the six CDR amino acid sequences of any one of the clones in Table 4 and any one of the Fc region amino acid sequences in Table 18. In some aspects, an anti-PD1 antibody may comprise an immunoglobulin heavy chain constant region comprising any one of the Fc region amino acid sequences in Table 18 and an immunoglobulin light chain constant region that is a kappa light chain constant region or a lambda light chain constant region.

In some aspects, disclosed herein is an anti-PD1 antibody or an antigen-binding portion thereof, wherein the antibody comprises a heavy chain variable (VH) region, a light chain variable (VL) region and a heavy chain constant region, wherein (a) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QLYGFDY (SEQ ID NO: 40); the VL region amino acid sequence comprises LCDR1 of RASQSISSWLN (SEQ ID NO: 41), LCDR2 of AASSLQS (SEQ ID NO: 42) and LCDR3 of QQSYSTPWT (SEQ ID NO: 43); and the heavy chain constant region comprises any one of SEQ ID NOS: 13-19;

(b) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QVYYFDY (SEQ ID NO: 44); the VL region amino acid sequence comprises LCDR1 of RASQSISSWLN (SEQ ID NO: 41), LCDR2 of AASSLQS (SEQ ID NO: 42) and LCDR3 of QQSYSTPWT (SEQ ID NO: 43); and the heavy chain constant region comprises any one of SEQ ID NOS: 13-19;

(c) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QLYFFDY (SEQ ID NO: 45); the VL region amino acid sequence comprises LCDR1 of RASQSISSWLN (SEQ ID NO: 41), LCDR2 of AASSLQS (SEQ ID NO: 42) and LCDR3 of QQSYSTPWT (SEQ ID NO: 43); and the heavy chain constant region comprises any one of SEQ ID NOS: 13-19;

(d) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QLYAFDY (SEQ ID NO: 46); the VL region amino acid sequence comprises LCDR1 of RASQSISSWLN (SEQ ID NO: 41), LCDR2 of AASSLQS (SEQ ID NO: 42) and LCDR3 of QQSYSTPWT (SEQ ID NO: 43); and the heavy chain constant region comprises any one of SEQ ID NOS: 13-19;

(e) the VH region amino acid sequence comprises HCDR1 of GFTFSSYLMS (SEQ ID NO: 38), HCDR2 of VATISGGGSETYYVDSVKG (SEQ ID NO: 48) and HCDR3 of QLYGFDY (SEQ ID NO: 40); the VL region amino acid sequence comprises LCDR1 of RASQSISSWLN (SEQ ID NO: 41), LCDR2 of AASSLQS (SEQ ID NO: 42) and LCDR3 of QQSYSIPWT (SEQ ID NO: 47); and the heavy chain constant region comprises any one of SEQ ID NOS: 13-19;

(f) the VH region amino acid sequence comprises HCDR1 of GFTFSSYLMS (SEQ ID NO: 38), HCDR2 of VATISGGGAEKYYVDSVKG (SEQ ID NO: 49) and HCDR3 of QLYGFDY (SEQ ID NO: 40); the VL region amino acid sequence comprises LCDR1 of RASQSISSWLN (SEQ ID NO: 41), LCDR2 of AASSLQD (SEQ ID NO: 50) and LCDR3 of QQSYSTPWT (SEQ ID NO: 43); and the heavy chain constant region comprises any one of SEQ ID NOS: 13-19;

(g) the VH region amino acid sequence comprises HCDR1 of GFTFSSYLMS (SEQ ID NO: 38), HCDR2 of VATISGGGSETYYVDSVKG (SEQ ID NO: 48), and HCDR3 of QLYGFDY (SEQ ID NO: 40); the VL region amino acid sequence comprises LCDR1 of RASQSISSWLN (SEQ ID NO: 41), LCDR2 of AASSLQS (SEQ ID NO: 42), and LCDR3 of QQSYSIPWT (SEQ ID NO: 47); and the heavy chain constant region comprises any one of SEQ ID NOS: 13-19;

(h) the VH region amino acid sequence comprises HCDR1 of GFTFSSYLMS (SEQ ID NO: 38), HCDR2 of VATISGGGAEKYYVDSVKG (SEQ ID NO: 49), and HCDR3 of QLYGFDY (SEQ ID NO: 40); the VL region amino acid sequence comprises LCDR1 of RASQSISSWLN (SEQ ID NO: 41), LCDR2 of AASSLQD (SEQ ID NO: 50), and LCDR3 of QQSYSTPWT (SEQ ID NO: 43); and the heavy chain constant region comprises any one of SEQ ID NOS: 13-19;

(i) the VH region amino acid sequence comprises HCDR1 of GFTFSSYLMS (SEQ ID NO: 38), HCDR2 of VATISGGGSNTYYVDSVKG (SEQ ID NO: 51), and HCDR3 of QLYGFDY (SEQ ID NO: 40); the VL region amino acid sequence comprises LCDR1 of RASQSISTWLN (SEQ ID NO: 52), LCDR2 of AASSLAS (SEQ ID NO: 53), and LCDR3 of QQSYSTPWT (SEQ ID NO: 43); and the heavy chain constant region comprises any one of SEQ ID NOS: 13-19;

(j) the VH region amino acid sequence comprises HCDR1 of GFTFSSYLMS (SEQ ID NO: 38), HCDR2 of VATISGGGSEKYYVDSVKG (SEQ ID NO: 39), and HCDR3 of QVYYFDY (SEQ ID NO: 44); the VL region amino acid sequence comprises LCDR1 of RASQSISSWLN (SEQ ID NO: 41), LCDR2 of AASSLHS (SEQ ID NO: 54), and LCDR3 of QQSYS- TPWT (SEQ ID NO: 43); and the heavy chain constant region comprises any one of SEQ ID NOS: 13-19; or (k) the VH region amino acid sequence comprises HCDR1 of GFTFSSYLMS (SEQ ID NO: 38), HCDR2 of VATISGGGSEKYYVDSVKG (SEQ ID NO: 39), and HCDR3 of QVYYFDY (SEQ ID NO: 44); the VL region amino acid sequence comprises LCDR1 of RASQSISSWLN (SEQ ID NO: 41), LCDR2 of AASSLQS (SEQ ID NO: 42), and LCDR3 of QQSYS-TPWT (SEQ ID NO: 43); and the heavy chain constant region comprises any one of SEQ ID NOS: 13-19.

In some aspects, disclosed herein is an anti-PD1 antibody or an antigen-binding portion thereof, wherein the antibody comprises a heavy chain variable (VH) region, a light chain variable (VL) region and a heavy chain constant region, wherein a) the VH region amino acid sequence comprises or consists of SEQ ID NO:1; the VL region amino acid sequence comprises or consists of SEQ ID NO:2; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;

(b) the VH region amino acid sequence comprises or consists of SEQ ID NO:3; the VL region amino acid sequence comprises or consists of SEQ ID NO:4; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;

(c) the VH region amino acid sequence comprises or consists of SEQ ID NO:5; the VL region amino acid sequence comprises or consists of SEQ ID NO:6; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;

(d) the VH region amino acid sequence comprises or consists of SEQ ID NO:7; the VL region amino acid sequence comprises or consists of SEQ ID NO:8; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A;

(e) the VH region amino acid sequence comprises or consists of SEQ ID NO:9; the VL region amino acid sequence comprises or consists of SEQ ID NO:10; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A; or (f) the VH region amino acid sequence comprises or consists of SEQ ID NO:11; the VL region amino acid sequence comprises or consists of SEQ ID NO:12; and the heavy chain constant region comprises a wild-type human IgG4 constant region, a human IgG4 constant region comprising the amino acid substitution S228P, a wild-type human IgG2 constant region; a wild-type human IgG1 constant region or a human IgG1 constant region comprising the amino acid substitutions L234A, L235A and G237A.

In some aspects, disclosed herein is an anti-PD1 antibody or an antigen-binding portion thereof, wherein the antibody comprises a heavy chain variable (VH) region, a light chain variable (VL) region and a heavy chain constant region, wherein a) the VH region amino acid sequence comprises or consists of SEQ ID NO:1; the VL region amino acid sequence comprises or consists of SEQ ID NO:2; and the heavy chain constant region comprises any one of SEQ ID NOS: 13-19;

(b) the VH region amino acid sequence comprises or consists of SEQ ID NO:3; the VL region amino acid sequence comprises or consists of SEQ ID NO:4; and the heavy chain constant region comprises any one of SEQ ID NOS: 13-19;

(c) the VH region amino acid sequence comprises or consists of SEQ ID NO:5; the VL region amino acid sequence comprises or consists of SEQ ID NO:6; and the heavy chain constant region comprises any one of SEQ ID NOS: 13-19;

(d) the VH region amino acid sequence comprises or consists of SEQ ID NO:7; the VL region amino acid sequence comprises or consists of SEQ ID NO:8; and the heavy chain constant region comprises any one of SEQ ID NOS: 13-19;

(e) the VH region amino acid sequence comprises or consists of SEQ ID NO:9; the VL region amino acid sequence comprises or consists of SEQ ID NO:10; and the heavy chain constant region comprises any one of SEQ ID NOS: 13-19; or (f) the VH region amino acid sequence comprises or consists of SEQ ID NO:11; the VL region amino acid sequence comprises or consists of SEQ ID NO:12; and the heavy chain constant region comprises any one of SEQ ID NOS: 13-19.

In some aspects, an anti-PD1 antibody may be immune effector null. In some aspects, an anti-PD1 antibody or an antigen-binding portion thereof does not induce immune effector function and, optionally, suppresses immune effector function. In some aspects, an anti-PD1 antibody may lack measurable binding to human FcγRI, FcγRIIa, FcγRIIIa and FcγRIIIb receptors but maintain binding to human FcγRIIb receptor and optionally maintain binding to human FcRn receptor. FcγRI, FcγRIIa, FcγRIIIa and FcγRIIIb are examples of activating receptors. FcγRIIb is an example of an inhibitory receptor. FcRn is an example of a recycling receptor. In some aspects, binding affinity of an anti-PD1 antibody or an antigen-binding portion thereof for human Fc receptors may be measured by BIACORE® analysis. In some aspects, Homogeneous Time Resolved Fluorescence (HTRF) can be used to study binding of an anti-PD1 antibody to human Fc receptors. In one example of HTRF, human IgG1 (wild type) is labelled, as is the full suite of Fc gamma receptors and then antibodies with engineered Fc fragments are used in titration competition. In some aspects, PD1-positive cells may be mixed with human white blood cells and anti-PD1 antibodies, and cell killing by CDC, ADCC and/or ADCP may be measured. In some aspects, an anti-PD1 antibody comprising an amino acid sequence of an Fc region of human IgG1-3M (see Table 18) is effector null. In some aspects, an anti-PD1 antibody comprising an amino acid sequence of an Fc region of human IgG1-3M (see Table 18) is not effector null.

The antibody molecule or antigen-binding portion thereof may be a Fab fragment, a F(ab)$_2$ fragment, an Fv fragment, a tetrameric antibody, a tetravalent antibody, a multispecific antibody (for example, a bivalent antibody), a domain-specific antibody, a single domain antibody, a monoclonal antibody or a fusion protein. In one embodiment, an antibody may be a bispecific antibody that binds specifically to a first antigen and a second antigen, wherein the first antigen is PD1 and the second antigen is not PD1. Antibody molecules and methods for their construction and use are described, in for example Holliger & Hudson (2005, Nature Biotechnol. 23(9): 1126-1136).

In another aspect of the invention, there is provided an immunoconjugate comprising the antibody molecule or antigen-binding portion thereof of the invention as defined herein linked a therapeutic agent.

Examples of suitable therapeutic agents include cytotoxins, radioisotopes, chemotherapeutic agents, immunomodulatory agents, anti-angiogenic agents, antiproliferative agents, pro-apoptotic agents, and cytostatic and cytolytic enzymes (for example RNAses). Further therapeutic agents include a therapeutic nucleic acid, such as a gene encoding an immunomodulatory agent, an anti-angiogenic agent, an anti-proliferative agent, or a pro-apoptotic agent. These drug descriptors are not mutually exclusive, and thus a therapeutic agent may be described using one or more of the above terms.

Examples of suitable therapeutic agents for use in immunoconjugates include the taxanes, maytansines, CC-1065 and the duocarmycins, the calicheamicins and other enediynes, and the auristatins. Other examples include the anti-folates, vinca alkaloids, and the anthracyclines. Plant toxins, other bioactive proteins, enzymes (i.e., ADEPT), radioisotopes, photosensitizers may also be used in immunoconjugates. In addition, conjugates can be made using secondary carriers as the cytotoxic agent, such as liposomes or polymers, Suitable cytotoxins include an agent that inhibits or prevents the function of cells and/or results in destruction of cells. Representative cytotoxins include antibiotics, inhibitors of tubulin polymerization, alkylating agents that bind to and disrupt DNA, and agents that disrupt protein synthesis or the function of essential cellular proteins such as protein kinases, phosphatases, topoisomerases, enzymes, and cyclins.

Representative cytotoxins include, but are not limited to, doxorubicin, daunorubicin, idarubicin, aclarubicin, zorubicin, mitoxantrone, epirubicin, carubicin, nogalamycin, menogaril, pitarubicin, valrubicin, cytarabine, gemcitabine, trifluridine, ancitabine, enocitabine, azacitidine, doxifluhdine, pentostatin, broxuhdine, capecitabine, cladhbine, decitabine, floxuhdine, fludarabine, gougerotin, puromycin, tegafur, tiazofuhn, adhamycin, cisplatin, carboplatin, cyclophosphamide, dacarbazine, vinblastine, vincristine, mitoxantrone, bleomycin, mechlorethamine, prednisone, procarbazine, methotrexate, flurouracils, etoposide, taxol, taxol analogs, platins such as cis-platin and carbo-platin, mitomycin, thiotepa, taxanes, vincristine, daunorubicin, epirubicin, actinomycin, authramycin, azaserines, bleomycins, tamoxifen, idarubicin, dolastatins/auristatins, hemiasterlins, esperamicins and maytansinoids.

Suitable immunomodulatory agents include anti-hormones that block hormone action on tumors and immunosuppressive agents that suppress cytokine production, downregulate self-antigen expression, or mask MHC antigens.

Also provided is a nucleic acid molecule encoding the antibody molecule or antigen-binding portion thereof of the invention as defined herein. A nucleic acid molecule may encode (a) the VH region amino acid sequence; (b) the VL region amino acid sequence; or (c) both the VH and the VL region amino acid sequences of an anti-PD1 antibody or an antigen-binding portion thereof described herein. In some aspects, the nucleic acid molecule as defined herein may be isolated.

Further provided is a vector comprising the nucleic acid molecule of the invention as defined herein. The vector may be an expression vector.

Also provided is a host cell comprising the nucleic acid molecule or the vector of the invention as defined herein. The host cell may be a recombinant host cell.

In a further aspect there is provided a method of producing an anti-PD1 antibody and/or an antigen-binding portion thereof, comprising culturing the host cell of the invention under conditions that result in expression and/or production of the antibody and/or the antigen-binding portion thereof, and isolating the antibody and/or the antigen-binding portion thereof from the host cell or culture.

In another aspect of the invention there is provided a pharmaceutical composition comprising the antibody molecule or antigen-binding portion thereof of the invention as defined herein, or the nucleic acid molecule of the invention as defined herein, or the vector of the invention as defined herein.

Further provided is a method for enhancing an immune response in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein.

In a further aspect there is provided a method for treating or preventing cancer in a subject, comprising administering to the subject an effective amount of the antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein. In some cases, the administration to a subject of the antibody molecule or antigen-binding portion thereof of the invention as defined herein, or the immunoconjugate of the invention as defined herein, or the nucleic acid molecule of the invention as defined herein, or the vector of the invention as defined herein does not induce or induces minimal hemangioma in the subject.

For example, the cancer may be pancreatic cancer, melanoma, breast cancer, lung cancer, bronchial cancer, colorectal cancer, prostate cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, or cancer of hematological tissues.

The invention also provides an antibody molecule or antigen-binding portion thereof of the invention as defined herein, or the immunoconjugate of the invention as defined herein, or the nucleic acid molecule of the invention as defined herein, or the vector of the invention as defined herein, or the pharmaceutical composition of the invention as defined herein, for use in the treatment of cancer.

In another aspect the invention provides the antibody molecule, or antigen-binding portion thereof, or the immunoconjugate, or the nucleic acid molecule, or the vector for use, or the method of treatment of the invention as defined herein, for separate, sequential or simultaneous use in a combination combined with a second therapeutic agent, for example an anti-cancer agent.

In a further aspect there is provided the use of an antibody molecule or antigen-binding portion thereof of the invention as defined herein, or an immunoconjugate of the invention as defined herein, or a nucleic acid molecule of the invention as defined herein, or a vector of the invention as defined herein, or a pharmaceutical composition of the invention as defined herein, in the manufacture of a medicament for the treatment of cancer.

The invention also provides a method for treating or preventing an infectious or immune disease in a subject, comprising administering to the subject an effective amount of the antibody molecule or antigen-binding portion thereof as defined herein, or the immunoconjugate as defined here, or the nucleic acid molecule as defined herein, or the vector as defined herein, or the pharmaceutical composition as defined herein.

In one embodiment, the invention provides an anti-PID1 antibody or an antigen-binding portion thereof comprising the amino acid sequences disclosed herein for use in therapy.

The pharmaceutical composition of the invention may comprise a pharmaceutically acceptable excipient, carrier, or diluent. A pharmaceutically acceptable excipient may be a compound or a combination of compounds entering into a pharmaceutical composition which does not provoke secondary reactions and which allows, for example, facilitation of the administration of the anti-PD1 antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-PID1 antibody molecule.

In some embodiments, the anti-PID1 antibody molecule may be provided in a lyophilised form for reconstitution prior to administration. For example, lyophilised antibody molecules may be re-constituted in sterile water and mixed with saline prior to administration to an individual.

The anti-PID1 antibody molecules will usually be administered in the form of a pharmaceutical composition, which may comprise at least one component in addition to the antibody molecule. Thus pharmaceutical compositions may comprise, in addition to the anti-PID1 antibody molecule, a pharmaceutically acceptable excipient, carrier, buffer, stabilizer or other materials well known to those skilled in the art. Such materials should be non-toxic and should not interfere with the efficacy of the anti-PID1 antibody molecule. The precise nature of the carrier or other material will depend on the route of administration, which may be by bolus, infusion, injection or any other suitable route, as discussed below.

For parenteral, for example sub-cutaneous or intra-venous administration, e.g. by injection, the pharmaceutical composition comprising the anti-PD1 antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringe's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

A pharmaceutical composition comprising an anti-PD1 antibody molecule may be administered alone or in combination with other treatments, either simultaneously or sequentially dependent upon the condition to be treated.

An anti-PD1 antibody molecule as described herein may be used in a method of treatment of the human or animal body, including prophylactic or preventative treatment (e.g. treatment before the onset of a condition in an individual to reduce the risk of the condition occurring in the individual; delay its onset; or reduce its severity after onset). The method of treatment may comprise administering the anti-PD1 antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. Appropriate doses of antibody molecules are well known in the art (Ledermann J. A. et al., 1991, Int. J. Cancer 47: 659-664; Bagshawe K. D. et al., 1991, Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 µg to 1 g for systemic applications, and 1 µg to 1 mg for topical applications. An initial higher loading dose, followed by one or more lower doses, may be administered. Typically, the antibody will be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. The treatment schedule for an individual may be dependent on the pharmocokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of surgical treatment or invasive procedure. Suitable formulations and routes of administration are described above.

In some embodiments, anti-PD1 antibody molecules as described herein may be administered as sub-cutaneous injections. Sub-cutaneous injections may be administered using an auto-injector, for example for long term prophylaxis/treatment.

In some embodiments, the therapeutic effect of the anti-PD1 antibody molecule may persist for several half-lives, depending on the dose. For example, the therapeutic effect of a single dose of the anti-PD1 antibody molecule may persist in an individual for 1 month or more, 2 months or more, 3 months or more, 4 months or more, 5 months or more, or 6 months or more.

The invention also provides a method of producing an antibody molecule which specifically binds to human PD1 and optionally also to cynomolgus monkey PD1, or an antigen-binding portion thereof, comprising the steps of:
(1) grafting anti-PD1 CDRs from a non-human source into a human v-domain framework to produce a humanized anti-PD1 antibody molecule or antigen-binding portion thereof;
(2) generating a library of clones of the humanized anti-PD1 antibody molecule or antigen-binding portion thereof comprising one or more mutations in the CDRs;
(3) screening the library for binding to human PD1 and optionally also to cynomolgus monkey PD1;
(4) selecting clones from the screening step (3) having binding specificity to human PD1 and optionally also to cynomolgus monkey PD1; and
(5) producing an antibody molecule which specifically binds to human PD1 and optionally also to cynomolgus monkey PD1, or an antigen-binding portion thereof from clones selected from step (4).

The method may comprise a further step of producing additional clones based on the clones selected in step (4), for example based on further exploratory mutagenesis at specific positions in the CDRs of the clones selected in step (4), to enhance humanization and/or minimise human T cell epitope content and/or improve manufacturing properties in the antibody molecule or antigen-binding portion thereof produced in step (5).

Refinements applicable to the above method are as described in Example 1 below.

As used herein, the term "PD1" refers to Programmed Cell Death Protein 1 and variants thereof that retain at least part of the biological activity of PD1. As used herein, PD1 includes all species of native sequence PD1, including human, rat, mouse and chicken. The term "PD1" is used to include variants, isoforms and species homologs of human PD1. Antibodies of the invention may cross-react with PD1 from species other than human, in particular PD1 from cynomolgus monkey (*Macaca fascicularis*). Examples of human and cynomolgus PD1 amino acid sequences are provided in Table 19. In certain embodiments, the antibodies may be completely specific for human PD1 and may not exhibit non-human cross-reactivity.

As used herein, an "antagonist" as used in the context of the antibody of the invention or an "anti-PD1 antagonist antibody" (interchangeably termed "anti-PD1 antibody") refers to an antibody which is able to bind to PD1 and inhibit PD1 biological activity and/or downstream pathway(s) mediated by PD1 signalling. An anti-PD1 antagonist antibody encompasses antibodies that can block, antagonize, suppress or reduce (including significantly) PD1 biological activity, including downstream pathways mediated by PD1 signalling, such as receptor binding and/or elicitation of a cellular response to PD1. For the purposes of the present invention, it will be explicitly understood that the term "anti-PD1 antagonist antibody" encompass all the terms, titles, and functional states and characteristics whereby PD1 itself, and PD1 biological activity (including but not limited to its ability to suppress the activation of anti-tumour cell activity of T cells), or the consequences of the activity or biological activity, are substantially nullified, decreased, or neutralized in any meaningful degree.

The antibody "specifically binds" "specifically interacts", "preferentially binds", "binds" or "interacts" with PD1 if it binds with greater affinity, avidity, more readily and/or with greater duration than it binds to other receptors.

An "antibody molecule" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody molecule" encompasses not only intact polyclonal or monoclonal antibodies, but also any antigen binding fragment (for example, an "antigen-binding portion") or single chain thereof, fusion proteins comprising an antibody, and any other modified configuration of the immunoglobulin molecule that comprises an antigen recognition site including, for example without limitation, scFv, single domain antibodies (for example, shark and camelid antibodies), maxibodies, minibodies, intrabodies, diabodies, triabodies, tetrabodies, v-NAR and bis-scFv.

An "antibody molecule" encompasses an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), for example IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding portion" of an antibody molecule, as used herein, refers to one or more fragments of an intact antibody that retain the ability to specifically bind to PD1. Antigen binding functions of an antibody molecule can be performed by fragments of an intact antibody. Examples of binding fragments encompassed within the term "antigen binding portion" of an antibody molecule include Fab; Fab'; F(ab')2; an Fd fragment consisting of the VH and CH1 domains; an Fv fragment consisting of the VL and VH domains of a single arm of an antibody; a single domain antibody (dAb) fragment, and an isolated complementarity determining region (CDR).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. The Fc region of an immunoglobulin generally comprises two constant domains, incorporates the lessons of all such prior insights and includes all appropriate loop positions required to sample the full residue landscape that potentially mediates target-binding complementarity.

Table 1 shows the amino acid sequences of the MAb005 murine anti-PD1 antibody CDRs as defined herein (a "Unified" scheme), in comparison to well-known alternative systems for defining the same CDRs.

The term "Mab005-IgG1 (humanized)" refers to an anti-PD1 antibody comprising the variable heavy region sequence labelled PD1-VH1 and the variable light region sequence labelled PD1-VL1 in Table 2 and a human IgG1 constant region.

As used herein the term "conservative substitution" refers to replacement of an amino acid with another amino acid which does not significantly deleteriously change the functional activity. A preferred example of a "conservative substitution" is the replacement of one amino acid with another amino acid which has a value ≥0 in the following BLOSUM 62 substitution matrix (see Henikoff & Henikoff, 1992, PNAS 89: 10915-10919):

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 |
| R | -1 | 5 | 0 | -2 | -3 | 1 | 0 | -2 | 0 | -3 | -2 | 2 | -1 | -3 | -2 | -1 | -1 | -3 | -2 | -3 |
| N | -2 | 0 | 6 | 1 | -3 | 0 | 0 | 0 | 1 | -3 | -3 | 0 | -2 | -3 | -2 | 1 | 0 | -4 | -2 | -3 |
| D | -2 | -2 | 1 | 6 | -3 | 0 | 2 | -1 | -1 | -3 | -4 | -1 | -3 | -3 | -1 | 0 | -1 | -4 | -3 | -3 |
| C | 0 | -3 | -3 | -3 | 9 | -3 | -4 | -3 | -3 | -1 | -1 | -3 | -1 | -2 | -3 | -1 | -1 | -2 | -2 | -1 |
| Q | -1 | 1 | 0 | 0 | -3 | 5 | 2 | -2 | 0 | -3 | -2 | 1 | 0 | -3 | -1 | 0 | -1 | -2 | -1 | -2 |
| E | -1 | 0 | 0 | 2 | -4 | 2 | 5 | -2 | 0 | -3 | -3 | 1 | -2 | -3 | -1 | 0 | -1 | -3 | -2 | -2 |
| G | 0 | -2 | 0 | -1 | -3 | -2 | -2 | 6 | -2 | -4 | -4 | -2 | -3 | -3 | -2 | 0 | -2 | -2 | -3 | -3 |
| H | -2 | 0 | 1 | -1 | -3 | 0 | 0 | -2 | 8 | -3 | -3 | -1 | -2 | -1 | -2 | -1 | -2 | -2 | 2 | -3 |
| I | -1 | -3 | -3 | -3 | -1 | -3 | -3 | -4 | -3 | 4 | 2 | -3 | 1 | 0 | -3 | -2 | -1 | -3 | -1 | 3 |
| L | -1 | -2 | -3 | -4 | -1 | -2 | -3 | -4 | -3 | 2 | 4 | -2 | 2 | 0 | -3 | -2 | -1 | -2 | -1 | 1 |
| K | -1 | 2 | 0 | -1 | -3 | 1 | 1 | -2 | -1 | -3 | -2 | 5 | -1 | -3 | -1 | 0 | -1 | -3 | -2 | -2 |
| M | -1 | -1 | -2 | -3 | -1 | 0 | -2 | -3 | -2 | 1 | 2 | -1 | 5 | 0 | -2 | -1 | -1 | -1 | -1 | 1 |
| F | -2 | -3 | -3 | -3 | -2 | -3 | -3 | -3 | -1 | 0 | 0 | -3 | 0 | 6 | -4 | -2 | -2 | 1 | 3 | -1 |
| P | -1 | -2 | -2 | -1 | -3 | -1 | -1 | -2 | -2 | -3 | -3 | -1 | -2 | -4 | 7 | -1 | -1 | -4 | -3 | -2 |
| S | 1 | -1 | 1 | 0 | -1 | 0 | 0 | 0 | -1 | -2 | -2 | 0 | -1 | -2 | -1 | 4 | 1 | -3 | -2 | -2 |
| T | 0 | -1 | 0 | -1 | -1 | -1 | -1 | -2 | -2 | -1 | -1 | -1 | -1 | -2 | -1 | 1 | 5 | -2 | -2 | 0 |
| W | -3 | -3 | -4 | -4 | -2 | -2 | -3 | -2 | -2 | -3 | -2 | -3 | -1 | 1 | -4 | -3 | -2 | 11 | 2 | -3 |
| Y | -2 | -2 | -2 | -3 | -2 | -1 | -2 | -3 | 2 | -1 | -1 | -2 | -1 | 3 | -3 | -2 | -2 | 2 | 7 | -1 |
| V | 0 | -3 | -3 | -3 | -1 | -2 | -2 | -3 | -3 | 3 | 1 | -2 | 1 | -1 | -2 | -2 | 0 | -3 | -1 | 4. |

CH2 and CH3. As is known in the art, an Fc region can be present in dimer or monomeric form.

A "variable region" of an antibody refers to the variable region of the antibody light chain or the variable region of the antibody heavy chain, either alone or in combination. As known in the art, the variable regions of the heavy and light chain each consist of four framework regions (FRs) connected by three complementarity determining regions (CDRs) also known as hypervariable regions, contribute to the formation of the antigen binding site of antibodies. When choosing FR to flank CDRs, for example when humanizing or optimizing an antibody, FRs from antibodies which contain CDR sequences in the same canonical class are preferred.

The CDR definitions used in the present application combine the domains used in the many disparate, often conflicting schemes that have been created in the field, which are based on the combination of immunoglobulin repertoire analyses and structural analyses of antibodies in isolation and in their co-crystals with antigens (see review by Swindells et al., 2016, abYsis: Integrated Antibody Sequence and Structure-Management, Analysis, and Prediction. J Mol Biol. [PMID: 27561707; Epub 22 August 2016]). The CDR definition used herein (a "Unified" definition)

The term "monoclonal antibody" (Mab) refers to an antibody, or antigen-binding portion thereof, that is derived from a single copy or clone, including for example any eukaryotic, prokaryotic, or phage clone, and not the method by which it is produced. Preferably, a monoclonal antibody of the invention exists in a homogeneous or substantially homogeneous population.

A "humanized" antibody molecule refers to a form of non-human (for example, murine) antibody molecules, or antigen-binding portion thereof, that are chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. Humanized antibodies may be human immunoglobulins (recipient antibody) in which residues from a CDR of the recipient are replaced by residues from a CDR of a non-human species (donor antibody) such as mouse, rat, or rabbit having the desired specificity, affinity, and capacity.

"Human antibody or fully human antibody" refers to an antibody molecule, or antigen-binding portion thereof, derived from transgenic mice carrying human antibody genes or from human cells.

The term "chimeric antibody" is intended to refer to an antibody molecule, or antigen-binding portion thereof, in which the variable region sequences are derived from one species and the constant region sequences are derived from another species, such as an antibody molecule in which the variable region sequences are derived from a mouse antibody and the constant region sequences are derived from a human antibody.

"Antibody-drug conjugate" and "immunoconjugate" refer to an antibody molecule, or antigen-binding portion thereof, including antibody derivatives that binds to PD1 and is conjugated to cytotoxic, cytostatic and/or therapeutic agents.

Antibody molecules of the invention, or antigen-binding portion thereof, can be produced using techniques well known in the art, for example recombinant technologies, phage display technologies, synthetic technologies or combinations of such technologies or other technologies readily known in the art.

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The term "epitope" refers to that portion of a molecule capable of being recognized by and bound by an antibody molecule, or antigen-binding portion thereof, at one or more of the antibody molecule's antigen-binding regions. Epitopes can consist of defined regions of primary secondary or tertiary protein structure and includes combinations of secondary structural units or structural domains of the target recognised by the antigen binding regions of the antibody, or antigen-binding portion thereof. Epitopes can likewise consist of a defined chemically active surface grouping of molecules such as amino acids or sugar side chains and have specific three-dimensional structural characteristics as well as specific charge characteristics. The term "antigenic epitope" as used herein, is defined as a portion of a polypeptide to which an antibody molecule can specifically bind as determined by any method well known in the art, for example, by conventional immunoassays, antibody competitive binding assays or by x-ray crystallography or related structural determination methods (for example NMR).

The term "binding affinity" or "KD" refers to the dissociation rate of a particular antigen-antibody interaction. The KD is the ratio of the rate of dissociation, also called the "off-rate ($k_{off}$)", to the association rate, or "on-rate ($k_{on}$)". Thus, $K_D$ equals $k_{off}/k_{on}$ and is expressed as a molar concentration (M). It follows that the smaller the $K_D$, the stronger the affinity of binding. Therefore, a $K_D$ of 1 µM indicates weak binding affinity compared to a $K_D$ of 1 nM. KD values for antibodies can be determined using methods well established in the art. One method for determining the KD of an antibody is by using surface plasmon resonance (SPR), typically using a biosensor system such as a Biacore® system.

The term "potency" is a measurement of biological activity and may be designated as $IC_{50}$, or effective concentration of an antibody or antibody drug conjugate to the antigen PD1 to inhibit 50% of activity measured in a PD1 activity assay as described herein.

The phrase "effective amount" or "therapeutically effective amount" as used herein refers to an amount necessary (at dosages and for periods of time and for the means of administration) to achieve the desired therapeutic result. An effective amount is at least the minimal amount, but less than a toxic amount, of an active agent which is necessary to impart therapeutic benefit to a subject.

The term "inhibit" or "neutralize" as used herein with respect to bioactivity of an antibody molecule of the invention means the ability of the antibody to substantially antagonize, prohibit, prevent, restrain, slow, disrupt, eliminate, stop, reduce or reverse for example progression or severity of that which is being inhibited including, but not limited to, a biological activity or binding interaction of the antibody molecule to PD1.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as defined above. The term "treating" also includes adjuvant and neo-adjuvant treatment of a subject. For the avoidance of doubt, reference herein to "treatment" includes reference to curative, palliative and prophylactic treatment. For the avoidance of doubt, references herein to "treatment" also include references to curative, palliative and prophylactic treatment.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the present invention encompasses not only the entire group listed as a whole, but each member of the group individually and all possible subgroups of the main group, but also the main group absent one or more of the group members. The present invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. Any example(s) following the term "e.g." or "for example" is not meant to be exhaustive or limiting.

The practice of the present invention will employ, unless otherwise indicated, conventional techniques of molecular biology (including recombinant techniques), microbiology, cell biology, biochemistry and immunology, which are within the skill of the art.

Particular non-limiting embodiments of the present invention will now be described with reference to accompanying drawings.

Example 1. Generation of Optimized Anti-PD1 Therapeutic Antibodies

Introduction

In this example, we successfully generate a panel of agonistic, optimized anti-PD1 antibodies. These anti-PD1 antibodies are well expressed, biophysically stable, highly soluble and of maximized identity to preferred human germlines.

Materials and Methods

PD1 Library Generation and Selection

The PD1 Fab repertoire was assembled by mass oligo synthesis and PCR. The amplified Fab repertoire was then cloned via restriction-ligation into a phagemid vector, transformed into *E. coli* TG-1 cells, and the phage repertoire rescued essentially as previously described in detail (Finlay et al., 2011, Methods Mol Biol 681: 383-401).

Phage selections were performed by coating streptavidin magnetic microbeads with biotinylated PD1 target protein (either human or cyno), washing the beads thrice with PBS and resuspending in PBS pH7.4 plus 5% skim milk protein. These beads were coated at 100 nM target protein in round 1 of selection, followed by reduced antigen concentrations in three successive rounds. In each round, phage were eluted using trypsin before re-infection into TG1 cells.

Periplasmic Extracts Production (Small-Scale)

Production of soluble Fabs in individual *E. coli* clones was performed. *E. coli* TG1 cells in logarhythmic growth phase were induced with isopropyl 1-thio-β-D-galactopyranoside. Periplasmic extracts containing soluble Fab were generated by a freeze/thaw cycle: BacteriaL cell pellets were frozen at −20° C. for overnight and then thawed at room temperature and resuspended in PBS pH 7.4. The supernatants containing the soluble Fab were collected after shaking at room temperature and centrifugation.

Fab Production and Purification

A panel of anti-PD1 Fabs were selected for larger-scale production. *E. coli* TG1 cultures (500 ml) were prepared and soluble Fab expressions induced, as above. Periplasmic extracts containing soluble Fab were extracted by a freeze/thaw cycle as above. The supernatants containing the soluble Fabs were collected after 1 hour with head-over-head rotation at room temperature, centrifugation and filtration through a 0.22 μm membrane. Soluble Fabs were purified by two step purification procedure using His-Trap HP Affinity column (for purification via the associated His tag) followed by purification on modified protein A or CaptureSelect™ IgG-CH1 Affinity Matrix columns.

IgG Expression and Purification

Mammalian codon-optimized synthetic genes encoding the heavy and light chain variable domains of the lead panel anti-PD1 antibodies plus the Mab005 variants and a Pembrolizumab analog were cloned into mammalian expression vectors comprising effector function null human IgG1 ('IgG1null'; human IgG1 containing L234A, L235A, G237A mutations in the lower hinge that abrogate normal immunoglobulin ADCC, ADCP and CDC functions) and human Cκ domains, respectively. Co-transfection of heavy and light chain containing vector in mammalian expression system was performed, followed by protein A-based purification of the IgG, quantification and QC on denaturing and non-denaturing SDS-PAGE.

Direct Binding ELISA for Fab and IgG

Binding and cross-reactivity of the lead panel to the recombinant proteins was initially assessed by binding ELISA. The human PD1 human Fc tagged recombinant protein and the cynomolgus monkey PD1 human Fc tagged recombinant protein were coated to the surface of MaxiSorp™ flat-bottom 96 well plate at 1 μg/ml. The purified Fab or IgG samples were titrated in two fold serial dilutions starting from 500 nM to 0.98 nM and allowed to bind to the coated antigens. The Fabs were detected using mouse anti-c-myc antibody followed by donkey anti-mouse IgG conjugated to horseradish peroxidase. The IgGs were detected using the mouse anti-human IgG conjugated to horseradish peroxidase. Binding signals were visualized with 3,3',5,5'-Tetramethylbenzidine Substrate Solution (TMB) and the absorbance measured at 450 nm.

Alphascreen Epitope Competition Assay for IgG1null Antibodies

The AlphaScreen assay (Perkin Elmer) was performed in a 25 μl final volume in 384-well white microtiter plates (Greiner). The reaction buffer contained 1×PBS pH 7.3 (Oxoid, Cat. nr. BR0014G) and 0.05% (v/v) Tween® 20 (Sigma, Cat. nr. P9416). Purified IgG samples were titrated in three fold serial dilutions starting at 500 nM final concentration and incubated with biotinylated human PD1-His/AviTag at 0.6 nM final concentration for 20 minutes at room temperature. The parental IgG at 0.3 nM and the anti-human IgG1 Acceptor beads at 20 μg/ml (final concentrations) were added and the mix was incubated for 1 hour at room temperature. Followed by addition of the Streptavidin Donor beads at 20 μg/ml (final concentration) and incubation for 30 minutes at room temperature. The emission of light was measured in the EnVision multilabel plate reader (Perkin Elmer) and analysed using the EnVision manager software. Values were reported as Counts Per Second (CPS) and corrected for crosstalk. The EC50 values were calculated using the MFI values in GraphPad Prism software (GraphPad Software, La Jolla, CA) and 4 parameters.

Biacore Analyses of IgG Affinity for Monomeric Human and Cyno PD1 in Solution

Affinity (KD) of purified IgGs was determined via SPR with antigen in-solution on a Biacore 3000 (GE). A mouse anti-human antibody (CH1 specific) was immobilized on a CM5 Sensor Chip to a level of 2000 RU in acetate buffer at pH 4.5 using amine coupling following the Wizard instructions for two channels. One channel was used for background signal correction. The standard running buffer HBS-EP pH 7.4 was used. Regeneration was performed with a single injection of 10 μl of 10 mM Glycine at pH 1.5 at 20 μl/minute. IgG samples were injected for 2 minutes at 50 nM at 30 μl/min followed by and off-rate of 60 seconds. The monomeric antigen (human PD1 His tagged or cynomolgus monkey PD1 His tag) was injected in two fold serial dilutions from 100 nM down to 3.1 nM, for 2 minutes at 30 μl/min followed by an off-rate of 300 seconds. The obtained sensorgrams were analysed using the Biacore 3000 evaluation (BIAevaluation) software. The KD was calculated by simultaneous fitting of the association and dissociation phases to a 1:1 Langmuir binding model.

Flow Cytometry of IgGs

Purified IgGs were tested in FACs for binding to human and cyno PD1 expressed on CHO-K1 stable cell lines and CHO-K1 wild-type cells. The IgG samples were titrated in three-fold serial dilutions starting at 500 nM to 0.98 nM. Binding of IgGs was detected with a mouse anti-human IgG conjugated to FITC. Results were analyzed by examining the Mean Fluorescence Intensity (MFI) of 10000 cells per sample in the BL-1 channel detector of a flow cytometer (Attune™ NxT Acoustic Focusing Cytometer, Invitrogen/ThermoFisher Scientific).

PD1/PD-L1 Cell-Based Antagonism Assay

The PD1/PD-L1 blockade cell-based bioassay (Promega), was used to measure the potency of antibodies in blocking the PD1/PD-L1 interaction. On the day before the assay, PD-L1 aAPC/CHO-K1 cells were thawed and transferred into cell recovery medium (90% Ham's F12/10% FBS). The cell suspension was dispensed to each of the inner 60 wells of two 96-well, white, flat-bottom assay plates, at 100 μl per well. Cell recovery medium was added to each of the outside wells and the assay plates and incubated overnight at 37° C./5% CO2. On the day of the assay the sample IgGs were diluted 4-fold in assay buffer (99% RPMI 1640/1% FBS) from 300 nM to 0.04 nM and 40 μl per dilution added to the assay plates containing the PD-L1 aAPC/CHO-K1 cells. Positive inhibition controls included the human PD1 Antibody AF1086 (R&D systems), mAb005 in IgG1null form and a pembrolizumab mab analogue in IgG1null form. As a negative inhibition control, an irrelevant IgG was included. PD1 Effector Cells were then thawed in assay buffer (99% RPMI 1640/1% FBS) and the cell suspension added to the wells of the assay plates containing the PD-L1 aAPC/CHO-K1 cells and the IgG titration samples. The assay plates were incubated for six hours in a 37° C./5% CO2 incubator, allowed to equilibrate to ambient temperature for 5-10 minutes, then 80 μl of Bio-Glo™ Reagent (Promega) was added. Assay plates were incubated at ambient temperature for a further 5-30 minutes and luminescence signals subsequently measured at 10, 20 and 30 minutes.

Antibody v-Domain T Cell Epitope Content: In Silico Analyses

In silico technologies (Abzena, Ltd.), which are based on identifying the location of T cell epitopes in therapeutic antibodies and proteins, were used for assessing potential immunogenicity in antibody v-domains. iTope™ was used to analyse the VL and a VH sequences of key leads for peptides with promiscuous high affinity binding to human MHC class II. Promiscuous high affinity MHC class II binding peptides are thought to correlate with the presence of T cell epitopes that are high risk indicators for clinical immunogenicity of drug proteins. The iTope™ software predicts favourable interactions between amino acid side chains of a peptide and specific binding pockets (in particular pocket positions; p1, p4, p6, p7 and p9) within the open-ended binding grooves of 34 human MHC class II alleles. These alleles represent the most common HLA-DR alleles found world-wide with no weighting attributed to those found most prevalently in any particular ethnic population. Twenty of the alleles contain the 'open' p1 configuration and 14 contain the 'closed' configuration where glycine at position 83 is replaced by a valine. The location of key binding residues is achieved by the in silico generation of 9mer peptides that overlap by eight amino acids spanning the test protein sequence. This process successfully discriminates with high accuracy between peptides that either bind or do not bind MHC class II molecules.

In addition, the sequences were analysed using TCED™ (T Cell Epitope Database™) search for matches to T cell epitopes previously identified by in vitro human T cell epitope mapping analyses of other protein sequences. The TCED™ is used to search any test sequence against a large (>10,000 peptides) database of peptides derived from unrelated protein and antibody sequences.

Antibody v-Domain Specificity Testing: Human Receptor Array Analyses

Human cell membrane receptor proteome arrays were performed at Retrogenix Ltd. Primary screens: 5 μg/ml of IgG1-Mab005 (humanized) antibody was screened for binding against fixed HEK293 cells/slides expressing 4975 human plasma membrane proteins individually (14 slide sets, n=2 slides per slide set). All transfection efficiencies exceeded the minimum threshold. Antibody binding was detected using AF647 fluorescent secondary anti-human IgG1 antibody. Primary hits (duplicate spots) were identified by analysing fluorescence (AF647 and ZsGreen1) on ImageQuant. Vectors encoding all hits were sequenced to confirm their correct identities. Confirmation/specificity screens: Vectors encoding all hits, plus control vectors encoding MS4A1 (CD20) and EGFR, were spotted in duplicate on new slides, and used to reverse transfect human HEK293 cells as before. All transfection efficiencies exceeded the minimum threshold. Identical fixed slides were treated with 5 μg/ml of each test antibody, 5 μg/ml of the negative control antibody, 1 μg/ml Rituximab biosimilar (positive control), Isotype IgG1 (Ab00102 human IgG1 anti-Fluorescein) or no test molecule (secondary only; negative control) (n=2 slides per treatment). Slides were analysed as above. Flow cytometry confirmation screen: Expression vectors encoding ZsGreen1 only, or ZsGreen1 and PD1, FZD5, KDR or ULBP2, were transfected into human HEK293 cells. Each live transfectant was incubated with 1 and 5 mg/ml of each of the test antibodies and the Isotype control antibody. Cells were washed, and incubated with the same AF647 anti-human IgG Fc detection antibody as used in the cell microarray screens. Cells were again washed, and analysed by flow cytometry using an Accuri flow cytometer (BD). A 7AAD live/dead dye was used to exclude dead cells, and ZsGreen1-positive cells (i.e. transfected cells) were selected for analyses.

DSC Analysis

The Tm of test articles was analysed using a MicroCal PEAQ-DSC (Malvern Instruments, Malvern, UK) running version 1.22 software. The samples were heated at a rate of 200° C./hour over a range of 20-110° C. Thermal data was normalised based on protein concentration. The Tm of the protein was determined from the heating scan data.

Forced Oxidation Analyses

For forced oxidation analysis of intact IgGs: IgG1null samples in PBS buffer were treated with 0.5% $H_2O_2$ at room temperature for 2 hours and then stored at −80° C. prior to RP analysis (intact antibodies and subunits, tryptic peptides) on a Dionex Ultimate 3000RS HPLC system (ThermoFisher Scientific, Hemel Hempstead, UK). For intact antibody reduction, DTT was added to a final concentration of 0.33 M and samples were incubated for 1 hour at room temperature and immediately analysed by RP. Chromatographic separation was performed using a PLRP-S 1000, 5 µm, 2.1 mm×50 mm column (Agilent Technologies, Stockport, UK) connected to a Dionex Ultimate 3000RS HPLC system (ThermoFisherScientific, Hemel Hempstead, UK). The method consisted of a linear gradient from 80% buffer A (0.02% TFA, 7.5% acetonitrile in H2O) to 50% buffer B (0.02% TFA, 7.5% $H_2O$ in acetonitrile) over 24 minutes. The flow rate was 0.5 mL/minute and the temperature was maintained at 70° C. throughout the analysis. Detection was carried out by UV absorption at 280 nm.

For forced oxidation analysis of digested IgGs: Native and oxidised IgG1null samples were digested with trypsin using the SMART Digest™ kit (ThermoFisher Scientific, Hemel Hempstead, UK) by following the manufacturer's protocol. The resulting tryptic peptides were immediately analysed by RP. Chromatographic separation was performed using an Acquity UPLC CSH C18 Column, 130 Å, 1.7 µm, 2.1 mm×150 mm (Waters, Elstree, UK) connected to a Dionex Ultimate 3000RS HPLC system (ThermoFisher Scientific, Hemel Hempstead, UK). The method consisted of a linear gradient from 95% buffer A (0.1% FA in H2O) to 15% buffer B (0.085% FA in 75% acetonitrile) over 4 minutes, followed by a linear gradient from 15% buffer B to 60% buffer B over 22 minutes. The flow rate was 0.2 mL/minute and the temperature was maintained at 40° C. throughout the analysis. Detection was carried out by UV absorption at 280 nm.

For HIC analyses, chromatographic separation was performed using a TSKgel Butyl-NPR 4.6 mm×35 mm HIC column (TOSOH Bioscience Ltd., Reading, UK) connected to a Dionex Ultimate 3000RS HPLC system (ThermoFisher Scientific, Hemel Hempstead, UK). The method consisted of a linear gradient from 60% Buffer A (100 mM sodium phosphate pH 7.0, 2 M ammonium sulphate) to 90% Buffer B (100 mM sodium phosphate pH 7.0) over 9 minutes. The flow rate was 1.2 mL/minute. Detection was carried out by UV absorption at 280 nm.

Results and Discussion

CDR Grafting onto Preferred Human Germline v-Genes

The CDRs of an agonistic murine anti-PD1 IgG MAb005 (mVH/mVL; see WO2015/085847A1 and Table 2) were initially introduced to human germline immunoglobulin v-domain framework sequence scaffolds using CDR grafting. To bias our engineering efforts towards final lead therapeutic IgG compounds with optimal drug-like properties, we chose to graft the CDRs of the parental antibody onto "preferred" germline scaffolds IGHV3-7 and IGKV1-39, which are known to have good solubility and drug development qualities, and are used at high frequency in the expressed human antibody repertoire.

Those scaffolds and grafted CDR definitions are outlined in Table 2. The heavy and light chain sequences for murine anti-PD1 antibody are also shown in Table 2. While this process of CDR grafting is well known, it is still problematic to predict whether a given set of human v-domain sequences will act as suitable acceptor frameworks for non-human CDR grafting. The use of unsuitable frameworks can lead to the loss of target binding function, protein stability issues or even impaired expression of the final IgG. The IGHV3-7/IGKV1-39 graft was therefore taken forward as the template for CDR mutagenesis and selection of improved clones.

Library Generation and Screening

The CDR-grafted IGHV3-7/IGKV1-39 v-domain sequences were combined into a Fab phage display format and a mutagenesis library cassette was generated by oligo synthesis and assembly. The final Fab library was ligated into a phage display vector and transformed into E. coli via electroporation to generate $1.3 \times 10^9$ independent clones. Library build quality was verified by sequencing 96 clones. This sequencing data showed that the positions encoding either the murine or human germline residue at each position of variance had been effectively sampled at a frequency of approximately 50%. Libraries were rescued using helper phage M13 and selections performed on biotinylated human and cynomolgus monkey PD1-Fc proteins in multiple separate branches.

Figure 1:
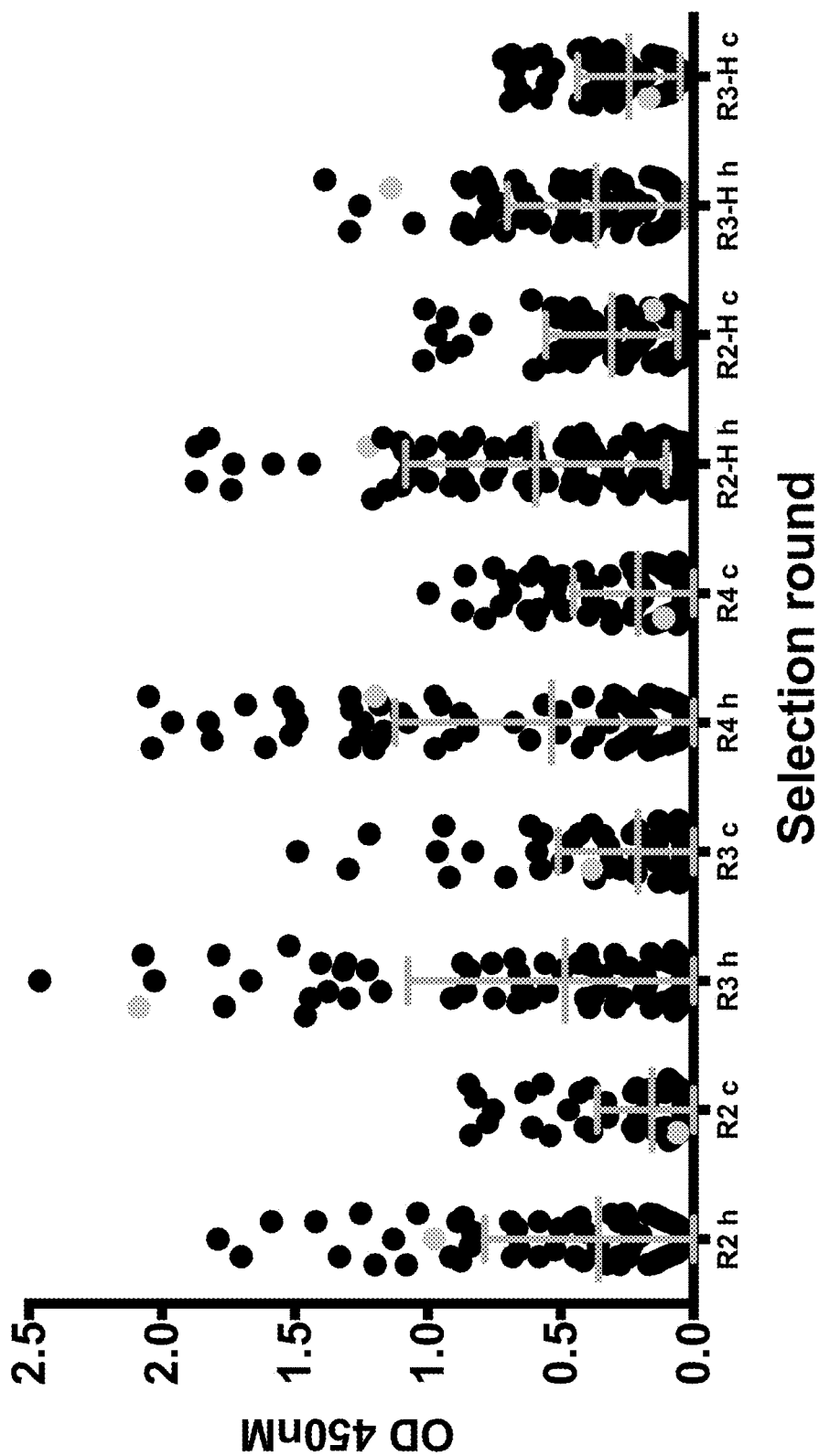
FIG. 1. Direct binding ELISA of library-derived anti-PD1 Fabs against human and cyno PD1-Fc proteins. Clones were derived from multiple phage selection branches where phage populations were selected on biotinylated human, or cynomolgus monkey PD1 proteins in each round. Standard selections are numbered R2-R4. 'Hammer-Hug' rounds are numbered R2-H and R3-H. After each round of selection, library-derived clones (black circles) were screened as periplasmically-expressed Fab proteins, against both human (h) and cyno (c) PD1. Mean±SD values in each round are represented in grey bars. mAb005 v-domains expressed as human IgG1 Fab were used as positive controls on each plate (grey circles).
Figure 2A:
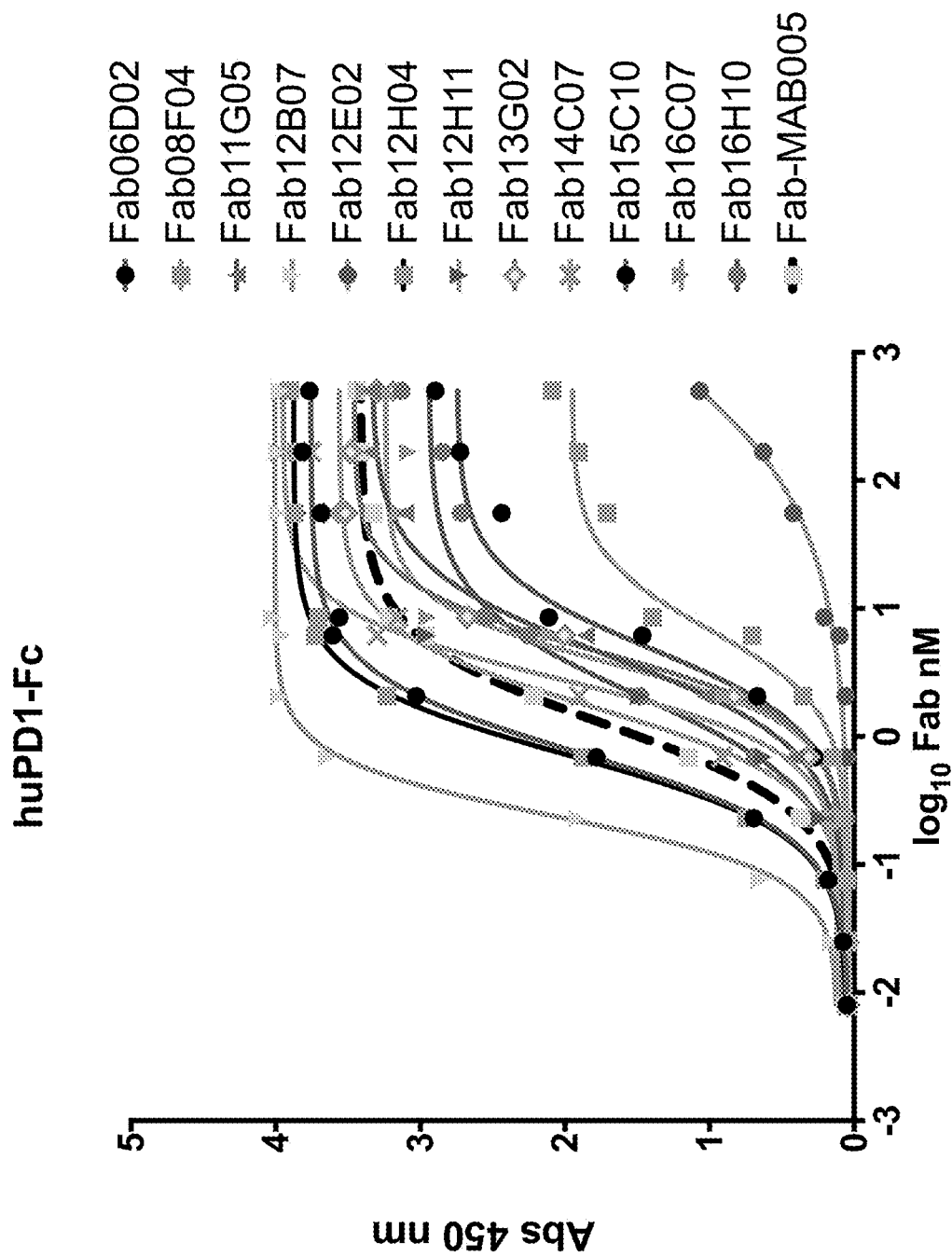
FIG. 2A-FIG. 2B. Direct titration ELISA for purified monomeric Fab binding to human and cyno PD1-Fc proteins. Mab005 and library-derived clones in human Fab format were titrated (in nM) in a direct binding ELISA against human (FIG. 2A) and cyno (FIG. 2B) PD1-Fc proteins.
Figure 2B:
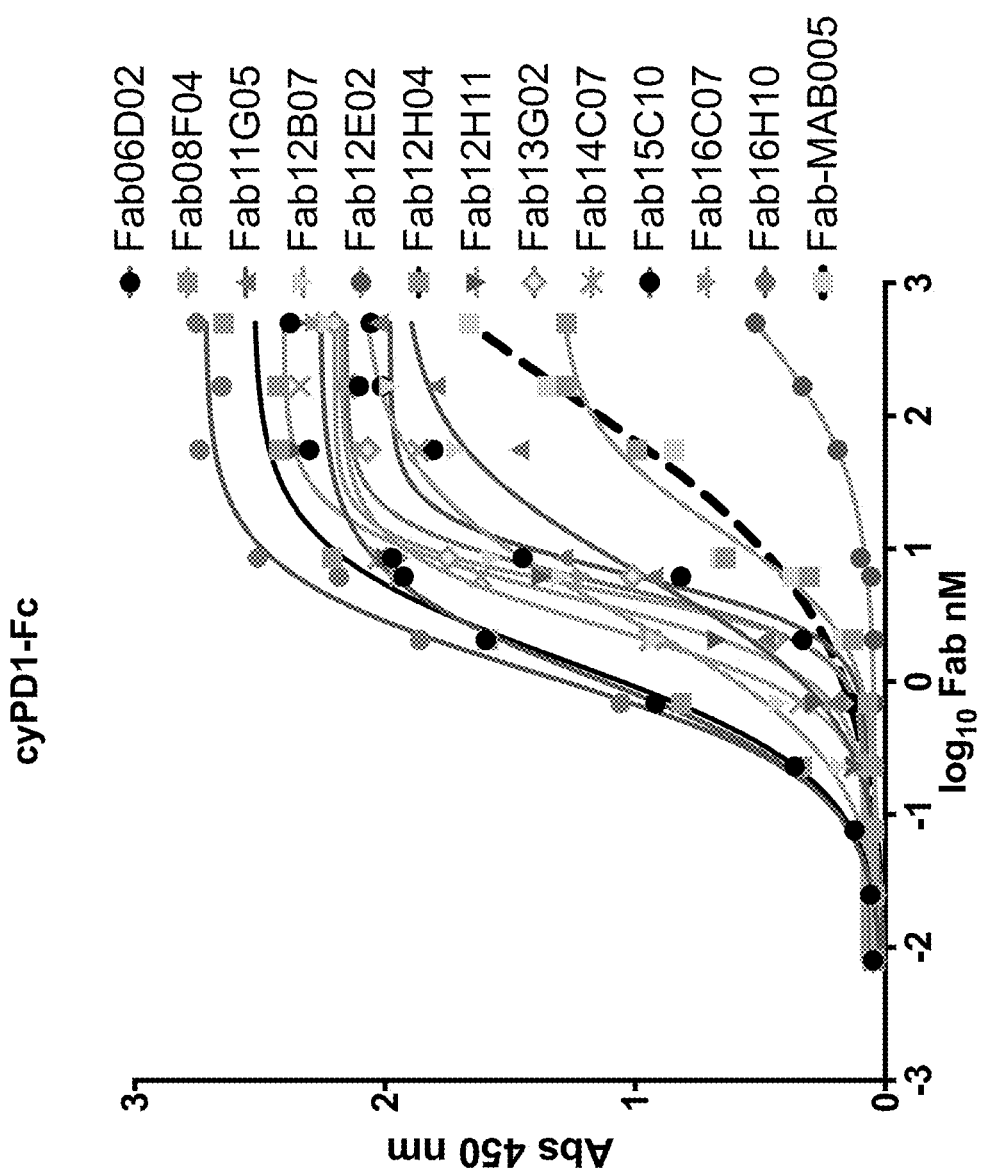

Post-selection screening (FIG. 1) and DNA sequencing revealed the presence of 64 unique, human and cyno PD1-binding Fab clones that exhibited strong binding to human and cyno PD1 in ELISA and >50% inhibition of IgG1-Mab005 (humanized) binding to human and cyno PD1 in Alphascreen assay. Amongst these 64 clones, the framework sequences remained fully germline while mutations were also observed in all CDRs (Table 3). Lead clones were ranked based on level of CDR germ-lining versus ELISA signals for binding to both human and cyno PD1-Fc. The v-domains of the 12 top clones from this ranking were then sub-cloned into IgG expression vectors for further testing as below (Table 4). The top 12 clones were also expressed as Fab protein from E. coli expression, purified to homogeneity, quantified, and applied in direct ELISA binding analyses on human PD1-Fc and cyno PD1-Fc (FIGS. 2A&B, Table 5). Unexpectedly, the titration of the Fab proteins on cyno PD1 protein demonstrated significantly improved binding EC50 values for several library-derived clones over that of the Mab005 (humanized) Fab (Table 5). This led to EC50 values for all library derived clones that were approximately equivalent to those observed for human PD1 binding, while the cyno binding of the Mab005 (humanized) Fab was significantly lower than for human. Indeed, binding of the Mab005 (humanized) Fab was sufficiently weak on cyno PD1 that it did not achieve binding signal saturation, even at the highest concentration applied (500 nM), meaning that a cyno PD1 EC50 value could not be calculated for this protein (Table 5). As these values were generated with proven monomeric Fab proteins, they reflected 1:1 binding improvements for cyno protein in several clones.

Figure 3A:
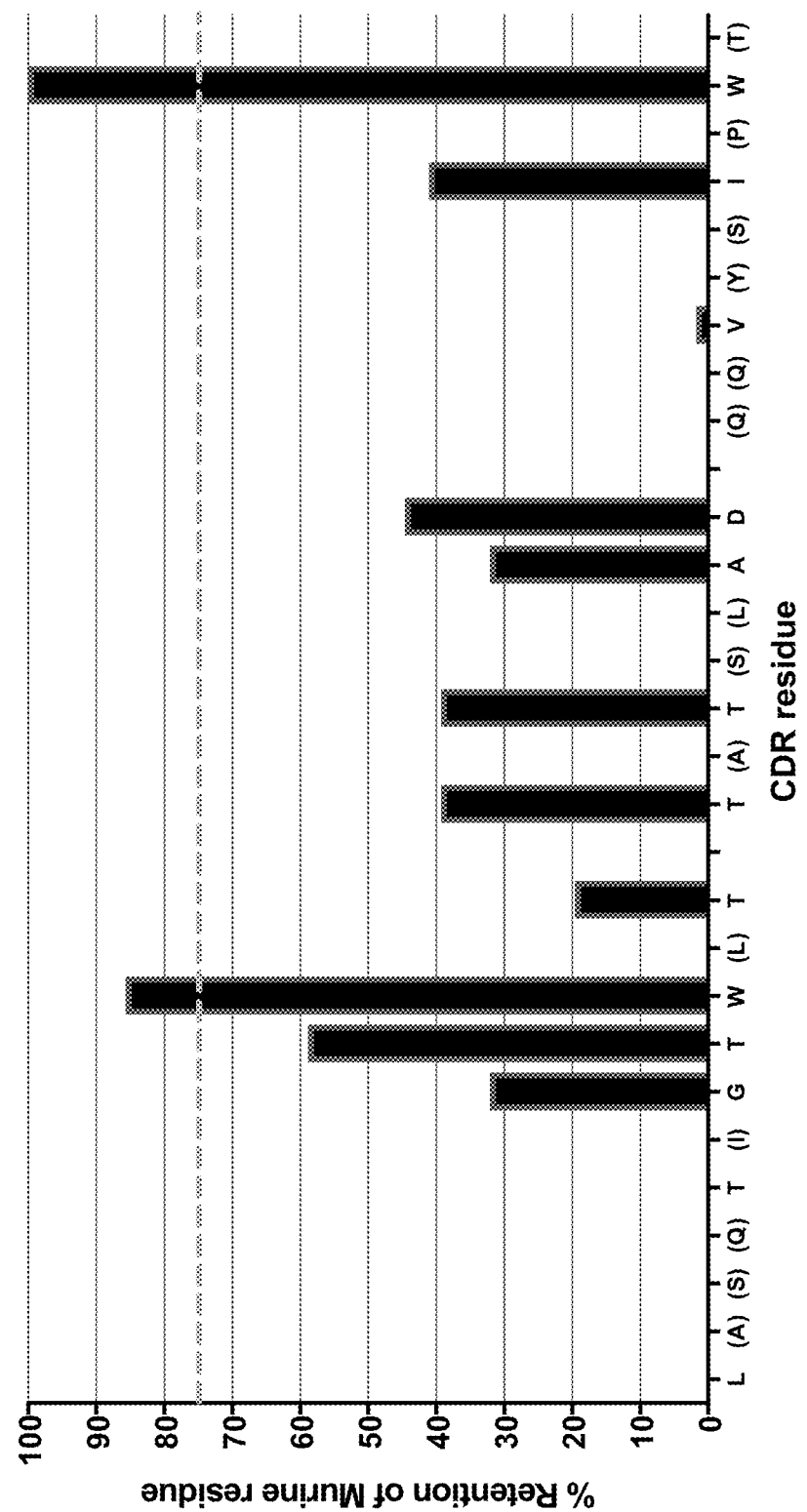
FIG. 3A-FIG. 3B. Analysis of CDR residue tolerance for mutation to germline. A plot of murine amino acid retention frequencies in the CDRs of the ELISA-positive population of 64 unique scFv clones is shown for $V_L$ (FIG. 3A; SEQ ID NOs: 110, 114 and 116) and $V_H$ (FIG. 3B; SEQ ID NOs: 95, 92 and 106) domains, respectively. Only those residues targeted for human/murine residue mutagenesis are plotted, other than in the HCDR3. CDR residues noted in parentheses on the X-axes were identical to those found in the human germlines used for grafting (IGKV1-39 and IGHV3-7). In both plots the dashed line in grey at 75% represents the cut-off for tolerance of murine residue replacement by human germline.
Figure 3B:
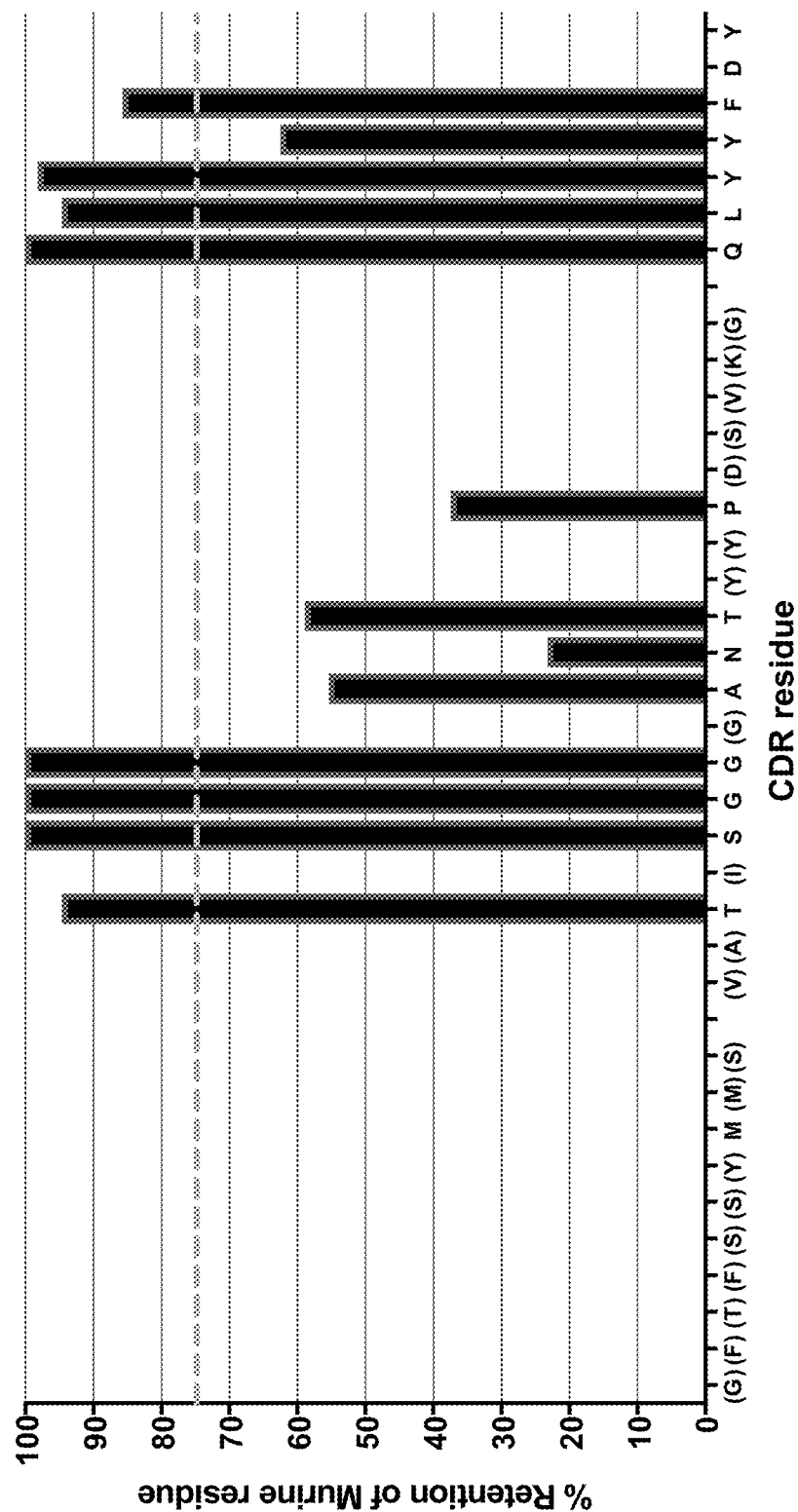

While germ-lining mutations were observed in all CDRs for the lead clones derived directly from library selections, it remained possible that sequence analyses might allow further clones to be designed to have maximal humanization. The 64 sequence-unique hits with binding signals against human and cyno protein were therefore used to analyse the retention frequency for murine amino acids in the CDRs of this functionally characterized population. Positional amino acid retention frequency was expressed as a percentage found in the $V_L$ and $V_H$ domains (FIGS. 3A&B, respectively). Murine residues with RF<75% were regarded as positions that are possibly not essential to the target-binding paratope and are likely to be open to germ-lining, in a series of combinatorial designs (Table 4). In the $V_H$ domain (excluding the CDR-H3), only 4 of 9 murine residues in the CDR-H1 and H2 exhibited retention frequency above 75% and the sole murine residue (M) found in the CDR-H1 was not found in any functional clones, giving it a frequency value of 0% (FIG. 3B). In the $V_L$ domain, only 2 of 13 murine CDR residues derived from the Mab005 sequence were retained with frequencies >75% (FIG. 3A). This analysis strongly suggested that the entire CDR-L2 sequence could be rendered germline identity to IGKV1-39. Importantly, the Tryptophan (W) residue found in the CDR-L3 of Mab005 and retained at almost 100% (FIG. 3A) is in a position donated by the J segment during light chain splicing, and was only regarded as non-human due to the use of the human JK4 sequence in the starting library. This observation allowed a redesign of the light chain in a series of designer clones to include the human JK1 sequence instead of JK4, as human JK1 naturally contains a W residue at that position, rendering the resulting light chain sequence fully germline in CDR-L2 and L3 (Table 4).

Designs containing only those murine residues with RF>75% were given the prefix "MH" (MH=Maximally Humanized). Another designer v-domain set ('TTP'=Total Theoretically Possible) was also created that combined the most humanized CDRs observed in the population, for both $V_L$ and $V_H$ domains. In total 5 designer $V_H$ and 3 designer $V_L$ domains were generated: VH domains MH-AA-VH, MH-LV-VH, MH-LG-VH, MH-LF-VH, MH-LA-VH sampled variant sequences in the CDR-H1 and H3, while MH-VL, MH-JK1-VL, TTP-JK1-VL sampled variants in the CDR-L1 and also the JK4>JK1 swap. Indeed, the W>Y and JK4>JK1 mutations in TTP-JK1-VL rendered this sequence fully human germline across the entire v-domain. These constructs were co-transfected in a matrixed fashion to create 15 final designer IgGs in total (Table 4). The MH and TTP clones were generated by gene synthesis and (along with the 12 library-derived clones outlined above and positive control IgG1-Mab005 (humanized)), cloned into human expression vectors for production in IgG1null format. All IgGs were readily expressed and purified from transient transfections of mammalian cells.

Lead IgG Specificity and Potency Characteristics

Figure 4A:
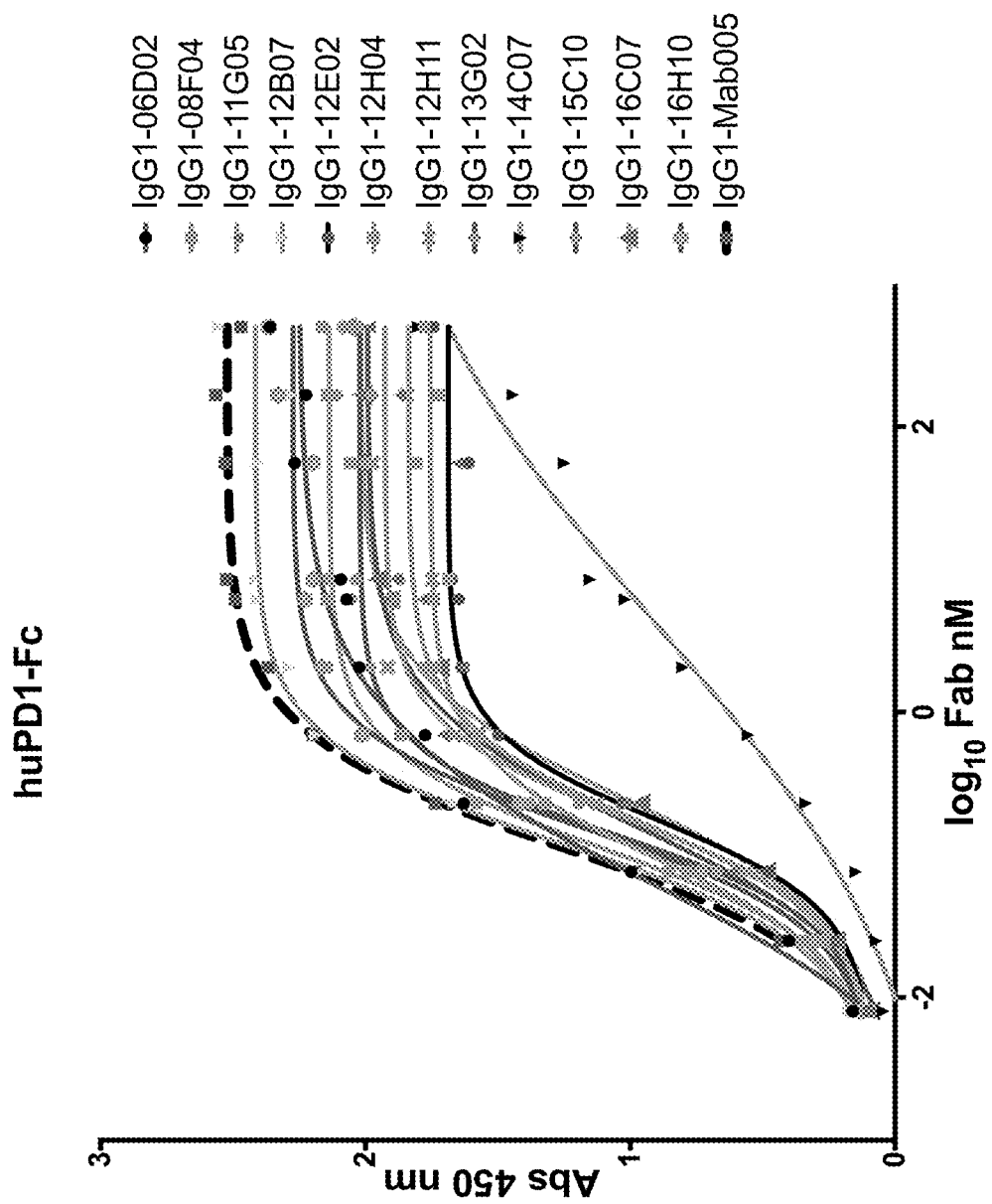
FIG. 4A-FIG. 4B. Direct titration ELISA for library-derived IgG1null clones binding to human and cyno PD1-Fc proteins. Mab005 and library-derived clones in human IgG1null format were titrated (in nM) in a direct binding ELISA against human (FIG. 4A) and cyno (FIG. 4B) PD1-Fc proteins.
Figure 4B:
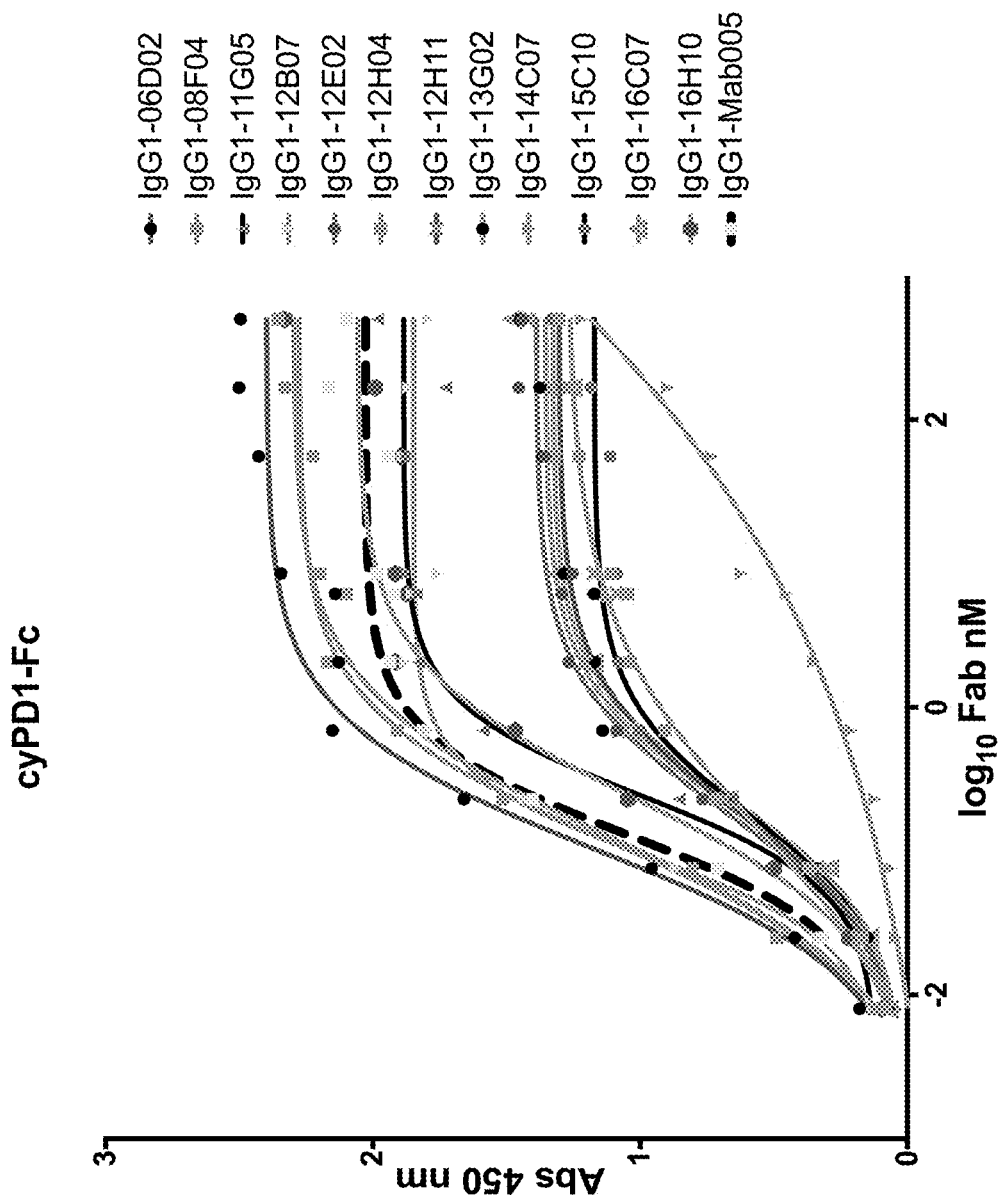
Figure 5A:
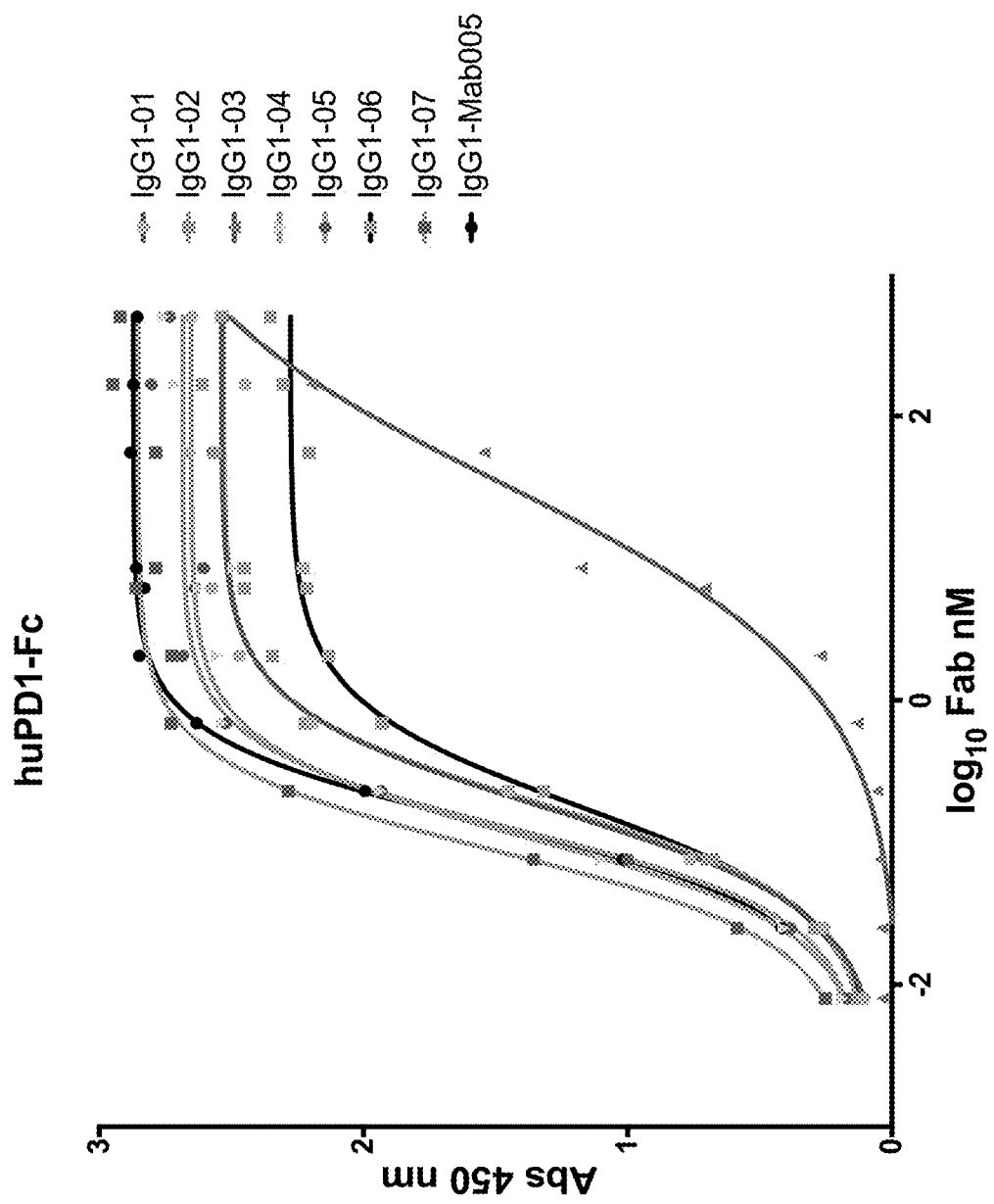
FIG. 5A-FIG. 5D. Direct titration ELISA for designer IgG1null clones IgG1-01 to IgG1-15 binding to human and cyno PD1-Fc proteins. Mab005 and designer clones in human IgG1null format were titrated (in nM) in a direct binding ELISA against human (FIG. 5A, FIG. 5B) and cyno (FIG. 5C, FIG. 5D) PD1-Fc proteins.
Figure 5B:
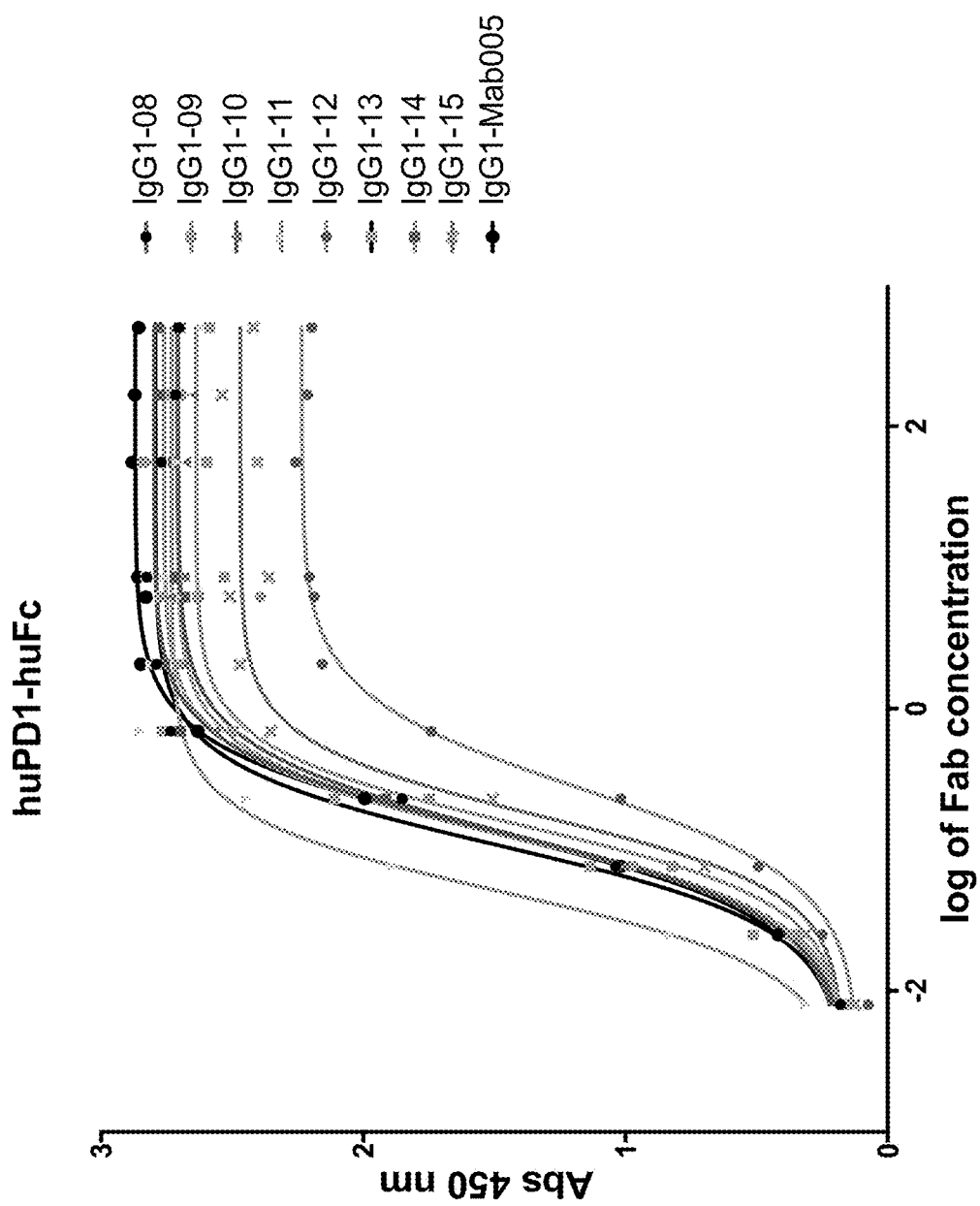
Figure 5C:
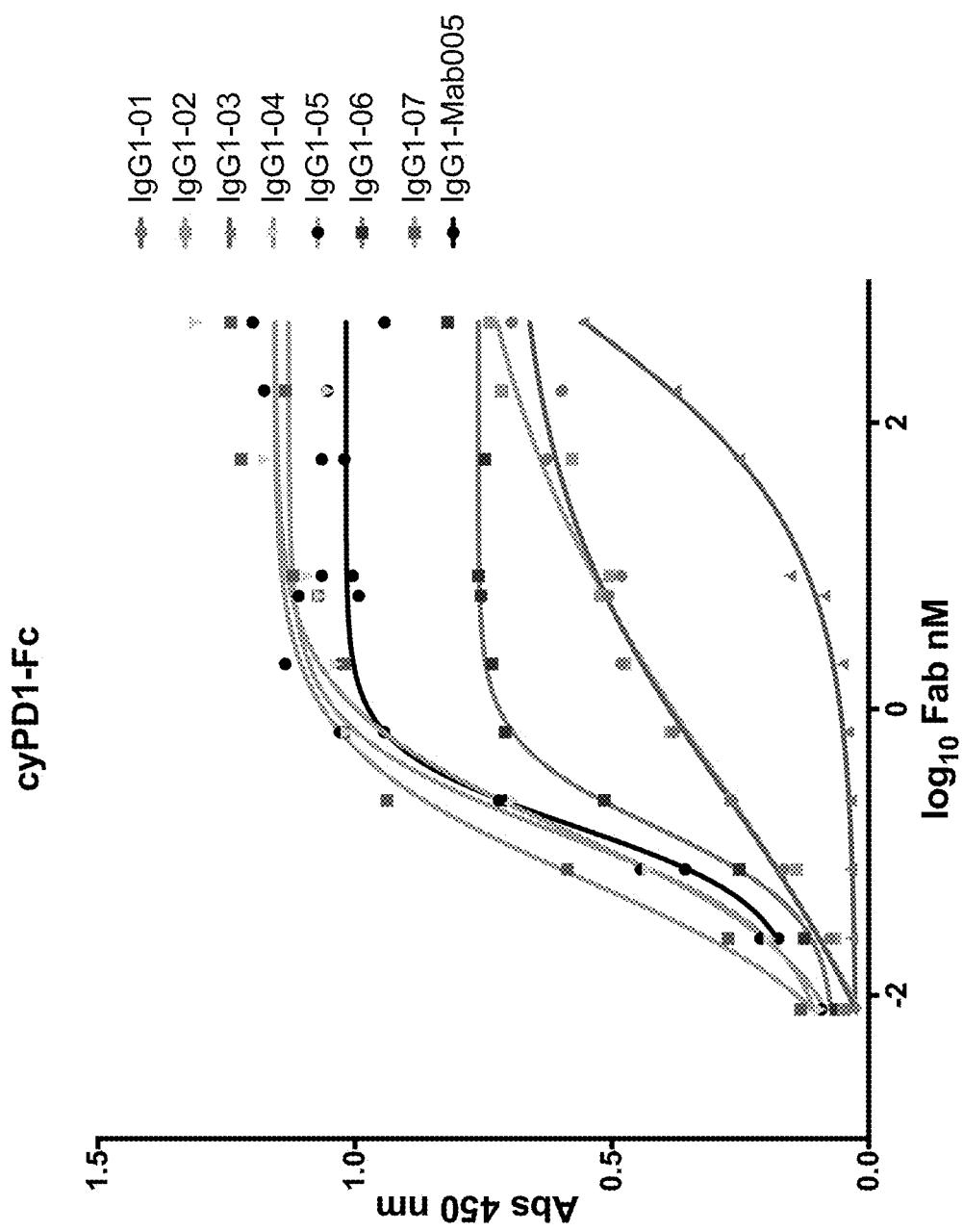
Figure 5D:
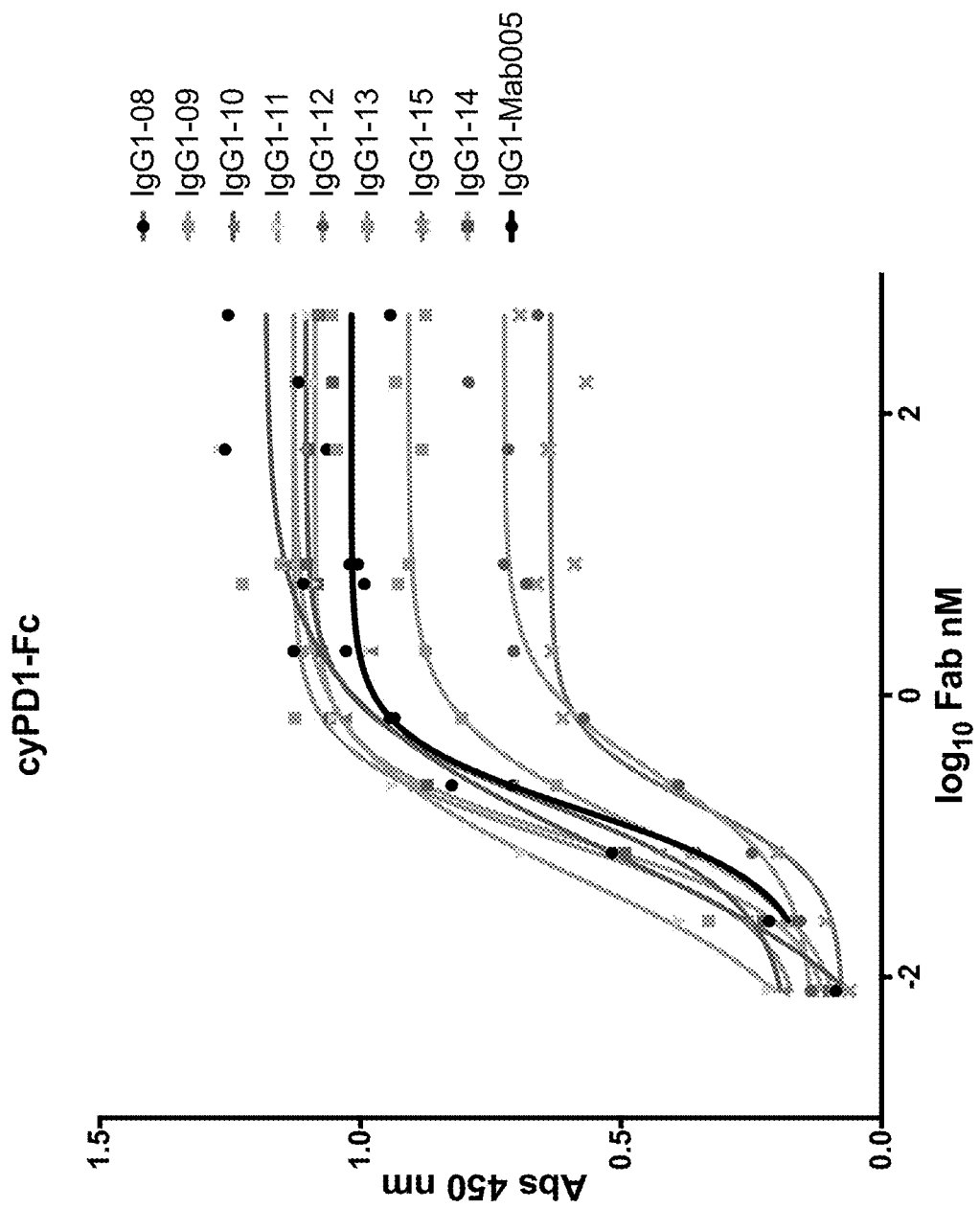

The purified IgGs described above were then tested for binding to human and cyno PD1-Fc in direct titration ELISA format. This analysis demonstrated that several library-derived clones had human and cyno PD1 binding profiles and EC50 values similar to (within 2-fold), or improved over, IgG1-Mab005 (humanized) (FIGS. 4A&B, Table 6). One notable exception was clone IgG1-14C07 which exhibited poor binding to both orthologs of PD1, making it impossible to determine an EC50 value for this clone. Similarly, the majority of designer IgGs had EC50 values similar to (within 3-fold), or improved over, IgG1-Mab005 (humanized) (FIG. 5A-D, Table 7). Clones IgG1-01, IgG1-02 and IgG1-03 exhibited poor binding to one or both orthologs of PD1, however, demonstrating that the CDR-H1 and H3 mutations found in these clones are disruptive to binding when used in combination. As the ELISA EC50 values for directly binding IgGs are strongly influenced by avidity, rather than true 1:1 binding affinity, we then proceeded to perform higher-sensitivity, solution-phase epitope competition and Biacore binding affinity determinations, as outlined below.

Figure 6A:
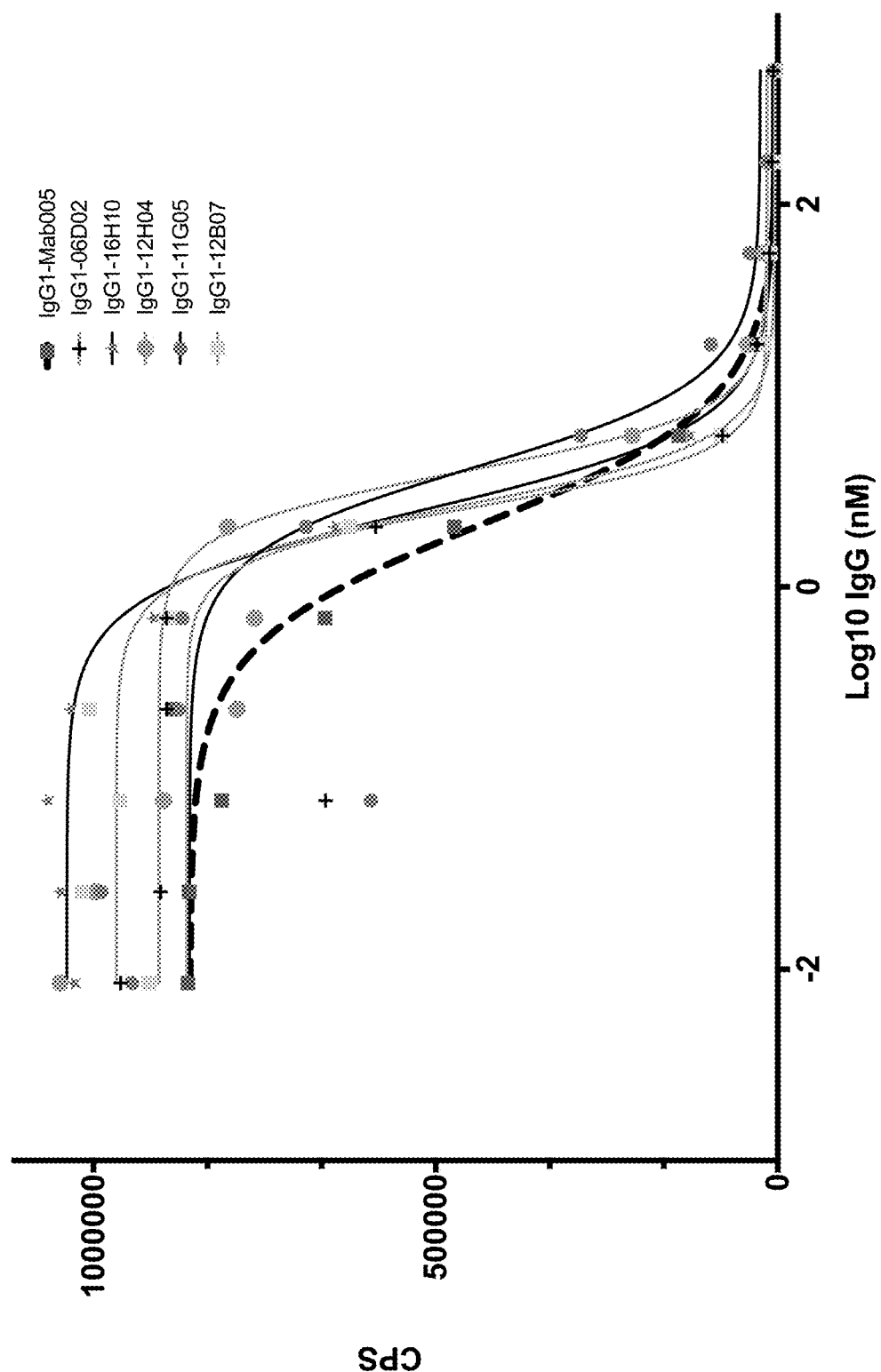
FIG. 6A-FIG. 6B. Epitope competition analysis of IgG1null proteins in Alphascreen Anti-PD1 IgG1null clones were applied in an epitope competition assay using Alphascreen technology. In this assay, library-derived (FIG. 6A) and designer (FIG. 6B) IgGs were analysed for their relative affinities and retention of the parental Mab005 epitope by competing for Mab005 IgG1null binding to human PD1 protein, in solution. All clones analysed showed strong, concentration-dependent neutralisation of Mab-005 binding to PD1.
Figure 6B:
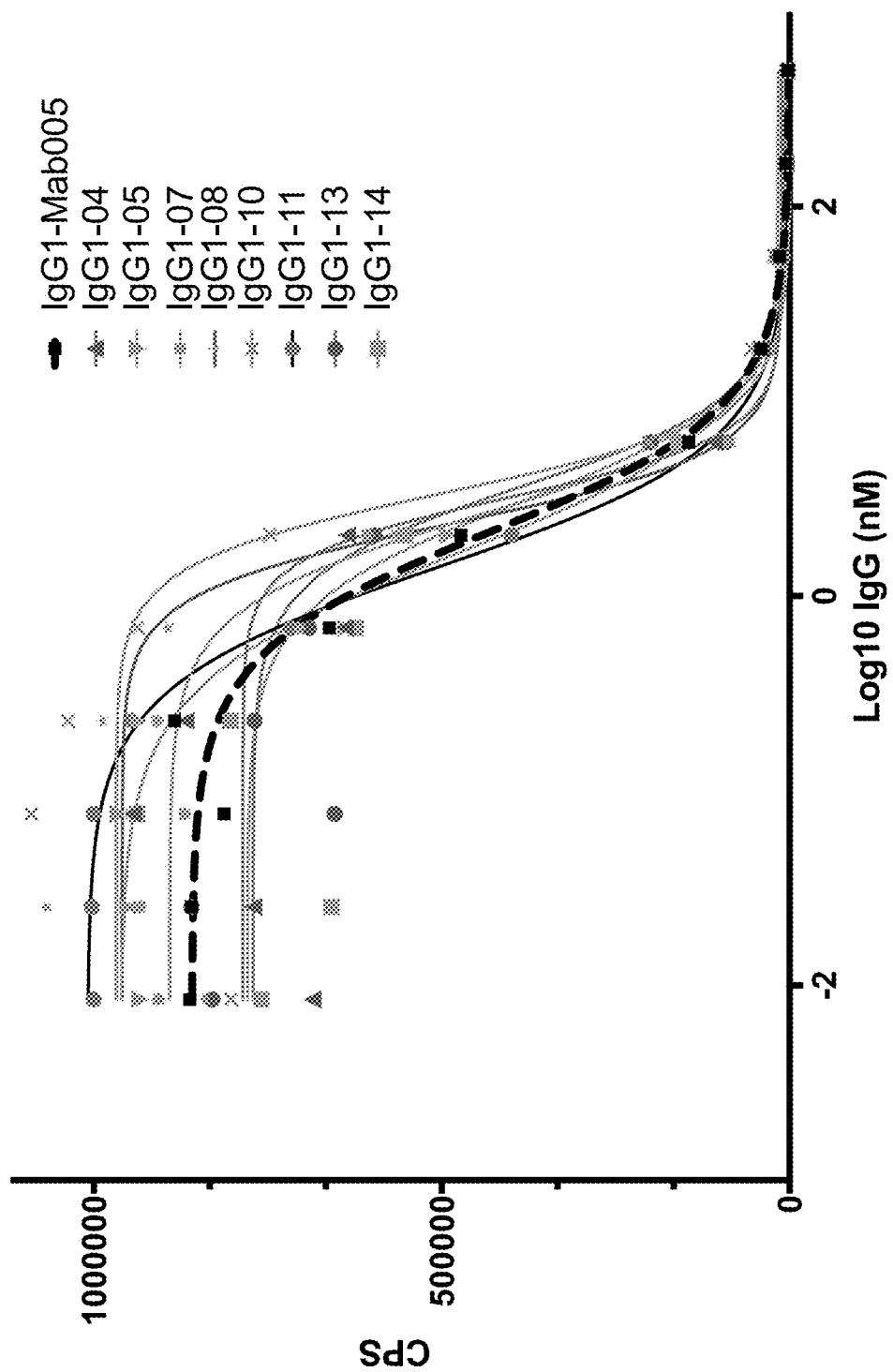

An Alphascreen assay was established to allow the testing of IgGs for epitope competition with IgG1-Mab005 (humanized) binding to biotinylated monomeric human PD1. In this assay, the top-performing library-derived and designer IgGs were more effectively differentiated via IC50 values (Table 8). While many clones exhibited equivalent or improved competition for the Mab005 epitope over IgG1-Mab005 (humanized) (FIGS. 6A&6B), several exhibited impaired epitope competition (>2-fold lower than Mab005) including: IgG1-15C10, IgG1-13G02, IgG1-08F04, IgG1-16C07, IgG1-12H11, IgG1-12E02, IgG1-14C07, IgG1-01, IgG1-02, IgG1-03, IgG1-06, IgG1-09, IgG1-12 and IgG1-15 (Table 8). Notably, the lowest-performing designer IgGs in this assay included those previously shown to have poor cyno ortholog cross-reactivity in the ELISA assay and also all clones that contained the CDR-L1 germlining mutation W>Y.

Biacore analyses of binding affinity was performed for all IgGs to solution-phase, monomeric human and cyno PD1 proteins. In all cases, accurate 1:1 binding affinities with low $Chi^2$ values were obtained (Table 9). These analyses showed that library-derived clones which consistently gave the highest EC50 and IC50 values in Fab and IgG ELISA and Alphascreen assays also showed highest affinity binding to human and cyno PD1. Importantly, library-derived clones IgG1-06D02, IgG1-12B07, IgG1-12H04 and IgG1-16H10 and designer clones IgG1-04, IgG1-05, IgG1-08, IgG1-10, IgG1-11, IgG1-13 and IgG1-14 all exhibited improved binding affinities for both human and cyno PD1 in comparison to IgG1-Mab005 (humanized). Importantly, these improvements in affinity unexpectedly normalised the human/cyno affinities for these clones to within 3-fold (all KD values <4.9 nM), as opposed to IgG1-Mab005 (humanized), which exhibited an 8-fold differential (human KD—4.0 nM, cyno KD—32.0 nM). Affinity differentials of less than 3-fold between human and cyno target orthologs are highly beneficial in pre-clinical drug development analyses as they allow significantly better design and interpretation of e.g. monkey safety, PK and PD modelling experiments. This relative normalisation of the binding to both PD1 orthologs rendered these lead clones highly similar in binding to the IgG1-Pembrolizumab analog, which exhibited an affinity differential of 2.7. In addition, comparison of the affinities of clones IgG1-14 and IgG1-15 confirmed the influence of the single 'murine' W residue in the CDR-L1 of IgG1-14 (Table 4), as mutation of this single residue to Y in IgG1-15 resulted in approximately 10-fold loss of KD against both human and cyno PD1 (Table 9). This finding highlighted the difficulty in deciding 'a priori' which CDR residues may or may not be converted to human germline identity, as the W>Y mutation would normally be assumed to be a relatively conservative substitution.

Flow Cytometric Analyses of Lead IgG Binding Specificity at the Cell Membrane

Figure 7A:
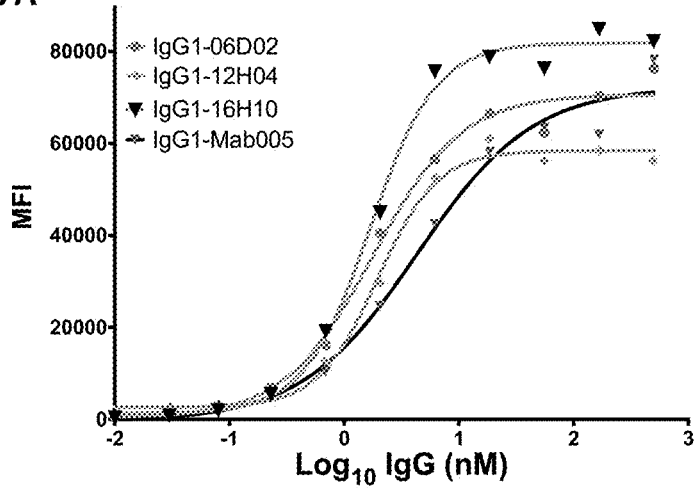
FIG. 7A-FIG. 7C. Flow cytometric binding to human PD1+ CHO cells. IgG1-Mab005 (humanized), lead library-derived (FIG. 7A) and designer (FIG. 7B) IgGs were examined for specific binding on CHO-K1 cells expressing human PD1. Concentration-dependent binding was observed against human PD1 for almost all clones, with weaker binding being observed for IgG1-Mab005 (humanized). Clone IgG1-15 was a single exception, showing weaker binding than IgG1-Mab005 (humanized) (FIG. 7C).
Figure 7B:
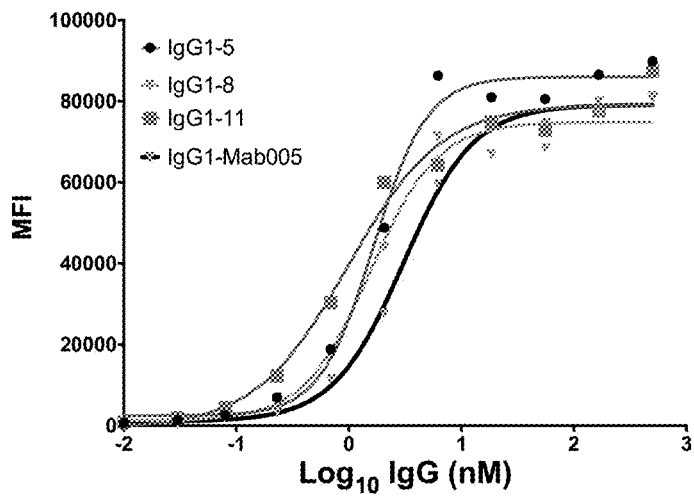
Figure 7C:
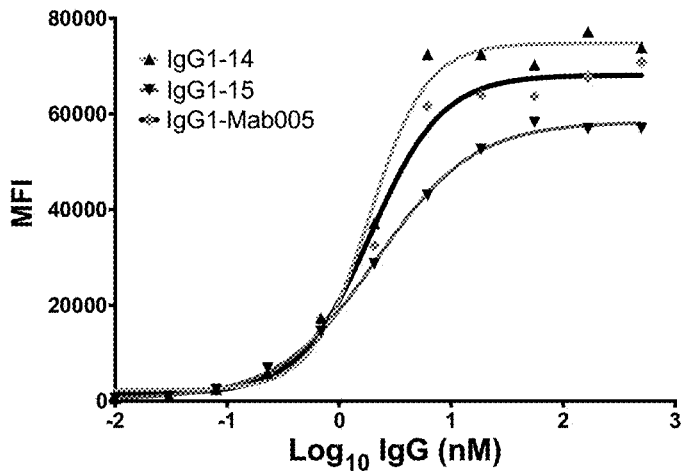
Figure 8A:
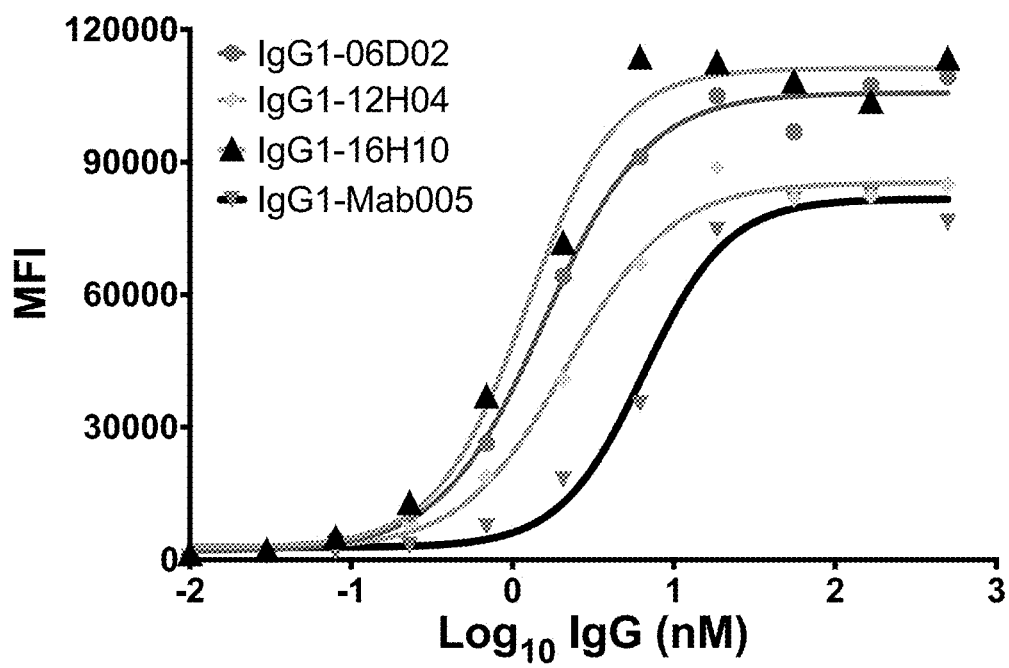
FIG. 8A-FIG. 8B. Flow cytometric testing of binding to cyno PD1+ CHO cells. IgG1-Mab005 (humanized), lead library-derived (FIG. 8A) and designer (FIG. 8B) IgGs were examined for specific binding on CHO-K1 cells expressing cyno PD1. Concentration-dependent binding was observed against cyno PD1 for all clones, with significantly stronger binding than that observed for IgG1-Mab005 (humanized).
Figure 8B:
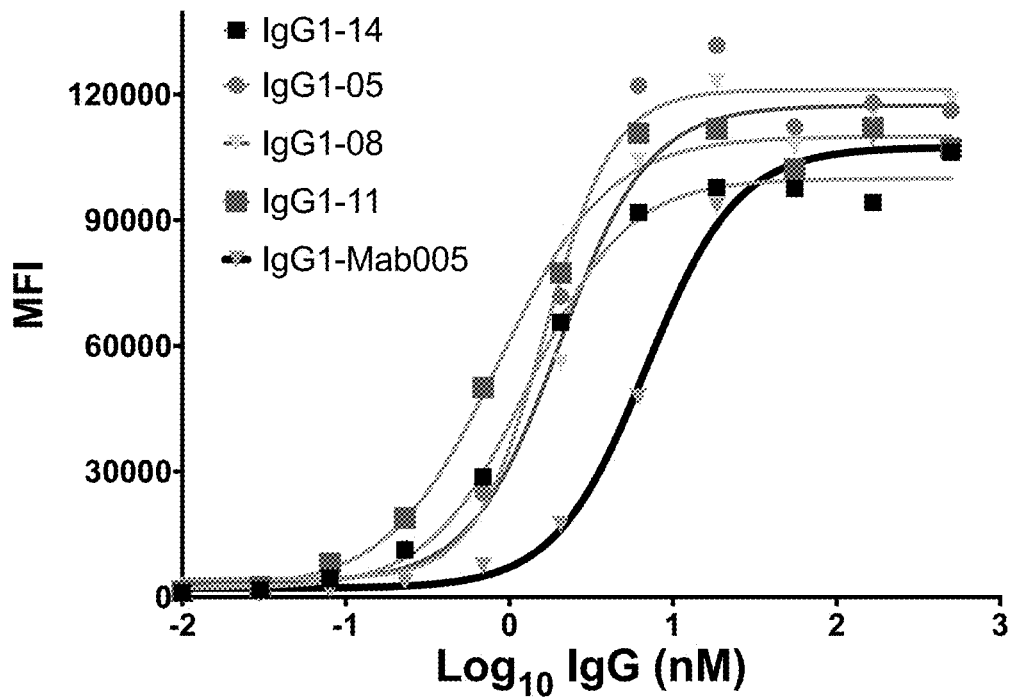

Antibodies to PD1 were analysed for concentration-dependent binding at the cell surface via flow cytometry. Initial analyses were performed on CHO cells stably-transfected with human or cyno PD1. These analyses showed that lead library-derived (FIG. 7A) and designer clones (FIG. 7B, 7C) exhibit concentration-dependent binding to membrane-presented human PD1 with potencies equivalent to, or improved over, the IgG1-Mab005 (humanized) (Table 10). Importantly, the influence of the CDR-L1 'W' residue was again observed as IgG1-14 exhibited stronger binding than IgG1-15 for human PD1 (FIG. 7C). Analyses performed on cyno PD1 CHO cells further confirmed that several library-derived (FIG. 8A) and designer leads (FIG. 8B) exhibited significantly improved binding for cyno PD1 in comparison to IgG1-Mab005 (humanized) (Table 10). No binding signals were observed for any clone, even at the highest concentrations, on untransfected CHO cells.

Lead IgG Analyses in PD1-PDL1 Blockade Assay

Figure 9:
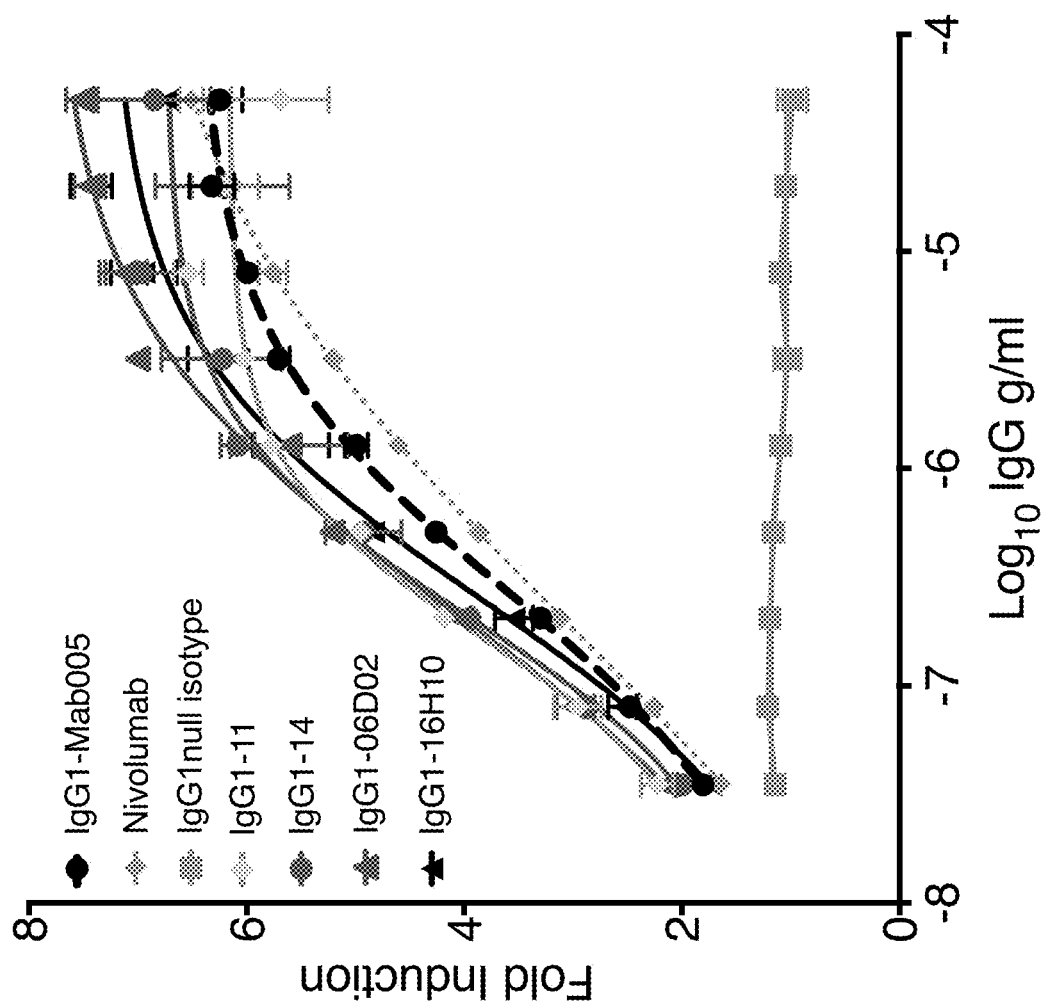
FIG. 9. Cell-based PD1/PD-L1 antagonism assay. Analyses of antagonism of human PD1 function at the cell surface, for lead clones IgG1-11, IgG1-14, IgG1-06D02 and IgG1-16H10 in human IgG1null format, showed that all novel clones exhibited concentration-dependent antagonistic activity, with higher relative potency in comparison to both IgG1-Mab005 (humanized) and IgG4 Nivolumab analog.

In a cell-based PD1/PD-L1 blockade reporter assay, all clones tested exhibited concentration-dependent antagonism of PD1. Importantly, multiple clones (including IgG1-06D02, IgG1-12H04, IgG1-16H10, IgG1-05, IgG1-08, IgG1-11 and IgG1-14) exhibited improved potency in PD1 blockade in comparison to IgG1-Mab005 (humanized) (Table 11). In addition, clones IgG1-06D02 and IgG1-16H10 exhibited increased maximal signal in the assay, over IgG1-Mab005 (humanized) and an IgG4 Nivolumab analogue (FIG. 9).

Antibody v-Domain T Cell Epitope Analyses

In silico technologies (Abzena, Ltd.), which are based on identifying the location of T cell epitopes in therapeutic antibodies and proteins, were used for assessing the immunogenicity of both the Mab005 and lead antibody v-domains. Analysis of the v-domain sequences was performed with overlapping 9mer peptides (with each overlapping the last peptide by 8 residues) which were tested against each of the 34 MHC class II allotypes. Each 9merwas scored based on the potential 'fit' and interactions with the MHC class II molecules. The peptide scores calculated by the software lie between 0 and 1. Peptides that produced a high mean binding score (>0.55 in the iTope™ scoring function) were highlighted and, if >50% of the MHC class II binding peptides (i.e. 17 out of 34 alleles) had a high binding affinity (score >0.6), such peptides were defined as 'high affinity' MHC class II binding peptides which are considered a high risk for containing CD4+ T cell epitopes. Low affinity MHC class II binding peptides bind a high number of alleles (>50%) with a binding score >0.55 (but without a majority >0.6). Further analysis of the sequences was performed using the TCED™. The sequences were used to interrogate the TCED™ by BLAST search in order to identify any high sequence homology between peptides (T cell epitopes) from unrelated proteins/antibodies that stimulated T cell responses in previous in vitro T cell epitope mapping studies performed at Abzena Ltd.

Peptides were grouped into four classes: High Affinity Foreign ('HAF'—high immunogenicity risk), Low Affinity Foreign ('LAF'—lower immunogenicity risk), TCED+ (previously identified epitope in TCED database), and Germline Epitope ('GE'—human germline peptide sequence with high MHC Class II binding affinity). Germline Epitope 9mer peptides are unlikely to have immunogenic potential due to T cell tolerance, as validated by previous studies with a wide range of germline peptides. Importantly, such germline v-domain epitopes (aided further by similar sequences in the human antibody constant regions) also compete for MHC Class II occupancy at the membrane of antigen presenting cells, reducing the risk of foreign peptide presentation being sufficient to achieve the 'activation threshold' required for T cell stimulation. High GE content is therefore a beneficial quality in clinical development of an antibody therapeutic.

As shown in Table 12, key lead v-domains exhibited significant beneficial changes in peptide epitope content in comparison to IgG1-Mab005 (humanized) (Table 12). As the v-domain framework regions (i.e. outside the CDR sequences) of IgG1-Mab005 (humanized) and all leads were germline in sequence (Table 2), all improvements in predicted immunogenicity came about as a result of the germlining of CDR residues (Tables 4, 12). Indeed, in several clones, the VL domains were found to be fully deimmunized. GE epitope content was also found to be significantly increased in the VL regions of lead clones (from 1 to ≥3 in all leads), and TCED+ epitopes were eliminated from the VL domains in all leads (Table 12). Importantly, multiple HAF and LAF epitopes were eliminated by germlining mutations found in the VL CDRs of lead clones. For example, a TCED+ and HAF peptide 'VTITCLASQ' (SEQ ID NO: 83) found in the LCDR-1 of IgG1-Mab005 (humanized) was eliminated in all lead clones by the mutation L>R at position 6, converting this sequence to the light chain GE 'VTITCRASQ' (SEQ ID NO: 84). Similarly, an LAF peptide 'IGTWLTWYQ' (SEQ ID NO: 85) found in the LCDR-1 of IgG1-Mab005 (humanized) was eliminated in all lead clones by retaining only a single murine residue W at position 4, converting this sequence to 'ISSWLNWYQ' (SEQ ID NO: 86) (Table 12). In clones 06D02, IgG1-05, IgG1-08, IgG1-11 and IgG1-14, the IgG1-Mab005 (humanized) HAF peptides 'LLIYTATSL' (SEQ ID NO: 87) and 'LIYTATSLA' (SEQ ID NO: 88), and LAF peptide 'IYTATSLAD' (SEQ ID NO: 89) were eliminated and converted to GE sequences by mutation of the LCDR-2 from the murine sequence 'TATSLAD' (SEQ ID NO: 36), to the fully germline sequence 'AASSLQS' (SEQ ID NO: 42). The IgG1-Mab005 (humanized) FW3/LCDR3 region also encoded for a LAF peptide 'YYCQQVYSI' (SEQ ID NO: 90). This epitope was eliminated in all leads by the germlining mutation V>S at position 6. In the VH region of IgG1-Mab005 (humanized), the peptide sequence 'LYYFDYWGQ' (SEQ ID NO:91) (spanning the HCDR3 and FW4) was found to be a LAF. The mutation Y>A at position 3 in this peptide allowed the elimination of this epitope in clones IgG1-14 (Tables 4, 12).

Antibody Binding Specificity Analyses

In early clinical trials, a humanized form of Mab005 has been reported to induce unusual toxicities in human patients, such as hemangiomas, which have not been seen with other anti-PD1 or anti-PD-L1 therapeutics. These reports suggested that humanized Mab005 might have unique, 'off-target' binding characteristics that are not found in other anti-PD1 antibodies. Hemangioma is a benign tumor formed by a collection of excess blood vessels, often developing in the skin, but they can also develop in the liver and other organs. We hypothesised that Mab005 might bind to unidentified and unpredictable receptors associated with vascular development or tissue differentiation. To examine this possibility, in vitro technologies (Retrogenix, Ltd.), which are based on using high-density arrays of cells expressing 4975 unique human membrane receptors, were used to screen for off-target binding specificities in IgG1-Mab005 (humanized). This receptor array binding screen identified that IgG1-Mab005 (humanized) exhibited strong binding to membrane-expressed PD1, but also had 4 potential off-target binding specificities: FZD5 (frizzled class receptor 5), ULBP2 (UL16 binding protein 2), EphB6 and KDR (also known as VEGFR2). Hemangiomas are known to develop spontaneously in patients with mutations in vascular biology-associated receptors such as VEGFR2 and are a reported side effect in the use of vascular-targeting antibodies for cancer therapy, such as ramucirumab (Anti-VEGFR2). In addition, FZD5 is a Wnt pathway signalling receptor associated with vascular development, so modulating the function of either of these receptors is likely to modulate vascular biology. In addition, ULBP2 is a known ligand for the natural killer cell activating receptor NKG2D, so binding to this protein during cancer therapy with an anti-PD1 is of unknown consequence.

Figure 10C:
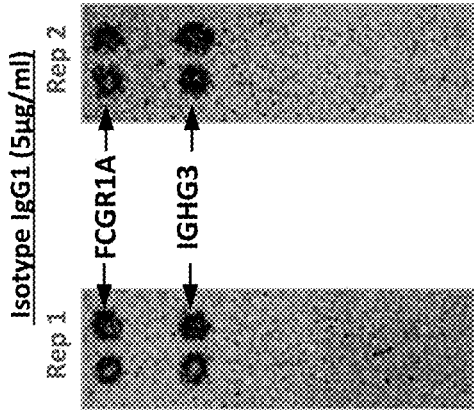
FIG. 10A-FIG. 10E. Off-target binding analysis chip array assay. After performing an array-based binding screen on 4975 human receptors for IgG1-Mab005 (humanized), confirmatory analyses of binding specificity were performed on chips in which plasmids encoding PD1 and putative Mab005 off-target binding proteins were arrayed and used to transfect HEK293 cells. Effective transfection of all plasmids was confirmed by screening for the co-encoded marker ZS green (FIG. 10A). Separate chips were then probed in duplicate using IgG1-Mab005 (humanized) (FIG. 10B), Isotype IgG1 (FIG. 10C), Rituximab (FIG. 10D), and no primary antibody (FIG. 10E). These analyses confirmed that only IgG1-Mab005 (humanized) exhibited binding to PD1, but IgG1-Mab005 (humanized) also exhibited unexpected off-target binding to KDR, FZD5 and ULBP2 proteins.
Figure 10E:
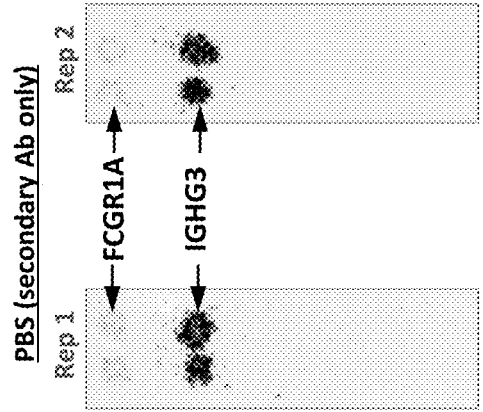
Figure 10B:
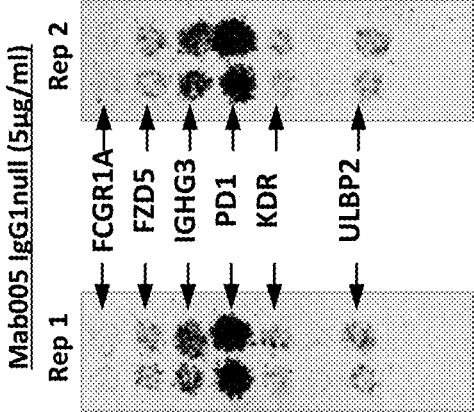
Figure 10D:
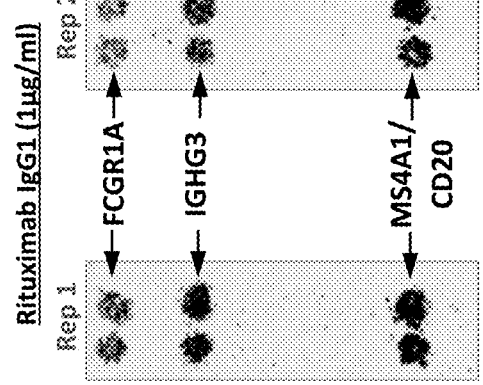
Figure 10A:
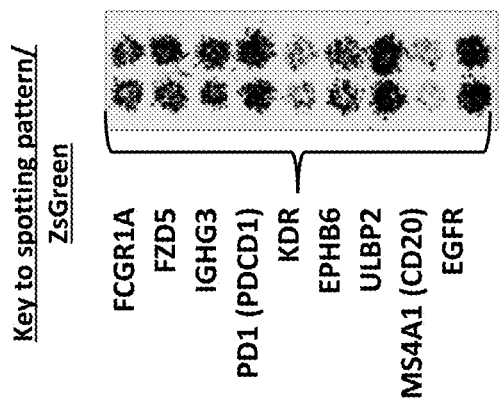

To confirm these off-target binding events, the plasmids encoding for these receptors and controls were submitted for DNA sequencing. These analyses confirmed that the encoded proteins were indeed the correct sequences. The plasmid samples for control and potential target receptors were then re-arrayed onto new chips for repeat analyses in duplicate. The effective induction of expression from all re-arrayed plasmids was confirmed via scanning the chips for ZS green, which is co-encoded on all expression plasmids as an internal control marker. This analysis showed clearly detectable ZS expression in all positions where plasmids were spotted (FIG. 10A). Further, identically-spotted slides were then used to re-probe transfected cells with IgG1-Mab005 (humanized) (FIG. 10B), isotype IgG1 (negative control, FIG. 10C), Rituximab (IgG1 positive control, FIG. 10D), and a chip where no primary antibody probe was applied (FIG. 10E). These analyses showed that IgG1-Mab005 (humanized) again demonstrated measurable binding over background (on both chips) on cells transfected with PD1, FZD5, ULBP2 and KDR, but no binding to FcγR1a (due to IgG1null isotype) or any other spots, including EphB6 (FIG. 10B). Rituximab demonstrated binding to CD20 and FcγR1a (due to IgG1 isotype) as expected, with no observable binding to PD1, FZD5, ULBP2, EphB6 and KDR (FIG. 10D). In the chips probed with isotype control antibody (FIG. 10C) and no primary antibody (FIG. 10E), only the expected control proteins showed any signal. This clean performance of the control chips confirmed that IgG1-Mab005 (humanized) binding signals on PD1, FZD5, ULBP2 and KDR were specific.

Figures 11G, 11H, 11I:
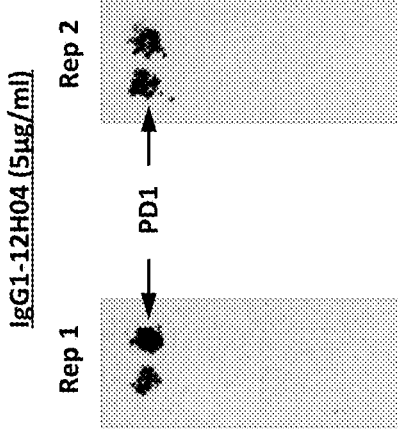
FIG. 11A-FIG. 11T. Off-target binding analysis re-array assay. Analyses of binding specificity were performed on chips in which plasmids encoding relevant targets were arrayed and used to transfect HEK293 cells. Transfection of all plasmids was confirmed by screening for the co-encoded marker ZS green (FIG. 11A). Separate chips were then probed in duplicate using Pembrolizumab analog (FIG. 11B), Rituximab (FIG. 11C), Isotype IgG1 (FIG. 11D), mVH/mVL Mab005-IgG1 (FIG. 11E), IgG1-Mab005 (humanized) (FIG. 11F) and library-derived and designer lead IgGs (FIG. 11G-FIG. 11T). These analyses confirmed that mVH/mVL Mab005 IgG1 (original murine hybridoma v-domains) and IgG1-Mab005 (humanized) (humanized v-domains) both exhibited binding to PD1, but also exhibited unexpected off-target binding to KDR, FZD5 and ULBP2 proteins. In contrast, none of the lead antibodies (FIG. 11G-FIG. 11T) exhibited measurable signal (i.e., binding) on any protein other than PD1.
Figures 11J, 11K, 11L:
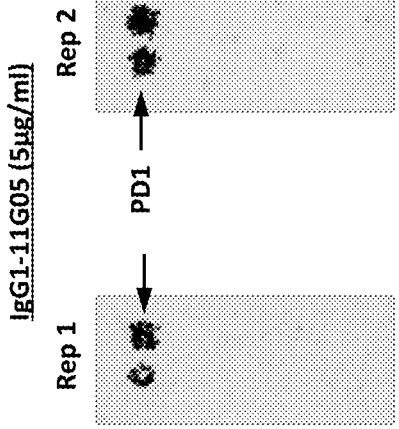
Figure 11S:
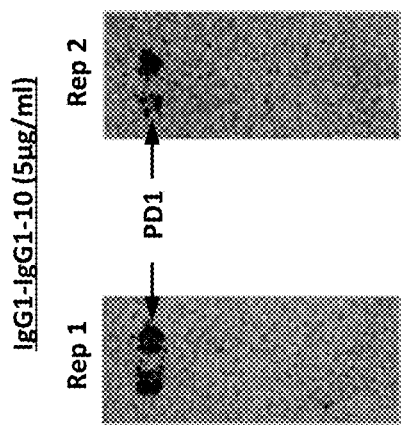
Figure 11T:
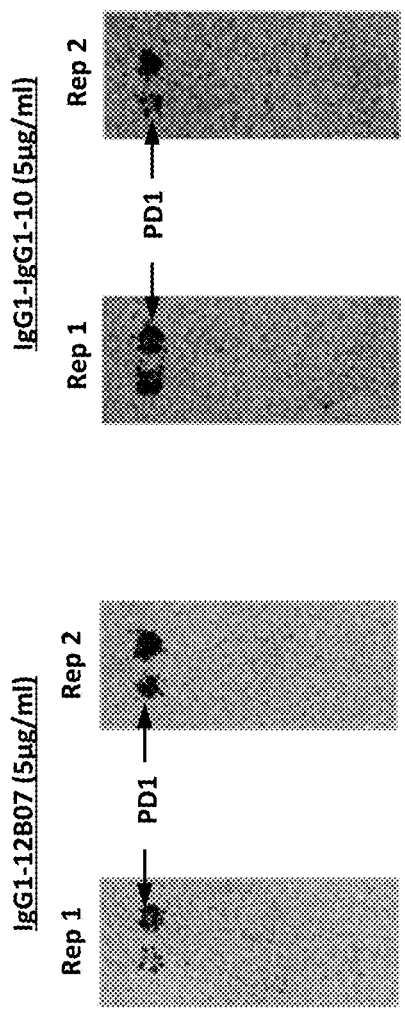

To investigate the origin of this off-target binding activity and whether or not it was retained in library-derived and designer IgGs generated in this study, further chip binding analyses were performed (FIG. 11A-T). As above, the re-arrayed plasmids were again checked for transfection quality and the induction of ZS green expression was confirmed (FIG. 11A). Additional control antibodies; Pembrolizumab analog (FIG. 11B) and Rituximab (FIG. 11C) both bound only their respective cognate targets and the isotype control IgG1 showed no binding (FIG. 11D). Primary analyses using mVH/mVL Mab005-IgG1 and IgG1-Mab005 (humanized) (FIGS. 11E and F, respectively), showed that the off-target binding signals previously only observed with IgG1-Mab005 (humanized) (FIG. 10B) were also present in chips probed with the mVH/mVL Mab005-IgG1. This finding confirmed that the off-target binding reactivity of IgG1-Mab005 (humanized) derived directly from the original murine hybridoma and was not a result of polyreactivity being induced during the humanization process. The off-target binding activity of IgG1-Mab005 (humanized) was therefore housed directly in the CDRs, as it was retained when the murine CDRs were grafted onto human germline frameworks.

Lead library-derived and designer antibodies were then also used to probe this same chip set. Surprisingly, none of the antibodies IgG1-06D02 (FIG. 11G), IgG1-11G05 (FIG. 11H), IgG1-12H04 (FIG. 11I), IgG1-16H10 (FIG. 1J), IgG1-04 (FIG. 11K), IgG1-05 (FIG. 11L), IgG1-06 (FIG. 11M), IgG1-08 (FIG. 11N), IgG1-11 (FIG. 11O), IgG1-13 (FIG. 11P), IgG1-14 (FIG. 11Q), IgG1-15 (FIG. 11R), IgG1-12B07 (FIG. 11S) and IgG1-10 (FIG. 11T) showed any measurable binding to any other target than PD1, on any of the duplicate analyses. This finding demonstrated that the lead antibodies retained highly specific and potent binding to PD1 only, and that the off-target reactivity observed for IgG1-Mab005 (humanized) had been ablated.

Figure 14D:
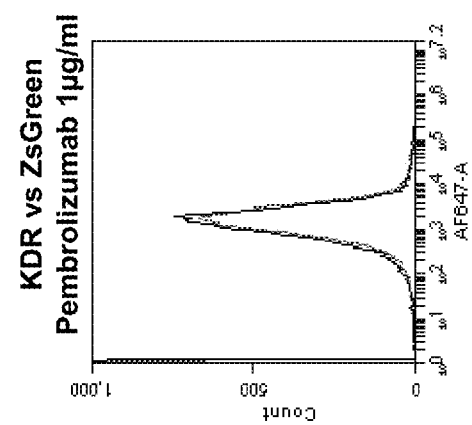
FIG. 14A-FIG. 14P. KDR binding analysis by flow cytometry using transiently-transfected HEK293 cells. Analyses of binding specificity were performed on HEK293 cells transiently transfected with plasmids encoding either human KDR (grey line) or ZS green marker (black line). Transfected cells were then stained using mVH/mVL Mab005-IgG1, IgG1-Mab005 (humanized), Pembrolizumab analog, isotype IgG1 and a subset of lead antibodies (IgG1-06D02, IgG1-12HO4, IgG1-05, IgG1-08). Each antibody was used in repeat staining at high (5 µg/ml) and moderate (1 µg/ml) concentration. These analyses confirmed that the only antibodies which exhibited binding to KDR-expressing cells were mVH/mVL Mab005-IgG1 and IgG1-Mab005 (humanized).
Figure 14C:
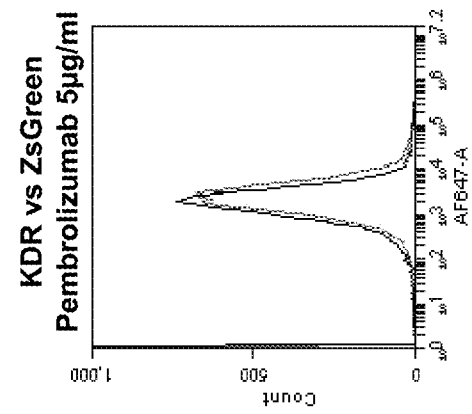
Figure 14B:
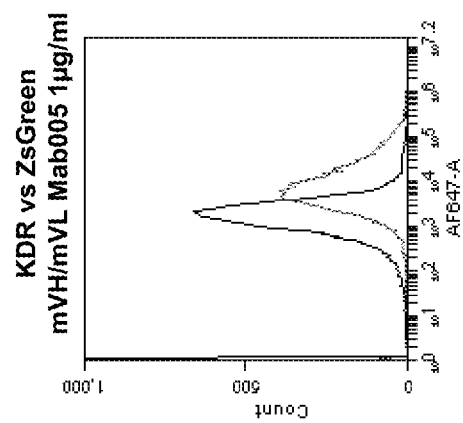
Figure 14A:
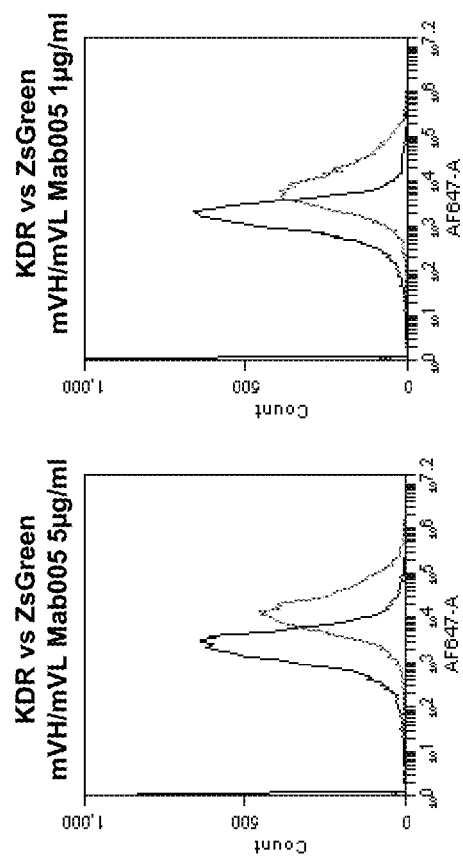
Figure 14H:
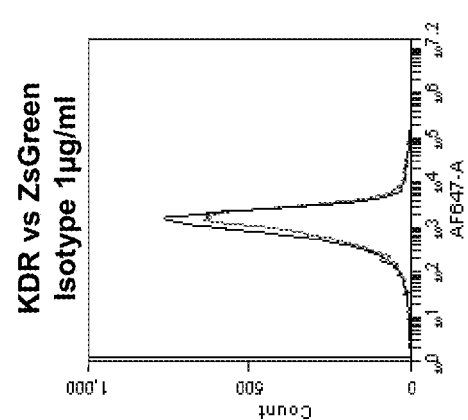
Figure 14G:
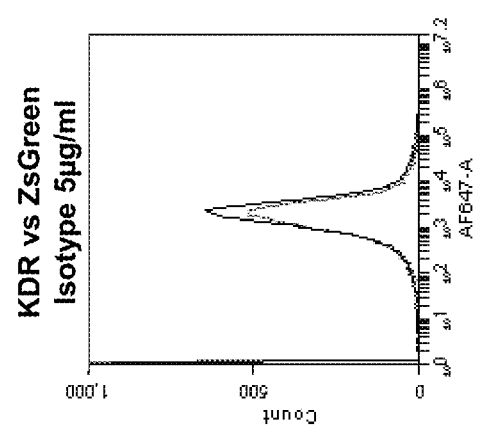
Figure 14F:
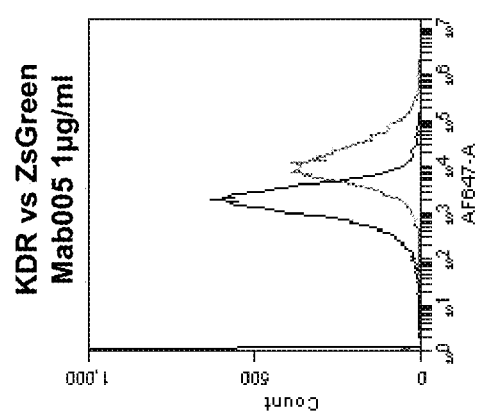
Figure 14E:
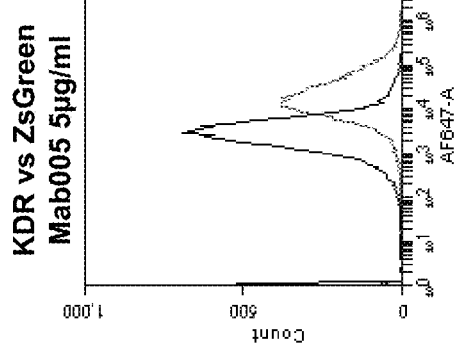
Figure 16B:
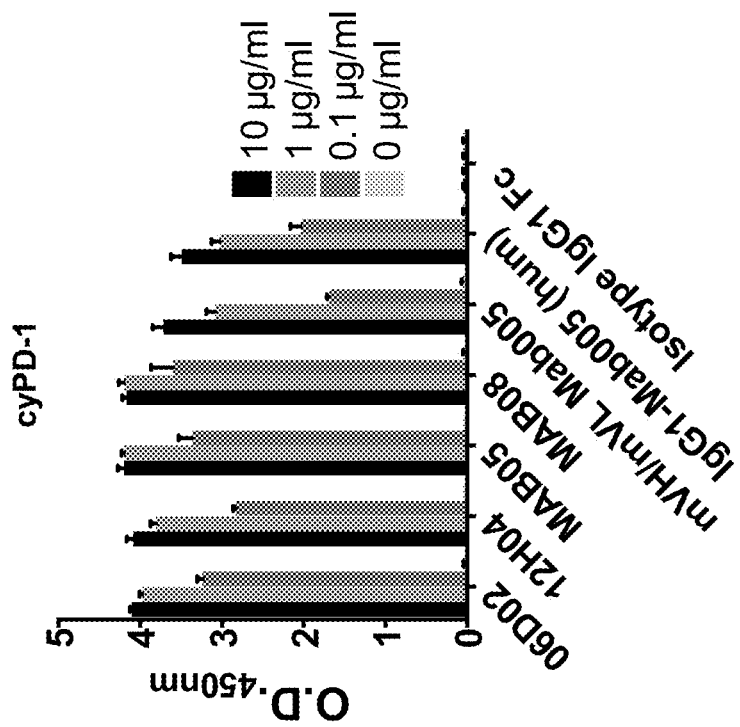
Figure 16A:
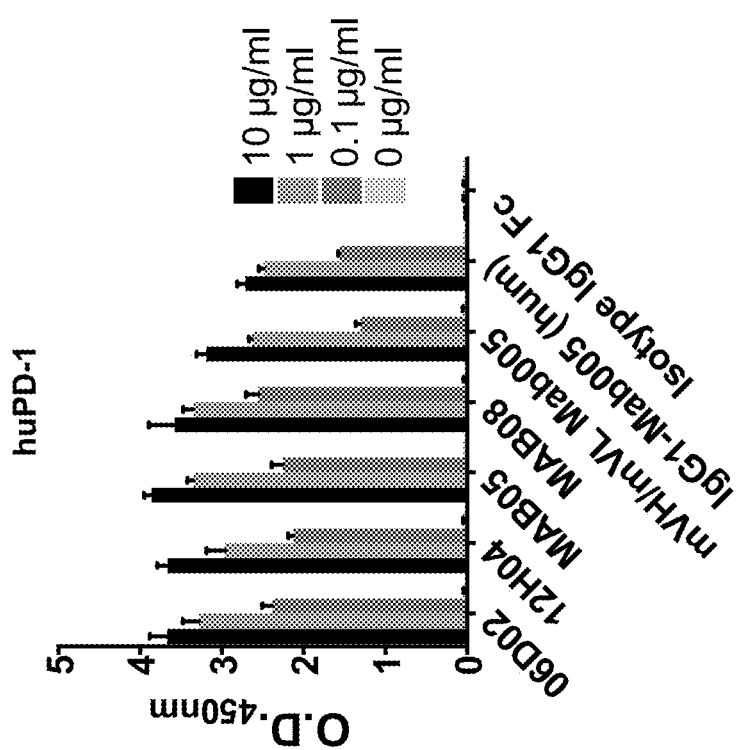
Figure 16D:
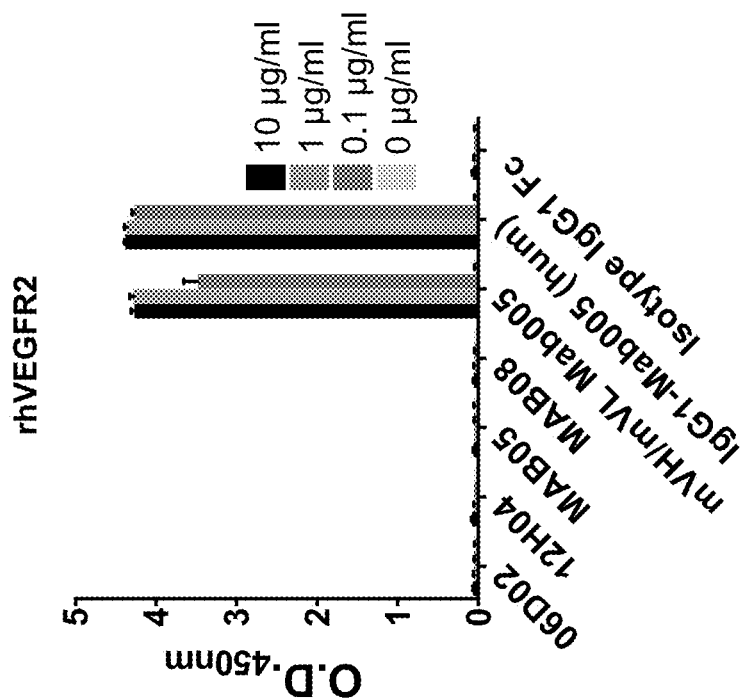
Figure 16C:
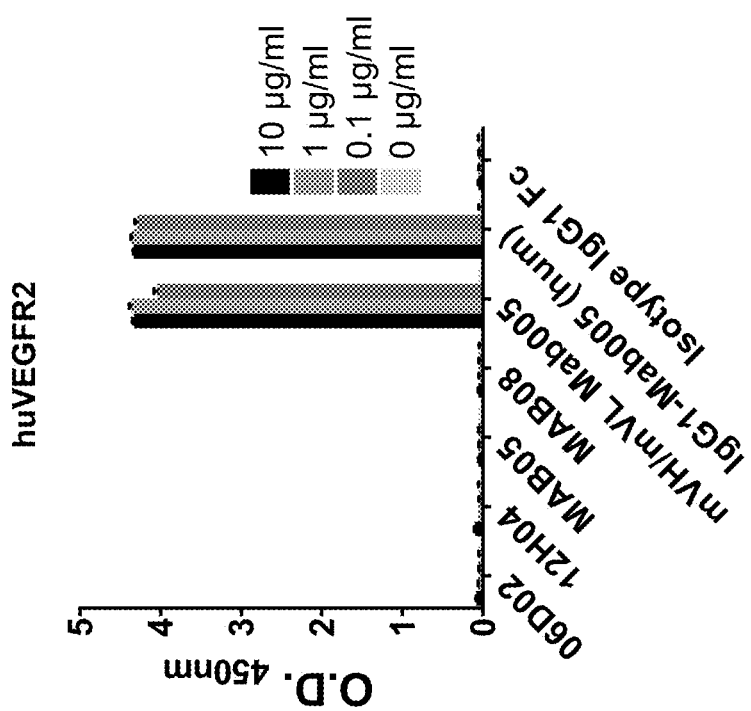
Figure 16E:
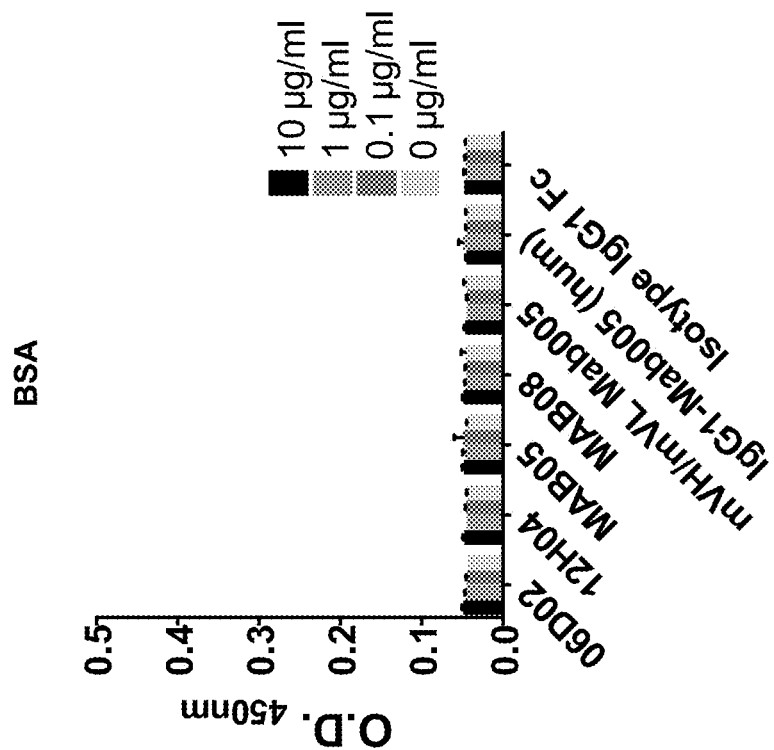
Figure 16F:
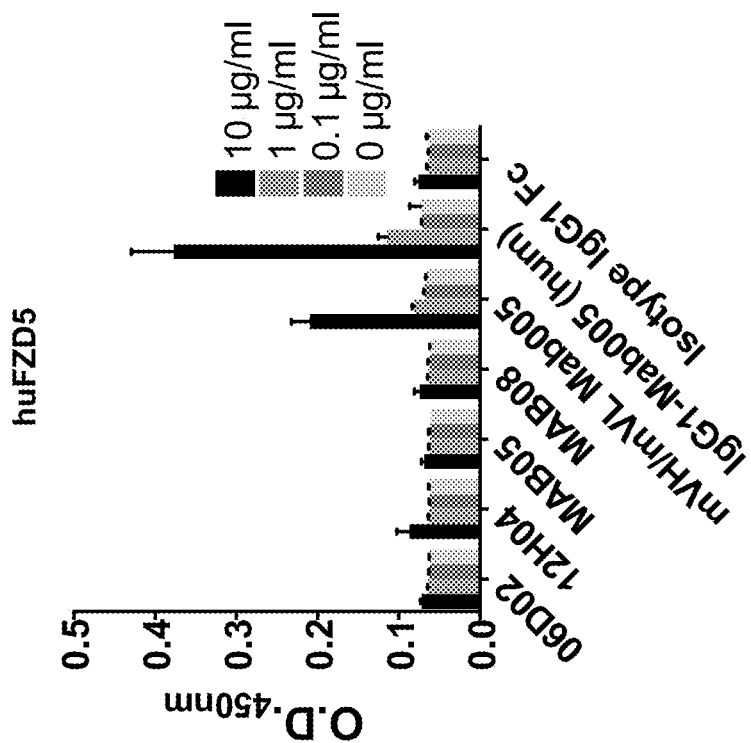

To finally confirm these findings with an orthogonal, high-sensitivity assay, the sequence-verified plasmids for KDR, ULBP2, FZD5, and ZS green only (negative control) were used to perform transient transfection of the human cell line HEK293. Transfected cells were then stained using mVH/mVL Mab005-IgG1, IgG1-Mab005 (humanized), Pembrolizumab analog, isotype IgG1 and a subset of lead antibodies (IgG1-06D02, IgG1-12HO4, IgG1-05, IgG1-08). Each antibody was used in repeat staining at high (5 µg/ml) and moderate (1 µg/ml) concentration against both receptor-transfected and ZS green-transfected cells (to measure background binding). In staining of PD1-transfected cells at both 5 and 1 µg/ml (FIGS. 12A-12P), all tested antibodies other than the isotype control showed the expected strong, specific staining of PD1-transfected cells but not ZS green-transfected. In contrast, staining of FZ5 (FIGS. 13A-13P), KDR (FIGS. 14A-14P) and ULBP2-transfected cells (FIGS. 15A-15P) fully correlated with the chip data from FIG. 11, with only mVH/mVL Mab005-IgG1 and IgG1-Mab005 (humanized) exhibiting strong binding signal on all 3 targets at both 5 and 1 µg/ml. None of the antibodies IgG1-06D02, IgG1-12HO4, IgG1-05, IgG1-08, Pembrolizumab analog, nor isotype IgG1 exhibited any measurable binding above background, at either concentration, to any of FZ5, KDR or ULBP2-transfected cells. In a further, high-sensitivity, ELISA assay, these antibodies were also found to bind human and cyno PD1 (FIG. 16 A,B) but not to bind to recombinant ectodomains of human or rhesus VEGFR2 (FIG. 16 C, D), human FZD5 (FIG. 16E), or to BSA protein (FIG. 16F). These findings fully confirmed that the CDR sequences derived in the mutagenesis and reselection process had unexpectedly ablated the off-target binding of receptors KDR, FZD5 and ULBP2 that may be primary drivers of the clinical toxicities associated with IgG1-Mab005 (humanized).

Finally, an attempt was made to estimate the affinity of mVH/mVL Mab005-IgG1 and IgG1-Mab005 (humanized) for VEGFR2 via Biacore, using the conditions described above for PD1 affinity evaluation. Human and rhesus monomeric VEGFR2-his proteins were titrated against mVH/mVL Mab005-IgG1 and IgG1-Mab005 (humanized). Both antibodies again exhibited binding to VEGFR2 recombinant protein, but binding signal was only observed at very high concentrations of soluble analyte (FIG. 17). As a result, complex curves with poor fit values ($Chi^2 > 6.6$) were all that could be generated and reliable KD values could not be accurately derived. This indicated that the affinity of both antibodies for either human or rhesus VEGFR2 was low, likely in the M range.

VEGFR2 Activation Analyses

To investigate whether the VEGFR2 reactivity in IgG1-Mab005 (humanized) was capable of activating the receptor, a human VEGFR2 reporter assay was used to examine induction of luciferase expression under control of the natural VEGF response element NFAT (Promega). In this assay, both IgG1-Mab005 (humanized) and mVH/mVL Mab005-IgG1 exhibited strong, concentration-dependent activation of VEGFR2 signalling (in the nM range), with IgG1-Mab005 (humanized) being more potent than mVH/mVL Mab005-IgG1 (FIG. 18). The activation potency of IgG1-Mab005 (humanized) was, however, significantly lower than that of recombinant human VEGF-163 (FIG. 18). Importantly, each of clones MAB04, MAB08, 06D02 and 12H04 were also analysed in this assay and demonstrated no observable activation signal, even at concentrations as high as 1 µM. Indeed, the signals at maximum concentration for the lead IgG clones were lower than the signals observed for the isotype control IgG1 (FIG. 18).

IgG Stability Analyses

Differential Scanning Calorimetry (DSC) is used to measure thermal stability of proteins, as an indicator of overall molecular structural stability. All IgG1null proteins tested were fully compatible with DSC analysis, presenting comparable sample homogeneity and cooperativity (FIG. 19). The measured thermal transition midpoints (Tm) for each antibody are indicated in Table 13. All five IgGs demonstrated similar CH2 domain Tm1 values from 72.2° C. to 72.4° C., indicating that all samples had high integrity. Unexpectedly, however, all lead IgGs (IgG1-05, IgG1-08, IgG1-06D02 and IgG1-12H04) demonstrated extremely high stability in their Fab domains, with Tm2 values ranging from 90.8° C. to 92.2° C. (Table 13). Mab005-IgG1 (humanized), in contrast, had a significantly lower stability Fab Tm value of 83.8° C. (Table 13). The significant increases in Fab stability for the lead antibodies over Mab005-IgG1 (humanized) were unexpected as the variable domain framework regions and antibody constant regions of all antibodies were identical in sequence and all improvements were therefore mediated solely by differences in CDR sequences.

Oxidation of exposed amino acid residues, such as tryptophan and methionine is a common degradation pathway for mAbs. Importantly, oxidation of critical side chains in the CDRs of antibodies can also potentially impact on their biological activity, by causing a reduction in target binding affinity. Oxidation is a process that usually happens over time in the storage of proteins, so the standard laboratory method of analysing oxidative risk in real time is to add an oxidative reagent to the protein. In this study, forced oxidation was applied to the IgGs by treating with 0.5% $H_2O_2$ in PBS, for 2 hours at room temperature. As oxidation can alter overall hydrophobicity of an antibody, for example by increasing the polarity of the oxidised form, potential changes induced by forced oxidation were analysed by Reverse Phase (RP) and Hydrophobic Interaction Chromatography (HIC) methods.

In RP analyses, no changes in retention times were observed for any of clones IgG1-05, IgG1-08, IgG1-06D02 and IgG1-12H04, in either intact (Table 14) or reduced (Table 15) IgG forms, suggesting that no significant oxidation of side chains had occurred. In contrast, upon $H_2O_2$ treatment of Mab005-IgG1 (humanized), a decrease of approximately 0.6 min in the column retention time of intact IgG (Table 14) and 0.8 min for the reduced light chain (Table 15) was observed, suggesting oxidation of exposed amino acids was specifically occurring in the antibody light chain. RP analysis of tryptic peptide fingerprints before and after $H_2O_2$ treatment also showed that side chain oxidation changes were minimal for all IgGs apart from for Mab005-IgG1 (humanized). For Mab005-IgG1 (humanized), the loss or reduction of 5 peptides after forced oxidation, was followed by appearance of 6 additional peptides (FIG. 20A). In contrast, clones IgG1-05, IgG1-08, IgG1-06D02 and IgG1-12H04 showed the concomitant loss of significantly fewer peptides. For example, IgG1-06D02 exhibited loss of just two tryptic peptides and appearance of two additional peaks after $H_2O_2$ treatment (FIG. 20B).

$H_2O_2$ treatment also induced a decrease in the retention time on HIC for all 5 test articles, suggesting minor oxidation of exposed amino acids (Table 16). Again, the highest decrease in the retention on HIC (1.1 min) was observed for Mab005-IgG1 (humanized), while for clones IgG1-05, IgG1-08, IgG1-06D02 and IgG1-12H04 the decrease is only 0.2-0.3 min. In total, these findings suggested that lead clones IgG1-05, IgG1-08, IgG1-06D02 and IgG1-12H04 had unexpectedly improved physical stability and resistance to oxidative challenge in comparison to Mab005-IgG1 (humanized).

The combined analyses outlined herein demonstrated that, surprisingly, deep sampling of both germline and non-germline amino acids in the CDRs of these antibodies allowed the simultaneous optimisation of target binding specificity, immunogenicity risk, potency, biophysical stability and chemical stability risks in multiple final molecules.

All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

Although the present invention has been described with reference to preferred or exemplary embodiments, those skilled in the art will recognize that various modifications and variations to the same can be accomplished without departing from the spirit and scope of the present invention and that such modifications are clearly contemplated herein. No limitation with respect to the specific embodiments disclosed herein and set forth in the appended claims is intended nor should any be inferred.

TABLE 1

Amino acid sequences murine anti-PD1 CDRs as defined here ("Unified" scheme) in comparison to alternative definitions.

| Scheme | HCDR1 | HCDR2 | HCDR3 | LCDR1 | LCDR2 | LCDR3 |
|---|---|---|---|---|---|---|
| Unified | GFTFSSYMMS (SEQ ID NO: 95) | VATISGGGANTYYPDSVKG (SEQ ID NO: 92) | QLYYFDY (SEQ ID NO: 106) | LASQTIGTWLT (SEQ ID NO: 110) | TATSLAD (SEQ ID NO: 114) | QQVYSIPWT (SEQ ID NO: 116) |
| Kabat | SYMMS (SEQ ID NO: 96) | TISGGGANTYYPDSVKG (SEQ ID NO: 100) | QLYYFDY (SEQ ID NO: 106) | LASQTIGTWLT (SEQ ID NO: 110) | TATSLAD (SEQ ID NO: 114) | QQVYSIPWT (SEQ ID NO: 116) |
| Chothia | GFTFSSY (SEQ ID NO: 97) | SGGGAN (SEQ ID NO: 101) | QLYYFDY (SEQ ID NO: 106) | LASQTIGTWLT (SEQ ID NO: 110) | TATSLAD (SEQ ID NO: 114) | QQVYSIPWT (SEQ ID NO: 116) |
| IMGT | GFTFSSYM (SEQ ID NO: 98) | ISGGGANT (SEQ ID NO: 102) | ARQLYYFDY (SEQ ID NO: 107) | QTIGTW (NO: 111) | TAT | QQVYSIPWT (SEQ ID NO: 116) |
| AHo | GFTFSSYMMS (SEQ ID NO: 95) | ISGGGANTYYPDSVKG (SEQ ID NO: 103) | QLYYFD (SEQ ID NO: 108) | ASQTIGTW (SEQ ID NO: 112) | TATSLAD (SEQ ID NO: 114) | VYSIPW (SEQ ID NO: 117) |
| AbM | GFTFSSYMMS (SEQ ID NO: 95) | TISGGGANTY (SEQ ID NO: 104) | QLYYFDY (SEQ ID NO: 106) | LASQTIGTWLT (SEQ ID NO: 110) | TATSLAD (SEQ ID NO: 114) | QQVYSIPWT (SEQ ID NO: 116) |

TABLE 1-continued

Amino acid sequences murine anti-PD1 CDRs as defined here
("Unified" scheme) in comparison to alternative definitions.

| Scheme | HCDR1 | HCDR2 | HCDR3 | LCDR1 | LCDR2 | LCDR3 |
|---|---|---|---|---|---|---|
| Contact | SSYMMS (SEQ ID NO: 99) | VATISGGGANTY (SEQ ID NO: 105) | ARQLYYFD (SEQ ID NO: 109) | GTWLTWY (SEQ ID NO: 113) | LLIYTATSLA (SEQ ID NO: 115) | QQVYSIPW (SEQ ID NO: 118) |

TABLE 2

Amino acid sequence of MAB005 murine anti-PD1 v-domains
(mVH/mVL) and human germline CDR grafts (VH1A/L1).

| V DOMAIN | Human germline[1] | Amino acid sequence[2] |
|---|---|---|
| PD1-mVH | n/a | EVMLVESGGGLVKPGGSLKLSCAASGFTFSSYMMSWVRQTPEKRLEWVATISGGGANTYYPDSVKGRFTISRDNAKNTLYLQMSSLRSEDTALTYCARQLYYFDYWGQGTTLTVSS (SEQ ID NO: 119) |
| PD1-VH1 | IGHV3-7 | EVQLVESGGGLVQPGGSLRLSCAASGFTFSSYMMSWVRQAPGKGLEWVATISGGGANTYYPDSVKGRFTISRDNAKNSLYLQMNSLRAEDTAVYYCARQLYYFDYWGQGTTVTVSS (SEQ ID NO: 120) |
| PD1-mVL | n/a | DIQMTQSPASQSASLGEGVTITCLASQTIGTWLTWYQQKPGKSPQLLIYTATSLADGVPSRFSGSGSGTKFSFKISSLQAEDFVTYYCQQVYSIPWTFGGGTKLEIK (SEQ ID NO: 121) |
| PD1-VL1 | IGKV1-39 | DIQMTQSPSSLSASVGDRVTITCLASQTIGTWLTWYQQKPGKAPKLLIYTATSLADGVPSRFSGSGSGTDFTLTISSLQPEDFATTYCQQVYSIPWTFGGGTKVEIK (SEQ ID NO: 122) |

[1]Human germline definitions used for grafting, based on IMGT system.
[2]CDR residues are in bold and underlined. As noted above, the "Unified" CDR definitions used in this manuscript are in expanded definition in comparison to the classical Kabat definition. Each sequence above shows the framework regions (FRs) and the CDRs in the following order: FR1-CDR1-FR2-CDR2-FR3-CDR3-FR4.

TABLE 3

Unique CDRs from Fab clones shown to bind human and cyno PD1 proteins.

| LCDR1 | LCDR2 | LCDR3 | HCDR1 | HCDR2 | HCDR3 |
|---|---|---|---|---|---|
| RASQSIGSWLT (SEQ ID NO: 123) | AASSLAD (SEQ ID NO: 128) | QQSYSIPLT (SEQ ID NO: 132) | GFTFSSYAMS (SEQ ID NO: 67) | VANISGGGAEKYYPDSVKG (SEQ ID NO: 147) | LLYYEDY (SEQ ID NO: 165) |
| RASQSIGSYLN (SEQ ID NO: 78) | AASSLAS (SEQ ID NO: 53) | QQSYSIPWT (SEQ ID NO: 47) | GFTFSSYDMS (SEQ ID NO: 135) | VANISGGGAEKYYPDSVKG (SEQ ID NO: 147) | MLYYDDY (SEQ ID NO: 166) |
| RASQSIGTWLN (SEQ ID NO: 124) | AASSLHS (SEQ ID NO: 54) | QQSYSTPWT (SEQ ID NO: 43) | GFTFSSYEMS (SEQ ID NO: 136) | VANISGGGAEKYYVDSVKG (SEQ ID NO: 148) | NLYYFDY (SEQ ID NO: 167) |
| RASQSIGTYLN (SEQ ID NO: 76) | AASSLQD (SEQ ID NO: 50) | QQVYSIPLT (SEQ ID NO: 133) | GFTFSSYFMS (SEQ ID NO: 137) | VANISGGGAEKYYVDSVKG (SEQ ID NO: 148) | QGYYFDY (SEQ ID NO: 168) |
| RASQSISSWLN (SEQ ID NO: 41) | AASSLQS (SEQ ID NO: 42) | QQVYSTPWT (SEQ ID NO: 134) | GFTFSSYGMS (SEQ ID NO: 138) | VANISGGGAETYYPDSVKG (SEQ ID NO: 149) | QKYYFDY (SEQ ID NO: 169) |
| RASQSISSWLT (SEQ ID NO: 125) | AATSLAS (SEQ ID NO: 69) | | GFTFSSYHMS (SEQ ID NO: 139) | VANISGGGAETYYVDSVKG (SEQ ID NO: 150) | QLHYFDY (SEQ ID NO: 170) |
| RASQSISSYLN (SEQ ID NO: 74) | AATSLQD (SEQ ID NO: 129) | | GFTFSSYIMS (SEQ ID NO: 140) | VANISGGGANKYYPDSVKG (SEQ ID NO: 151) | QLYAFDY (SEQ ID NO: 46) |
| RASQSISTWLN (SEQ ID NO: 52) | AATSLQS (SEQ ID NO: 77) | | GFTFSSYLMS (SEQ ID NO: 38) | VANISGGGANKYYVDSVKG (SEQ ID NO: 152) | QLYDFDY (SEQ ID NO: 171) |

TABLE 3-continued

Unique CDRs from Fab clones shown to bind human and cyno PD1 proteins.

| LCDR1 | LCDR2 | LCDR3 | HCDR1 | HCDR2 | HCDR3 |
|---|---|---|---|---|---|
| RASQSISTWLT (SEQ ID NO: 126) | TASSLAD (SEQ ID NO: 73) | | GFTFSSYNMS (SEQ ID NO: 141) | VANISGGGSEKYYPDSVKG (SEQ ID NO: 153) | QLYFFDY (SEQ ID NO: 45) |
| RASQSISTYLN (SEQ ID NO: 127) | TASSLQD (SEQ ID NO: 71) | | GFTFSSYPMS (SEQ ID NO: 80) | VANISGGGSEKYYVDSVKG (SEQ ID NO: 154) | QLYGFDY (SEQ ID NO: 40) |
| | TASSLQS (SEQ ID NO: 79) | | GFTFSSYQMS (SEQ ID NO: 142) | VANISGGGSETYYPDSVKG (SEQ ID NO: 155) | QLYMFDY (SEQ ID NO: 172) |
| | TATSLAS (SEQ ID NO: 130) | | GFTFSSYSMS (SEQ ID NO: 75) | VANISGGGSETYYVDSVKG (SEQ ID NO: 156) | QLYYADY (SEQ ID NO: 72) |
| | TATSLQD (SEQ ID NO: 131) | | GFTFSSYTMS (SEQ ID NO: 143) | VANISGGGSNKYYPDSVKG (SEQ ID NO: 157) | QLYYEDY (SEQ ID NO: 173) |
| | | | GFTFSSYVMS (SEQ ID NO: 144) | VANISGGGSNKYYVDSVKG (SEQ ID NO: 158) | QLYYIDY (SEQ ID NO: 174) |
| | | | GFTFSSYWMS (SEQ ID NO: 145) | VATISGGGAEKYYPDSVKG (SEQ ID NO: 159) | QLYYKDY (SEQ ID NO: 175) |
| | | | GFTFSSYYMS (SEQ ID NO: 146) | VATISGGGAEKYYPDSVKG (SEQ ID NO: 159) | QLYYMDY (SEQ ID NO: 176) |
| | | | | VATISGGGAEKYYVDSVKG (SEQ ID NO: 49) | QLYYSDY (SEQ ID NO: 177) |
| | | | | VATISGGGAEKYYVDSVKG (SEQ ID NO: 49) | QLYYWDY (SEQ ID NO: 178) |
| | | | | VATISGGGAETYYPDSVKG (SEQ ID NO: 160) | QMYYFDY (SEQ ID NO: 179) |
| | | | | VATISGGGAETYYPDSVKG (SEQ ID NO: 70) | QQYYFDY (SEQ ID NO: 180) |
| | | | | VATISGGGANKYYPDSVKG (SEQ ID NO: 164) | QSYYFDY (SEQ ID NO: 181) |
| | | | | VATISGGGANKYYVDSVKG (SEQ ID NO: 161) | QVYYFDY (SEQ ID NO: 44) |
| | | | | VATISGGGSEKYYPDSVKG (SEQ ID NO: 162) | TLYYFDY (SEQ ID NO: 182) |
| | | | | VATISGGGSEKYYVDSVKG (SEQ ID NO: 39) | |
| | | | | VATISGGGSETYYPDSVKG (SEQ ID NO: 162) | |
| | | | | VATISGGGSETYYVDSVKG (SEQ ID NO: 48) | |
| | | | | VATISGGGSNKYYPDSVKG (SEQ ID NO: 163) | |
| | | | | VATISGGGSNKYYVDSVKG (SEQ ID NO: 68) | |

TABLE 4

CDR sequences of unique, library-derived and designer, PD1 antagonistic IgGs.

| Clone name | LCDR1 | LCDR2 | LCDR3 | HCDR1 | HCDR2 | HCDR3 |
|---|---|---|---|---|---|---|
| 06D02 | RASQSISSWLN (SEQ ID NO: 41) | AASSLQS (SEQ ID NO: 42) | QQSYSIPWT (SEQ ID NO: 47) | GFTFSSYLMS (SEQ ID NO: 38) | VATISGGGSETYYVDSVKG (SEQ ID NO: 48) | QLFGFDY (SEQ ID NO: 40) |
| 08F04 | RASQSISTWLN (SEQ ID NO: 52) | AATSLAS (SEQ ID NO: 69) | QQSYSIPWT (SEQ ID NO: 47) | GFTFSSYAMS (SEQ ID NO: 67) | VATISGGGSNKYYVDSVKG (SEQ ID NO: 687) | QLYGFDY (SEQ ID NO: 40) |
| 11G05 | RASQSISSWLN (SEQ ID NO: 41) | TASSLQD (SEQ ID NO: 71) | QQSYSTPWT (SEQ ID NO: 43) | GFTFSSYLMS (SEQ ID NO: 38) | VATISGGGAETYYVDSVKG (SEQ ID NO: 70) | QLYFFDY (SEQ ID NO: 45) |
| 12E02 | RASQSISSWLN (SEQ ID NO: 41) | TASSLAD (SEQ ID NO: 73) | QQSYSIPWT (SEQ ID NO: 47) | GFTFSSYAMS (SEQ ID NO: 67) | VATISGGGSEKYYVDSVKG (SEQ ID NO: 39) | QLYYADY (SEQ ID NO: 72) |
| 12H04 | RASQSISSWLN (SEQ ID NO: 41) | AASSLQD (SEQ ID NO: 50) | QQSYSTPWT (SEQ ID NO: 43) | GFTFSSYLMS (SEQ ID NO: 38) | VATISGGGAEKYYVDSVKG (SEQ ID NO: 49) | QLYGFDY (SEQ ID NO: 40) |
| 12B07 | RASQSISTWLN (SEQ ID NO: 52) | AASSLAS (SEQ ID NO: 53) | QQSYSTPWT (SEQ ID NO: 43) | GFTFSSYLMS (SEQ ID NO: 38) | VATISGGGSNTYYVDSVKG (SEQ ID NO: 51) | QLYGFDY (SEQ ID NO: 40) |
| 13G02 | RASQSISSYLN (SEQ ID NO: 74) | AASSLQS (SEQ ID NO: 42) | QQSYSTPWT (SEQ ID NO: 43) | GFTFSSYLMS (SEQ ID NO: 38) | VATISGGGAEKYYVDSVKG (SEQ ID NO: 49) | QLYGFDY (SEQ ID NO: 40) |
| 14C07 | RASQSISSWLN (SEQ ID NO: 41) | AASSLQS (SEQ ID NO: 42) | QQSYSIPWT (SEQ ID NO: 47) | GFTFSSYSMS (SEQ ID NO: 75) | VANISGGGAETYYVDSVKG (SEQ ID NO: 150) | QLYGFDY (SEQ ID NO: 40) |
| 15C10 | RASQSIGTYLN (SEQ ID NO: 76) | AATSLQS (SEQ ID NO: 77) | QQSYSIPWT (SEQ ID NO: 47) | GFTFSSYLMS (SEQ ID NO: 38) | VATISGGGSNKYYVDSVKG (SEQ ID NO: 68) | QLYGFDY (SEQ ID NO: 40) |
| 16C07 | RASQSIGSYLN (SEQ ID NO: 78) | TASSLQS (SEQ ID NO: 79) | QQSYSIPWT (SEQ ID NO: 47) | GFTFSSYLMS (SEQ ID NO: 38) | VATISGGGAEKYYVDSVKG (SEQ ID NO: 49) | QLYAFDY (SEQ ID NO: 46) |
| 16H10 | RASQSISSWLN (SEQ ID NO: 41) | AASSLHS (SEQ ID NO: 54) | QQSYSTPWT (SEQ ID NO: 43) | GFTFSSYLMS (SEQ ID NO: 38) | VATISGGGSEKYYVDSVKG (SEQ ID NO: 39) | QVYYFDY (SEQ ID NO: 44) |
| 12H11 | RASQSISTWLN (SEQ ID NO: 52) | AASSLQY (SEQ ID NO: 82) | QQSYSTPWT (SEQ ID NO: 43) | GFTFSSYPMS (SEQ ID NO: 80) | VATISGGGSETYYPDSVKG (SEQ ID NO: 162) | QLYYYDY (SEQ ID NO: 81) |
| MH-AA-VH | | | | GFTFSSYAMS (SEQ ID NO: 67) | VATISGGGSEKYYVDSVKG (SEQ ID NO: 39) | QLYYADY (SEQ ID NO: 72) |
| MH-LV-VH | | | | GFTFSSYLMS (SEQ ID NO: 38) | VATISGGGSEKYYVDSVKG (SEQ ID NO: 39) | QVYYFDY (SEQ ID NO: 44) |
| MH-LG-VH | | | | GFTFSSYLMS (SEQ ID NO: 38) | VATISGGGSEKYYVDSVKG (SEQ ID NO: 39) | QLYGFDY (SEQ ID NO: 40) |
| MH-LF-VH | | | | GFTFSSYLMS (SEQ ID NO: 38) | VATISGGGSEKYYVDSVKG (SEQ ID NO: 39) | QLYFFDY (SEQ ID NO: 45) |
| MH-LA-VH | | | | GFTFSSYLMS (SEQ ID NO: 38) | VATISGGGSEKYYVDSVKG (SEQ ID NO: 39) | GLYAFDY (SEQ ID NO: 46) |
| MH-VL | RASQSISSWLN (SEQ ID NO: 41) | AASSLQS (SEQ ID NO: 42) | QQSYSTPWT (SEQ ID NO: 43) | | | |
| MH-JK1-VL | RASQSISSWLN (SEQ ID NO: 41) | AASSLQS (SEQ ID NO: 42) | QQSYSTPWT (SEQ ID NO: 43) | | | |

TABLE 4-continued

CDR sequences of unique, library-derived and designer, PD1 antagonistic IgGs.

| Clone name | LCDR1 | LCDR2 | LCDR3 | HCDR1 | HCDR2 | HCDR3 |
|---|---|---|---|---|---|---|
| TTP-JK1-VL | RASQSISSYLN (SEQ ID NO: 74) | AASSLQS (SEQ ID NO: 42) | QQSYSTPWT (SEQ ID NO: 43) | | | |
| IgG1-01 | RASQSISSWLN (SEQ ID NO: 41) | AASSLQS (SEQ ID NO: 42) | QQSYSTPWT (SEQ ID NO: 43) | GFTFSSYAMS (SEQ ID NO: 67) | VATISGGGSEKYYVDSVKG (SEQ ID NO: 39) | QLYYADY (SEQ ID NO: 72) |
| IgG1-02 | RASQSISSWLN (SEQ ID NO: 41) | AASSLQS (SEQ ID NO: 42) | QQSYSTPWT (SEQ ID NO: 43) | GFTFSSYAMS (SEQ ID NO: 67) | VATISGGGSEKYYVDSVKG (SEQ ID NO: 39) | QLYYADY (SEQ ID NO: 72) |
| IgG1-03 | RASQSISSYLN (SEQ ID NO: 74) | AASSLQS (SEQ ID NO: 42) | QQSYSTPWT (SEQ ID NO: 43) | GFTFSSYAMS (SEQ ID NO: 67) | VATISGGGSEKYYVDSVKG (SEQ ID NO: 39) | QLYYADY (SEQ ID NO: 72) |
| IgG1-04 | RASQSISSWLN (SEQ ID NO: 41) | AASSLQS (SEQ ID NO: 42) | QQSYSTPWT (SEQ ID NO: 43) | GFTFSSYLMS (SEQ ID NO: 38) | VATISGGGSEKYYVDSVKG (SEQ ID NO: 39) | QVYYFDY (SEQ ID NO: 44) |
| IgG1-05 | RASQSISSWLN (SEQ ID NO: 41) | AASSLQS (SEQ ID NO: 42) | QQSYSTPWT (SEQ ID NO: 43) | GFTFSSYLMS (SEQ ID NO: 38) | VATISGGGSEKYYVDSVKG (SEQ ID NO: 39) | QVYYFDY (SEQ ID NO: 44) |
| IgG1-06 | RASQSISSYLN (SEQ ID NO: 74) | AASSLQS (SEQ ID NO: 42) | QQSYSTPWT (SEQ ID NO: 43) | GFTFSSYLMS (SEQ ID NO: 38) | VATISGGGSEKYYVDSVKG (SEQ ID NO: 39) | QVYYFDY (SEQ ID NO: 44) |
| IgG1-07 | RASQSISSWLN (SEQ ID NO: 41) | AASSLQS (SEQ ID NO: 42) | QQSYSTPWT (SEQ ID NO: 43) | GFTFSSYLMS (SEQ ID NO: 38) | VATISGGGSEKYYVDSVKG (SEQ ID NO: 39) | QLYGFDY (SEQ ID NO: 40) |
| IgG1-08 | RASQSISSWLN (SEQ ID NO: 41) | AASSLQS (SEQ ID NO: 42) | QQSYSTPWT (SEQ ID NO: 43) | GFTFSSYLMS (SEQ ID NO: 38) | VATISGGGSEKYYVDSVKG (SEQ ID NO: 39) | QLYGFDY (SEQ ID NO: 40) |
| IgG1-09 | RASQSISSYLN (SEQ ID NO: 74) | AASSLQS (SEQ ID NO: 42) | QQSYSTPWT (SEQ ID NO: 43) | GFTFSSYLMS (SEQ ID NO: 38) | VATISGGGSEKYYVDSVKG (SEQ ID NO: 39) | QLYGFDY (SEQ ID NO: 40) |
| IgG1-10 | RASQSISSWLN (SEQ ID NO: 41) | AASSLQS (SEQ ID NO: 42) | QQSYSTPWT (SEQ ID NO: 43) | GFTFSSYLMS (SEQ ID NO: 38) | VATISGGGSEKYYVDSVKG (SEQ ID NO: 39) | QLYFFDY (SEQ ID NO: 45) |
| IgG1-11 | RASQSISSWLN (SEQ ID NO: 41) | AASSLQS (SEQ ID NO: 42) | QQSYSTPWT (SEQ ID NO: 43) | GFTFSSYLMS (SEQ ID NO: 38) | VATISGGGSEKYYVDSVKG (SEQ ID NO: 39) | QLYFFDY (SEQ ID NO: 45) |
| IgG1-12 | RASQSISSYLN (SEQ ID NO: 74) | AASSLQS (SEQ ID NO: 42) | QQSYSTPWT (SEQ ID NO: 43) | GFTFSSYLMS (SEQ ID NO: 38) | VATISGGGSEKYYVDSVKG (SEQ ID NO: 39) | QLYFFDY (SEQ ID NO: 45) |
| IgG1-13 | RASQSISSWLN (SEQ ID NO: 41) | AASSLQS (SEQ ID NO: 42) | QQSYSTPWT (SEQ ID NO: 43) | GFTFSSYLMS (SEQ ID NO: 38) | VATISGGGSEKYYVDSVKG (SEQ ID NO: 39) | QLYAFDY (SEQ ID NO: 46) |
| IgG1-14 | RASQSISSWLN (SEQ ID NO: 41) | AASSLQS (SEQ ID NO: 42) | QQSYSTPWT (SEQ ID NO: 43) | GFTFSSYLMS (SEQ ID NO: 38) | VATISGGGSEKYYVDSVKG (SEQ ID NO: 39) | QLYAFDY (SEQ ID NO: 46) |
| IgG1-15 | RASQSISSYLN (SEQ ID NO: 74) | AASSLQS (SEQ ID NO: 42) | QQSYSTPWT (SEQ ID NO: 43) | GFTFSSYLMS (SEQ ID NO: 38) | VATISGGGSEKYYVDSVKG (SEQ ID NO: 39) | QLYAFDY (SEQ ID NO: 46) |

TABLE 5

ELISA EC50 values of unique, library-derived anti-PD1 Fabs.

| Clone name | huPD1-Fc EC50 (nM) | cyPD1-Fc EC50 (nM) |
|---|---|---|
| Fab12B07 | 0.2374 | 3.116 |
| Fab12H04 | 0.7078 | 1.402 |
| Fab06D02 | 0.7434 | 1.013 |
| Fab-Mab005 | 1.245 | ND |
| Fab14C07 | 1.704 | 2.551 |
| Fab16H10 | 2.055 | 1.105 |
| Fab12H11 | 2.804 | 4.269 |
| Fab16C07 | 3.703 | 4.874 |
| Fab11G05 | 4.27 | 6.379 |
| Fab13G02 | 4.626 | 5.445 |
| Fab15C10 | 4.838 | 6.408 |
| Fab08F04 | 6.861 | 14.2 |
| Fab12E02 | ND | ND |

N.D. = Not Determined

TABLE 6

ELISA EC50 values of unique, library-derived anti-PD1 IgG1null sequences.

| Clone name | huPD-1-Fc EC50 (nM) | cyPD-1-Fc EC50 (nM) |
|---|---|---|
| IgG1-06D02 | 0.065 | 0.1036 |
| IgG1-08F04 | 0.096 | 0.126 |
| IgG1-12H04 | 0.1116 | 0.1204 |
| IgG1-Mab005 | 0.1141 | 0.1322 |
| IgG1-12B07 | 0.117 | 0.0932 |
| IgG1-15C10 | 0.1393 | 0.1826 |
| IgG1-16H10 | 0.1543 | 0.2337 |
| IgG1-13G02 | 0.1595 | 0.21 |
| IgG1-11G05 | 0.1671 | 0.2451 |
| IgG1-12E02 | 0.1741 | 0.1943 |
| IgG1-12H11 | 0.1795 | 0.2088 |
| IgG1-16C07 | 0.2445 | 0.2372 |
| IgG1-14C07 | N.D. | N.D. |

N.D. = Not Determined.

TABLE 7

ELISA EC50 values of unique, designer anti-PD1 IgG1null sequences.

| Clone name | huPD-1-Fc EC50 (nM) | cyPD-1-Fc EC50 (nM) |
|---|---|---|
| IgG1-11 | 0.04921 | 0.04975 |
| IgG1-07 | 0.08801 | 0.06449 |
| IgG1-13 | 0.107 | 0.09845 |
| IgG1-04 | 0.1083 | 0.138 |
| IgG1-05 | 0.1213 | 0.1349 |
| IgG1-14 | 0.1246 | 0.09586 |
| IgG1-10 | 0.128 | 0.1692 |
| IgG1-08 | 0.1339 | 0.07714 |
| IgG1-Mab005 | 0.1368 | 0.1525 |
| IgG1-09 | 0.1497 | 0.1253 |
| IgG1-15 | 0.172 | 0.1695 |
| IgG1-06 | 0.1752 | 0.1482 |
| IgG1-01 | 0.1781 | N.D. |
| IgG1-02 | 0.1832 | N.D. |
| IgG1-12 | 0.2718 | 0.2704 |
| IgG1-03 | N.D. | N.D. |

N.D. = Not Determined.

TABLE 8

Alphascreen IC50 values of anti-PD1 IgG1null sequences.

| Clone ID | CPS IC50 nM |
|---|---|
| IgG1-11 | 1.413 |
| IgG1-05 | 1.66 |
| IgG1-Mab005 | 2.142 |
| IgG1-08 | 2.361 |
| IgG1-16H10 | 2.498 |
| IgG1-12B07 | 2.557 |
| IgG1-07 | 2.615 |
| IgG1-06D02 | 2.626 |
| IgG1-14 | 3.004 |
| IgG1-04 | 3.24 |
| IgG1-10 | 3.416 |
| IgG1-13 | 3.615 |
| IgG1-12H04 | 4.013 |
| IgG1-11G05 | 4.225 |
| IgG1-15C10 | 5.868 |
| IgG1-13G02 | 7.169 |
| IgG1-08F04 | 7.744 |
| IgG1-16C07 | 9.267 |
| IgG1-12H11 | 15.47 |
| IgG1-15 | ND |
| IgG1-12E02 | ND |
| IgG1-14C07 | ND |
| IgG1-01 | ND |
| IgG1-02 | ND |
| IgG1-03 | ND |
| IgG1-06 | ND |
| IgG1-09 | ND |
| IgG1-12 | ND |

ND = not determined

TABLE 9

Biacore affinity values for IgG1null binding to human and cyno monomeric PD1.

| | Human PD1 | | | | Cyno PD1 | | | |
|---|---|---|---|---|---|---|---|---|
| Clone name | ka (1/Ms) | kd (1/s) | Chi2 | KD (nM) | ka (1/Ms) | kd (1/s) | Chi2 | KD (nM) |
| IgG1-Pembro* | 4.9E+05 | 2.4E−03 | 1.3 | 4.8 | 3.9E+05 | 6.8E−04 | 1.7 | 1.8 |
| IgG1-Mab005 | 1.2E+05 | 4.7E−04 | 1.3 | 4.0 | 8.8E+04 | 2.8E−03 | 0.4 | 32.0 |
| IgG1-16H10 | 1.6E+05 | 3.4E−04 | 1.2 | 2.1 | 9.3E+04 | 4.2E−04 | 0.3 | 4.5 |
| IgG1-12H04 | 2.0E+05 | 3.2E−04 | 1.1 | 1.6 | 1.4E+05 | 6.4E−04 | 0.8 | 4.7 |
| IgG1-06D02 | 2.0E+05 | 2.5E−04 | 3.0 | 1.3 | 1.3E+05 | 6.2E−04 | 0.4 | 4.9 |
| IgG1-12B07 | 1.7E+05 | 2.5E−04 | 2.2 | 1.5 | 1.1E+05 | 1.6E−03 | 0.5 | 14.2 |
| IgG1-11G05 | 1.2E+05 | 5.8E−04 | 0.4 | 4.7 | 5.5E+04 | 1.3E−03 | 0.3 | 24.0 |
| IgG1-13G02 | 1.5E+05 | 2.0E−03 | 0.4 | 13.4 | 9.7E+04 | 6.4E−03 | 0.4 | 65.5 |
| IgG1-16C07 | 1.5E+05 | 1.8E−03 | 0.3 | 12.0 | 9.6E+04 | 7.5E−03 | 0.4 | 77.7 |
| IgG1-12H11 | 1.5E+05 | 2.8E−03 | 0.3 | 18.1 | 9.9E+04 | 1.0E−02 | 0.4 | 103.0 |
| IgG1-15C10 | 1.4E+05 | 1.8E−03 | 1.3 | 12.3 | 9.6E+04 | 1.4E−02 | 0.4 | 144.0 |
| IgG1-08F04 | 1.3E+05 | 2.5E−03 | 1.1 | 19.5 | 1.5E+05 | 2.6E−02 | 0.7 | 174.0 |

TABLE 9-continued

Biacore affinity values for IgG1null binding to human and cyno monomeric PD1.

| | Human PD1 | | | | Cyno PD1 | | | |
|---|---|---|---|---|---|---|---|---|
| Clone name | ka (1/Ms) | kd (1/s) | Chi2 | KD (nM) | ka (1/Ms) | kd (1/s) | Chi2 | KD (nM) |
| IgG1-08 | 1.9E+05 | 2.8E-04 | 3.4 | 1.47 | 1.5E+05 | 5.2E-04 | 1.6 | 3.4 |
| IgG1-06 | 1.8E+05 | 2.9E-04 | 2.9 | 1.59 | 1.5E+05 | 5.2E-04 | 1.6 | 3.4 |
| IgG1-04 | 1.5E+05 | 2.7E-04 | 1.6 | 1.87 | 1.2E+05 | 3.2E-04 | 0.8 | 2.7 |
| IgG1-05 | 1.5E+05 | 2.9E-04 | 1.1 | 1.91 | 1.2E+05 | 3.3E-04 | 1.3 | 2.8 |
| IgG1-13 | 1.8E+05 | 4.4E-04 | 1.9 | 2.45 | 1.4E+05 | 9.8E-04 | 1.2 | 6.8 |
| IgG1-14 | 1.8E+05 | 4.6E-04 | 2.2 | 2.57 | 1.4E+05 | 9.7E-04 | 1.2 | 6.9 |
| IgG1-10 | 1.5E+05 | 4.0E-04 | 1.2 | 2.7 | 1.2E+05 | 7.1E-04 | 1.4 | 6.1 |
| IgG1-11 | 1.3E+05 | 4.0E-04 | 1.4 | 3.01 | 1.0E+05 | 7.3E-04 | 0.9 | 7.1 |
| IgG1-015 | 1.6E+05 | 3.5E-03 | 1.6 | 21.5 | 1.2E+05 | 8.6E-03 | 0.9 | 69.9 |

*Pembrolizumab analog

TABLE 10

EC50 values for IgG1null binding to human and cyno PD1-CHO cells.

| Clone name | huPD-1-Fc EC50 (nM) | cyPD-1-Fc EC50 (nM) |
|---|---|---|
| IgG1-Mab005 | 2.319 | 6.532 |
| IgG1-06D02 | 1.779 | 1.561 |
| IgG1-12H04 | 1.952 | 2.172 |
| IgG1-16H10 | 1.681 | 1.221 |
| IgG1-05 | 1.656 | 2.521 |
| IgG1-08 | 1.551 | 2.031 |
| IgG1-11 | 0.978 | 0.861 |
| IgG1-14 | 1.866 | 1.326 |
| IgG1-15 | 2.133 | ND |

ND = Not Determined

TABLE 11

EC50 values for IgG1null blockade of human PD1/PD-L1.

| Clone name | EC50 (ng/ml) |
|---|---|
| IgG1-Mab005 | 285 |
| IgG1-16H10 | 252 |
| IgG1-12H04 | 188 |
| IgG1-06D02 | 224 |
| IgG1-08 | 127 |
| IgG1-05 | 156 |
| IgG1-14 | 212 |
| IgG1-11 | 172 |

TABLE 12

Human T cell epitope content in v-domains predicted by iTOPE ™ and TCED ™.

| Clone Name | Germline epitopes | Low Affinity Foreign | High Affinity Foreign | TCED+ |
|---|---|---|---|---|
| Mab005 V1 | 1 | 4 | 2 | 1 |
| Mab005 VH | 9 | 3 | 1 | 2 |
| 06D02 V1 | 5 | 0 | 0 | 0 |
| 06D02 VH | 9 | 3 | 1 | 2 |
| 12H04 V1 | 4 | 1 | 0 | 0 |
| 12H04 VH | 9 | 3 | 1 | 2 |
| 16H10 V1 | 3 | 0 | 2 | 0 |
| 16H10 VH | 9 | 3 | 1 | 2 |
| IgG1-05 V1 | 5 | 0 | 0 | 0 |
| IgG1-05 VH | 9 | 3 | 1 | 2 |
| IgG1-08 V1 | 5 | 0 | 0 | 0 |
| IgG1-08 VH | 9 | 3 | 1 | 2 |
| IgG1-11 V1 | 5 | 0 | 0 | 0 |
| IgG1-11 VH | 9 | 3 | 1 | 2 |
| IgG1-14 V1 | 5 | 0 | 0 | 0 |
| IgG1-14 VH | 9 | 2 | 1 | 2 |

TABLE 13

IgG thermal stability analysis by DSC - TM values in Degrees C.

| IgG | TM1 (CH2) | TM2 (Fab) |
|---|---|---|
| Mab005-IgG1 (hum) | 72.2 | 83.8 |
| IgG1-05 | 72.4 | 90.8 |
| IgG1-08 | 72.4 | 91.1 |
| IgG1-06D02 | 72.4 | 92.2 |
| IgG1-12H04 | 72.4 | 91.5 |

TABLE 14

Reverse Phase Chromatography retention time for intact IgGs - before (0 mins) and after 120 mins of forced oxidation with 0.5% $H_2O_2$

| IgG | 0 mins | 120 mins |
|---|---|---|
| Mab005-IgG1 (hum) | 16.4 | 15.8 |
| IgG1-05 | 15.5 | 15.5 |
| IgG1-08 | 15.5 | 15.5 |
| IgG1-06D02 | 15.8 | 15.8 |
| IgG1-12H04 | 15.7 | 15.7 |

TABLE 15

Reverse Phase Chromatography retention time for light and heavy chains of reduced IgGs - before (0 mins) and after 120 mins of forced oxidation with 0.5% $H_2O_2$

| | Light Chain | | Heavy Chain | |
|---|---|---|---|---|
| IgG | 0 mins | 120 mins | 0 mins | 120 mins |
| Mab005-IgG1 (hum) | 13.8 | 13 | 14.2 | 14.4 |
| IgG1-05 | 11.8 | 11.9 | 14.3 | 14.3 |
| IgG1-08 | 11.9 | 11.9 | 14.4 | 14.4 |
| IgG1-06D02 | 12.2 | 12.2 | 14.5 | 14.5 |
| IgG1-12H04 | 11.9 | 11.9 | 14.5 | 14.5 |

TABLE 16

Hydrophobic Interaction Chromatography retention time for IgGs - before (0 mins) and after 120 mins of forced oxidation with 0.5% $H_2O_2$

| IgG | 0 mins | 120 mins |
| --- | --- | --- |
| Mab005-IgG1 (hum) | 7.7 | 6.6 |
| IgG1-05 | 7 | 6.7 |
| IgG1-08 | 7.3 | 7 |
| IgG1-06D02 | 7.8 | 7.6 |
| IgG1-12H04 | 7.4 | 7.1 |

TABLE 17

Examples of antibody variable region amino acid sequences.

Antibody IgG1-08 heavy chain variable (VH) region
EVQLVESGGGLVQPGGSLRLSCAASGFTFSSYLMSWVRQAPGKGLEWVAT
ISGGGSEKYYVDSVKGRFTISRDNAKNSLYLQMNSLRAEDTAVYYCARQL
YGFDYWGQGTLVTVSS
(SEQ ID NO: 1)

Antibody IgG1-08 light chain variable (VL) region
DIQMTQSPSSLSASVGDRVTITCRASQSISSWLNWYQQKPGKAPKLLIYA
ASSLQSGVPSRFSGSGSGTDFTLTISSLQPEDFATYYCQQSYSTPWTFGQ
GTKVEIK
(SEQ ID NO: 2)

Antibody IgG1-05 heavy chain variable (VH) region
EVQLVESGGGLVQPGGSLRLSCAASGFTFSSYLMSWVRQAPGKGLEWVAT
ISGGGSEKYYVDSVKGRFTISRDNAKNSLYLQMNSLRAEDTAVYYCARQV
YYFDYWGQGTLVTVSS
(SEQ ID NO: 3)

Antibody IgG1-05 light chain variable (VL) region
DIQMTQSPSSLSASVGDRVTITCRASQSISSWLNWYQQKPGKAPKLLIYA
ASSLQSGVPSRFSGSGSGTDFTLTISSLQPEDFATYYCQQSYSTPWTFGQ
GTKVEIK
(SEQ ID NO: 4)

Antibody IgG1-11 heavy chain variable (VH) region
EVQLVESGGGLVQPGGSLRLSCAASGFTFSSYLMSWVRQAPGKGLEWVAT
ISGGGSEKYYVDSVKGRFTISRDNAKNSLYLQMNSLRAEDTAVYYCARQL
YFFDYWGQGTLVTVSS
(SEQ ID NO: 5)

Antibody IgG1-11 light chain variable (VL) region
DIQMTQSPSSLSASVGDRVTITCRASQSISSWLNWYQQKPGKAPKLLIYA
ASSLQSGVPSRFSGSGSGTDFTLTISSLQPEDFATYYCQQSYSTPWTFGQ
GTKVEIK
(SEQ ID NO: 6)

Antibody IgG1-14 heavy chain variable (VH) region
EVQLVESGGGLVQPGGSLRLSCAASGFTFSSYLMSWVRQAPGKGLEWVAT
ISGGGSEKYYVDSVKGRFTISRDNAKNSLYLQMNSLRAEDTAVYYCARQL
YAFDYWGQGTLVTVSS
(SEQ ID NO: 7)

Antibody IgG1-14 light chain variable (VL) region
DIQMTQSPSSLSASVGDRVTITCRASQSISSWLNWYQQKPGKAPKLLIYA
ASSLQSGVPSRFSGSGSGTDFTLTISSLQPEDFATYYCQQSYSTPWTFGQ
GTKVEIK
(SEQ ID NO: 8)

Antibody 06D02 heavy chain variable (VH) region
EVQLVESGGGLVQPGGSLRLSCAASGFTFSSYLMSWVRQAPGKGLEWVAT
ISGGGSETYYVDSVKGRFTISRDNAKNSLYLQMNSLRAEDTAVYYCARQL
YGFDYWGQGTLVTVSS
(SEQ ID NO: 9)

Antibody 06D02 light chain variable (VL) region
DIQMTQSPSSLSASVGDRVTITCRASQSISSWLNWYQQKPGKAPKLLIYA
ASSLQSGVPSRFSGSGSGTDFTLTISSLQPEDFATYYCQQSYSIPWTFGG
GTKVEIK
(SEQ ID NO: 10)

TABLE 17-continued

Examples of antibody variable region amino acid sequences.

Antibody 12H04 heavy chain variable (VH) region
EVQLVESGGGLVQPGGSLRLSCAASGFTFSSYLMSWVRQAPGKGLEWVAT
ISGGGAEKYYVDSVKGRFTISRDNAKNSLYLQMNSLRAEDTAVYYCARQL
YGFDYWGQGTLVTVSS
(SEQ ID NO: 11)

Antibody 12H04 light chain variable (VL) region
DIQMTQSPSSLSASVGDRVTITCRASQSISSWLNWYQQKPGKAPKLLIYA
ASSLQDGVPSRFSGSGSGTDFTLTISSLQPEDFATYYCQQSYSTPWTFGG
GTKVEIK
(SEQ ID NO: 12)

TABLE 18

Examples of antibody Fc region amino acid sequences.

Human IgG4 wild type
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPSCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQE
GNVFSCSVMHEALHNHYTQKSLSLSLGK
(SEQ ID NO: 13)

Human IgG4(S228P)
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK
(SEQ ID NO: 14)

Human IgG1 wild type
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK
(SEQ ID NO: 15)

Human IgG1-3M
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPEAAGAPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK
(SEQ ID NO: 16)

Human IgG2 wild type
ASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSHEDP
EVQFNWYVDGVEVHNAKTKPREEQFNSTFRVVSVLTVVHQDWLNGKEYKC
KVSNKGLPAPIEKTISKTKGQPREPQVYTLPPSREEMTKNQVSLTCLVKG
FYPSDISVEWESNGQPENNYKTTPPMLDSDGSFFLYSKLTVDKSRWQQGN
VFSCSVMHEALHNHYTQKSLSLSPGK
(SEQ ID NO: 17)

Human IgG1 wild type "REEM" allotype
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK

TABLE 18-continued

Examples of antibody Fc region amino acid sequences.

EYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRW
QQGNVFSCSVMHEALHNHYTQKSLSLSPGK
(SEQ ID NO: 18)

Human IgG1-3M "REEM" allotype
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPEAAGAPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSREEMKNQVSLTCL
VKGFYPSDIAVEWESNGQPENNYKTTPPVLDSDGSFFLYSKLTVDKSRWQ
QGNVFSCSVMHEALHNHYTQKSLSLSPGK
(SEQ ID NO: 19)

TABLE 19

Examples of membrane protein amino acid sequences.

Human PD1 sequence
MQIPQAPWPVVWAVLQLGWRPGWFLDSPDRPWNPPTFSPALLVVTEGDNA
TFTCSFSNTSESFVLNWYRMSPSNQTDKLAAFPEDRSQPGQDCRFRVTQL
PNGRDFHMSVVRARRNDSGTYLCGAISLAPKAQIKESLRAELRVTERRAE
VPTAHPSPSPRPAGQFQTLVVGVVGGLLGSLVLLVWVLAVICSRAARGTI
GARRTGQPLKEDPSAVPVFSVDYGELDFQWREKTPEPPVPCVPEQTEYAT
IVFPSGMGTSSPARRGSADGPRSAQPLRPEDGHCSWPL
(SEQ ID NO: 20)

Cynomolgus monkey PD1 sequence
MQIPQAPWPVVWAVLQLGWRPGWFLESPDRPWNAPTFSPALLLVTEGDNA
TFTCSFSNASESFVLNWYRMSPSNQTDKLAAFPEDRSQPGQDCRFRVTRL
PNGRDFHMSVVRARRNDSGTYLCGAISLAPKAQIKESLRAELRVTERRAE
VPTAHPSPSPRPAGQFQALVVGVVGGLLGSLVLLVWVLAVICSRAAQGTI
EARRTGQPLKEDPSAVPVFSVDYGELDFQWREKTPEPPAPCVPEQTEYAT
IVFPSGLGTSSPARRGSADGPRSPRPLRPEDGHCSWPL
(SEQ ID NO: 21)

Human KDR (VEGFR2) sequence
MQSKVLLAVALWLCVETRAASVGLPSVSLDLPRLSIQKDILTIKANTTLQ
ITCRGQRDLDWLWPNNQSGSEQRVEVTECSDGLFCKTLTIPKVIGNDTGA
YKCFYRETDLASVIYVYVQDYRSPFIASVSDQHGVVYITENKNKTVVIPC
LGSISNLNVSLCARYPEKRFVPDGNRISWDSKKGFTIPSYMISYAGMVFC
EAKINDESYQSIMYIVVVVGYRIYDVVLSPSHGIELSVGEKLVLNCTART
ELNVGIDFNWEYPSSKHQHKKLVNRDLKTQSGSEMKKFLSTLTIDGVTRS
DQGLYTCAASSGLMTKKNSTFVRVHEKPFVAFGSGMESLVEATVGERVRI
PAKYLGYPPPEIKWYKNGIPLESNHTIKAGHVLTIMEVSERDTGNYTVIL
TNPISKEKQSHVVSLVVYVPPQIGEKSLISPVDSYQYGTTQTLTCTVYAI
PPPHHIHWYWQLEEECANEPSQAVSVTNPYPCEEWRSVEDFQGGNKIEVN
KNQFALIEGKNKTVSTLVIQAANVSALYKCEAVNKVGRGERVISFHVTRG
PEITLQPDMQPTEQESVSLWCTADRSTFENLTWYKLGPQPLPIHVGELPT
PVCKNLDTLWKLNATMFSNSTNDILIMELKNASLQDQGDYVCLAQDRKTK
KRHCVVRQLTVLERVAPTITGNLENQTTSIGESIEVSCTASGNPPPQIMW
FKDNETLVEDSGIVLKDGNRNLTIRRVRKEDEGLYTCQACSVLGCAKVEA
FFIIEGAQEKTNLEIIILVGTAVIAMFFWLLLVIILRTVKRANGGELKTG
YLSIVMDPDELPLDEHCERLPYDASKWEFPRDRLKLGKPLGRGAFGQVIE
ADAFGIDKTATCRTVAVKMLKEGATHSEHRALMSELKILIHIGHHLNVVN
LLGACTKPGGPLMVIEFCKFGNLSTYLRSKRNEFVPYKTKGARFRQGKD
YVGAIPVDLKRRLDSITSSQSSASSGFVEEKSLSDVEEEEAPEDLYKDFL
TLEHLICYSFQVAKGMEFLASRKCIHRDLAARNILLSEKNVVKICDFGLA
RDIYKDPDYVRKGDARLPLKWMAPETIFDRVYTIQSDVWSFGVLLWEIFS
LGASPYPGVKIDEEFCRRLKEGTRMRAPDYTTPEMYQTMLDCWHGEPSQR
PTFSELVEHLGNLLQANAQQDGKDYIVLPISETLSMEEDSGLSLPTSPVS
CMEEEEVCDPKFHYDNTAGISQYLQNSKRKSRPVSVKTFEDIPLEEPEVK
VIPDDNQTDSGMVLASEELKTLEDRTKLSPSFGGMVPSKSRESVASEGSN
QTSGYQSGYHSDDTDTTVYSSEEAELLKLIEIGVQTGSTAQILQPDSGTT
LSSPPV
(SEQ ID NO: 22)

Rhesus KDR (VEGFR2) sequence
MASKVLLAVALWLCVETRAASVGLPSVSLDLPRLSIQKDILTIKANTTLQ
ITCRGQRDLDWLWPNNQSGSEQRVEVTECSDGLFCKTLTIPKVIGNDTGA
YKCFYRETDLASVIYVYVQDYRSPFIASVSDQHGVVYITENKNKTVVIPC
LGSISNLNVSLCARYPEKRFVPDGNRISWDSKKGFTIPSYMISYAGMVFC
EAKINDESYQSIMYIVVVVGYRIYDVVLSPSHGVELSVGEKLVLNCTART
ELNVGIDFNWEYPSSKHQHKKLVNRDLKTQSGSEMKKFLSTLTIDGVTRS
DQGLYTCAASSGLMTKKNSTFVRVHEKPFVAFGSGMESLVEATVGERVRI
PVKYLGYPPPEIKWYKNGIPLESNHTVKVGHVLTIMEVSERDTGNYTVIL
TNPISKEKQSHVVSLVVYVPPQIGEKSLISPVDSYQYGTTQTLTCTVYAI
PPPHHIHWYWQLEEECPNEPSQAVSVTNPYPCEEWRSVEDFQGGNKIEVN
KNQFALIEGKNKTVSTLVIQAANVSALYKCEAVNKVGRGERVISFHVTRG
PEITLQPDLQPTEQESVSLWCTADKSTFENLTWYKLGPQPLPVHVGELPT
PVCKNLDTLWKLNATIFSNSTNDILIMELKNASLQDQGDYVCVAQDRKTK
KRHCVVRQLTVLERVAPMITGNLENQTTSIGETIEVSCTASGNPPPQIMW
FKDNETLVEDSGIVLKDGNRNLTIRRVRKEDEGLYTCQACSVLGCAKVEA
FFIIEGAQEKTNLEIIILVGTAVIAMFFWLLLVIILRTVKRANGGELKTG
YLSIVMDPDELPLDEHCERLPYDASKWEFPRDRLKLGKPLGRGAFGQVIE
ADAFGIDKTATCRTVAVKMLKEGATHSEHRALMSELKILIHIGHHLNVVN
LLGACTKPGGPLMVIEFCKFGNLSTYLRSKRNEFVPYKTKGARFRQGKD
YVGAIPVDLKRRLDSITSSQSSASSGFVEEKSLSDVEEEEAPEDLYKDFL
TLEHLICYSFQVAKGMEFLASRKCIHRDLAARNILLSEKNVVKICDFGLA
RDIYKDPDYVRKGDARLPLKWMAPETIFDRVYTIQSDVWSFGVLLWEIFS
LGASPYPGVKIDEEFCRRLKEGTRMRAPDYTTPEMYQTMLDCWHGEPSQR
PTFSELVEHLGNLLQANAQQDGKDYIVLPISETLSMEEDSGLSLPTSPVS
CMEEEEVCDPKFHYDNTAGISQYLQNSKRKSRPVSVKTFEDIPLEEPEVK
VIPDDNQTDSGMVLASEELKTLEDRTKLAPSFSGMVSSKSRESVASEGSN
QTSGYQSGYHSDDTDTTVYSSEEAELLKLIEIGVQTGSTAQILQPDSGTT
LSSPPV
(SEQ ID NO: 23)

Human FZD5 sequence
MARPDPSAPPSLLLLLAQLVGRAAAASKAPVCQEITVPMCRGIGYNLTH
MPNQFNHDTQDEAGLEVHQFWPLVEIQCSPDLRFFLCSMYTPICLPDYHK
PLPPCRSVCERAKAGCSPLMRQYGFAWPERMSCDRLPVLGRDAEVLCMDY
NRSEATTAPPRPFPAKPTLPGPPGPAPASGGECPAGGPFVCKCREPFVPIL
KESHPLYNKVRTGQVPNCAVPCYQPSFSADERTFATFWIGLWSVLCFIST
STTVATFLIDMERFRYPERPIIFLSACYLCVSLGFVRLVVGHASVACSR
EHNHIHYETTGPALCTIVFLLVYFFGMASSIWWVILSLTWFLAAGMKWGN
EAIAGYAQYFHLAAWLIPSVKSITALALSSVDGDPVAGICYVGNQNLNSL
RGFVLGPLVLYLLVGTLFLLAGFVSLFRIRSVIKQGGTKTDKLEKLMIRI
GIFTLLYTVPASIVVACYLYEQHYRESWEAALTCACPGHDTGQPRAKPEY
WVLMLKYFMCLVVGITSGVWIWSGKTVESWRRFSTRCCCRPRRGHKSGGA
MAAGDYPEASAALTGRTGPPGPAATYHKQVSLSHV
(SEQ ID NO: 24)

Human ULBP2 sequence
MAAAAATKILLCLPLLLLLSGWSRAGRADPHSLCYDITVIPKFRPGPRWC
AVQGQVDEKTFLHYDCGNKTVTPVSPLGKKLNVTTAWKAQNPVLREVVDI
LTEQLRDIQLENYTPKEPLTLQARMSCEQKAEGHSSGSWQFSFDGQIFLL
FDSEKRMWTTVHPGARKMKEKWENDKVVAMSFHYFSMGDCIGWLEDFLMG
MDSTLEPSAGAPLAMSSGTTQLRATATTLILCCLLIILPCFILPGI
(SEQ ID NO: 25)

What is claimed is:

1. A nucleic acid molecule encoding the heavy chain variable (VH) region amino acid sequence and the light chain variable (VL) region amino acid sequence of an anti-PD1 antibody or an antigen-binding portion thereof, wherein
   (a) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QLYGFDY (SEQ ID NO: 40); and the VL region amino acid sequence comprises LCDR1 of RASQSISSWLN (SEQ ID NO: 41), LCDR2 of AASSLQS (SEQ ID NO: 42) and LCDR3 of QQSYSTPWT (SEQ ID NO: 43);
   (b) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QVYYFDY (SEQ ID NO: 44); and the VL region amino acid sequence comprises LCDR1 of RASQSISSWLN (SEQ ID NO: 41), LCDR2 of AASSLQS (SEQ ID NO: 42) and LCDR3 of QQSYSTPWT (SEQ ID NO: 43);
   (c) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QLYFFDY (SEQ ID NO: 45); and the VL region amino acid sequence comprises LCDR1 of RASQSISSWLN (SEQ ID NO: 41), LCDR2 of AASSLQS (SEQ ID NO: 42) and LCDR3 of QQSYSTPWT (SEQ ID NO: 43);
   (d) the VH region amino acid sequence comprises HCDR1 of GFTFSSYLMS (SEQ ID NO: 38), HCDR2 of VATISGGGSEKYYVDSVKG (SEQ ID NO: 39) and HCDR3 of QLYAFDY (SEQ ID NO: 46); and the VL region amino acid sequence comprises LCDR1 of RASQSISSWLN (SEQ ID NO: 41), LCDR2 of AASSLQS (SEQ ID NO: 42) and LCDR3 of QQSYSTPWT (SEQ ID NO: 43);
   (e) the VH region amino acid sequence comprises HCDR1 of GFTFSSYLMS (SEQ ID NO: 38), HCDR2 of VATISGGGSETYYVDSVKG (SEQ ID NO: 48) and HCDR3 of QLYGFDY (SEQ ID NO: 40); and the VL region amino acid sequence comprises LCDR1 of RASQSISSWLN (SEQ ID NO: 41), LCDR2 of AASSLQS (SEQ ID NO: 42) and LCDR3 of QQSYSIPWT (SEQ ID NO: 47); or
   (f) the VH region amino acid sequence comprises HCDR1 of GFTFSSYLMS (SEQ ID NO: 38), HCDR2 of VATISGGGAEKYYVDSVKG (SEQ ID NO: 49) and HCDR3 of QLYGFDY (SEQ ID NO: 40); and the VL region amino acid sequence comprises LCDR1 of RASQSISSWLN (SEQ ID NO: 41), LCDR2 of AASSLQD (SEQ ID NO: 50) and LCDR3 of QQSYSTPWT (SEQ ID NO: 43).

2. The nucleic acid molecule of claim 1, wherein
   (a) the VH region amino acid sequence comprises SEQ ID NO:1 and the VL region amino acid sequence comprises SEQ ID NO:2;
   (b) the VH region amino acid sequence comprises SEQ ID NO:3 and the VL region amino acid sequence comprises SEQ ID NO:4;
   (c) the VH region amino acid sequence comprises SEQ ID NO:5 and the VL region amino acid sequence comprises SEQ ID NO:6;
   (d) the VH region amino acid sequence comprises SEQ ID NO:7 and the VL region amino acid sequence comprises SEQ ID NO:8;
   (e) the VH region amino acid sequence comprises SEQ ID NO:9 and the VL region amino acid sequence comprises SEQ ID NO:10; or
   (f) the VH region amino acid sequence comprises SEQ ID NO:11 and the VL region amino acid sequence comprises SEQ ID NO:12.

3. The nucleic acid molecule of claim 1, wherein the antibody or antigen-binding portion is humanized or chimeric.

4. The nucleic acid molecule of claim 1, wherein the VH region, the VL region, or both the VH and the VL region comprise one or more human framework region amino acid sequences.

5. The nucleic acid molecule of claim 1, wherein the VH region, the VL region, or both the VH and the VL region comprise a human variable region framework scaffold amino acid sequence into which the CDRs have been inserted.

6. The nucleic acid molecule of claim 1, wherein the VH region comprises an IGHV3-7 human germline scaffold amino acid sequence into which the HCDR1, HCDR2 and HCDR3 amino acid sequences have been inserted.

7. The nucleic acid molecule of claim 1, wherein the VL region comprises an IGKV1-39 human germline scaffold amino acid sequence into which the LCDR1, LCDR2 and LCDR3 amino acid sequences have been inserted.

8. The nucleic acid molecule of claim 1, wherein the nucleic acid molecule further encodes an immunoglobulin constant region.

9. The nucleic acid molecule of claim 8, wherein the immunoglobulin constant region is IgG, IgE, IgM, IgD, IgA or IgY.

10. The nucleic acid molecule of claim 9, wherein the immunoglobulin constant region is IgG1, IgG2, IgG3, IgG4, IgA1 or IgA2.

11. The nucleic acid molecule of claim 8, wherein the immunoglobulin constant region is immunologically inert.

12. The nucleic acid molecule of claim 8, wherein the immunoglobulin constant region is a wild-type human IgG4 constant region, a human IgG4 constant region comprising the amino acid substitution S228P, a wild-type human IgG1 constant region, a human IgG1 constant region comprising the amino acid substitutions L234A, L235A and G237A or a wild-type human IgG2 constant region, wherein numbering is according to the EU index as in Kabat.

13. The nucleic acid molecule of claim 8, wherein the immunoglobulin constant region comprises any one of SEQ ID NOS:13-19.

14. The nucleic acid molecule of claim 1, wherein the antibody or antigen-binding portion is an Fab, an Fab', an F(ab')$_2$, an Fv, an scFv, a maxibody, a minibody a diabody, a triabody, a tetrabody, or a bis-scFv.

15. An expression vector comprising the nucleic acid molecule of claim 1.

16. A recombinant host cell comprising the expression vector of claim 15.

17. A recombinant host cell comprising the nucleic acid molecule of claim 1.

* * * * *

SEQUENCE LISTING

<160> NUMBER OF SEQ ID NOS: 182

<210> SEQ ID NO 1
<211> LENGTH: 116
<212> TYPE: PRT
<213> ORGANISM: Artificial Sequence
<220> FEATURE:
<223> OTHER INFORMATION: Antibody IgG1-08 heavy chain variable (VH)

-continued region

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Leu Met Ser Trp Val Arg Gln Ala Pro Gly Lys Gly Leu Glu Trp Val
        35                  40                  45

Ala Thr Ile Ser Gly Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Gly Phe Asp Tyr Trp Gly Gln Gly Thr Leu Val
            100                 105                 110

Thr Val Ser Ser
        115

<210> SEQ ID NO 2
<211> LENGTH: 107
<212> TYPE: PRT
<213> ORGANISM: Artificial Sequence
<220> FEATURE:
<223> OTHER INFORMATION: Antibody IgG1-08 light chain variable (VL)
      region

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 3
<211> LENGTH: 116
<212> TYPE: PRT
<213> ORGANISM: Artificial Sequence
<220> FEATURE:
<223> OTHER INFORMATION: Antibody IgG1-05 heavy chain variable (VH)
      region

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Leu Met Ser Trp Val Arg Gln Ala Pro Gly Lys Gly Leu Glu Trp Val
        35                  40                  45

```
Ala Thr Ile Ser Gly Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Val Tyr Tyr Phe Asp Tyr Trp Gly Gln Gly Thr Leu Val
            100                 105                 110

Thr Val Ser Ser
        115
```

```
<210> SEQ ID NO 4
<211> LENGTH: 107
<212> TYPE: PRT
<213> ORGANISM: Artificial Sequence
<220> FEATURE:
<223> OTHER INFORMATION: Antibody IgG1-05 light chain variable (VL)
      region

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105
```

```
<210> SEQ ID NO 5
<211> LENGTH: 116
<212> TYPE: PRT
<213> ORGANISM: Artificial Sequence
<220> FEATURE:
<223> OTHER INFORMATION: Antibody IgG1-11 heavy chain variable (VH)
      region

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Leu Met Ser Trp Val Arg Gln Ala Pro Gly Lys Gly Leu Glu Trp Val
        35                  40                  45

Ala Thr Ile Ser Gly Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Phe Phe Asp Tyr Trp Gly Gln Gly Thr Leu Val
            100                 105                 110
```

Thr Val Ser Ser
        115

<210> SEQ ID NO 6
<211> LENGTH: 107
<212> TYPE: PRT
<213> ORGANISM: Artificial Sequence
<220> FEATURE:
<223> OTHER INFORMATION: Antibody IgG1-11 light chain variable (VL)
      region

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 7
<211> LENGTH: 116
<212> TYPE: PRT
<213> ORGANISM: Artificial Sequence
<220> FEATURE:
<223> OTHER INFORMATION: Antibody IgG1-14 heavy chain variable (VH)
      region

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Leu Met Ser Trp Val Arg Gln Ala Pro Gly Lys Gly Leu Glu Trp Val
        35                  40                  45

Ala Thr Ile Ser Gly Gly Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Ala Phe Asp Tyr Trp Gly Gln Gly Thr Leu Val
            100                 105                 110

Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Antibody IgG1-14 light chain variable (VL)
      region

```
<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Val Glu Ile Lys
            100                 105

<210> SEQ ID NO 9
<211> LENGTH: 116
<212> TYPE: PRT
<213> ORGANISM: Artificial Sequence
<220> FEATURE:
<223> OTHER INFORMATION: Antibody 06D02 heavy chain variable (VH)
      region

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Leu Met Ser Trp Val Arg Gln Ala Pro Gly Lys Gly Leu Glu Trp Val
        35                  40                  45

Ala Thr Ile Ser Gly Gly Gly Ser Glu Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Gly Phe Asp Tyr Trp Gly Gln Gly Thr Leu Val
            100                 105                 110

Thr Val Ser Ser
        115

<210> SEQ ID NO 10
<211> LENGTH: 107
<212> TYPE: PRT
<213> ORGANISM: Artificial Sequence
<220> FEATURE:
<223> OTHER INFORMATION: Antibody 06D02 light chain variable (VL)
      region

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Ile Pro Trp
                 85                  90                  95

Thr Phe Gly Gly Gly Thr Lys Val Glu Ile Lys
            100                 105

<210> SEQ ID NO 11
<211> LENGTH: 116
<212> TYPE: PRT
<213> ORGANISM: Artificial Sequence
<220> FEATURE:
<223> OTHER INFORMATION: Antibody 12H04 heavy chain variable (VH)
      region

<400> SEQUENCE: 11

Glu Val Gln Leu Val Glu Ser Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Leu Met Ser Trp Val Arg Gln Ala Pro Gly Lys Gly Leu Glu Trp Val
         35                  40                  45

Ala Thr Ile Ser Gly Gly Gly Ala Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Leu Tyr Gly Phe Asp Tyr Trp Gly Gln Gly Thr Leu Val
            100                 105                 110

Thr Val Ser Ser
        115

<210> SEQ ID NO 12
<211> LENGTH: 107
<212> TYPE: PRT
<213> ORGANISM: Artificial Sequence
<220> FEATURE:
<223> OTHER INFORMATION: Antibody 12H04 light chain variable (VL)
      region

<400> SEQUENCE: 12

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Trp
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Trp
                 85                  90                  95

Thr Phe Gly Gly Gly Thr Lys Val Glu Ile Lys
            100                 105
```

<210> SEQ ID NO 13
<211> LENGTH: 327
<212> TYPE: PRT
<213> ORGANISM: Homo sapiens

<400> SEQUENCE: 13

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 14
<211> LENGTH: 327
<212> TYPE: PRT
<213> ORGANISM: Homo sapiens

<400> SEQUENCE: 14

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 15
<211> LENGTH: 330
<212> TYPE: PRT
<213> ORGANISM: Homo sapiens

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45
```

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 16
<211> LENGTH: 330
<212> TYPE: PRT
<213> ORGANISM: Homo sapiens

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys

```
            85                  90                  95
Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 17
<211> LENGTH: 326
<212> TYPE: PRT
<213> ORGANISM: Homo sapiens

<400> SEQUENCE: 17

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125
```

Thr Leu Met Ile Ser Arg Thr Pro Glu Val Thr Cys Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 18
<211> LENGTH: 330
<212> TYPE: PRT
<213> ORGANISM: Homo sapiens

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 19
<211> LENGTH: 329
<212> TYPE: PRT
<213> ORGANISM: Homo sapiens

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
                210                 215                 220
Gln Pro Arg Glu Pro Gln Val Tyr Thr Leu Pro Pro Ser Arg Glu Glu
225                 230                 235                 240

Met Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
                260                 265                 270

Tyr Lys Thr Thr Pro Pro Val Leu Asp Ser Asp Gly Ser Phe Phe Leu
                275                 280                 285

Tyr Ser Lys Leu Thr Val Asp Lys Ser Arg Trp Gln Gln Gly Asn Val
                290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 20
<211> LENGTH: 288
<212> TYPE: PRT
<213> ORGANISM: Homo sapiens

<400> SEQUENCE: 20

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
                50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
                115                 120                 125

Ala Pro Lys Ala Gln Ile Lys Glu Ser Leu Arg Ala Glu Leu Arg Val
                130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
                195                 200                 205

Leu Lys Glu Asp Pro Ser Ala Val Pro Val Phe Ser Val Asp Tyr Gly
                210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255
```

```
Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 21
<211> LENGTH: 288
<212> TYPE: PRT
<213> ORGANISM: Macaca fascicularis

<400> SEQUENCE: 21

```
Met Gln Ile Pro Gln Ala Pro Trp Pro Val Val Trp Ala Val Leu Gln
1               5                   10                  15

Leu Gly Trp Arg Pro Gly Trp Phe Leu Glu Ser Pro Asp Arg Pro Trp
            20                  25                  30

Asn Ala Pro Thr Phe Ser Pro Ala Leu Leu Leu Val Thr Glu Gly Asp
            35                  40                  45

Asn Ala Thr Phe Thr Cys Ser Phe Ser Asn Ala Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Arg Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Gln Gly Thr Ile Glu Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
                245                 250                 255

Leu Gly Thr Ser Ser Pro Ala Arg Arg Gly Ser Ala Asp Gly Pro Arg
            260                 265                 270

Ser Pro Arg Pro Leu Arg Pro Glu Asp Gly His Cys Ser Trp Pro Leu
        275                 280                 285
```

<210> SEQ ID NO 22
<211> LENGTH: 1356
<212> TYPE: PRT
<213> ORGANISM: Homo sapiens

<400> SEQUENCE: 22

```
Met Gln Ser Lys Val Leu Leu Ala Val Ala Leu Trp Leu Cys Val Glu
1               5                   10                  15
```

-continued

```
Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
```

|   |   |   |   |   |   |   |   |   |   |   |   |
|---|---|---|---|---|---|---|---|---|---|---|---|
| | | | 435 | | | | 440 | | | 445 | |
| Ala | Ile | Pro | Pro | His | His | Ile | His | Trp | Tyr | Trp | Gln | Leu | Glu | Glu |
| 450 | | | | 455 | | | | 460 | | | | | | |
| Glu | Cys | Ala | Asn | Glu | Pro | Ser | Gln | Ala | Val | Ser | Val | Thr | Asn | Pro | Tyr |
| 465 | | | | 470 | | | | 475 | | | | 480 | | | |
| Pro | Cys | Glu | Glu | Trp | Arg | Ser | Val | Glu | Asp | Phe | Gln | Gly | Gly | Asn | Lys |
| | | | | 485 | | | | 490 | | | | 495 | | | |
| Ile | Glu | Val | Asn | Lys | Asn | Gln | Phe | Ala | Leu | Ile | Glu | Gly | Lys | Asn | Lys |
| | | | 500 | | | | 505 | | | | 510 | | | | |
| Thr | Val | Ser | Thr | Leu | Val | Ile | Gln | Ala | Ala | Asn | Val | Ser | Ala | Leu | Tyr |
| | | 515 | | | | 520 | | | | 525 | | | | | |
| Lys | Cys | Glu | Ala | Val | Asn | Lys | Val | Gly | Arg | Gly | Glu | Arg | Val | Ile | Ser |
| 530 | | | | 535 | | | | 540 | | | | | | | |
| Phe | His | Val | Thr | Arg | Gly | Pro | Glu | Ile | Thr | Leu | Gln | Pro | Asp | Met | Gln |
| 545 | | | | 550 | | | | 555 | | | | 560 | | | |
| Pro | Thr | Glu | Gln | Glu | Ser | Val | Ser | Leu | Trp | Cys | Thr | Ala | Asp | Arg | Ser |
| | | | | 565 | | | | 570 | | | | 575 | | | |
| Thr | Phe | Glu | Asn | Leu | Thr | Trp | Tyr | Lys | Leu | Gly | Pro | Gln | Pro | Leu | Pro |
| | | | 580 | | | | 585 | | | | 590 | | | | |
| Ile | His | Val | Gly | Glu | Leu | Pro | Thr | Pro | Val | Cys | Lys | Asn | Leu | Asp | Thr |
| | | 595 | | | | 600 | | | | 605 | | | | | |
| Leu | Trp | Lys | Leu | Asn | Ala | Thr | Met | Phe | Ser | Asn | Ser | Thr | Asn | Asp | Ile |
| 610 | | | | 615 | | | | 620 | | | | | | | |
| Leu | Ile | Met | Glu | Leu | Lys | Asn | Ala | Ser | Leu | Gln | Asp | Gln | Gly | Asp | Tyr |
| 625 | | | | 630 | | | | 635 | | | | 640 | | | |
| Val | Cys | Leu | Ala | Gln | Asp | Arg | Lys | Thr | Lys | Arg | His | Cys | Val | Val |
| | | | | 645 | | | | 650 | | | | 655 | | | |
| Arg | Gln | Leu | Thr | Val | Leu | Glu | Arg | Val | Ala | Pro | Thr | Ile | Thr | Gly | Asn |
| | | | 660 | | | | 665 | | | | 670 | | | | |
| Leu | Glu | Asn | Gln | Thr | Thr | Ser | Ile | Gly | Glu | Ser | Ile | Glu | Val | Ser | Cys |
| | | 675 | | | | 680 | | | | 685 | | | | | |
| Thr | Ala | Ser | Gly | Asn | Pro | Pro | Pro | Gln | Ile | Met | Trp | Phe | Lys | Asp | Asn |
| 690 | | | | 695 | | | | 700 | | | | | | | |
| Glu | Thr | Leu | Val | Glu | Asp | Ser | Gly | Ile | Val | Leu | Lys | Asp | Gly | Asn | Arg |
| 705 | | | | 710 | | | | 715 | | | | 720 | | | |
| Asn | Leu | Thr | Ile | Arg | Arg | Val | Arg | Lys | Glu | Asp | Glu | Gly | Leu | Tyr | Thr |
| | | | | 725 | | | | 730 | | | | 735 | | | |
| Cys | Gln | Ala | Cys | Ser | Val | Leu | Gly | Cys | Ala | Lys | Val | Glu | Ala | Phe | Phe |
| | | | 740 | | | | 745 | | | | 750 | | | | |
| Ile | Ile | Glu | Gly | Ala | Gln | Glu | Lys | Thr | Asn | Leu | Glu | Ile | Ile | Ile | Leu |
| | | 755 | | | | 760 | | | | 765 | | | | | |
| Val | Gly | Thr | Ala | Val | Ile | Ala | Met | Phe | Phe | Trp | Leu | Leu | Leu | Val | Ile |
| | 770 | | | | 775 | | | | 780 | | | | | | |
| Ile | Leu | Arg | Thr | Val | Lys | Arg | Ala | Asn | Gly | Gly | Glu | Leu | Lys | Thr | Gly |
| 785 | | | | 790 | | | | 795 | | | | 800 | | | |
| Tyr | Leu | Ser | Ile | Val | Met | Asp | Pro | Asp | Glu | Leu | Pro | Leu | Asp | Glu | His |
| | | | 805 | | | | 810 | | | | 815 | | | | |
| Cys | Glu | Arg | Leu | Pro | Tyr | Asp | Ala | Ser | Lys | Trp | Glu | Phe | Pro | Arg | Asp |
| | | 820 | | | | 825 | | | | 830 | | | | | |
| Arg | Leu | Lys | Leu | Gly | Lys | Pro | Leu | Gly | Arg | Gly | Ala | Phe | Gly | Gln | Val |
| | 835 | | | | 840 | | | | 845 | | | | | | |
| Ile | Glu | Ala | Asp | Ala | Phe | Gly | Ile | Asp | Lys | Thr | Ala | Thr | Cys | Arg | Thr |
| 850 | | | | 855 | | | | 860 | | | | | | | |

-continued

```
Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
                900                 905                 910

Met Val Ile Val Glu Phe Cys Lys Phe Gly Asn Leu Ser Thr Tyr Leu
                915                 920                 925

Arg Ser Lys Arg Asn Glu Phe Val Pro Tyr Lys Thr Lys Gly Ala Arg
930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
                980                 985                 990

Glu Asp Leu Tyr Lys Asp Phe Leu Thr Leu Glu His Leu Ile Cys Tyr
                995                 1000                1005

Ser Phe Gln Val Ala Lys Gly Met Glu Phe Leu Ala Ser Arg Lys
        1010                1015                1020

Cys Ile His Arg Asp Leu Ala Ala Arg Asn Ile Leu Leu Ser Glu
        1025                1030                1035

Lys Asn Val Val Lys Ile Cys Asp Phe Gly Leu Ala Arg Asp Ile
        1040                1045                1050

Tyr Lys Asp Pro Asp Tyr Val Arg Lys Gly Asp Ala Arg Leu Pro
        1055                1060                1065

Leu Lys Trp Met Ala Pro Glu Thr Ile Phe Asp Arg Val Tyr Thr
        1070                1075                1080

Ile Gln Ser Asp Val Trp Ser Phe Gly Val Leu Leu Trp Glu Ile
        1085                1090                1095

Phe Ser Leu Gly Ala Ser Pro Tyr Pro Gly Val Lys Ile Asp Glu
        1100                1105                1110

Glu Phe Cys Arg Arg Leu Lys Glu Gly Thr Arg Met Arg Ala Pro
        1115                1120                1125

Asp Tyr Thr Thr Pro Glu Met Tyr Gln Thr Met Leu Asp Cys Trp
        1130                1135                1140

His Gly Glu Pro Ser Gln Arg Pro Thr Phe Ser Glu Leu Val Glu
        1145                1150                1155

His Leu Gly Asn Leu Leu Gln Ala Asn Ala Gln Gln Asp Gly Lys
        1160                1165                1170

Asp Tyr Ile Val Leu Pro Ile Ser Glu Thr Leu Ser Met Glu Glu
        1175                1180                1185

Asp Ser Gly Leu Ser Leu Pro Thr Ser Pro Val Ser Cys Met Glu
        1190                1195                1200

Glu Glu Glu Val Cys Asp Pro Lys Phe His Tyr Asp Asn Thr Ala
        1205                1210                1215

Gly Ile Ser Gln Tyr Leu Gln Asn Ser Lys Arg Lys Ser Arg Pro
        1220                1225                1230

Val Ser Val Lys Thr Phe Glu Asp Ile Pro Leu Glu Glu Pro Glu
        1235                1240                1245

Val Lys Val Ile Pro Asp Asp Asn Gln Thr Asp Ser Gly Met Val
        1250                1255                1260
```

```
Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 23
<211> LENGTH: 1356
<212> TYPE: PRT
<213> ORGANISM: Macaca mulatta

<400> SEQUENCE: 23

Met Ala Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Val Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270
```

```
Val Asn Arg Asp Leu Lys Thr Gln Ser Gly Ser Glu Met Lys Lys Phe
            275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Val
            340                 345                 350

Lys Tyr Leu Gly Tyr Pro Pro Pro Glu Ile Lys Trp Tyr Lys Asn Gly
                355                 360                 365

Ile Pro Leu Glu Ser Asn His Thr Val Lys Val Gly His Val Leu Thr
            370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
            435                 440                 445

Ala Ile Pro Pro Pro His His Ile His Trp Tyr Trp Gln Leu Glu Glu
            450                 455                 460

Glu Cys Pro Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
            515                 520                 525

Lys Cys Glu Ala Val Asn Lys Val Gly Arg Gly Glu Arg Val Ile Ser
            530                 535                 540

Phe His Val Thr Arg Gly Pro Glu Ile Thr Leu Gln Pro Asp Leu Gln
545                 550                 555                 560

Pro Thr Glu Gln Glu Ser Val Ser Leu Trp Cys Thr Ala Asp Lys Ser
                565                 570                 575

Thr Phe Glu Asn Leu Thr Trp Tyr Lys Leu Gly Pro Gln Pro Leu Pro
            580                 585                 590

Val His Val Gly Glu Leu Pro Thr Pro Val Cys Lys Asn Leu Asp Thr
            595                 600                 605

Leu Trp Lys Leu Asn Ala Thr Ile Phe Ser Asn Ser Thr Asn Asp Ile
            610                 615                 620

Leu Ile Met Glu Leu Lys Asn Ala Ser Leu Gln Asp Gln Gly Asp Tyr
625                 630                 635                 640

Val Cys Val Ala Gln Asp Arg Lys Thr Lys Lys Arg His Cys Val Val
                645                 650                 655

Arg Gln Leu Thr Val Leu Glu Arg Val Ala Pro Met Ile Thr Gly Asn
            660                 665                 670

Leu Glu Asn Gln Thr Thr Ser Ile Gly Glu Thr Ile Glu Val Ser Cys
            675                 680                 685
```

```
Thr Ala Ser Gly Asn Pro Pro Gln Ile Met Trp Phe Lys Asp Asn
690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
                740                 745                 750

Ile Ile Glu Gly Ala Gln Lys Thr Asn Leu Glu Ile Ile Leu
        755                 760                 765

Val Gly Thr Ala Val Ile Ala Met Phe Phe Trp Leu Leu Leu Val Ile
770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
                820                 825                 830

Arg Leu Lys Leu Gly Lys Pro Leu Gly Arg Gly Ala Phe Gly Gln Val
                835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
                900                 905                 910

Met Val Ile Val Glu Phe Cys Lys Phe Gly Asn Leu Ser Thr Tyr Leu
        915                 920                 925

Arg Ser Lys Arg Asn Glu Phe Val Pro Tyr Lys Thr Lys Gly Ala Arg
        930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Ala Pro
                980                 985                 990

Glu Asp Leu Tyr Lys Asp Phe Leu Thr Leu Glu His Leu Ile Cys Tyr
        995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
```

```
                  1100               1105                1110

Glu Phe Cys Arg Arg Leu Lys Glu Gly Thr Arg Met Arg Ala Pro
        1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ala Pro Ser Phe Ser Gly Met Val Ser Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 24
<211> LENGTH: 585
<212> TYPE: PRT
<213> ORGANISM: Homo sapiens

<400> SEQUENCE: 24

Met Ala Arg Pro Asp Pro Ser Ala Pro Ser Leu Leu Leu Leu Leu
1               5                   10                  15

Leu Ala Gln Leu Val Gly Arg Ala Ala Ala Ala Ser Lys Ala Pro Val
            20                  25                  30

Cys Gln Glu Ile Thr Val Pro Met Cys Arg Gly Ile Gly Tyr Asn Leu
            35                  40                  45

Thr His Met Pro Asn Gln Phe Asn His Asp Thr Gln Asp Glu Ala Gly
        50                  55                  60

Leu Glu Val His Gln Phe Trp Pro Leu Val Glu Ile Gln Cys Ser Pro
65                  70                  75                  80

Asp Leu Arg Phe Phe Leu Cys Ser Met Tyr Thr Pro Ile Cys Leu Pro
                85                  90                  95
```

-continued

Asp Tyr His Lys Pro Leu Pro Pro Cys Arg Ser Val Cys Glu Arg Ala
            100                 105                 110

Lys Ala Gly Cys Ser Pro Leu Met Arg Gln Tyr Gly Phe Ala Trp Pro
            115                 120                 125

Glu Arg Met Ser Cys Asp Arg Leu Pro Val Leu Gly Arg Asp Ala Glu
    130                 135                 140

Val Leu Cys Met Asp Tyr Asn Arg Ser Glu Ala Thr Thr Ala Pro Pro
145                 150                 155                 160

Arg Pro Phe Pro Ala Lys Pro Thr Leu Pro Gly Pro Pro Gly Ala Pro
                165                 170                 175

Ala Ser Gly Gly Glu Cys Pro Ala Gly Gly Pro Phe Val Cys Lys Cys
            180                 185                 190

Arg Glu Pro Phe Val Pro Ile Leu Lys Glu Ser His Pro Leu Tyr Asn
        195                 200                 205

Lys Val Arg Thr Gly Gln Val Pro Asn Cys Ala Val Pro Cys Tyr Gln
    210                 215                 220

Pro Ser Phe Ser Ala Asp Glu Arg Thr Phe Ala Thr Phe Trp Ile Gly
225                 230                 235                 240

Leu Trp Ser Val Leu Cys Phe Ile Ser Thr Ser Thr Thr Val Ala Thr
                245                 250                 255

Phe Leu Ile Asp Met Glu Arg Phe Arg Tyr Pro Glu Arg Pro Ile Ile
            260                 265                 270

Phe Leu Ser Ala Cys Tyr Leu Cys Val Ser Leu Gly Phe Leu Val Arg
        275                 280                 285

Leu Val Val Gly His Ala Ser Val Ala Cys Ser Arg Glu His Asn His
    290                 295                 300

Ile His Tyr Glu Thr Thr Gly Pro Ala Leu Cys Thr Ile Val Phe Leu
305                 310                 315                 320

Leu Val Tyr Phe Phe Gly Met Ala Ser Ser Ile Trp Trp Val Ile Leu
                325                 330                 335

Ser Leu Thr Trp Phe Leu Ala Ala Gly Met Lys Trp Gly Asn Glu Ala
            340                 345                 350

Ile Ala Gly Tyr Ala Gln Tyr Phe His Leu Ala Ala Trp Leu Ile Pro
        355                 360                 365

Ser Val Lys Ser Ile Thr Ala Leu Ala Leu Ser Ser Val Asp Gly Asp
    370                 375                 380

Pro Val Ala Gly Ile Cys Tyr Val Gly Asn Gln Asn Leu Asn Ser Leu
385                 390                 395                 400

Arg Gly Phe Val Leu Gly Pro Leu Val Leu Tyr Leu Leu Val Gly Thr
                405                 410                 415

Leu Phe Leu Leu Ala Gly Phe Val Ser Leu Phe Arg Ile Arg Ser Val
            420                 425                 430

Ile Lys Gln Gly Gly Thr Lys Thr Asp Lys Leu Glu Lys Leu Met Ile
        435                 440                 445

Arg Ile Gly Ile Phe Thr Leu Leu Tyr Thr Val Pro Ala Ser Ile Val
    450                 455                 460

Val Ala Cys Tyr Leu Tyr Glu Gln His Tyr Arg Glu Ser Trp Glu Ala
465                 470                 475                 480

Ala Leu Thr Cys Ala Cys Pro Gly His Asp Thr Gly Gln Pro Arg Ala
                485                 490                 495

Lys Pro Glu Tyr Trp Val Leu Met Leu Lys Tyr Phe Met Cys Leu Val
            500                 505                 510

Val Gly Ile Thr Ser Gly Val Trp Ile Trp Ser Gly Lys Thr Val Glu

```
            515                 520                 525

Ser Trp Arg Arg Phe Thr Ser Arg Cys Cys Cys Arg Pro Arg Gly
530                 535                 540

His Lys Ser Gly Gly Ala Met Ala Ala Gly Asp Tyr Pro Glu Ala Ser
545                 550                 555                 560

Ala Ala Leu Thr Gly Arg Thr Gly Pro Pro Gly Pro Ala Ala Thr Tyr
                565                 570                 575

His Lys Gln Val Ser Leu Ser His Val
            580                 585

<210> SEQ ID NO 25
<211> LENGTH: 246
<212> TYPE: PRT
<213> ORGANISM: Homo sapiens

<400> SEQUENCE: 25

Met Ala Ala Ala Ala Thr Lys Ile Leu Leu Cys Leu Pro Leu Leu
1               5                   10                  15

Leu Leu Leu Ser Gly Trp Ser Arg Ala Gly Arg Ala Asp Pro His Ser
                20                  25                  30

Leu Cys Tyr Asp Ile Thr Val Ile Pro Lys Phe Arg Pro Gly Pro Arg
            35                  40                  45

Trp Cys Ala Val Gln Gly Gln Val Asp Glu Lys Thr Phe Leu His Tyr
        50                  55                  60

Asp Cys Gly Asn Lys Thr Val Thr Pro Val Ser Pro Leu Gly Lys Lys
65                  70                  75                  80

Leu Asn Val Thr Thr Ala Trp Lys Ala Gln Asn Pro Val Leu Arg Glu
                85                  90                  95

Val Val Asp Ile Leu Thr Glu Gln Leu Arg Asp Ile Gln Leu Glu Asn
            100                 105                 110

Tyr Thr Pro Lys Glu Pro Leu Thr Leu Gln Ala Arg Met Ser Cys Glu
        115                 120                 125

Gln Lys Ala Glu Gly His Ser Ser Gly Ser Trp Gln Phe Ser Phe Asp
130                 135                 140

Gly Gln Ile Phe Leu Leu Phe Asp Ser Glu Lys Arg Met Trp Thr Thr
145                 150                 155                 160

Val His Pro Gly Ala Arg Lys Met Lys Glu Lys Trp Glu Asn Asp Lys
                165                 170                 175

Val Val Ala Met Ser Phe His Tyr Phe Ser Met Gly Asp Cys Ile Gly
            180                 185                 190

Trp Leu Glu Asp Phe Leu Met Gly Met Asp Ser Thr Leu Glu Pro Ser
        195                 200                 205

Ala Gly Ala Pro Leu Ala Met Ser Ser Gly Thr Thr Gln Leu Arg Ala
210                 215                 220

Thr Ala Thr Thr Leu Ile Leu Cys Cys Leu Leu Ile Ile Leu Pro Cys
225                 230                 235                 240

Phe Ile Leu Pro Gly Ile
                245

<210> SEQ ID NO 26
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1
<220> FEATURE:
```

```
<221> NAME/KEY: misc_feature
<222> LOCATION: (8)..(8)
<223> OTHER INFORMATION: Xaa is Leu or any other amino acid

<400> SEQUENCE: 26

Gly Phe Thr Phe Ser Ser Tyr Xaa Met Ser
1               5                   10

<210> SEQ ID NO 27
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2
<220> FEATURE:
<221> NAME/KEY: misc_feature
<222> LOCATION: (1)..(1)
<223> OTHER INFORMATION: Xaa is Val or a conservative substitution of
      Val
<220> FEATURE:
<221> NAME/KEY: misc_feature
<222> LOCATION: (3)..(3)
<223> OTHER INFORMATION: Xaa is Thr or Asn
<220> FEATURE:
<221> NAME/KEY: misc_feature
<222> LOCATION: (9)..(9)
<223> OTHER INFORMATION: Xaa is Ala or Ser
<220> FEATURE:
<221> NAME/KEY: misc_feature
<222> LOCATION: (10)..(10)
<223> OTHER INFORMATION: Xaa is Glu or Asn
<220> FEATURE:
<221> NAME/KEY: misc_feature
<222> LOCATION: (11)..(11)
<223> OTHER INFORMATION: Xaa is Thr or Lys
<220> FEATURE:
<221> NAME/KEY: misc_feature
<222> LOCATION: (14)..(14)
<223> OTHER INFORMATION: Xaa is Pro or Val

<400> SEQUENCE: 27

Xaa Ala Xaa Ile Ser Gly Gly Gly Xaa Xaa Xaa Tyr Tyr Xaa Asp Ser
1               5                   10                  15

Val Lys Gly

<210> SEQ ID NO 28
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3
<220> FEATURE:
<221> NAME/KEY: misc_feature
<222> LOCATION: (1)..(1)
<223> OTHER INFORMATION: Xaa is Gln or any other amino acid
<220> FEATURE:
<221> NAME/KEY: misc_feature
<222> LOCATION: (2)..(2)
<223> OTHER INFORMATION: Xaa is Leu or any other amino acid
<220> FEATURE:
<221> NAME/KEY: misc_feature
<222> LOCATION: (3)..(3)
<223> OTHER INFORMATION: Xaa is Tyr or a conservative substitution of
      Tyr
<220> FEATURE:
<221> NAME/KEY: misc_feature
<222> LOCATION: (4)..(4)
<223> OTHER INFORMATION: Xaa is Tyr or any other amino acid
<220> FEATURE:
<221> NAME/KEY: misc_feature
<222> LOCATION: (5)..(5)
<223> OTHER INFORMATION: Xaa is Phe or any other amino acid
```

<400> SEQUENCE: 28

Xaa Xaa Xaa Xaa Xaa Asp Tyr
1               5

<210> SEQ ID NO 29
<211> LENGTH: 10
<212> TYPE: PRT
<213> ORGANISM: Artificial Sequence
<220> FEATURE:
<223> OTHER INFORMATION: MAb005 murine/humanized antibody HCDR1

<400> SEQUENCE: 29

Gly Phe Thr Phe Ser Ser Tyr Met Met Ser
1               5                   10

<210> SEQ ID NO 30
<211> LENGTH: 17
<212> TYPE: PRT
<213> ORGANISM: Artificial Sequence
<220> FEATURE:
<223> OTHER INFORMATION: MAb005 murine/humanized antibody HCDR2

<400> SEQUENCE: 30

Thr Ile Ser Gly Gly Gly Ala Asn Thr Tyr Tyr Pro Asp Ser Val Lys
1               5                   10                  15
Gly

<210> SEQ ID NO 31
<211> LENGTH: 7
<212> TYPE: PRT
<213> ORGANISM: Artificial Sequence
<220> FEATURE:
<223> OTHER INFORMATION: MAb005 murine/humanized antibody HCDR3

<400> SEQUENCE: 31

Gln Leu Tyr Tyr Phe Asp Tyr
1               5

<210> SEQ ID NO 32
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      LCDR1
<220> FEATURE:
<221> NAME/KEY: misc_feature
<222> LOCATION: (7)..(7)
<223> OTHER INFORMATION: Xaa is Ser or a conservative substitution of
      Ser
<220> FEATURE:
<221> NAME/KEY: misc_feature
<222> LOCATION: (8)..(8)
<223> OTHER INFORMATION: Xaa is Ser or a conservative substitution of
      Ser
<220> FEATURE:
<221> NAME/KEY: misc_feature
<222> LOCATION: (9)..(9)
<223> OTHER INFORMATION: Xaa is Tyr or a conservative substitution of
      Tyr
<220> FEATURE:
<221> NAME/KEY: misc_feature
<222> LOCATION: (10)..(10)
<223> OTHER INFORMATION: Xaa is Leu or a conservative substitution of
      Leu
<220> FEATURE:
<221> NAME/KEY: misc_feature
<222> LOCATION: (11)..(11)
<223> OTHER INFORMATION: Xaa is Asn or Thr or a conservative

```
            substitution of Asn or Thr

<400> SEQUENCE: 32

Arg Ala Ser Gln Ser Ile Xaa Xaa Xaa Xaa Xaa
1               5                   10

<210> SEQ ID NO 33
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2
<220> FEATURE:
<221> NAME/KEY: misc_feature
<222> LOCATION: (1)..(1)
<223> OTHER INFORMATION: Xaa is Ala or Thr or a conservative
      substitution of Ala or Thr
<220> FEATURE:
<221> NAME/KEY: misc_feature
<222> LOCATION: (3)..(3)
<223> OTHER INFORMATION: Xaa is Ser or a conservative substitution of
      Ser
<220> FEATURE:
<221> NAME/KEY: misc_feature
<222> LOCATION: (6)..(6)
<223> OTHER INFORMATION: Xaa is Gln or any other amino acid
<220> FEATURE:
<221> NAME/KEY: misc_feature
<222> LOCATION: (7)..(7)
<223> OTHER INFORMATION: Xaa is Ser or any other amino acid

<400> SEQUENCE: 33

Xaa Ala Xaa Ser Leu Xaa Xaa
1               5

<210> SEQ ID NO 34
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      LCDR3
<220> FEATURE:
<221> NAME/KEY: misc_feature
<222> LOCATION: (3)..(3)
<223> OTHER INFORMATION: Xaa is Ser or any other amino acid
<220> FEATURE:
<221> NAME/KEY: misc_feature
<222> LOCATION: (6)..(6)
<223> OTHER INFORMATION: Xaa is Thr or any other amino acid
<220> FEATURE:
<221> NAME/KEY: misc_feature
<222> LOCATION: (8)..(8)
<223> OTHER INFORMATION: Xaa is Trp or any other amino acid

<400> SEQUENCE: 34

Gln Gln Xaa Tyr Ser Xaa Pro Xaa Thr
1               5

<210> SEQ ID NO 35
<211> LENGTH: 11
<212> TYPE: PRT
<213> ORGANISM: Artificial Sequence
<220> FEATURE:
<223> OTHER INFORMATION: MAb005 murine/humanized antibody LCDR1

<400> SEQUENCE: 35

Leu Ala Ser Gln Thr Ile Gly Thr Trp Leu Thr
1               5                   10
```

```
<210> SEQ ID NO 36
<211> LENGTH: 7
<212> TYPE: PRT
<213> ORGANISM: Artificial Sequence
<220> FEATURE:
<223> OTHER INFORMATION: MAb005 murine/humanized antibody LCDR2

<400> SEQUENCE: 36

Thr Ala Thr Ser Leu Ala Asp
1               5

<210> SEQ ID NO 37
<211> LENGTH: 9
<212> TYPE: PRT
<213> ORGANISM: Artificial Sequence
<220> FEATURE:
<223> OTHER INFORMATION: MAb005 murine/humanized antibody LCDR3

<400> SEQUENCE: 37

Gln Gln Val Tyr Ser Ile Pro Trp Thr
1               5

<210> SEQ ID NO 38
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 38

Gly Phe Thr Phe Ser Ser Tyr Leu Met Ser
1               5                   10

<210> SEQ ID NO 39
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 39

Val Ala Thr Ile Ser Gly Gly Gly Ser Glu Lys Tyr Tyr Val Asp Ser
1               5                   10                  15

Val Lys Gly

<210> SEQ ID NO 40
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 40

Gln Leu Tyr Gly Phe Asp Tyr
1               5

<210> SEQ ID NO 41
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      LCDR1

<400> SEQUENCE: 41
```

Arg Ala Ser Gln Ser Ile Ser Ser Trp Leu Asn
1               5                   10

<210> SEQ ID NO 42
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 42

Ala Ala Ser Ser Leu Gln Ser
1               5

<210> SEQ ID NO 43
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      LCDR3

<400> SEQUENCE: 43

Gln Gln Ser Tyr Ser Thr Pro Trp Thr
1               5

<210> SEQ ID NO 44
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 44

Gln Val Tyr Tyr Phe Asp Tyr
1               5

<210> SEQ ID NO 45
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 45

Gln Leu Tyr Phe Phe Asp Tyr
1               5

<210> SEQ ID NO 46
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 46

Gln Leu Tyr Ala Phe Asp Tyr
1               5

<210> SEQ ID NO 47
<211> LENGTH: 9
<212> TYPE: PRT
<213> ORGANISM: Artificial Sequence -continued

```
<220> FEATURE:
<223> OTHER INFORMATION: anti-PD1 antibody molecule or antigen-binding
      LCDR3

<400> SEQUENCE: 47

Gln Gln Ser Tyr Ser Ile Pro Trp Thr
1               5

<210> SEQ ID NO 48
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 48

Val Ala Thr Ile Ser Gly Gly Gly Ser Glu Thr Tyr Tyr Val Asp Ser
1               5                   10                  15

Val Lys Gly

<210> SEQ ID NO 49
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 49

Val Ala Thr Ile Ser Gly Gly Gly Ala Glu Lys Tyr Tyr Val Asp Ser
1               5                   10                  15

Val Lys Gly

<210> SEQ ID NO 50
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 50

Ala Ala Ser Ser Leu Gln Asp
1               5

<210> SEQ ID NO 51
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 51

Val Ala Thr Ile Ser Gly Gly Gly Ser Asn Thr Tyr Tyr Val Asp Ser
1               5                   10                  15

Val Lys Gly

<210> SEQ ID NO 52
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      LCDR1
```

```
<400> SEQUENCE: 52

Arg Ala Ser Gln Ser Ile Ser Thr Trp Leu Asn
1               5                   10

<210> SEQ ID NO 53
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 53

Ala Ala Ser Ser Leu Ala Ser
1               5

<210> SEQ ID NO 54
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 54

Ala Ala Ser Ser Leu His Ser
1               5

<210> SEQ ID NO 55
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1
<220> FEATURE:
<221> NAME/KEY: misc_feature
<222> LOCATION: (8)..(8)
<223> OTHER INFORMATION: Xaa is Ala, Asp, Glu, Phe, His, Ile, Leu, Asn,
      Pro, Gln, Ser, Thr, Val, Trp or Tyr

<400> SEQUENCE: 55

Gly Phe Thr Phe Ser Ser Tyr Xaa Met Ser
1               5                   10

<210> SEQ ID NO 56
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2
<220> FEATURE:
<221> NAME/KEY: misc_feature
<222> LOCATION: (3)..(3)
<223> OTHER INFORMATION: Xaa is Thr or Asn
<220> FEATURE:
<221> NAME/KEY: misc_feature
<222> LOCATION: (9)..(9)
<223> OTHER INFORMATION: Xaa is Ser or Ala
<220> FEATURE:
<221> NAME/KEY: misc_feature
<222> LOCATION: (10)..(10)
<223> OTHER INFORMATION: Xaa is Glu or Asn
<220> FEATURE:
<221> NAME/KEY: misc_feature
<222> LOCATION: (11)..(11)
<223> OTHER INFORMATION: Xaa is Thr or Lys
<220> FEATURE:
<221> NAME/KEY: misc_feature
```

<222> LOCATION: (14)..(14)
<223> OTHER INFORMATION: Xaa is Val or Pro

<400> SEQUENCE: 56

Val Ala Xaa Ile Ser Gly Gly Gly Xaa Xaa Xaa Tyr Tyr Xaa Asp Ser
1 5 10 15

Val Lys Gly

<210> SEQ ID NO 57
<211> LENGTH: 7
<212> TYPE: PRT
<213> ORGANISM: Artificial Sequence
<220> FEATURE:
<223> OTHER INFORMATION: anti-PD1 antibody molecule or antigen-binding HCDR3
<220> FEATURE:
<221> NAME/KEY: misc_feature
<222> LOCATION: (1)..(1)
<223> OTHER INFORMATION: Xaa is Gln, Leu, Met, Asn or Thr
<220> FEATURE:
<221> NAME/KEY: misc_feature
<222> LOCATION: (2)..(2)
<223> OTHER INFORMATION: Xaa is Leu, Gly, Lys, Gln, Met, Ser or Val
<220> FEATURE:
<221> NAME/KEY: misc_feature
<222> LOCATION: (3)..(3)
<223> OTHER INFORMATION: Xaa is Tyr or His
<220> FEATURE:
<221> NAME/KEY: misc_feature
<222> LOCATION: (4)..(4)
<223> OTHER INFORMATION: Xaa is Tyr, Ala, Asp, Gly, Phe or Met
<220> FEATURE:
<221> NAME/KEY: misc_feature
<222> LOCATION: (5)..(5)
<223> OTHER INFORMATION: Xaa is Phe, Ala, Asp, Glu, Ile, Lys, Met, Ser, Trp or Tyr

<400> SEQUENCE: 57

Xaa Xaa Xaa Xaa Xaa Asp Tyr
1 5

<210> SEQ ID NO 58
<211> LENGTH: 10
<212> TYPE: PRT
<213> ORGANISM: Artificial Sequence
<220> FEATURE:
<223> OTHER INFORMATION: anti-PD1 antibody molecule or antigen-binding HCDR1
<220> FEATURE:
<221> NAME/KEY: misc_feature
<222> LOCATION: (8)..(8)
<223> OTHER INFORMATION: Xaa is Leu, Ala or Ser

<400> SEQUENCE: 58

Gly Phe Thr Phe Ser Ser Tyr Xaa Met Ser
1 5 10

<210> SEQ ID NO 59
<211> LENGTH: 19
<212> TYPE: PRT
<213> ORGANISM: Artificial Sequence
<220> FEATURE:
<223> OTHER INFORMATION: anti-PD1 antibody molecule or antigen-binding HCDR2
<220> FEATURE:
<221> NAME/KEY: misc_feature
<222> LOCATION: (9)..(9)
<223> OTHER INFORMATION: Xaa is Ser or Ala
<220> FEATURE:
<221> NAME/KEY: misc_feature
<222> LOCATION: (10)..(10)
<223> OTHER INFORMATION: Xaa is Glu or Asn

```
<220> FEATURE:
<221> NAME/KEY: misc_feature
<222> LOCATION: (11)..(11)
<223> OTHER INFORMATION: Xaa is Thr or Lys

<400> SEQUENCE: 59

Val Ala Thr Ile Ser Gly Gly Gly Xaa Xaa Xaa Tyr Tyr Val Asp Ser
1               5                   10                  15

Val Lys Gly

<210> SEQ ID NO 60
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3
<220> FEATURE:
<221> NAME/KEY: misc_feature
<222> LOCATION: (2)..(2)
<223> OTHER INFORMATION: Xaa is Leu or Val
<220> FEATURE:
<221> NAME/KEY: misc_feature
<222> LOCATION: (4)..(4)
<223> OTHER INFORMATION: Xaa is Tyr, Gly, Phe or Ala
<220> FEATURE:
<221> NAME/KEY: misc_feature
<222> LOCATION: (5)..(5)
<223> OTHER INFORMATION: Xaa is Phe, Tyr or Ala

<400> SEQUENCE: 60

Gln Xaa Tyr Xaa Xaa Asp Tyr
1               5

<210> SEQ ID NO 61
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      LCDR1
<220> FEATURE:
<221> NAME/KEY: misc_feature
<222> LOCATION: (5)..(5)
<223> OTHER INFORMATION: Xaa is Thr or Ser
<220> FEATURE:
<221> NAME/KEY: misc_feature
<222> LOCATION: (7)..(7)
<223> OTHER INFORMATION: Xaa is Gly or Ser
<220> FEATURE:
<221> NAME/KEY: misc_feature
<222> LOCATION: (8)..(8)
<223> OTHER INFORMATION: Xaa is Thr or Ser
<220> FEATURE:
<221> NAME/KEY: misc_feature
<222> LOCATION: (9)..(9)
<223> OTHER INFORMATION: Xaa is Trp or Tyr
<220> FEATURE:
<221> NAME/KEY: misc_feature
<222> LOCATION: (11)..(11)
<223> OTHER INFORMATION: Xaa is Thr or Asn

<400> SEQUENCE: 61

Arg Ala Ser Gln Xaa Ile Xaa Xaa Xaa Leu Xaa
1               5                   10

<210> SEQ ID NO 62
<211> LENGTH: 7
<212> TYPE: PRT
<213> ORGANISM: Artificial Sequence
<220> FEATURE:
<223> OTHER INFORMATION: anti-PD1 antibody molecule or antigen-binding
```

```
          LCDR2
<220> FEATURE:
<221> NAME/KEY: misc_feature
<222> LOCATION: (1)..(1)
<223> OTHER INFORMATION: Xaa is Thr or Ala
<220> FEATURE:
<221> NAME/KEY: misc_feature
<222> LOCATION: (3)..(3)
<223> OTHER INFORMATION: Xaa is Thr or Ser
<220> FEATURE:
<221> NAME/KEY: misc_feature
<222> LOCATION: (6)..(6)
<223> OTHER INFORMATION: Xaa is Ala, Gln or His
<220> FEATURE:
<221> NAME/KEY: misc_feature
<222> LOCATION: (7)..(7)
<223> OTHER INFORMATION: Xaa is Asp or Ser

<400> SEQUENCE: 62

Xaa Ala Xaa Ser Leu Xaa Xaa
1               5

<210> SEQ ID NO 63
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      LCDR3
<220> FEATURE:
<221> NAME/KEY: misc_feature
<222> LOCATION: (3)..(3)
<223> OTHER INFORMATION: Xaa is Val or Ser
<220> FEATURE:
<221> NAME/KEY: misc_feature
<222> LOCATION: (6)..(6)
<223> OTHER INFORMATION: Xaa is Ile or Thr
<220> FEATURE:
<221> NAME/KEY: misc_feature
<222> LOCATION: (8)..(8)
<223> OTHER INFORMATION: Xaa is Trp or Leu

<400> SEQUENCE: 63

Gln Gln Xaa Tyr Ser Xaa Pro Xaa Thr
1               5

<210> SEQ ID NO 64
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      LCDR1
<220> FEATURE:
<221> NAME/KEY: misc_feature
<222> LOCATION: (7)..(7)
<223> OTHER INFORMATION: Xaa is Gly or Ser
<220> FEATURE:
<221> NAME/KEY: misc_feature
<222> LOCATION: (8)..(8)
<223> OTHER INFORMATION: Xaa is Thr or Ser
<220> FEATURE:
<221> NAME/KEY: misc_feature
<222> LOCATION: (9)..(9)
<223> OTHER INFORMATION: Xaa is Trp or Tyr

<400> SEQUENCE: 64

Arg Ala Ser Gln Ser Ile Xaa Xaa Xaa Leu Asn
1               5                   10

<210> SEQ ID NO 65
<211> LENGTH: 7
<212> TYPE: PRT
```

```
<213> ORGANISM: Artificial Sequence
<220> FEATURE:
<223> OTHER INFORMATION: anti-PD1 antibody molecule or antigen-binding
      LCDR2
<220> FEATURE:
<221> NAME/KEY: misc_feature
<222> LOCATION: (6)..(6)
<223> OTHER INFORMATION: Xaa is Gln or His

<400> SEQUENCE: 65

Ala Ala Ser Ser Leu Xaa Ser
1               5

<210> SEQ ID NO 66
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      LCDR3
<220> FEATURE:
<221> NAME/KEY: misc_feature
<222> LOCATION: (6)..(6)
<223> OTHER INFORMATION: Xaa is Ile or Thr

<400> SEQUENCE: 66

Gln Gln Ser Tyr Ser Xaa Pro Trp Thr
1               5

<210> SEQ ID NO 67
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 67

Gly Phe Thr Phe Ser Ser Tyr Ala Met Ser
1               5                   10

<210> SEQ ID NO 68
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 68

Val Ala Thr Ile Ser Gly Gly Gly Ser Asn Lys Tyr Tyr Val Asp Ser
1               5                   10                  15

Val Lys Gly

<210> SEQ ID NO 69
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 69

Ala Ala Thr Ser Leu Ala Ser
1               5

<210> SEQ ID NO 70
<211> LENGTH: 19
```

```
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 70

Val Ala Thr Ile Ser Gly Gly Gly Ala Glu Thr Tyr Tyr Val Asp Ser
1               5                  10                  15

Val Lys Gly

<210> SEQ ID NO 71
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 71

Thr Ala Ser Ser Leu Gln Asp
1               5

<210> SEQ ID NO 72
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 72

Gln Leu Tyr Tyr Ala Asp Tyr
1               5

<210> SEQ ID NO 73
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 73

Thr Ala Ser Ser Leu Ala Asp
1               5

<210> SEQ ID NO 74
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      LCDR1

<400> SEQUENCE: 74

Arg Ala Ser Gln Ser Ile Ser Ser Tyr Leu Asn
1               5                  10

<210> SEQ ID NO 75
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 75
```

Gly Phe Thr Phe Ser Ser Tyr Ser Met Ser
1               5                   10

<210> SEQ ID NO 76
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      LCDR1

<400> SEQUENCE: 76

Arg Ala Ser Gln Ser Ile Gly Thr Tyr Leu Asn
1               5                   10

<210> SEQ ID NO 77
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 77

Ala Ala Thr Ser Leu Gln Ser
1               5

<210> SEQ ID NO 78
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      LCDR1

<400> SEQUENCE: 78

Arg Ala Ser Gln Ser Ile Gly Ser Tyr Leu Asn
1               5                   10

<210> SEQ ID NO 79
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 79

Thr Ala Ser Ser Leu Gln Ser
1               5

<210> SEQ ID NO 80
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 80

Gly Phe Thr Phe Ser Ser Tyr Pro Met Ser
1               5                   10

<210> SEQ ID NO 81
<211> LENGTH: 7
<212> TYPE: PRT
<213> ORGANISM: Artificial Sequence

```
<220> FEATURE:
<223> OTHER INFORMATION: anti-PD1 antibody molecule or antigen-binding
      HCDR3

<400> SEQUENCE: 81

Gln Leu Tyr Tyr Tyr Asp Tyr
1               5

<210> SEQ ID NO 82
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 82

Ala Ala Ser Ser Leu Gln Tyr
1               5

<210> SEQ ID NO 83
<211> LENGTH: 9
<212> TYPE: PRT
<213> ORGANISM: Artificial Sequence
<220> FEATURE:
<223> OTHER INFORMATION: TCED+ and HAF peptide

<400> SEQUENCE: 83

Val Thr Ile Thr Cys Leu Ala Ser Gln
1               5

<210> SEQ ID NO 84
<211> LENGTH: 9
<212> TYPE: PRT
<213> ORGANISM: Artificial Sequence
<220> FEATURE:
<223> OTHER INFORMATION: converted TCED+ and HAF peptide

<400> SEQUENCE: 84

Val Thr Ile Thr Cys Arg Ala Ser Gln
1               5

<210> SEQ ID NO 85
<211> LENGTH: 9
<212> TYPE: PRT
<213> ORGANISM: Artificial Sequence
<220> FEATURE:
<223> OTHER INFORMATION: LAF peptide

<400> SEQUENCE: 85

Ile Gly Thr Trp Leu Thr Trp Tyr Gln
1               5

<210> SEQ ID NO 86
<211> LENGTH: 9
<212> TYPE: PRT
<213> ORGANISM: Artificial Sequence
<220> FEATURE:
<223> OTHER INFORMATION: converted LAF peptide

<400> SEQUENCE: 86

Ile Ser Ser Trp Leu Asn Trp Tyr Gln
1               5

<210> SEQ ID NO 87
<211> LENGTH: 9
<212> TYPE: PRT
```

```
<213> ORGANISM: Artificial Sequence
<220> FEATURE:
<223> OTHER INFORMATION: HAF peptide

<400> SEQUENCE: 87

Leu Leu Ile Tyr Thr Ala Thr Ser Leu
1               5

<210> SEQ ID NO 88
<211> LENGTH: 9
<212> TYPE: PRT
<213> ORGANISM: Artificial Sequence
<220> FEATURE:
<223> OTHER INFORMATION: HAF peptide

<400> SEQUENCE: 88

Leu Ile Tyr Thr Ala Thr Ser Leu Ala
1               5

<210> SEQ ID NO 89
<211> LENGTH: 9
<212> TYPE: PRT
<213> ORGANISM: Artificial Sequence
<220> FEATURE:
<223> OTHER INFORMATION: LAF peptide

<400> SEQUENCE: 89

Ile Tyr Thr Ala Thr Ser Leu Ala Asp
1               5

<210> SEQ ID NO 90
<211> LENGTH: 9
<212> TYPE: PRT
<213> ORGANISM: Artificial Sequence
<220> FEATURE:
<223> OTHER INFORMATION: LAF peptide

<400> SEQUENCE: 90

Tyr Tyr Cys Gln Gln Val Tyr Ser Ile
1               5

<210> SEQ ID NO 91
<211> LENGTH: 9
<212> TYPE: PRT
<213> ORGANISM: Artificial Sequence
<220> FEATURE:
<223> OTHER INFORMATION: LAF peptide

<400> SEQUENCE: 91

Leu Tyr Tyr Phe Asp Tyr Trp Gly Gln
1               5

<210> SEQ ID NO 92
<211> LENGTH: 19
<212> TYPE: PRT
<213> ORGANISM: Mus musculus

<400> SEQUENCE: 92

Val Ala Thr Ile Ser Gly Gly Gly Ala Asn Thr Tyr Tyr Pro Asp Ser
1               5                   10                  15

Val Lys Gly

<210> SEQ ID NO 93
<211> LENGTH: 5
<212> TYPE: PRT
<213> ORGANISM: Homo sapiens
```

<400> SEQUENCE: 93

Arg Asp Glu Leu Thr
1               5

<210> SEQ ID NO 94
<211> LENGTH: 4
<212> TYPE: PRT
<213> ORGANISM: Homo sapiens

<400> SEQUENCE: 94

Arg Glu Glu Met
1

<210> SEQ ID NO 95
<211> LENGTH: 10
<212> TYPE: PRT
<213> ORGANISM: Mus musculus

<400> SEQUENCE: 95

Gly Phe Thr Phe Ser Ser Tyr Met Met Ser
1               5                   10

<210> SEQ ID NO 96
<211> LENGTH: 5
<212> TYPE: PRT
<213> ORGANISM: Mus musculus

<400> SEQUENCE: 96

Ser Tyr Met Met Ser
1               5

<210> SEQ ID NO 97
<211> LENGTH: 7
<212> TYPE: PRT
<213> ORGANISM: Mus musculus

<400> SEQUENCE: 97

Gly Phe Thr Phe Ser Ser Tyr
1               5

<210> SEQ ID NO 98
<211> LENGTH: 8
<212> TYPE: PRT
<213> ORGANISM: Mus musculus

<400> SEQUENCE: 98

Gly Phe Thr Phe Ser Ser Tyr Met
1               5

<210> SEQ ID NO 99
<211> LENGTH: 6
<212> TYPE: PRT
<213> ORGANISM: Mus musculus

<400> SEQUENCE: 99

Ser Ser Tyr Met Met Ser
1               5

<210> SEQ ID NO 100
<211> LENGTH: 17
<212> TYPE: PRT
<213> ORGANISM: Mus musculus

<400> SEQUENCE: 100

Thr Ile Ser Gly Gly Gly Ala Asn Thr Tyr Tyr Pro Asp Ser Val Lys
1               5                   10                  15

Gly

<210> SEQ ID NO 101
<211> LENGTH: 6
<212> TYPE: PRT
<213> ORGANISM: Mus musculus

<400> SEQUENCE: 101

Ser Gly Gly Gly Ala Asn
1               5

<210> SEQ ID NO 102
<211> LENGTH: 8
<212> TYPE: PRT
<213> ORGANISM: Mus musculus

<400> SEQUENCE: 102

Ile Ser Gly Gly Gly Ala Asn Thr
1               5

<210> SEQ ID NO 103
<211> LENGTH: 16
<212> TYPE: PRT
<213> ORGANISM: Mus musculus

<400> SEQUENCE: 103

Ile Ser Gly Gly Gly Ala Asn Thr Tyr Tyr Pro Asp Ser Val Lys Gly
1               5                   10                  15

<210> SEQ ID NO 104
<211> LENGTH: 10
<212> TYPE: PRT
<213> ORGANISM: Mus musculus

<400> SEQUENCE: 104

Thr Ile Ser Gly Gly Gly Ala Asn Thr Tyr
1               5                   10

<210> SEQ ID NO 105
<211> LENGTH: 12
<212> TYPE: PRT
<213> ORGANISM: Mus musculus

<400> SEQUENCE: 105

Val Ala Thr Ile Ser Gly Gly Gly Ala Asn Thr Tyr
1               5                   10

<210> SEQ ID NO 106
<211> LENGTH: 7
<212> TYPE: PRT
<213> ORGANISM: Mus musculus

<400> SEQUENCE: 106

Gln Leu Tyr Tyr Phe Asp Tyr
1               5

<210> SEQ ID NO 107
<211> LENGTH: 9
<212> TYPE: PRT
<213> ORGANISM: Mus musculus

<400> SEQUENCE: 107

Ala Arg Gln Leu Tyr Tyr Phe Asp Tyr
1               5

<210> SEQ ID NO 108
<211> LENGTH: 6
<212> TYPE: PRT
<213> ORGANISM: Mus musculus

<400> SEQUENCE: 108

Gln Leu Tyr Tyr Phe Asp
1               5

<210> SEQ ID NO 109
<211> LENGTH: 8
<212> TYPE: PRT
<213> ORGANISM: Mus musculus

<400> SEQUENCE: 109

Ala Arg Gln Leu Tyr Tyr Phe Asp
1               5

<210> SEQ ID NO 110
<211> LENGTH: 11
<212> TYPE: PRT
<213> ORGANISM: Mus musculus

<400> SEQUENCE: 110

Leu Ala Ser Gln Thr Ile Gly Thr Trp Leu Thr
1               5                   10

<210> SEQ ID NO 111
<211> LENGTH: 6
<212> TYPE: PRT
<213> ORGANISM: Mus musculus

<400> SEQUENCE: 111

Gln Thr Ile Gly Thr Trp
1               5

<210> SEQ ID NO 112
<211> LENGTH: 8
<212> TYPE: PRT
<213> ORGANISM: Mus musculus

<400> SEQUENCE: 112

Ala Ser Gln Thr Ile Gly Thr Trp
1               5

<210> SEQ ID NO 113
<211> LENGTH: 7
<212> TYPE: PRT
<213> ORGANISM: Mus musculus

<400> SEQUENCE: 113

Gly Thr Trp Leu Thr Trp Tyr
1               5

<210> SEQ ID NO 114
<211> LENGTH: 7
<212> TYPE: PRT
<213> ORGANISM: Mus musculus

<400> SEQUENCE: 114

Thr Ala Thr Ser Leu Ala Asp

```
1               5
```

<210> SEQ ID NO 115
<211> LENGTH: 10
<212> TYPE: PRT
<213> ORGANISM: Mus musculus

<400> SEQUENCE: 115

```
Leu Leu Ile Tyr Thr Ala Thr Ser Leu Ala
1               5                   10
```

<210> SEQ ID NO 116
<211> LENGTH: 9
<212> TYPE: PRT
<213> ORGANISM: Mus musculus

<400> SEQUENCE: 116

```
Gln Gln Val Tyr Ser Ile Pro Trp Thr
1               5
```

<210> SEQ ID NO 117
<211> LENGTH: 6
<212> TYPE: PRT
<213> ORGANISM: Mus musculus

<400> SEQUENCE: 117

```
Val Tyr Ser Ile Pro Trp
1               5
```

<210> SEQ ID NO 118
<211> LENGTH: 8
<212> TYPE: PRT
<213> ORGANISM: Mus musculus

<400> SEQUENCE: 118

```
Gln Gln Val Tyr Ser Ile Pro Trp
1               5
```

<210> SEQ ID NO 119
<211> LENGTH: 116
<212> TYPE: PRT
<213> ORGANISM: Mus musculus

<400> SEQUENCE: 119

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Met Met Ser Trp Val Arg Gln Thr Pro Glu Lys Arg Leu Glu Trp Val
        35                  40                  45

Ala Thr Ile Ser Gly Gly Ala Asn Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ala Arg Gln Leu Tyr Tyr Phe Asp Tyr Trp Gly Gln Gly Thr Thr Leu
            100                 105                 110

Thr Val Ser Ser
            115
```

<210> SEQ ID NO 120
<211> LENGTH: 116
<212> TYPE: PRT
<213> ORGANISM: Artificial Sequence
<220> FEATURE:
<223> OTHER INFORMATION: PD1-VH1 IGHV3-7

<400> SEQUENCE: 120

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Met Met Ser Trp Val Arg Gln Ala Pro Gly Lys Gly Leu Glu Trp Val
        35                  40                  45

Ala Thr Ile Ser Gly Gly Gly Ala Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Tyr Phe Asp Tyr Trp Gly Gln Gly Thr Thr Val
            100                 105                 110

Thr Val Ser Ser
        115
```

<210> SEQ ID NO 121
<211> LENGTH: 107
<212> TYPE: PRT
<213> ORGANISM: Mus musculus

<400> SEQUENCE: 121

```
Asp Ile Gln Met Thr Gln Ser Pro Ala Ser Gln Ser Ala Ser Leu Gly
1               5                   10                  15

Glu Gly Val Thr Ile Thr Cys Leu Ala Ser Gln Thr Ile Gly Thr Trp
            20                  25                  30

Leu Thr Trp Tyr Gln Gln Lys Pro Gly Lys Ser Pro Gln Leu Leu Ile
        35                  40                  45

Tyr Thr Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Thr Tyr Tyr Cys Gln Gln Val Tyr Ser Ile Pro Trp
                85                  90                  95

Thr Phe Gly Gly Gly Thr Lys Leu Glu Ile Lys
            100                 105
```

<210> SEQ ID NO 122
<211> LENGTH: 107
<212> TYPE: PRT
<213> ORGANISM: Artificial Sequence
<220> FEATURE:
<223> OTHER INFORMATION: PD1-VL1 IGKV1-39

<400> SEQUENCE: 122

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Gln Thr Ile Gly Thr Trp
            20                  25                  30

Leu Thr Trp Tyr Gln Gln Lys Pro Gly Lys Ala Pro Lys Leu Leu Ile
```

```
                35                  40                  45
Tyr Thr Ala Thr Ser Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Tyr Ser Ile Pro Trp
                85                  90                  95

Thr Phe Gly Gly Gly Thr Lys Val Glu Ile Lys
            100                 105

<210> SEQ ID NO 123
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      LCDR1

<400> SEQUENCE: 123

Arg Ala Ser Gln Ser Ile Gly Ser Trp Leu Thr
1               5                   10

<210> SEQ ID NO 124
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      LCDR1

<400> SEQUENCE: 124

Arg Ala Ser Gln Ser Ile Gly Thr Trp Leu Asn
1               5                   10

<210> SEQ ID NO 125
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      LCDR1

<400> SEQUENCE: 125

Arg Ala Ser Gln Ser Ile Ser Ser Trp Leu Thr
1               5                   10

<210> SEQ ID NO 126
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      LCDR1

<400> SEQUENCE: 126

Arg Ala Ser Gln Ser Ile Ser Thr Trp Leu Thr
1               5                   10

<210> SEQ ID NO 127
<211> LENGTH: 11
<212> TYPE: PRT
<213> ORGANISM: Artificial Sequence
<220> FEATURE:
<223> OTHER INFORMATION: anti-PD1 antibody molecule or antigen-binding
      LCDR1
```

```
<400> SEQUENCE: 127

Arg Ala Ser Gln Ser Ile Ser Thr Tyr Leu Asn
1               5                   10

<210> SEQ ID NO 128
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 128

Ala Ala Ser Ser Leu Ala Asp
1               5

<210> SEQ ID NO 129
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 129

Ala Ala Thr Ser Leu Gln Asp
1               5

<210> SEQ ID NO 130
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 130

Thr Ala Thr Ser Leu Ala Ser
1               5

<210> SEQ ID NO 131
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      LCDR2

<400> SEQUENCE: 131

Thr Ala Thr Ser Leu Gln Asp
1               5

<210> SEQ ID NO 132
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      LCDR3

<400> SEQUENCE: 132

Gln Gln Ser Tyr Ser Ile Pro Leu Thr
1               5

<210> SEQ ID NO 133
<211> LENGTH: 9
<212> TYPE: PRT
```

```
<213> ORGANISM: Artificial Sequence
<220> FEATURE:
<223> OTHER INFORMATION: anti-PD1 antibody molecule or antigen-binding
      LCDR3

<400> SEQUENCE: 133

Gln Gln Val Tyr Ser Ile Pro Leu Thr
1               5

<210> SEQ ID NO 134
<211> LENGTH: 9
<212> TYPE: PRT
<213> ORGANISM: Artificial Sequence
<220> FEATURE:
<223> OTHER INFORMATION: anti-PD1 antibody molecule or antigen-binding
      LCDR3

<400> SEQUENCE: 134

Gln Gln Val Tyr Ser Thr Pro Trp Thr
1               5

<210> SEQ ID NO 135
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 135

Gly Phe Thr Phe Ser Ser Tyr Asp Met Ser
1               5                   10

<210> SEQ ID NO 136
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 136

Gly Phe Thr Phe Ser Ser Tyr Glu Met Ser
1               5                   10

<210> SEQ ID NO 137
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 137

Gly Phe Thr Phe Ser Ser Tyr Phe Met Ser
1               5                   10

<210> SEQ ID NO 138
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 138

Gly Phe Thr Phe Ser Ser Tyr Gly Met Ser
1               5                   10
```

<210> SEQ ID NO 139
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 139

Gly Phe Thr Phe Ser Ser Tyr His Met Ser
1               5                   10

<210> SEQ ID NO 140
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 140

Gly Phe Thr Phe Ser Ser Tyr Ile Met Ser
1               5                   10

<210> SEQ ID NO 141
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 141

Gly Phe Thr Phe Ser Ser Tyr Asn Met Ser
1               5                   10

<210> SEQ ID NO 142
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 142

Gly Phe Thr Phe Ser Ser Tyr Gln Met Ser
1               5                   10

<210> SEQ ID NO 143
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 143

Gly Phe Thr Phe Ser Ser Tyr Thr Met Ser
1               5                   10

<210> SEQ ID NO 144
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

-continued

<400> SEQUENCE: 144

Gly Phe Thr Phe Ser Ser Tyr Val Met Ser
1               5                   10

<210> SEQ ID NO 145
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 145

Gly Phe Thr Phe Ser Ser Tyr Trp Met Ser
1               5                   10

<210> SEQ ID NO 146
<211> LENGTH: 10
<212> TYPE: PRT
<213> ORGANISM: Artificial Sequence
<220> FEATURE:
<223> OTHER INFORMATION: anti-PD1 antibody molecule or antigen-binding
      HCDR1

<400> SEQUENCE: 146

Gly Phe Thr Phe Ser Ser Tyr Tyr Met Ser
1               5                   10

<210> SEQ ID NO 147
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 147

Val Ala Asn Ile Ser Gly Gly Gly Ala Glu Lys Tyr Tyr Pro Asp Ser
1               5                   10                  15

Val Lys Gly

<210> SEQ ID NO 148
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 148

Val Ala Asn Ile Ser Gly Gly Gly Ala Glu Lys Tyr Tyr Val Asp Ser
1               5                   10                  15

Val Lys Gly

<210> SEQ ID NO 149
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 149

Val Ala Asn Ile Ser Gly Gly Gly Ala Glu Thr Tyr Tyr Pro Asp Ser
1               5                   10                  15

Val Lys Gly

<210> SEQ ID NO 150
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 150

Val Ala Asn Ile Ser Gly Gly Gly Ala Glu Thr Tyr Tyr Val Asp Ser
1               5                   10                  15

Val Lys Gly

<210> SEQ ID NO 151
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 151

Val Ala Asn Ile Ser Gly Gly Gly Ala Asn Lys Tyr Tyr Pro Asp Ser
1               5                   10                  15

Val Lys Gly

<210> SEQ ID NO 152
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 152

Val Ala Asn Ile Ser Gly Gly Gly Ala Asn Lys Tyr Tyr Val Asp Ser
1               5                   10                  15

Val Lys Gly

<210> SEQ ID NO 153
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 153

Val Ala Asn Ile Ser Gly Gly Gly Ser Glu Lys Tyr Tyr Pro Asp Ser
1               5                   10                  15

Val Lys Gly

<210> SEQ ID NO 154
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 154

Val Ala Asn Ile Ser Gly Gly Gly Ser Glu Lys Tyr Tyr Val Asp Ser

```
1               5                  10                  15

Val Lys Gly

<210> SEQ ID NO 155
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 155

Val Ala Asn Ile Ser Gly Gly Gly Ser Glu Thr Tyr Tyr Pro Asp Ser
1               5                  10                  15

Val Lys Gly

<210> SEQ ID NO 156
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 156

Val Ala Asn Ile Ser Gly Gly Gly Ser Glu Thr Tyr Tyr Val Asp Ser
1               5                  10                  15

Val Lys Gly

<210> SEQ ID NO 157
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 157

Val Ala Asn Ile Ser Gly Gly Gly Ser Asn Lys Tyr Tyr Pro Asp Ser
1               5                  10                  15

Val Lys Gly

<210> SEQ ID NO 158
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 158

Val Ala Asn Ile Ser Gly Gly Gly Ser Asn Lys Tyr Tyr Val Asp Ser
1               5                  10                  15

Val Lys Gly

<210> SEQ ID NO 159
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 159
```

```
Val Ala Thr Ile Ser Gly Gly Gly Ala Glu Lys Tyr Tyr Pro Asp Ser
1               5                   10                  15

Val Lys Gly

<210> SEQ ID NO 160
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 160

Val Ala Thr Ile Ser Gly Gly Gly Ala Glu Thr Tyr Tyr Pro Asp Ser
1               5                   10                  15

Val Lys Gly

<210> SEQ ID NO 161
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 161

Val Ala Thr Ile Ser Gly Gly Gly Ala Asn Lys Tyr Tyr Val Asp Ser
1               5                   10                  15

Val Lys Gly

<210> SEQ ID NO 162
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 162

Val Ala Thr Ile Ser Gly Gly Gly Ser Glu Thr Tyr Tyr Pro Asp Ser
1               5                   10                  15

Val Lys Gly

<210> SEQ ID NO 163
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 163

Val Ala Thr Ile Ser Gly Gly Gly Ser Asn Lys Tyr Tyr Pro Asp Ser
1               5                   10                  15

Val Lys Gly

<210> SEQ ID NO 164
<211> LENGTH: 19
<212> TYPE: PRT
<213> ORGANISM: Artificial Sequence
<220> FEATURE:
<223> OTHER INFORMATION: anti-PD1 antibody molecule or antigen-binding
      HCDR2

<400> SEQUENCE: 164
```

```
Val Ala Thr Ile Ser Gly Gly Ala Asn Lys Tyr Tyr Pro Asp Ser
1               5                   10                  15

Val Lys Gly

<210> SEQ ID NO 165
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 165

Leu Leu Tyr Tyr Glu Asp Tyr
1               5

<210> SEQ ID NO 166
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 166

Met Leu Tyr Tyr Asp Asp Tyr
1               5

<210> SEQ ID NO 167
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 167

Asn Leu Tyr Tyr Phe Asp Tyr
1               5

<210> SEQ ID NO 168
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 168

Gln Gly Tyr Tyr Phe Asp Tyr
1               5

<210> SEQ ID NO 169
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 169

Gln Lys Tyr Tyr Phe Asp Tyr
1               5

<210> SEQ ID NO 170
<211> LENGTH: 7
```

```
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 170

Gln Leu His Tyr Phe Asp Tyr
1               5

<210> SEQ ID NO 171
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 171

Gln Leu Tyr Asp Phe Asp Tyr
1               5

<210> SEQ ID NO 172
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 172

Gln Leu Tyr Met Phe Asp Tyr
1               5

<210> SEQ ID NO 173
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 173

Gln Leu Tyr Tyr Glu Asp Tyr
1               5

<210> SEQ ID NO 174
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 174

Gln Leu Tyr Tyr Ile Asp Tyr
1               5

<210> SEQ ID NO 175
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 175

Gln Leu Tyr Tyr Lys Asp Tyr
```

```
1               5

<210> SEQ ID NO 176
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 176

Gln Leu Tyr Tyr Met Asp Tyr
1               5

<210> SEQ ID NO 177
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 177

Gln Leu Tyr Tyr Ser Asp Tyr
1               5

<210> SEQ ID NO 178
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 178

Gln Leu Tyr Tyr Trp Asp Tyr
1               5

<210> SEQ ID NO 179
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 179

Gln Met Tyr Tyr Phe Asp Tyr
1               5

<210> SEQ ID NO 180
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 180

Gln Gln Tyr Tyr Phe Asp Tyr
1               5

<210> SEQ ID NO 181
<211> LENGTH: 7
<212> TYPE: PRT
<213> ORGANISM: Artificial Sequence
<220> FEATURE:
<223> OTHER INFORMATION: anti-PD1 antibody molecule or antigen-binding
```

HCDR3

<400> SEQUENCE: 181

Gln Ser Tyr Tyr Phe Asp Tyr
1               5

<210> SEQ ID NO 182
<211> LENGTH: 7
<212> TYPE: PRT
<213> ORGANISM: Artificial Sequence
<220> FEATURE:
<223> OTHER INFORMATION: anti-PD1 antibody molecule or antigen-binding
      HCDR3

<400> SEQUENCE: 182

Thr Leu Tyr Tyr Phe Asp Tyr
1               5